United States Patent
Wang et al.

(10) Patent No.: US 11,739,162 B2
(45) Date of Patent: Aug. 29, 2023

(54) SIDE CHAIN MODIFIED PEPTOIDS USEFUL AS STRUCTURE-STABILIZING COATINGS FOR BIOMATERIALS

(71) Applicants: Brookhaven Science Associates, LLC, Upton, NY (US); The Regents of the University of California, Oakland, CA (US); The Board of Trustees of the Leland Stanford Junior University, Stanford, CA (US); The Trustees of Columbia University in the City of New York, New York, NY (US)

(72) Inventors: Shih-Ting Wang, Mastic, NY (US); Oleg Gang, Setauket, NY (US); Ronald N. Zuckermann, El Cerrito, CA (US); Carolyn R. Bertozzi, Menlo Park, CA (US)

(73) Assignees: Brookhaven Science Associates LLC, Upton, NY (US); The Board of Trustees of the Leland Stanford Junior University, Stanford, CA (US); The Regents of the University of California, Oakland, CA (US); The Trustees of Columbia University in the City of New York, New York, NY (US)

( * ) Notice: Subject to any disclaimer, the term of this patent is extended or adjusted under 35 U.S.C. 154(b) by 232 days.

(21) Appl. No.: 17/015,532

(22) Filed: Sep. 9, 2020

(65) Prior Publication Data
US 2021/0070886 A1    Mar. 11, 2021

Related U.S. Application Data

(60) Provisional application No. 62/897,451, filed on Sep. 9, 2019.

(51) Int. Cl.
*C07K 7/06* (2006.01)
*C07K 17/06* (2006.01)
*A61K 47/69* (2017.01)
*C07K 1/10* (2006.01)
*B82Y 5/00* (2011.01)

(52) U.S. Cl.
CPC .......... *C07K 17/06* (2013.01); *A61K 47/6923* (2017.08); *C07K 1/10* (2013.01); *C07K 7/06* (2013.01); *B82Y 5/00* (2013.01)

(58) Field of Classification Search
None
See application file for complete search history.

(56) References Cited

U.S. PATENT DOCUMENTS

| 8,952,127 | B2 * | 2/2015 | Chen ...................... C08G 69/10 423/430 |
| 9,073,977 | B2 * | 7/2015 | Zuckermann ........ C07K 14/001 |
| 9,764,953 | B2 * | 9/2017 | Zuckermann ......... C01B 25/455 |

FOREIGN PATENT DOCUMENTS

WO    WO-2021030218 A1 *  2/2021  ........... A61K 47/543

OTHER PUBLICATIONS

Mahmoudi, Neda et al; "PEG-mimetic peptoid reduces protein fouling of polysulfone hollow fibers." Colloids Surf. B (2017) 149 p. 23-29.*
Seeman, Nadrian C., "DNA in a Material World," Nature 421.6921, pp. 427-431 (2003).
Lin C, et al., "Designer DNA Nanoarchitectures," Biochemistry 48, pp. 1663-1674 (2009).
Pinheiro A V, et al., "Challenges and Opportunities for Structural DNA Nanotechnology," Nature Nanotechnology 6, pp. 763-772 (2011).
Rothemund, Paul WK. "Folding DNA to Create Nanoscale Shapes and Patterns," Nature 440.7082, pp. 297-302 (2006).
Mirkin, Chad A., et al. "A DNA-Based Method for Rationally Assembling Nanoparticles into Macroscopic Materials," Nature 382.6592, pp. 607-609 (1996).
Niemeyer, Christof M., et al., "Covalent DNA—Streptavidin Conjugates as Building Blocks for Novel Biometallic Nanostructures," Angewandte Chemie International Edition 37(16), pp. 2265-2268 (1998).
Keren, Kinneret, et al. "Sequence-Specific Molecular Lithography on Single DNA Molecules," Science 297.5578, pp. 72-75 (2002).
Ford, William E., et al. "Platinated DNA as Precursors to Templated Chains of Metal Nanoparticles," Advanced Materials 13(23) pp. 1793-1797 (2001).
Alivisatos, A. Paul, et al. "Organization of 'Nanocrystal Molecules' using DNA," Nature 382.6592, pp. 609-611 (1996).
Nykypanchuk, Dmytro, et al. "DNA-Guided Crystallization of Colloidal Nanoparticles," Nature 451.7178, pp. 549-552 (2008).
Zhang, Yugang, et al. "A General Strategy for the DNA-Mediated Self-Assembly of Functional Nanoparticles into Heterogeneous Systems," Nature Nanotechnology 8(11), pp. 865-872 (2013).
Chandrasekaran, Arun Richard, et al., "DNA Nanocages," Chemistry of Materials 28(16), pp. 5569-5581 (2016).
Schneider, Ann-Kathrin, et al., "DNA Surface Technology: From Gene Sensors to Integrated Systems for Life and Materials Sciences," Angewandte Chemie International Edition 57(52), pp. 16959-16967 (2018).
Zhu, Bing, et al. "Precisely Tailored DNA Nanostructures and Their Theranostic Applications," The Chemical Record 17(12) pp. 1213-1230 (2017).

(Continued)

*Primary Examiner* — Fred H Reynolds
(74) *Attorney, Agent, or Firm* — Baker Botts LLP

(57) ABSTRACT

The current invention pertains compositions and methods to generate compositions providing stability to biomolecules, including providing physiologically stable and functional DNA origami-based drug/gene delivery carriers by surface coating with the oligo-ethylene glycol conjugated peptoids of Formulas (I), (II), and (III).

2 Claims, 78 Drawing Sheets

Specification includes a Sequence Listing.

(56) References Cited

OTHER PUBLICATIONS

Zhang, Yuezhou, et al. "Programmable and Multifunctional DNA-Based Materials for Biomedical Applications," Advanced Materials 30(24) 1703658 (2018).
Fu, Jinglin, et al. "Spatially-Interactive Biomolecular Networks Organized by Nucleic Acid Nanostructures," Accounts of Chemical Research 45(8) pp. 1215-1226 (2012).
Li, Jiang, et al. "Smart Drug Delivery Nanocarriers with Self-Assembled DNA Nanostructures," Advanced Materials 25(32) pp. 4386-4396 (2013).
Amir, Yaniv, et al. "Universal Computing by DNA Origami Robots in a Living Animal," Nature Nanotechnology 9(5) pp. 353-357 (2014).
Douglas, Shawn M., et al., "A Logic-Gated Nanorobot for Targeted Transport of Molecular Payloads," Science 335.6070, pp. 831-834 (2012).
Bujold, Katherine E., et al., "Optimized DNA "Nanosuitcases" for Encapsulation and Conditional Release of siRNA," Journal of the American Chemical Society 138(42), pp. 14030-14038 (2016).
Schuller, Verena J., et al. "Cellular Immunostimulation by CpG-Sequence-Coated DNA Origami Structures," ACS Nano 5(12) pp. 9696-9702 (2011).
Grossi G, et al., "Control of Enzyme Reactions by a Reconfigurable DNA Nanovault," Nat Commun 8:992, pp. 1-8 (2017).
Ora A, et al. (2016) Cellular delivery of enzyme-loaded DNA origami. Chem Commun 52:14161-14164.
Jiang, Qiao, et al. "DNA Origami as a Carrier for Circumvention of Drug Resistance," Journal of the American Chemical Society 134(32) pp. 13396-13403 (2012).
Zhang, Qian, et al. "DNA Origami as an In Vivo Drug Delivery Vehicle for Cancer Therapy," ACS Nano 8(7), pp. 6633-6643 (2014).
Sun W, et al. "Cocoon-Like Self-Degradable DNA Nanoclew for Anticancer Drug Delivery," Journal of the American Chemical Society 136, pp. 14722-14725 (2014).
Douglas S. M., et al. "Self-Assembly of DNA into Nanoscale Three-Dimensional Shapes," Nature 459.7245, pp. 414-418 (2009).
Hahn, Jaeseung, et al. "Addressing the Instability of DNA Nanostructures in Tissue Culture," ACS Nano 8(9), pp. 8765-8775 (2014).
Kielar C, et al. "On the Stability of DNA Origami Nanostructures in Low-Magnesium Buffers," Angew Chemie Int Ed 57, pp. 9470-9474 (2018).
Kim, Hyojeong, et al., "Stability of DNA Origami Nanostructure under Diverse Chemical Environments," Chem Mater 26, pp. 5265-5273 (2014).
Benson E, et al. "Effects of Design Choices on the Stiffness of Wireframe DNA Origami Structures," ACS Nano 12, pp. 9291-9299 (2018).
Benson E, et al., "DNA Rendering of Polyhedral Meshes at the Nanoscale," Nature 523.7561, pp. 441-444 (2015).
Veneziano, R., et al. "Designer Nanoscale DNA Assemblies Programmed from the Top Down," Science 352.6293 pp. 1534-1534 (2016).
Gerling T, et al., "Sequence-Programmable Covalent Bonding of Designed DNA Assemblies," Science Advances 4: eaau1157 (2018).
Cassinelli, Valentina, et al. "One-Step Formation of "Chain-Armor"-Stabilized DNA Nanostructures," Angewandte Chemie International Edition 54.27, pp. 7795-7798 (2015).
Ponnuswamy N, et al. "Oligolysine-Based Coating Protects DNA Nanostructures from Low-Salt Denaturation and Nuclease Degradation," Nat Commun 8:15654 (2017).
Kiviaho J.K., et al. "Cationic Polymers for DNA Origami Coating—Examining Their Binding Efficiency and Tuning the Enzymatic Reaction Rates," Nanoscale 8, pp. 11674-11680 (2016).
Agarwal, N.P., et al., "Block Copolymer Micellization as a Protection Strategy for DNA Origami," Angew Chemie Int Ed 56, pp. 5460-5464 (2017).
Mikkila J, et al. "Virus-Encapsulated DNA Origami Nanostructures for Cellular Delivery," Nano Lett 14, pp. 2196-2200 (2014).
Auvinen H, et al. Protein Coating of DNA Nanostructures for Enhanced Stability and Immunocompatibility, Advanced Healthcare Materials, 6:1700692 (2017).
Sun, Jing, et al., "Peptoid Polymers: A Highly Designable Boinspired Material," ACS Nano 7.6, pp. 4715-4732 (2013).
Figliozzi G.M., et al. "[25] Synthesis of N-Substituted Glycine Peptoid Libraries," Methods in Enzymology 267, pp. 437-447 (1996).
Webster A.M., et al. "Recent Advances in the Synthesis of Peptoid Macrocycles," Chemistry—A European Journal 24.30. pp. 7560-7573 (2018).
Miller, Susan M., et al. "Proteolytic Studies of Homologous Peptide and N-Substituted Glycine Peptoid Oligomers," Bioorganic & Medicinal Chemistry Letters 4.22, pp. 2657-2662 (1994).
Wender, Paul A., et al. "The Design, Synthesis, and Evaluation of Molecules that Enable or Enhance Cellular Uptake: Peptoid Molecular Transporters." Proceedings of the National Academy of Sciences 97.24 pp. 13003-13008 (2000).
Rothbard, Jonathan B., et al. "Arginine-Rich Molecular Transporters for Drug Delivery: Role of Backbone Spacing in Cellular Uptake," Journal of Medicinal Chemistry 45.17, pp. 3612-3618 (2002).
Schroder, Tina, et al. "Peptoidic Amino-and Guanidinium-Carrier Systems: Targeted Drug Delivery Into the Cell Cytosol or the Nucleus," Journal of Medicinal Chemistry 51.3, pp. 376-379 (2008).
Murphy, John E., et al. "A Combinatorial Approach to the Discovery of Efficient Cationic Peptoid Reagents for Gene Delivery. " Proceedings of the National Academy of Sciences 95.4 (1998): 1517-1522.
Tian, Y, et al. "Prescribed Nanoparticle Cluster Architectures and Low-Dimensional Arrays Built Using Octahedral DNA Origami Frames," Nature Nanotechnology 10, pp. 637-644 (2015).
Tian, Ye, et al. "Lattice Engineering Through Nanoparticle-DNA Frameworks," Nature Materials 15.6, pp. 654-661 (2016).
Statz, Andrea R., et al. "New Peptidomimetic Polymers for Antifouling Surfaces," Journal of the American Chemical Society 127. 22, pp. 7972-7973 (2005).
Xuan, Sunting, et al. "Synthesis and Characterization of Well-Defined PEGylated Polypeptoids as Protein-Resistant Polymers," Biomacromolecules 18.3, pp. 951-964 (2017).
Dragan, A. I., et al. "SYBR Green I: Fluorescence Properties and Interaction with DNA," Journal of Fluorescence 22.4, pp. 1189-1199 (2012).
Zipper, Hubert, et al. "Investigations on DNA Intercalation and Surface Binding by SYBR Green I, its Structure Determination and Methodological Implications," Nucleic Acids Research 32.12, pp. e103-e103 (2004).
Krishnamoorthy, G., et al., "Structure and Dynamics of Condensed DNA Probed by 1, 1 '-(4, 4, 8, 8-Tetramethyl-4, 8-Diazaundecamethylene) bis [4-[[3-Methylbenz-1, 3-Oxazol-2-yl] Methylidine]-1, 4-Dihydroquinolinium] Tetraiodide Fluorescence," Biochemistry 41.51, pp. 15277-15287 (2002).
Guarnieri, Frank, et al., "Simulated Annealing of Chemical Potential: A General Procedure for Locating Bound Waters. Application to the Study of the Differential Hydration Propensities of the Major and Minor Grooves of DNA," Journal of the American Chemical Society 118.35, pp. 8493-8494 (1996).
Spink, Charles H., et al., "Effects of Hydration, Ion Release, and Excluded Volume on the Melting of Triplex and Duplex DNA," Biochemistry 38.1, pp. 496-508 (1999).
Tateishi-Karimta, et al., "Control of Stability and Structure of Nucleic Acids Using Cosolutes," Methods 67.2, pp. 151-158 (2014).
Miyoshi, Daisuke, et al. "Hydration Regulates Thermodynamics of G-Quadruplex Formation Under Molecular Crowding Conditions" Journal of the American Chemical Society 128.24, pp. 7957-7963 (2006).
Munkholm, Christiane, et al., "Intramolecular Fluorescence Self-Quenching of Fluoresceinamine," Journal of the American Chemical Society 112.7, pp. 2608-2612 (1990).
Hu, Lianzhe, et al. "Highly Sensitive Fluorescent Detection of Trypsin Based on BSA-Stabilized Gold Nanoclusters," Biosensors and Bioelectronics 32.1, pp. 297-299 (2012).

(56) References Cited

OTHER PUBLICATIONS

Xiao, Han, et al. "Precision Glycocalyx Editing as a Strategy for Cancer Immunotherapy" Proceedings of the National Academy of Sciences 113.37, pp. 10304-10309 (2016).

* cited by examiner

Brush-type          Block-type

PE7

SEQUENCE LISTING

<160> NUMBER OF SEQ ID NOS: 127

<210> SEQ ID NO 1
<211> LENGTH: 18
<212> TYPE: DNA
<213> ORGANISM: Artificial Sequence
<220> FEATURE:
<223> OTHER INFORMATION: Description of artificial sequence: DBCO-
      modified ssDNA

<400> SEQUENCE: 1
tatgaagtga tggatgat                                                       18

<210> SEQ ID NO 2
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 2
tcaaagcgaa ccagaccgtt ttatatagtc                                          30

<210> SEQ ID NO 3
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 3
gctttgagga ctaaagagca acggggagtt                                          30

<210> SEQ ID NO 4
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 4
gtaaatcgtc gctattgaat aactcaagaa                                          30

<210> SEQ ID NO 5
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 5
aagccttaaa tcaagacttg cggagcaaat                                          30

<210> SEQ ID NO 6
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 6
attttaagaa ctggcttgaa ttatcagtga                                          30

```
<210> SEQ ID NO 7
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 7
gttaaaattc gcattataaa cgtaaactag                                      30

<210> SEQ ID NO 8
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 8
agcaccatta ccattacagc aaatgacgga                                      30

<210> SEQ ID NO 9
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 9
attgcgtaga ttttcaaaac agattgtttg                                      30

<210> SEQ ID NO 10
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 10
taacctgttt agctattttc gcattcattc                                      30

<210> SEQ ID NO 11
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 11
gtcagagggt aattgagaac accaaaatag                                      30

<210> SEQ ID NO 12
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 12
ctccagccag ctttcccctc aggacgttgg                                      30
```

<210> SEQ ID NO 13
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 13
gtccactatt aaagaaccag ttttggttcc                                    30

<210> SEQ ID NO 14
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 14
taaaggtggc aacatagtag aaaataataa                                    30

<210> SEQ ID NO 15
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 15
gataagtcct gaacaactgt ttaaagagaa                                    30

<210> SEQ ID NO 16
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 16
ggtaatagta aaatgtaagt tttacactat                                    30

<210> SEQ ID NO 17
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 17
tcagaaccgc caccctctca gagtattagc                                    30

<210> SEQ ID NO 18
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 18
aagggaaccg aactgagcag acggtatcat                                    30

```
<210> SEQ ID NO 19
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 19
gtaaagattc aaaaggcctg agttgaccct                                    30

<210> SEQ ID NO 20
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 20
aggcgttaaa taagaagacc gtgtcgcaag                                    30

<210> SEQ ID NO 21
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 21
caggtcgact ctagagcaag cttcaaggcg                                    30

<210> SEQ ID NO 22
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 22
cagagccacc accctctcag aactcgagag                                    30

<210> SEQ ID NO 23
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 23
ttcacgttga aaatcttgcg aatgggattt                                    30

<210> SEQ ID NO 24
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 24
aagttttaac ggggtcggag tgtagaatgg                                    30

<210> SEQ ID NO 25
```

```
<211> LENGTH: 30
<212> TYPE: DNA
<213> ORGANISM: Artificial Sequence
<220> FEATURE:
<223> OTHER INFORMATION: Description of artificial sequence: DNA
      origamis

<400> SEQUENCE: 25
ttgcgtattg ggcgcccgcg gggtgcgctc                                        30

<210> SEQ ID NO 26
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 26
gtcaccagag ccatggtgaa ttatcaccaa tcagaaaagc ct                          42

<210> SEQ ID NO 27
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 27
ggacagagtt actttgtcga aatccgcgtg tatcaccgta cg                          42

<210> SEQ ID NO 28
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 28
caacatgatt tacgagcatg gaataagtaa gacgacaata aa                          42

<210> SEQ ID NO 29
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 29
aaccagacgc tacgttaata aaacgaacat accacattca gg                          42

<210> SEQ ID NO 30
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 30
tgacctacta gaaaaagccc caggcaaagc aatttcatct tc                          42

<210> SEQ ID NO 31
<211> LENGTH: 42
```

<212> TYPE: DNA
<213> ORGANISM: Artificial Sequence
<220> FEATURE:
<223> OTHER INFORMATION: Description of artificial sequence: DNA
      origamis

<400> SEQUENCE: 31
tgccggaagg ggactcgtaa ccgtgcatta tattttagtt ct                          42

<210> SEQ ID NO 32
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 32
agaaccccaa atcaccatct gcggaatcga ataaaaattt tt                          42

<210> SEQ ID NO 33
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 33
gctccattgt gtaccgtaac actgagttag ttagcgtaac ct                          42

<210> SEQ ID NO 34
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 34
agtaccgaat aggaacccaa acggtgtaac ctcaggaggt tt                          42

<210> SEQ ID NO 35
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 35
cagtttgaat gtttagtatc atatgcgtag aatcgccata gc                          42

<210> SEQ ID NO 36
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 36
aagattgttt tttaaccaag aaaccatcga cccaaaaaca gg                          42

<210> SEQ ID NO 37
<211> LENGTH: 42
<212> TYPE: DNA

```
<213> ORGANISM: Artificial Sequence
<220> FEATURE:
<223> OTHER INFORMATION: Description of artificial sequence: DNA
      origamis

<400> SEQUENCE: 37
tcagagcgcc accacataat caaaatcaga acgagtagta tg                          42

<210> SEQ ID NO 38
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 38
gatggttggg aagaaaaatc caccagaaat aattgggctt ga                          42

<210> SEQ ID NO 39
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 39
ctccttaacg tagaaaccaa tcaataattc atcgagaaca ga                          42

<210> SEQ ID NO 40
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 40
agacaccttg cgcagaactg gcatgatttt ctgtccagac aa                          42

<210> SEQ ID NO 41
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 41
gccagctagg cgatagctta gattaagacc ttttaacct gt                           42

<210> SEQ ID NO 42
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 42
ccgacttatt aggaacgcca tcaaaaatga gtaacaaccc ca                          42

<210> SEQ ID NO 43
<211> LENGTH: 42
<212> TYPE: DNA
<213> ORGANISM: Artificial Sequence
```

<220> FEATURE:
<223> OTHER INFORMATION: Description of artificial sequence: DNA
      origamis

<400> SEQUENCE: 43
gtccaatagc gagaaccaga cgacgatatt caacgcaagg ga                              42

<210> SEQ ID NO 44
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 44
ccaaaataca atatgatatt caaccgttag gctatcaggt aa                              42

<210> SEQ ID NO 45
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 45
aacagtactt gaaaacatat gagacgggtc tttttaatg ga                               42

<210> SEQ ID NO 46
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 46
tttcaccgca ttaaagtcgg gaaacctgat ttgaattacc ca                              42

<210> SEQ ID NO 47
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 47
gagaatagag ccttaccgtc tatcaaatgg agcggaatta ga                              42

<210> SEQ ID NO 48
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 48
ataattaaat ttaaaaaact ttttcaaact tttaacaacg cc                              42

<210> SEQ ID NO 49
<211> LENGTH: 42
<212> TYPE: DNA
<213> ORGANISM: Artificial Sequence
<220> FEATURE:

<223> OTHER INFORMATION: Description of artificial sequence: DNA
      origamis

<400> SEQUENCE: 49
gcacccagcg tttttatcc ggtattctag gcgaattatt ca                              42

<210> SEQ ID NO 50
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 50
ggaagcgccc acaaacagtt aatgccccga ctcctcaaga ta                              42

<210> SEQ ID NO 51
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 51
gtttgcctat tcacaggcag gtcagacgcc accacaccac cc                              42

<210> SEQ ID NO 52
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 52
cgcgagctta gttttttccca attctgcgca agtgtaaagc ct                             42

<210> SEQ ID NO 53
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 53
agaagcaacc aagccaaaag aatacactaa tgccaaaact cc                              42

<210> SEQ ID NO 54
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 54
attaagtata aagcggcaag gcaaagaaac taatagggta cc                              42

<210> SEQ ID NO 55
<211> LENGTH: 42
<212> TYPE: DNA
<213> ORGANISM: Artificial Sequence
<220> FEATURE:
<223> OTHER INFORMATION: Description of artificial sequence: DNA origamis

<400> SEQUENCE: 55
cagtgcctac atgggaattt accgttccac aagtaagcag at                             42

<210> SEQ ID NO 56
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 56
ataaggcgcc aaaagttgag atttaggata acggaccagt ca                             42

<210> SEQ ID NO 57
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 57
tgctaaacag atgaagaaac caccagaatt taaaaaaagg ct                             42

<210> SEQ ID NO 58
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 58
cagccttggt tttgtattaa gaggctgact gcctatatca ga                             42

<210> SEQ ID NO 59
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 59
cggaataatt caacccagcg ccaaagactt attttaacgc aa                             42

<210> SEQ ID NO 60
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 60
cgcctgaatt accctaatct tgacaagaca gaccatgaaa ga                             42

<210> SEQ ID NO 61
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 61
acgcgaggct acaacagtac cttttacaaa tcgcgcagag aa        42

<210> SEQ ID NO 62
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 62
cagcgaacat taaaagagag tacctttact gaatataatg aa        42

<210> SEQ ID NO 63
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 63
ggacgtttaa tttcgacgag aaacaccacc actaatgcag at        42

<210> SEQ ID NO 64
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 64
aaagcgccaa agtttatctt accgaagccc aataatgagt aa        42

<210> SEQ ID NO 65
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 65
gagctcgttg taaacgccag ggttttccaa agcaataaag cc        42

<210> SEQ ID NO 66
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 66
aattattgtt ttcatgcctt tagcgtcaga tagcacggaa ac        42

<210> SEQ ID NO 67
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 67
aagtttcaga cagccgggat cgtcaccctt ctgtagctca ac        42

<210> SEQ ID NO 68
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 68
acaaagaaat ttaggtaggg cttaattgta tacaacggaa tc        42

<210> SEQ ID NO 69
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 69
aacaaaaata actaggtctg agagactacg ctgagtttcc ct        42

<210> SEQ ID NO 70
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 70
cataacctaa atcaacagtt cagaaaacgt cataaggata gc        42

<210> SEQ ID NO 71
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 71
cacgacgaat tcgtgtggca tcaattcttt agcaaaatta cg        42

<210> SEQ ID NO 72
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 72
cctaccaaca gtaattttat cctgaatcaa acagccatat ga        42

<210> SEQ ID NO 73
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 73
gattataaag aaacgccagt tacaaaattt accaacgtca ga                                42

<210> SEQ ID NO 74
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 74
agtagattga aaagaatcat ggtcatagcc ggaagcataa gt                                42

<210> SEQ ID NO 75
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 75
tagaatccat aaatcattta acaatttctc ccggcttagg tt                                42

<210> SEQ ID NO 76
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 76
aaaggccaaa tatgttagag cttaattgat tgctccatga gg                                42

<210> SEQ ID NO 77
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 77
ccaaaaggaa aggacaacag tttcagcgaa tcatcatatt cc                                42

<210> SEQ ID NO 78
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 78
gaaatcgata accggatacc gatagttgta tcagctccaa cg                                42

<210> SEQ ID NO 79
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 79
tgaatattat caaaataatg gaagggttaa tatttatccc aa            42

<210> SEQ ID NO 80
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 80
gaggaagcag gattcgggta aaatacgtaa aacaccccccc ag           42

<210> SEQ ID NO 81
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 81
ggttgatttt ccagcagaca gccctcattc gtcacgggat ag            42

<210> SEQ ID NO 82
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 82
caagccccca cccttagccc ggaataggac gatctaaagt tt            42

<210> SEQ ID NO 83
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 83
tgtagatatt acgcggcgat cggtgcgggc gccatcttct gg            42

<210> SEQ ID NO 84
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 84
catcctattc agctaaaagg taaagtaaaa agcaagccgt tt            42

<210> SEQ ID NO 85
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 85
cagctcatat aagcgtaccc cggttgatgt gtcggattct cc            42

```
<210> SEQ ID NO 86
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 86
catgtcacaa acggcattaa atgtgagcaa ttcgcgttaa at                     42

<210> SEQ ID NO 87
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 87
agcgtcacgt ataagaattg agttaagccc tttttaagaa ag                     42

<210> SEQ ID NO 88
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 88
tataaagcat cgtaaccaag taccgcaccg gctgtaatat cc                     42

<210> SEQ ID NO 89
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 89
atagcccgcg aaaataattg tatcggttcg ccgacaatga gt                     42

<210> SEQ ID NO 90
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 90
agacagttca tataggagaa gcctttataa cattgcctga ga                     42

<210> SEQ ID NO 91
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 91
aacaggtccc gaaattgcat caaaaagatc tttgatcatc ag                     42
```

<210> SEQ ID NO 92
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 92
actgcccttg ccccgttgca gcaagcggca acagcttttt ct                              42

<210> SEQ ID NO 93
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 93
tcaaagggag atagcccotta taaatcaaga caacaaccat cg                             42

<210> SEQ ID NO 94
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 94
gtaatacgca aacatgagag atctacaact agctgaggcc gg                              42

<210> SEQ ID NO 95
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 95
gagataacat tagaagaata acataaaaag gaaggattag ga                              42

<210> SEQ ID NO 96
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 96
cagatattac ctgaatacca agttacaatc gggagctatt tt                              42

<210> SEQ ID NO 97
<211> LENGTH: 42
<212> TYPE: DNA
<213> ORGANISM: Artificial Sequence
<220> FEATURE:
<223> OTHER INFORMATION: Description of artificial sequence: DNA
      origamis

<400> SEQUENCE: 97
catataacta atgaacacaa catacgagct gtttctttgg gg                              42

-continued

```
<210> SEQ ID NO 98
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 98
atgttttgct tttgatcgga acgagggtac tttttctttt gataagaggt catt          54

<210> SEQ ID NO 99
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 99
ggggtgccag ttgagaccat tagatacaat tttcactgtg tgaaattgtt atcc          54

<210> SEQ ID NO 100
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 100
cttcgctggg cgcagacgac agtatcgggg caccgtcgcc attcaggctg cgca          54

<210> SEQ ID NO 101
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 101
tcagagctgg gtaaacgacg gccagtgcga tccccgtagt agcattaaca tcca          54

<210> SEQ ID NO 102
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 102
ttagcggtac agagcgggag aattaactgc gctaatttcg gaacctatta ttct          54

<210> SEQ ID NO 103
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 103
gatattctaa attgagccgg aacgaggccc aacttggcgc ataggctggc tgac          54

<210> SEQ ID NO 104
```

```
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 104
tgtcgtcata agtacagaac cgccacccat tttcacagta caaactacaa cgcc          54

<210> SEQ ID NO 105
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 105
cgattataag cggagacttc aaatatcgcg gaagcctacg aaggcaccaa ccta          54

<210> SEQ ID NO 106
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 106
aacatgtacg cgagtggttt gaaataccta aacacattct taccagtata aagc          54

<210> SEQ ID NO 107
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 107
gtctggattt tgcgttttaa atgcaatggt gagaaataaa ttaatgccgg agag          54

<210> SEQ ID NO 108
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 108
gccttgaatc ttttccggaa ccgcctccca gagcccagag ccgccgccag catt          54

<210> SEQ ID NO 109
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 109
cgctggtgct ttcctgaatc ggccaacgag ggtggtgatt gcccttcacc gcct          54

<210> SEQ ID NO 110
<211> LENGTH: 54
```

```
<212> TYPE: DNA
<213> ORGANISM: Artificial Sequence
<220> FEATURE:
<223> OTHER INFORMATION: Description of artificial sequence: DNA
      origamis

<400> SEQUENCE: 110
tgattatcaa ctttacaact aaaggaatcc aaaaagtttg agtaacatta tcat        54

<210> SEQ ID NO 111
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 111
acataacttg ccctaacttt aatcattgca ttataacaac attattacag gtag        54

<210> SEQ ID NO 112
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 112
gtagcgccat taaattggga attagagcgc aaggcgcacc gtaatcagta gcga        54

<210> SEQ ID NO 113
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 113
ttatttttac cgacaatgca gaacgcgcga aaaatctttc cttatcattc caag        54

<210> SEQ ID NO 114
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 114
tttcaataga aggcagcgaa cctcccgatt agttgaaaca ataacggatt cgcc        54

<210> SEQ ID NO 115
<211> LENGTH: 54
<212> TYPE: DNA
<213> ORGANISM: Artificial Sequence
<220> FEATURE:
<223> OTHER INFORMATION: Description of artificial sequence: DNA
      origamis

<400> SEQUENCE: 115
gggcgacccc aaaagtatgt tagcaaacta aaagagtcac aatcaataga aaat        54

<210> SEQ ID NO 116
<211> LENGTH: 54
<212> TYPE: DNA
```

<213> ORGANISM: Artificial Sequence
<220> FEATURE:
<223> OTHER INFORMATION: Description of artificial sequence: DNA origamis

<400> SEQUENCE: 116
agccgaaagt ctctcttttg atgatacaag tgccttaaga gcaagaaaca atga    54

<210> SEQ ID NO 117
<211> LENGTH: 54
<212> TYPE: DNA
<213> ORGANISM: Artificial Sequence
<220> FEATURE:
<223> OTHER INFORMATION: Description of artificial sequence: DNA origamis

<400> SEQUENCE: 117
gtgggaaatc atataaatat ttaaattgaa tttttgtctg gccttcctgt agcc    54

<210> SEQ ID NO 118
<211> LENGTH: 54
<212> TYPE: DNA
<213> ORGANISM: Artificial Sequence
<220> FEATURE:
<223> OTHER INFORMATION: Description of artificial sequence: DNA origamis

<400> SEQUENCE: 118
cccacgcgca aaatggttga gtgttgttcg tggacttgct ttcgaggtga attt    54

<210> SEQ ID NO 119
<211> LENGTH: 54
<212> TYPE: DNA
<213> ORGANISM: Artificial Sequence
<220> FEATURE:
<223> OTHER INFORMATION: Description of artificial sequence: DNA origamis

<400> SEQUENCE: 119
atgaccactc gtttggcttt tgcaaaagtt agactatatt cattgaatcc ccct    54

<210> SEQ ID NO 120
<211> LENGTH: 54
<212> TYPE: DNA
<213> ORGANISM: Artificial Sequence
<220> FEATURE:
<223> OTHER INFORMATION: Description of artificial sequence: DNA origamis

<400> SEQUENCE: 120
tccaaatctt ctgaattatt tgcacgtagg tttaacgcta acgagcgtct ttcc    54

<210> SEQ ID NO 121
<211> LENGTH: 54
<212> TYPE: DNA
<213> ORGANISM: Artificial Sequence
<220> FEATURE:
<223> OTHER INFORMATION: Description of artificial sequence: DNA origamis

<400> SEQUENCE: 121
gggttattta attacaatat atgtgagtaa ttaataagag tcaatagtga attt    54

<210> SEQ ID NO 122
<211> LENGTH: 30
<212> TYPE: DNA
<213> ORGANISM: Artificial Sequence
<220> FEATURE:
<223> OTHER INFORMATION: Description of artificial sequence:
      encapsulating sequence

<400> SEQUENCE: 122

```
atccatcact tcatactcta cgttgttgtt                                      30
```

<210> SEQ ID NO 123
<211> LENGTH: 7249
<212> TYPE: DNA
<213> ORGANISM: bacteriophage M13

<400> SEQUENCE: 123

```
tgatagacgg ttttttcgccc tttgacgttg gagtccacgt tctttaatag tggactcttg     60
ttccaaactg gaacaacact caaccctatc tcgggctatt cttttgattt ataagggatt    120
ttgccgattt cggaaccacc atcaaacagg attttcgcct gctggggcaa accagcgtgg    180
accgcttgct gcaactctct cagggccagg cggtgaaggg caatcagctg ttgcccgtct    240
cactggtgaa aagaaaaacc accctggcgc ccaatacgca aaccgcctct ccccgcgcgt    300
tggccgattc attaatgcag ctggcacgac aggtttcccg actggaaagc gggcagtgag    360
cgcaacgcaa ttaatgtgag ttagctcact cattaggcac cccaggcttt acactttatg    420
cttccggctc gtatgttgtg tggaattgtg agcggataac aatttcacac aggaaacagc    480
tatgaccatg attacgaatt cgagctcggt acccggggat cctctagagt cgacctgcag    540
gcatgcaagc ttggcactgg ccgtcgtttt acaacgtcgt gactgggaaa accctggcgt    600
tacccaactt aatcgccttg cagcacatcc ccctttcgcc agctggcgta atagcgaaga    660
ggcccgcacc gatcgccctt cccaacagtt gcgcagcctg aatggcgaat ggcgctttgc    720
ctggtttccg gcaccagaag cggtgccgga aagctggctg gagtgcgatc ttcctgaggc    780
cgatactgtc gtcgtcccct caaactggca gatgcacggt tacgatgcgc ccatctacac    840
caacgtgacc tatcccatta cggtcaatcc gccgtttgtt cccacggaga atccgacggg    900
ttgttactcg ctcacattta atgttgatga agctggcta caggaaggcc agacgcgaat    960
tatttttgat ggcgttccta ttggttaaaa aatgagctga tttaacaaaa atttaatgcg   1020
aattttaaca aaatattaac gtttacaatt taaatatttg cttatacaat cttcctgttt   1080
ttggggcttt tctgattatc aaccggggta catatgattg acatgctagt tttacgatta   1140
ccgttcatcg attctcttgt ttgctccaga ctctcaggca atgacctgat agcctttgta   1200
gatctctcaa aaatagctac cctctccggc attaatttat cagctagaac ggttgaatat   1260
catattgatg gtgatttgac tgtctccggc cttttctcacc cttttgaatc tttacctaca   1320
cattactcag gcattgcatt taaaatatat gagggttcta aaaatttta tccttgcgtt   1380 gaaataaagg cttctcccgc aaaagtatta cagggtcata atgtttttgg tacaaccgat   1440
ttagctttat gctctgaggc tttattgctt aattttgcta attctttgcc ttgcctgtat   1500
gatttattgg atgttaatgc tactactatt agtagaattg atgccacctt tcagctcgc    1560 gccccaaatg aaaatatagc taaacaggtt attgaccatt tgcgaaatgt atctaatggt   1620
caaactaaat ctactcgttc gcagaattgg gaatcaactg ttatatggaa tgaaacttcc   1680
agacaccgta ctttagttgc atatttaaaa catgttgagc tacagcatta tattcagcaa   1740
ttaagctcta agccatccgc aaaaatgacc tcttatcaaa aggagcaatt aaaggtactc   1800
tctaatcctg acctgttgga gtttgcttcc ggtctggttc gctttgaagc tcgaattaaa   1860
acgcgatatt tgaagtcttt cgggcttcct cttaatcttt ttgatgcaat ccgctttgct   1920
```

-continued

```
tctgactata atagtcaggg taaagacctg attttttgatt tatggtcatt ctcgttttct    1980
gaactgttta aagcatttga gggggattca atgaatattt atgacgattc cgcagtattg    2040
gacgctatcc agtctaaaca ttttactatt accccctctg gcaaaacttc ttttgcaaaa    2100
gcctctcgct attttggttt ttatcgtcgt ctggtaaacg agggttatga tagtgttgct    2160
cttactatgc ctcgtaattc cttttggcgt tatgtatctg cattagttga atgtggtatt    2220
cctaaatctc aactgatgaa tctttctacc tgtaataatg ttgttccgtt agttcgtttt    2280
attaacgtag atttttcttc ccaacgtcct gactggtata atgagccagt tcttaaaatc    2340
gcataaggta attcacaatg attaaagttg aaattaaacc atctcaagcc caatttacta    2400
ctcgttctgg tgtttctcgt cagggcaagc cttattcact gaatgagcag ctttgttacg    2460
ttgatttggg taatgaatat ccggttcttg tcaagattac tcttgatgaa ggtcagccag    2520
cctatgcgcc tggtctgtac accgttcatc tgtcctcttt caaagttggt cagttcggtt    2580
cccttatgat tgaccgtctg cgcctcgttc cggctaagta acatggagca ggtcgcggat    2640
ttcgacacaa tttatcaggc gatgatacaa atctccgttg tactttgttt cgcgcttggt    2700
ataatcgctg ggggtcaaag atgagtgttt tagtgtattc ttttgcctct ttcgttttag    2760
gttggtgcct tcgtagtggc attacgtatt ttacccgttt aatggaaact tcctcatgaa    2820
aaagtcttta gtcctcaaag cctctgtagc cgttgctacc ctcgttccga tgctgtcttt    2880
cgctgctgag ggtgacgatc ccgcaaaagc ggcctttaac tccctgcaag cctcagcgac    2940
cgaatatatc ggttatgcgt gggcgatggt tgttgtcatt gtcggcgcaa ctatcggtat    3000
caagctgttt aagaaattca cctcgaaagc aagctgataa accgatacaa ttaaaggctc    3060
cttttggagc ctttttttttg gagattttca acgtgaaaaa attattattc gcaattcctt    3120
tagttgttcc tttctattct cactccgctg aaactgttga agttgtttta gcaaaatccc    3180
atacagaaaa ttcatttact aacgtctgga agacgacaa aactttagat cgttacgcta    3240
actatgaggg ctgtctgtgg aatgctacag gcgttgtagt ttgtactggt gacgaaactc    3300
agtgttacgg tacatgggtt cctattgggc ttgctatccc tgaaaatgag ggtggtggct    3360
ctgagggtgg cggttctgag ggtggcggtt ctgagggtgg cggtactaaa cctcctgagt    3420
acggtgatac acctattccg ggctatactt atatcaaccc tctcgacggc acttatccgc    3480
ctggtactga gcaaaacccc gctaatccta atccttctct tgaggagtct cagcctctta    3540
atactttcat gtttcagaat aataggttcc gaaataggca gggggcatta actgtttata    3600
cgggcactgt tactcaaggc actgacccccg ttaaaactta ttaccagtac actcctgtat    3660
catcaaaagc catgtatgac gcttactgga acggtaaatt cagagactgc gctttccatt    3720
ctggctttaa tgaggattta tttgtttgtg aatatcaagg ccaatcgtct gacctgcctc    3780
aacctcctgt caatgctggc ggcggctctg gtggtggttc tggtggcggc tctgagggtg    3840
gtggctctga gggtggcggt tctgagggtg cggctctga gggaggcggt tccggtggtg    3900
gctctggttc cggtgatttt gattatgaaa agatggcaaa cgctaataag ggggctatga    3960
ccgaaaatgc cgatgaaaac gcgctacagt ctgacgctaa aggcaaactt gattctgtcg    4020
ctactgatta cggtgctgct atcgatggtt tcattggtga cgtttccggc cttgctaatg    4080
gtaatggtgc tactggtgat tttgctggct ctaattccca aatggctcaa gtcggtgacg    4140
gtgataattc acctttaatg aataatttcc gtcaatattt accttccctc cctcaatcgg    4200
ttgaatgtcg cccttttgtc tttggcgctg gtaaaccata tgaattttct attgattgtg    4260
```

```
acaaaataaa cttattccgt ggtgtctttg cgtttcttt  atatgttgcc  accttatgt   4320
atgtattttc tacgtttgct aacatactgc gtaataagga gtcttaatca tgccagttct   4380
tttgggtatt ccgttattat tgcgtttcct cggtttcctt ctggtaactt tgttcggcta   4440
tctgcttact tttcttaaaa agggcttcgg taagatagct attgctattt cattgtttct   4500
tgctcttatt attgggctta actcaattct tgtgggttat ctctctgata ttagcgctca   4560
attaccctct gactttgttc agggtgttca gttaattctc ccgtctaatg cgcttccctg   4620
tttttatgtt attctctctg taaaggctgc tattttcatt tttgacgtta aacaaaaaat   4680
cgtttcttat ttggattggg ataaataata tggctgttta ttttgtaact ggcaaattag   4740
gctctggaaa gacgctcgtt agcgttggta agattcagga taaaattgta gctgggtgca   4800
aaatagcaac taatcttgat ttaaggcttc aaaacctccc gcaagtcggg aggttcgcta   4860
aaacgcctcg cgttcttaga ataccggata agccttctat atctgatttg cttgctattg   4920
ggcgcggtaa tgattcctac gatgaaaata aaaacggctt gcttgttctc gatgagtgcg   4980
gtacttggtt taatacccgt tcttggaatg ataaggaaag acagccgatt attgattggt   5040
ttctacatgc tcgtaaatta ggatgggata ttatttttct tgttcaggac ttatctattg   5100
ttgataaaca ggcgcgttct gcattagctg aacatgttgt ttattgtcgt cgtctggaca   5160
gaattacttt accttttgtc ggtactttat attctcttat tactggctcg aaaatgcctc   5220
tgcctaaatt acatgttggc gttgttaaat atggcgattc tcaattaagc cctactgttg   5280
agcgttggct ttatactggt aagaatttgt ataacgcata tgatactaaa caggcttttt   5340
ctagtaatta tgattccggt gtttattctt atttaacgcc ttatttatca cacggtcggt   5400
atttcaaacc attaaattta ggtcagaaga tgaaattaac taaaatatat ttgaaaagt    5460
tttctcgcgt tctttgtctt gcgattggat ttgcatcagc atttacatat agttatataa   5520
cccaacctaa gccggaggtt aaaaaggtag tctctcagac ctatgatttt gataaattca   5580
ctattgactc ttctcagcgt cttaatctaa gctatcgcta tgttttcaag gattctaagg   5640
gaaaattaat taatagcgac gatttacaga agcaaggtta ttcactcaca tatattgatt   5700
tatgtactgt ttccattaaa aaaggtaatt caaatgaaat tgttaaatgt aattaatttt   5760
gttttcttga tgtttgtttc atcatcttct tttgctcagg taattgaaat gaataattcg   5820
cctctgcgcg attttgtaac ttggtattca aagcaatcag gcgaatccgt tattgtttct   5880
cccgatgtaa aaggtactgt tactgtatat tcatctgacg ttaaacctga aaatctacgc   5940
aatttcttta tttctgtttt acgtgcaaat aattttgata tggtaggttc taacccttcc   6000
attattcaga agtataatcc aaacaatcag gattatattg atgaattgcc atcatctgat   6060
aatcaggaat atgatgataa ttccgctcct tctggtggtt tctttgttcc gcaaaatgat   6120
aatgttactc aaacttttaa aattaataac gttcgggcaa aggatttaat acgagttgtc   6180
gaattgtttg taaagtctaa tacttctaaa tcctcaaatg tattatctat tgacggctct   6240
aatctattag ttgttagtgc tcctaaagat attttagata accttcctca attcctttca   6300
actgttgatt tgccaactga ccagatattg attgagggtt tgatatttga ggttcagcaa   6360
ggtgatgctt tagattttc atttgctgct ggctctcagc gtggcactgt tgcaggcggt   6420
gttaatactg accgcctcac ctctgtttta tcttctgctg tggttcgtt cggtattttt    6480
aatggcgatg ttagggct atcagttcgc gcattaaaga ctaatagcca ttcaaaaata    6540
ttgtctgtgc cacgtattct tacgctttca ggtcagaagg gttctatctc tgttggccag   6600
aatgtcccctt ttattactgg tcgtgtgact ggtgaatctg ccaatgtaaa taatccattt   6660
```

-continued

```
cagacgattg agcgtcaaaa tgtaggtatt ccatgagcg ttttcctgt tgcaatggct      6720 ggcggtaata ttgttctgga tattaccagc aaggccgata gtttgagttc ttctactcag      6780
gcaagtgatg ttattactaa tcaaagaagt attgctacaa cggttaattt gcgtgatgga      6840
cagactcttt tactcggtgg cctcactgat tataaaaaca cttctcagga ttctggcgta      6900
ccgttcctgt ctaaaatccc tttaatcggc ctcctgttta gctcccgctc tgattctaac      6960
gaggaaagca cgttatacgt gctcgtcaaa gcaaccatag tacgcgccct gtagcggcgc      7020
attaagcgcg gcgggtgtgg tggttacgcg cagcgtgacc gctacacttg ccagcgccct      7080
agcgcccgct cctttcgctt tcttcccttc ctttctcgcc acgttcgccg gctttccccg      7140
tcaagctcta atcgggggc tccctttagg gttccgattt agtgctttac ggcacctcga      7200
ccccaaaaaa cttgatttgg gtgatggttc acgtagtggg ccatcgccc                  7249
```

<210> SEQ ID NO 124
<211> LENGTH: 15
<212> TYPE: DNA
<213> ORGANISM: Artificial Sequence
<220> FEATURE:
<223> OTHER INFORMATION: Description of artificial sequence:
      fluorescence assay sequence

<400> SEQUENCE: 124
attaccgtat agcat                                                        15

<210> SEQ ID NO 125
<211> LENGTH: 15
<212> TYPE: DNA
<213> ORGANISM: Artificial Sequence
<220> FEATURE:
<223> OTHER INFORMATION: Description of artificial sequence:
      fluorescence assay sequence

<400> SEQUENCE: 125
atgctatacg gtaat                                                        15

<210> SEQ ID NO 126
<211> LENGTH: 15
<212> TYPE: DNA
<213> ORGANISM: Artificial Sequence
<220> FEATURE:
<223> OTHER INFORMATION: Description of artificial sequence: MD
      simulation nucleic acid

<400> SEQUENCE: 126
attaccgtat agcat                                                        15

<210> SEQ ID NO 127
<211> LENGTH: 6
<212> TYPE: PRT
<213> ORGANISM: Artificial Sequence
<220> FEATURE:
<223> OTHER INFORMATION: Description of artificial sequence: AuCoated
      OC structure

<400> SEQUENCE: 127

Cys Ala Leu Asp Asp Lys
1               5

SIDE CHAIN MODIFIED PEPTOIDS USEFUL AS STRUCTURE-STABILIZING COATINGS FOR BIOMATERIALS

STATEMENT OF GOVERNMENT RIGHTS

This invention was made with government support under DE-SC0012704 and DE-AC02-05CH11231 awarded by Department of Energy. The government has certain rights in the invention(s).

FIELD OF THE INVENTION

This invention relates to stabilizing biomaterials for biomedical applications.

BACKGROUND OF THE INVENTION

DNA nanotechnology allows to program self-assembly of synthetic oligonucleotides into structures with prescribed topologies and spatial configurations. One of such approaches is called DNA origami. Advancement in DNA origami design and synthesis with high-precision structural controls has enabled potential biomedical applications, including smart drug/gene delivery carriers and biomolecular devices at the cellular level. Additionally, DNA origamis designed with controlled shape, biocompatibility and responsiveness toward other biomolecules (e.g., proteins, lipids, DNAs, and RNAs), may serve as a reliable molecular interface and augment functionalities of the hybrid bio/nano system. This technology applies a bottom-up approach in nanocarrier design and synthesis that may bring potential solutions in targeted drug/gene delivery and biomedical imaging and sensing, in which translation of nanoformulation carriers into clinical applications has remained challenging due to the difficulty to regulate interfaces between the nanocarriers and biological systems.

There are some roadblocks to maximizing this technology, however. For example, biomedical applications of DNA origamis with precisely defined nanostructures are often incompatible with the comparatively high content (10-20 mM) of magnesium ions required for the DNA origami self-assembly and its long-term stability. In fact, low transfection due to poor structural integrity of DNA origamis in physiological fluids, which typically contain low content of the magnesium ions (~1 mM), has been identified as a major challenge. Moreover, change in solution components and pH as well as nuclease degradation have also been shown to affect the DNA origami superstructures. It is therefore crucial to stabilize DNA origami structures under the damaging factors in order for them to be effectively used for broader biomedical applications.

Therefore, there is a need to overcome these obstacles and create a composition which can stabilize a biomaterial, such as pre-defined nucleic acid based nanostructures (e.g., DNA origami).

SUMMARY OF THE INVENTION

The present invention relates to compositions and methods for the stabilization of biomaterials.

In some embodiments, the invention relates to a composition for stabilizing a biomaterial, said composition including a compound of Formula (I).

$$T_1\text{-}[A_m\text{-}E_n]_{b1}\text{-}[G_p\text{-}J_q]_{b2}\text{-}[L_r\text{-}M_s]_{b3}\text{-}[Q_t\text{-}U_u]_{b4}\text{-}T_2 \quad (I)$$

wherein

A is

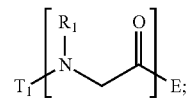

E is

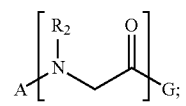

G is

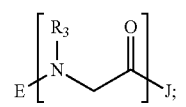

J is

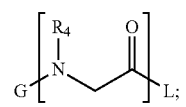

L is

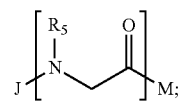

M is

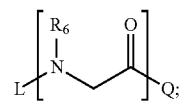

Q is

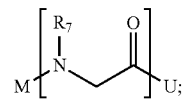

U is

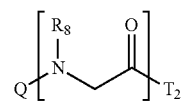

m, n, p, q, r, s, t, and u are independently 0, 1, 2, 3, 4, or 5;

b1, b2, b3, and b4 are independently 0, 1, 2, 3, 4, 5, 6, 7, 8, 9, 10, 15, or 20;

$R_1$, $R_2$, $R_3$, $R_4$, $R_5$, $R_6$, $R_7$, $R_8$ are independently H, OH, $(C_1-C_8)$alkyl, $(C_2-C_6)$alkenyl, $(C_2-C_6)$alkynyl, $(C_1-C_8)$alkoxy, $(C_1-C_6)$alkylene-O—$(C_1-C_6)$alkyl, $(C_1-C_6)$alkylene-O—$(C_1-C_6)$alkylene-O—$(C_1-C_6)$alkyl, —$((CH_2)_{1-8}$—$O)_{1-14}$—$CH_3$, —$((CH_2)_{1-8}$—$O)_{1-14}$-alkyl, $(C_1-C_8)$alkylene-C(O)OH, $(C_1-C_8)$alkylene-$SO_{1-3}H_{1-2}$, $(C_1-C_8)$alkylene-$PO_{1-3}H_{1-2}$, $(C_1-C_8)$alkylene-$SO_2$—$NH_2$, $(C_1-C_8)$alkoxy, $(C_1-C_6)$alkylene-(NH)$NR_{10}R_{11}$, $(C_1-C_8)$alkylene-$NR_{12}R_{13}$, $(C_1-C_8)$alkylene-C(O)$NR_{14}R_{15}$, or —$(C_1-C_6)$alkylene-$R_{16}$, where alkyl, alkenyl, alkynyl, alkylene, and alkoxy are optionally substituted with one or more substituent each independently selected from $(C_1-C_3)$alkyl, oxo, $NH_2$, —COOH, halogen, hydroxyl, methoxy, ethoxy, $N_3$, biotinyl, sulfhydryl, cyano, hydrazido, carbodiimide, succinimide, or maleimide;

$T_1$ is

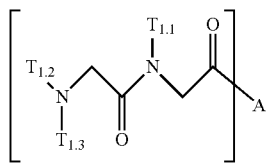

or H;

$T_2$ is

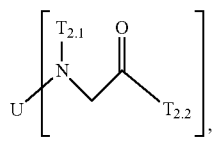

H, —OH, or $NH_2$;

$T_{1.1}$, $T_{1.2}$, $T_{1.3}$, $T_{2.1}$, and $T_{2.2}$ are independently $R_1$, $R_8$, —$(C_1-C_6)$alkylene($NR_{17}R_{18}$), —$NR_{14}R_{15}$, $(C_1-C_6)$alkylene-C(O)$R_{16}$, —C(O)$R_{16}$, —C(O)$(C_1-C_6)$alkyl, —C(O)$NR_{17}R_{18}$, $SO_2$, —OH, —SH, —COOH, —$(C_1-C_6)$alkylene-$N_3$, —$(C_2-C_6)$alkynyl, or alkyl, alkenyl, alkynyl, alkylene, or alkoxy that is substituted with at least one of biotinyl, sulfhydryl, cyano, hydrazido, carbodiimide, halo, succinimide, and maleimide;

$R_{16}$ is partially or fully saturated $(C_3-C_8)$carbocyclic, phenyl, 4- to 8-membered heterocycle containing 1 to 4 heteroatoms each independently selected from O, S, or N, 5- to 7-membered heteroaryl containing 1 to 3 heteroatoms each independently selected from O, N, or S, where $R_{16}$ is optionally substituted with one or more substituents each independently selected from $(C_1-C_3)$alkyl, $(C_1-C_3)$alkyl-$NH_2$, $(C_1-C_3)$alkoxy, halogen, hydroxyl, —C(O)$NH_2$, —COOH, or —CN; and $R_{10}$, $R_{11}$, $R_{12}$, $R_{13}$, $R_{14}$, $R_{15}$, $R_{16}$, $R_{17}$, and $R_{18}$ are each independently H, $(C_1-C_6)$alkyl, $(C_2-C_6)$alkenyl, $(C_2-C_6)$alkynyl, or halo-substituted $(C_1-C_6)$alkyl; wherein $R_1$-$R_8$, each defines a submonomer, and wherein Formula (I) defines a peptoid.

In some embodiments, the invention relates to a composition for stabilizing a biomaterial, said composition includes a compound of Formula (II).

$$T_1\text{-}[X_{b1}\text{—}Y_{b2}\text{—}Z_{b3}]_n\text{-}T_2 \qquad (II)$$

wherein

X is

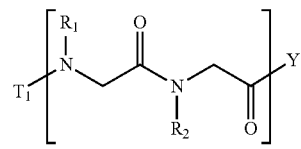

Y is

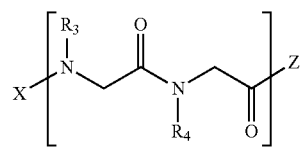

Z is

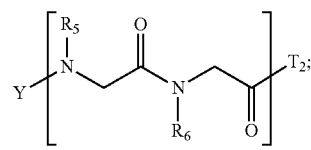

$T_1$ is

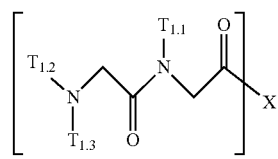

or H; and $T_2$ is

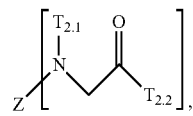

H, —OH, or $NH_2$;

wherein, n is 1, 2, 3, 4, or 5;

b1, b2, and b3 are independently 0, 1, 2, 3, 4, 5, 6, 7, 8, 9, 10, 15, and 20;

$R_1$, $R_2$, $R_3$, $R_4$, $R_5$, $R_6$, are independently H, OH, $(C_1-C_8)$alkyl, $(C_2-C_6)$alkenyl, $(C_2-C_6)$alkynyl, $(C_1-C_8)$alkoxy, $(C_1-C_6)$alkylene-O—$(C_1-C_6)$alkyl, $(C_1-C_6)$alkylene-O—$(C_1-C_6)$alkylene-O—$(C_1-C_6)$alkyl, —$((CH_2)_{1-8}$—$O)_{1-14}$—$CH_3$, —$((CH_2)_{1-8}$—$O)_{1-14}$-alkyl, $(C_1-C_8)$alkylene-C(O)OH, $(C_1-C_8)$alkylene-$SO_{1-3}H_{1-2}$, $(C_1-C_8)$alkylene-$PO_{1-3}H_{1-2}$, $(C_1-C_8)$alkylene-$SO_2$—$NH_2$, $(C_1-C_8)$alkoxy, $(C_1-C_6)$alkylene-(NH)$NR_{10}R_{11}$, $(C_1-C_8)$alkylene-$NR_{12}R_{13}$, $(C_1-C_8)$alkylene-C(O)$NR_{14}R_{15}$, or —$(C_1-C_6)$alkylene-$R_{16}$, where alkyl, alkenyl, alkynyl, alkylene, and alkoxy are optionally substituted with one or more substituent each independently selected from $(C_1$-$C_3)$alkyl, oxo, $NH_2$, —COOH, halogen, hydroxyl, methoxy, ethoxy, $N_3$, biotinyl, sulfhydryl, cyano, hydrazido, carbodiimide, succinimide, or maleimide;

$R_{16}$ is partially or fully saturated $(C_3$-$C_8)$carbocyclic, phenyl, 4- to 8-membered heterocycle containing 1 to 4 heteroatoms each independently selected from O, S, or N, 5- to 7-membered heteroaryl containing 1 to 3 heteroatoms each independently selected from O, N, or S, where $R_{16}$ is optionally substituted with one or more substituents each independently selected from $(C_1$-$C_3)$alkyl, $(C_1$-$C_3)$alkyl-$NH_2$, $(C_1$-$C_3)$alkoxy, halogen, hydroxyl, —C(O)$NH_2$, —COOH, or —CN;

$T_{1.1}$, $T_{1.2}$, $T_{1.3}$, $T_{2.1}$, and $T_{2.2}$ are independently $R_1$, $R_6$, —$(C_1$-$C_6)$alkylene(NR$_{17}R_{18}$), —NR$_{14}R_{15}$, $(C_1$-$C_6)$alkylene-C(O)R$_{16}$, —C(O)(C$_1$-$C_6$)alkyl, —C(O)NR$_{17}R_{18}$, $SO_2$, —OH, —SH, —COOH, —$(C_1$-$C_6)$ alkyl azide, —$(C_2$-$C_6)$alkynyl, or alkyl, alkenyl, alkynyl, alkylene, or alkoxy that is substituted with at least one of biotinyl, sulfhydryl, cyano, hydrazido, carbodiimide, halo, succinimide, and maleimide; and $R_{10}$, $R_{11}$, $R_{12}$, $R_{13}$, $R_{14}$, $R_{15}$, $R_{16}$, $R_{17}$, and $R_{18}$ are each independently H, $(C_1$-$C_6)$alkyl, $(C_2$-$C_6)$alkenyl, $(C_2$-$C_6)$alkynyl, or halo-substituted $(C_1$-$C_6)$alkyl; wherein $R_1$-$R_6$, each defines a submonomer, and wherein Formula (II) defines a peptoid.

In some embodiments, the invention relates to a composition for stabilizing a biomaterial, said composition including a compound of Formula (III).

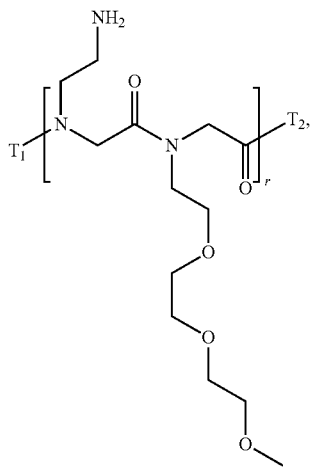

wherein r is 1, 2, 3, 4, 5, 6, 7, 8, 9, 10, 11, 12, 13, 14, 15, 20, 25, 50, 100, or 200;

$T_1$ is

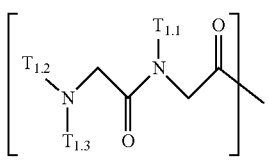

or H; and $T_2$ is

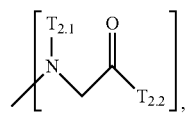

H, —OH, or $NH_2$;

wherein $T_{1.1}$, $T_{1.2}$, $T_{1.3}$, $T_{2.1}$, and $T_{2.2}$ are independently —$(CH_2)$—$NH_2$, —$((CH_2)_2$—O)$_3$—$CH_3$, —$(C_1$-$C_6)$alkylene(NR$_{17}R_{18}$), —NR$_{14}R_{15}$, $(C_1$-$C_6)$alkylene-C(O)R$_{16}$, —C(O)(C$_1$-$C_6$)alkyl, —C(O)NR$_{17}R_{18}$, $SO_2$, —OH, —SH, —COOH, —$(C_1$-$C_6)$alkylene-azide, —$(C_2$-$C_6)$alkynyl, or alkyl, alkenyl, alkynyl, alkylene, or alkoxy that is substituted with at least one of biotinyl, sulfhydryl, cyano, hydrazido, carbodiimide, halo, succinimide, and maleimide; and $R_{14}$, $R_{15}$, $R_{16}$, $R_{17}$, and $R_{18}$ are each independently H, $(C_1$-$C_6)$alkyl, $(C_2$-$C_6)$alkenyl, $(C_2$-$C_6)$alkynyl, or halo-substituted $(C_1$-$C_6)$alkyl; wherein formula (III) defines a peptoid.

In some embodiments, the invention relates to a drug delivery carrier having a pre-defined nucleic acid nanostructure and a compound of Formula (I), (II), or (III).

In some embodiments, the invention relates to a stabilized complex having a pre-defined nucleic acid nanostructure; a compound of Formula (I), (II), or (III); and a drug molecule or protein.

In some embodiments, the invention relates to a method of stabilizing a pre-defined nucleic acid nanostructure, said method including (i) complexing a pre-defined nucleic acid nanostructure with a composition comprising a compound of Formula (I), (II), or (III).

In some embodiments, the invention relates to a stabilized nanoparticle complex having a nanoparticle; and a compound according to Formula (I), (II), or (III).

DETAILED DESCRIPTION

Figure 1A:
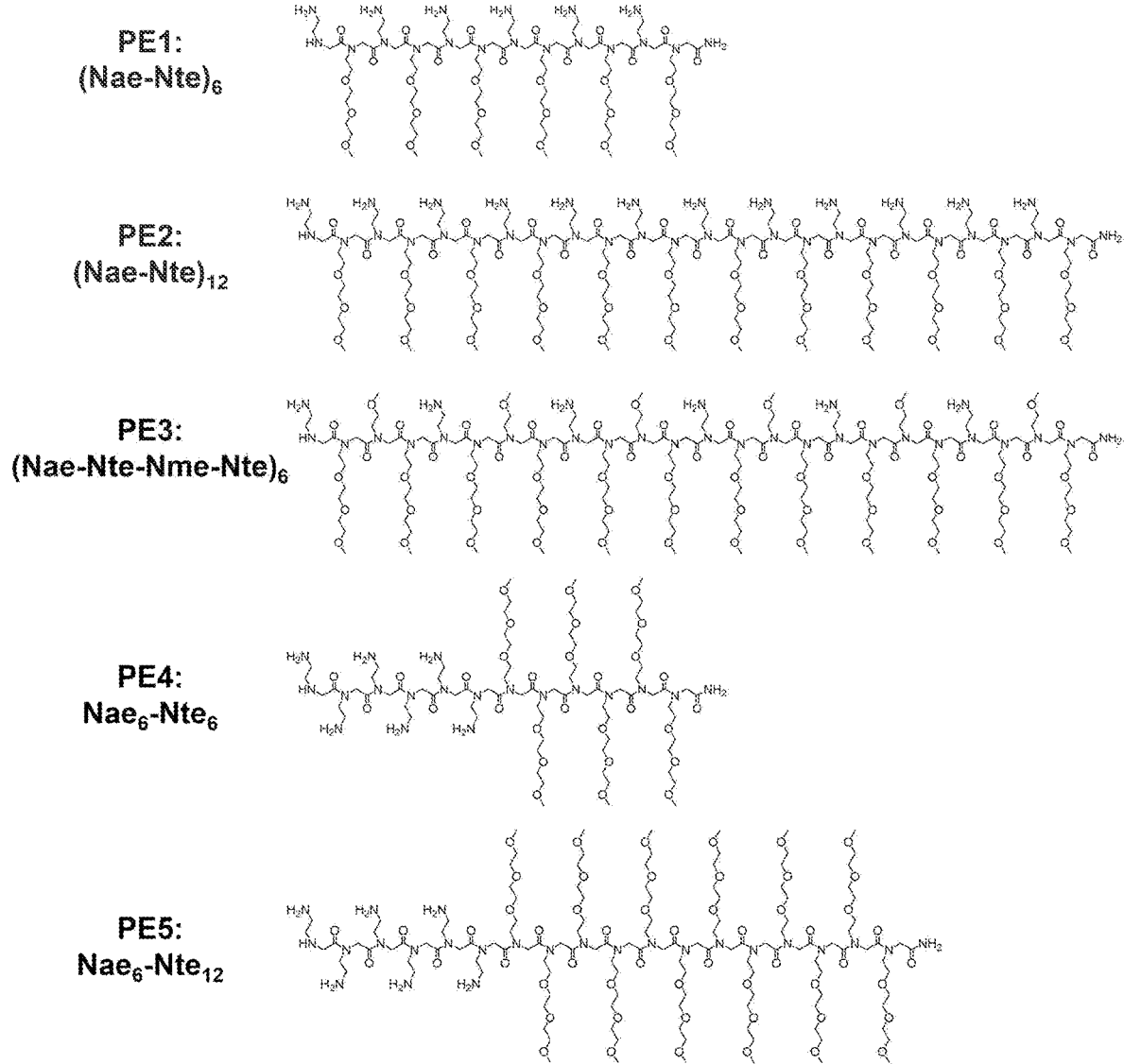
FIG. 1. (A) Chemical structures of peptoids designed to protect 3D octahedra-shaped DNA origamis (OC). Nae: (2-aminoethyl)glycine, Nte: N-2-(2-(2-methoxyethoxy)ethoxy)ethylglycine and Nme: N-(2-methoxyethyl)glycine. (B) Transmission electron microscope (TEM) image and schematic view (inset) of the OC structure (scale bar: 50 nm). (C) Schematic view showing the different surface coating of the two types ("brush" and "block") of peptoids on the OC structure proposed in this work, which leads to varied protection effect.

The present invention relates to compositions and methods for the stabilization of biomaterials.

As used herein, compositions of the present invention for stabilization of biomaterials are referred to as "peptoids". In other words, the peptoids of the present invention can also be referred to as a series of N-substituted glycines. Peptoids according to the present invention are exemplified by Formulas (I), (II), and (III) described herein.

In one embodiment, the composition of the invention includes a compound of Formula (I).

$$T_1\text{-}[A_m\text{-}E_n]_{b1}\text{-}[G_p\text{-}J_q]_{b2}\text{-}[L_r\text{-}M_s]_{b3}\text{-}[Q_r\text{-}U_u]_{b4}\text{-}T_2 \quad (I)$$

wherein
A is

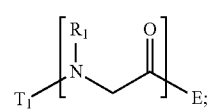

E is

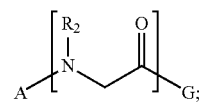

G is

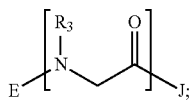

J is

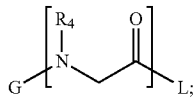

L is

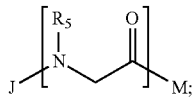

M is

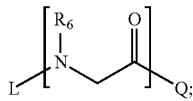

Q is

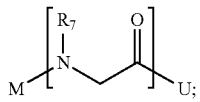

U is

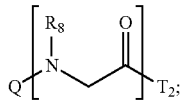

wherein m, n, p, q, r, s, t, and u are independently 0, 1, 2, 3, 4, or 5;
b1, b2, b3, and b4 are independently 0, 1, 2, 3, 4, 5, 6, 7, 8, 9, 10, 15, or 20;
$R_1$, $R_2$, $R_3$, $R_4$, $R_5$, $R_6$, $R_7$, $R_8$ are independently H, OH, $(C_1-C_8)$alkyl, $(C_2-C_6)$alkenyl, $(C_2-C_6)$alkynyl, $(C_1-C_8)$alkoxy, $(C_1-C_6)$alkylene-O—$(C_1-C_6)$alkyl, $(C_1-C_6)$alkylene-O—$(C_1-C_6)$alkylene-O—$(C_1-C_6)$alkyl, —$((CH_2)_{1-8}$—O$)_{1-14}$—$CH_3$, —$((CH_2)_{1-8}$—O$)_{1-14}$-alkyl, $(C_1-C_8)$alkylene-C(O)OH, $(C_1-C_8)$alkylene-SO$_{1-3}$H$_{1-2}$, $(C_1-C_8)$alkylene-PO$_{1-3}$H$_{1-2}$, $(C_1-C_8)$alkylene-SO$_2$—NH$_2$, $(C_1-C_8)$alkoxy, $(C_1-C_6)$alkylene-(NH)NR$_{10}$R$_{11}$, $(C_1-C_8)$alkylene-NR$_{12}$R$_{13}$, $(C_1-C_8)$alkylene-C(O)NR$_{14}$R$_{15}$, or —$(C_1-C_6)$alkylene-R$_{16}$, where alkyl, alkenyl, alkynyl, alkylene, and alkoxy are optionally substituted with one or more substituent each independently selected from $(C_1-C_3)$alkyl, oxo, NH$_2$, —COOH, halogen, hydroxyl, methoxy, ethoxy, N3, biotinyl, sulfhydryl, cyano, hydrazido, carbodiimide, succinimide, or maleimide;
$T_1$ is

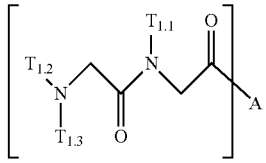

or H;
$T_2$ is

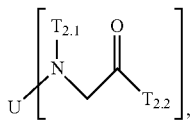

H, —OH, or NH$_2$;
$T_{1.1}$, $T_{1.2}$, $T_{1.3}$, $T_{2.1}$, and $T_{2.2}$ are independently $R_1$, $R_8$, —$(C_1-C_6)$alkylene(NR$_{17}$R$_{18}$), —NR$_{14}$R$_{15}$, $(C_1-C_6)$alkylene-C(O)R$_{16}$, —C(O)(C$_1$-C$_6$)alkyl, —C(O)NR$_{17}$R$_{18}$, SO$_2$, —OH, —SH, —COOH, —(C$_1$-C$_6$)alkylene N$_3$, —(C$_2$-C$_6$)alkynyl, or alkyl, alkenyl, alkynyl, alkylene, or alkoxy that is substituted with at least one of biotinyl, sulfhydryl, cyano, hydrazido, carbodiimide, halo, succinimide, and maleimide;
wherein R1-R8, each defines a submonomer,
$R_{16}$ is partially or fully saturated $(C_3-C_8)$carbocyclic, phenyl, 4- to 8-membered heterocycle containing 1 to 4 heteroatoms each independently selected from O, S, or N, 5- to 7-membered heteroaryl containing 1 to 3 heteroatoms each independently selected from O, N, or S, where $R_{16}$ is optionally substituted with one or more substituents each independently selected from $(C_1-C_3)$alkyl, $(C_1-C_3)$alkyl-NH$_2$, $(C_1-C_3)$alkoxy, halogen, hydroxyl, —C(O)NH$_2$, —COOH, or —CN; and
$R_{10}$, $R_{11}$, $R_{12}$, $R_{13}$, $R_{14}$, $R_{15}$, $R_{16}$, $R_{17}$, and $R_{18}$ are each independently H, $(C_1-C_6)$alkyl, $(C_2-C_6)$alkenyl, $(C_2-C_6)$alkynyl, or halo-substituted $(C_1-C_6)$alkyl;
wherein Formula (I) defines a peptoid, and
wherein $T_1$ and $T_2$ define terminal groups.

For purposes of interpreting this specification, the following definitions will apply and whenever appropriate, terms used in the singular will also include the plural and vice versa.

As used herein, the term "alkyl" refers to a fully saturated branched or unbranched hydrocarbon moieties having up to 12 carbon atoms. Unless otherwise provided, alkyl refers to hydrocarbon moieties having 1 to 12 carbon atoms, 1 to 8 carbon atoms, 1 to 6 carbon atoms (i.e., $(C_1-C_6)$alkyl), or 1 to 3 carbon atoms (i.e., $(C_1-C_3)$alkyl). Representative examples of alkyl include, but are not limited to, methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like.

As used herein, "alkylene" or "alkylenyl" refers to a branched or unbranched alkyl (as defined herein) chain having two free radicals available for bonding. Alkylene refers to divalent alkyl group as defined herein above having 1 to 12 carbon atoms. Unless otherwise provided, alkylene refers to moieties having 1 to 12 carbon atoms, 1 to 8 carbon atoms, 1 to 6 carbon atoms, or 1 to 3 carbon atoms. For example, methylene or methylenyl (e.g, —CH$_2$—), ethylene or ethylenyl (e.g, —CH$_2$—CH$_2$— or —CH(CH$_3$)—), propylene or propylenyl (e.g., —CH$_2$—CH$_2$—CH$_2$—, —CH(CH$_3$)—CH$_2$—, —CH$_2$—CH(CH$_3$)—, or —C(CH$_3$)$_2$—. Representative examples of alkylene further include, but are not limited to (—CH$_2$—CH$_2$—CH$_2$—CH$_2$—, —CH(CH$_3$)—CH$_2$—CH$_2$—, —CH$_2$—CH(CH$_3$)—CH$_2$—, —C(CH$_3$)(CH$_3$)—CH$_2$—), and the like.

As used herein, the term "alkenyl" refers to a monovalent group derived from a hydrocarbon having at least one carbon-carbon double bond. The term "C$_2$-C$_6$-alkenyl" refers to a monovalent group derived from a hydrocarbon having two to six carbon atoms and comprising at least one carbon-carbon double bond. The alkenyl group can be unbranched or branched. Representative examples of alkenyl include vinyl, 1-propenyl, 2-propenyl, 1-methyl-1-propenyl, 1-methyl-2-propenyl, 2-methyl-1-propenyl, 2-methyl-2-propenyl, 1-butenyl, 2-butenyl, 3-butenyl, and so on.

As used herein, the term "alkynyl" refers to a monovalent group derived from a hydrocarbon having at least one carbon-carbon triple bond. The term "(C$_2$-C$_6$)alkynyl" refers to a monovalent group derived from a hydrocarbon having 2 to 6 carbon atoms and comprising at least one carbon-carbon triple bond. The alkynyl group can be unbranched or branched. Representative examples include ethynyl, propynyl, butyn-1-yl, butyn-2-yl, and so on.

As used herein, the term "alkoxy" refers to —O-alkyl, wherein alkyl is as defined herein. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. In some embodiments, alkoxy groups may have about 1 to 8 carbon atoms. Typically, alkoxy groups have about 1 to 6 carbons, and more preferably about 1 to 3 carbons.

As used herein, the term "partially or fully saturated carbocyclic" (also referred to as "partially or fully saturated cycloalkyl") refers to nonaromatic rings that are either partially or fully hydrogenated and may exist as a single ring of 3 to 8 members or bicyclic ring of 9 to 14 members. Unless specified otherwise, the carbocyclic ring is generally a 3- to 8-membered ring. In another embodiment, the carbocyclic ring is a 3- to 6-membered ring. For example, partially or fully saturated carbocyclic rings (or cycloalkyl) include groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, norbornyl, norbornenyl, and the like. The term "cycloalkylene" refers to cycloalkyl as defined herein having two free radicals available for bonding.

As used herein, the term "heteroaryl" refers to a 5- to 14-membered monocyclic- or bicyclic- or tricyclic-aromatic ring system, having 1 to 8 heteroatoms selected from N, O, or S. Typically, the heteroaryl is a 5- to 10-membered ring system (e.g., 5- to 7-membered monocycle or an 8- to 10-membered bicycle). A 5-7 membered monocyclic ring system preferably contains 1 to 3 heteroatoms each independently selected from O, N, or S. Typical heteroaryl groups include 2- or 3-thienyl, 2- or 3-furyl, 2- or 3-pyrrsolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2, 3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl. As used herein, the term "heteroarylene" refers to heteroaryl as defined herein having two free radicals available for bonding.

As used herein, the term "halogen" or "halo" refers to fluoro, chloro, bromo, and iodo. It is to be understood that the terminology oxo or C(O) refers to a —C=O group, whether it be ketone, aldehyde or acid or acid derivative. Similarly, S(O) refers to a —S=O group.

Submonomers

As used herein, the term "submonomer" refers to a substituent that is covalently bonded to the amino group of the peptoid backbone of Formulas (I), (II), and (III). More specifically, in the case of Formula (I), submonomer refers to $R_1$-$R_8$ (individually or collectively); in the case of Formula (II), submonomer refers to $R_1$-$R_6$ (individually or collectively); and in the case of Formula (III), submonomer refers to the groups bound to the amino group of the peptoid backbone (individually or collectively). More specifically, submonomers of Formula (III) include —(CH$_2$)$_2$NH$_2$, and —(CH$_2$)$_2$—O—(CH$_2$)$_2$—O—(CH$_2$)$_2$O—CH$_3$.

In general, each of the submonomer moiety has a molecular weight of 1 to 250 daltons or 1 to 500 daltons. The submonomers can be positively charged, negatively charged, or neutrally charged. Submonomers may include functional groups that add functionality to the peptoid.

In some embodiments, the N-substitutions can include guanidoalkyl, alkylphenyl, indolylalkyl, alkoxyphenyl, hydroxyphenylalkyl, and halophenylalkyl and without limitation to (S, R)-α-methylbenzyl, benzyl, phenethyl, naphthylmethyl, methoxyethyl, (S)-α-methylnaphthylmethyl, N-pyrrolidinopropyl, furfurylmethyl, cyclohexylmethyl, 3,4,5-trimethoxybenzyl, phenylpropyl, 6-galactosyl, 3'-indolylethyl, p-methoxyphenylethyl, p-chlorophenylethyl, or p-hydroxyphenylethyl groups.

The submonomers may be protected by tert-butyloxycarbonyl (Boc), fluorenylmethoxycarbonyl (Fmoc), or allyloxycarbonyl (Aloc) and cleaved after the peptoid synthesis.

Positively-Charged Submonomers

In some embodiments, the positively charged submonomers are aminoalkyl groups having about 1-20 carbon atoms. The N-substitutions can include guanidoalkyl, alkylphenyl, halophenylalkyl, indolylalkyl, alkoxyphenyl, hydroxyphenylalkyl and without limitation to (S, R)-α-methylbenzyl, benzyl, phenethyl, naphthylmethyl, methoxyethyl, (S)-α-methylnaphthylmethyl, N-pyrrolidinopropyl, furfurylmethyl, cyclohexylmethyl, 3,4,5-trimethoxybenzyl, phenylpropyl, 6-galactosyl, 3'-indolylethyl, p-methoxyphenylethyl, p-chlorophenylethyl, or p-hydroxyphenylethyl groups. The cationic side chains can include the following: aminoethyl, aminopropyl, aminohexyl, 1,4-butadiamine (lysine mimic), (S)-1-methylethylenediamine, trimethylaminoethyl, quanidinoethyl, or quanidinopropyl.

The positively charged submonomers can include functional groups discussed herein.

Examples of positively charged submonomers are shown in Table 1.

TABLE 1

Positively-charged submonomers

H$_2$N\~\~\~X

H$_2$N\~\~\~\~X

TABLE 1-continued

Positively-charged submonomers

[Structures of positively-charged submonomers including: H₂N-(CH₂)₃-X; H₂N-(CH₂)₅-X; H₂N-(CH₂)₇-X; H₂N-CH(CH₃)-X; H₂N-CH(CH₃)-C(=O)-NH-CH₂-X; H₂N-C(=NH)-NH-CH₂-X; H₂N-C(=NH)-NH-(CH₂)₄-X; guanidino-phenyl-CH(CH₃)-X; guanidino-phenyl-CH₂CH₂-X; H₂N-CH₂-triazole-(CH₂)₃-X]

Wherein n is an integer between 1 and 100. Wherein X represents the amino group of the peptoid backbone.

Negatively-Charged Submonomers

In some embodiments, negatively charged submonomers are carboxyalkyl groups having 1-20 carbon atoms. The anionic side chain can include carboxyl, carbonyl, sulfonic acid, sulfonamide, phosphate, and phosphonic acid-based submonomers. Similar to the positively charged submonomers, the N-substituted side chains can include functional groups discussed herein.

The negatively charged submonomers can include functional groups discussed herein.

Examples of negatively-charged submonomers are shown in Table 2.

TABLE 2

Negative submonomers

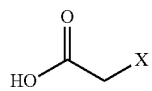

TABLE 2-continued

Negative submonomers

[Structures of negatively-charged submonomers including: HO-C(=O)-CH(CH₃)-X; HO-C(=O)-CH₂CH₂-X; HO-C(=O)-(CH₂)₃-C(=O)-CH(CH₃)-X; HO-C(=O)-phenyl-CH(CH₃)-X; HO₃S-CH₂CH₂-X; H₂NO₂S-CH₂CH₂-X; H₂O₃P-CH₂CH₂-X; H₂O₃P-CH₂CH₂-X; H₂O₃P-(CH₂)₄-X]

Wherein n is an integer between 1 and 100. Wherein X represents the amino group of the peptoid backbone.

Neutrally-Charged Oligo-Ethylene Glycol Motifs:

The term "oligo" as in "oligo-ethylene glycol" includes without limitation to polymers, copolymers, and interpolymers of any length. In addition, the oligomers may consist of a single repeating monomer, two alternating monomer units, and two or more monomer units randomly or purposely spaced relative to each other. The oligo-ethylene glycol comprises at least 1 ethylene glycol unit (i.e., submonomer: methoxyethylamine) moiety, typically at least 2 repeating units (i.e., submonomer: 2-(2-methoxyethoxy)ethanamine) and preferably at least 3 repeating units (i.e., submonomer: 2-(2-(2-methoxyethoxy)ethoxy)ethanamine).

The water-soluble motifs can also be substituted with oligomers or polymers composed of α-methylbenzylamine which typically comprise 2 to 13 repeating units. Examples can be found in works by Kirshenbaum (44), Zuckermann (45), Barron (46) and their co-workers. Carboxyamide, taurine- and phosphonate-based submonomers may also be used (47-49).

Examples of neutrally-charged submonomers are shown in Table 3.

TABLE 3

Neutral submonomers

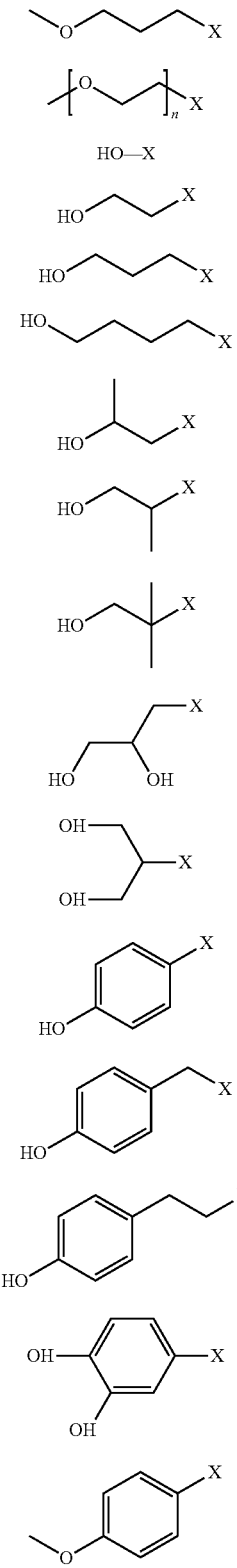

TABLE 3-continued

Neutral submonomers

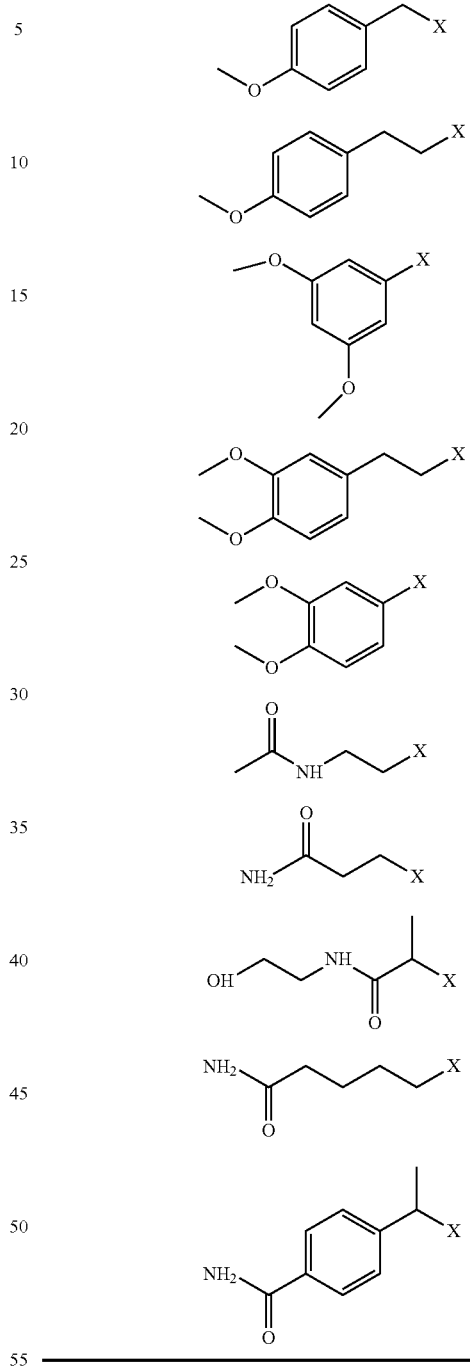

Wherein n is an integer between 1 and 100. Wherein X represents the amino group of the peptoid backbone.

Neutrally Charged Functional Submonomers:

The functional groups exhibit no net positive or negative charge. Functional groups include any group that allows for chemical conjugatison (or strong binding) to a chemical compound, imaging reagents, biomolecules, ligands, polymers, or glycans discussed above on the surfaces of DNA origami and nanoformulation carriers. Examples of a functional group includes alkyne, azide, sulfhydryl, maleimide biotinyl, cyano, hydrazido, carbodiimide, halo, succinimide, and maleimide.

Examples of functional submonomers are shown in Table 4.

TABLE 4

Functional submonomers

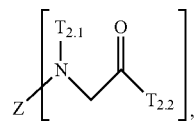

Wherein n is an integer between 1 and 100. Wherein X represents the amino group of the peptoid backbone.

In one embodiment, the composition of the invention includes a compound of Formula (II).

$$T_1\text{-}[X_{b1}\text{—}Y_{b2}\text{—}Z_{b3}]_n\text{-}T_2 \qquad (II)$$

wherein

X is

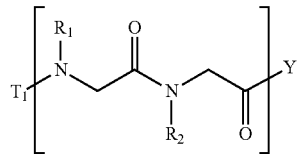

Y is

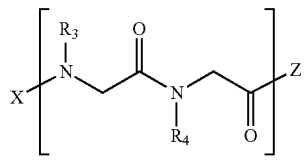

Z is

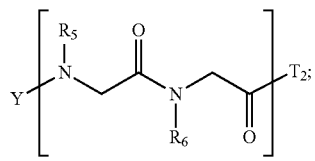

$T_1$ is

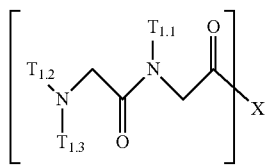

or H; and $T_2$ is

[diagram: $Z\left[\begin{array}{c}T_{2.1}\\|\\N\end{array}\stackrel{O}{\text{—}}T_{2.2}\right]$], H, —OH, or NH$_2$;

wherein, n is 1, 2, 3, 4, or 5;

b1, b2, and b3 are independently 0, 1, 2, 3, 4, 5, 6, 7, 8, 9, 10, 15, or 20;

$T_{1.1}$, $T_{1.2}$, $T_{1.3}$, $T_{2.1}$, and $T_{2.2}$ are independently $R_1$, $R_6$, —(C$_1$-C$_6$)alkylene(NR$_{17}$R$_{18}$), —NR$_{14}$R$_{15}$, (C$_1$-C$_6$)alkylene-C(O)R$_{16}$, —C(O)(C$_1$-C$_6$)alkyl, —C(O)NR$_{17}$R$_{18}$, SO$_2$, —OH, —SH, —COOH, —(C$_1$-C$_6$)alkylene-N$_3$, —(C$_2$-C$_6$)alkynyl, or alkyl, alkenyl, alkynyl, alkylene, or alkoxy that is substituted with at least one of biotinyl, sulfhydryl, cyano, hydrazido, carbodiimide, halo, succinimide, and maleimide;

$R_1$, $R_2$, $R_3$, $R_4$, $R_5$, $R_6$, are independently H, OH, (C$_1$-C$_8$)alkyl, (C$_2$-C$_6$)alkenyl, (C$_2$-C$_6$)alkynyl, (C$_1$-C$_8$) alkoxy, (C$_1$-C$_6$)alkylene-O—(C$_1$-C$_6$)alkyl, (C$_1$-C$_6$)alkylene-O—(C$_1$-C$_6$)alkylene-O—(C$_1$-C$_6$)alkyl, —((CH$_2$)$_{1-8}$—O)$_{1-14}$—CH$_3$, —((CH$_2$)$_{1-8}$—O)$_{1-14}$-alkyl, (C$_1$-C$_8$)alkylene-C(O)OH, (C$_1$-C$_8$)alkylene-SO$_{1-3}$H$_{1-2}$, (C$_1$-C$_8$)alkylene-PO$_{1-3}$H$_{1-2}$, (C$_1$-C$_8$)alkylene-SO$_2$—NH$_2$, (C$_1$-C$_8$)alkoxy, (C$_1$-C$_6$)alkylene-(NH)NR$_{10}$R$_{11}$, (C$_1$-C$_8$)alkylene-NR$_{12}$R$_{13}$, (C$_1$-C$_8$)alkylene-C(O)NR$_{14}$R$_{15}$, or —(C$_1$-C$_6$)alkylene-R$_{16}$, where alkyl, alkenyl, alkynyl, alkylene, and alkoxy are optionally substituted with one or more substituent each independently selected from (C$_1$-C$_3$)alkyl, oxo, NH$_2$, —COOH, halogen, hydroxyl, methoxy, ethoxy, N3, biotinyl, sulfhydryl, cyano, hydrazido, carbodiimide, succinimide, or maleimide;

$R_{16}$ is partially or fully saturated (C$_3$-C$_8$)carbocyclic, phenyl, 4- to 8-membered heterocycle containing 1 to 4 heteroatoms each independently selected from O, S, or N, 5- to 7-membered heteroaryl containing 1 to 3 heteroatoms each independently selected from O, N, or S, where R$_{16}$ is optionally substituted with one or more substituents each independently selected from (C$_1$-C$_3$) alkyl, (C$_1$-C$_3$)alkyl-NH$_2$, (C$_1$-C$_3$)alkoxy, halogen, hydroxyl, —C(O)NH$_2$, —COOH, or —CN; and $R_{10}$, $R_{11}$, $R_{12}$, $R_{13}$, $R_{14}$, $R_{15}$, $R_{16}$, $R_{17}$, and $R_{18}$ are each independently H, (C$_1$-C$_6$)alkyl, (C$_2$-C$_6$)alkenyl, (C$_2$-C$_6$)alkynyl, or halo-substituted (C$_1$-C$_5$)alkyl;

wherein $R_1$-$R_6$, each defines a submonomer, wherein Formula (II) defines a peptoid, and wherein $T_1$ and $T_2$ define terminal groups.

In some embodiments, the peptoid of Formula (I) or Formula (II) may include alternating submonomers across a portion of the peptoid sequence, or across the entirety of the peptoid sequence, excluding the terminal groups. For example, the peptoid may include submonomers that alternate between any combination of positive submonomers, negative submonomers, and neutral submonomers.

In one embodiment, the peptoid may include submonomers that alternate between positive submonomers and neutral submonomers. In one embodiment, the peptoid may include submonomers that alternate between negative submonomers and neutral submonomers. In one embodiment, the peptoid may include submonomers that alternate between positive submonomers and negative submonomers. In one embodiment, the peptoid may include submonomers that alternate between two types of negative submonomers, two types of positive submonomers, or two types of neutral submonomers.

In some embodiments, the peptoid sequence may include semi-alternating submonomers. For example, the peptoid sequence may alternate between one pair of submonomers for one portion of the peptoid sequence, and alternate between a second pair of submonomers for another portion of the peptoid sequence.

As used herein, the term "repeat unit" or "repeating unit" corresponds to the smallest constitutional unit, the repetition of which constitutes a regular macromolecule (or oligomer molecule or block).

By way of example, with reference to Formula (I), "$[A_m, -E_n]$" defines a repeat unit having two monomers; with reference to Formula (II), "$[X_{b1}—Y_{b2}—Z_{b3}]$" defines a repeat unit, having three monomers.

By way of further example, in the case of peptoid PE1, the repeat unit is —$(CH_2)_2$—$NH_2$ and —$((CH_2)_2$—$O)_3$—$CH_3$. By way of further example, in the case of peptoid PE3, the repeat unit is —$(CH_2)_2$—$NH_2$, —$((CH_2)_2$—$O)_3$—$CH_3$, —$(CH_2)_2O$—$CH_3$, and —$((CH_2)_2$—$O)_3$—$CH_3$, wherein one monomer is repeated in this repeat unit. In some embodiments, the repeating unit may contain a sequence of four unique submonomers.

In one embodiment, the peptoid sequence may have alternating groups of submonomers, wherein each repeating unit includes a unique sequence of 2, 3, 4, 5, or 6 submonomers. By way of example, see peptoid PE3 of FIG. 1. In the case of PE3, group 1 includes two monomers, having the following submonomers —$(CH_2)_2$—$NH_2$, —$((CH_2)_2$—$O)_3$—$CH_3$; and group 2 includes two monomers having the following two submonomers —$(CH_2)_2O$—$CH_3$, and —$((CH_2)_2$—$O)_3$—$CH_3$. In this way, peptoid PE3 alternates between group 1 and group 2 along its sequence.

In some embodiments, the peptoids of the present invention may have the charged submonomers distributed across the length of the peptoid. For example, the charged submonomers may be sporadically, evenly, or periodically distributed across the length of the peptoid. This type of peptoid structure is herein referred to as a brush structure.

In some embodiments, the peptoids of the present invention may have an uneven distribution of charged submonomers across the length of the peptoid. In some embodiments, positively-charged submonomers, negatively-charged submonomers, or neutrally-charged submonomers are clustered at the N-terminus, at the C-terminus, or internally, resulting in uneven charge distribution across the length of the peptoid. Such peptoids are referred to as having a block structure. In one aspect of this embodiment, positively-charged submonomers are clustered at the N-terminus. For example, in the case of a peptoid of Formula (I), submonomers $R_1$-$R_4$ include at least one positive submonomer and no more than four positive submonomers, and submonomers $R_5$-$R_8$ include no positive submonomers, or less submonomers than submonomers $R_1$-$R_4$. In another aspect of this embodiment, negatively-charged submonomers are clustered at the C-terminus.

Examples of peptoids having a brush structure and block structure are shown in FIG. 1. Accordingly, brush-type peptoids and block-type peptoids interact differently with the subject biomaterial. In the case of the brush-type peptoids, both termini of the peptoid are proximal to the biomaterial (e.g., pre-defined nucleic acid nanostructure). In the case of block-type peptoids, one terminus is proximal to the biomaterial (e.g., pre-defined nucleic acid nanostructure and one terminus is distal to the biomaterial (e.g., pre-defined nucleic acid nanostructure).

In some embodiments, the peptoids described herein may have a net positive charge. Such peptoids can interact with nucleic acid to facilitate their binding thereto.

In some embodiments, out of the total submonomers present in a peptoid of the invention, and described herein, 0-80%, 20-80%, 20-50%, 20-40%, 20-30%, 30-60%, 30-50%, or 30-40% of the submonomers are positively charged.

In some embodiments, out of the total submonomers present in a peptoid of the invention, and described herein, 0-80%, 20-80%, 20-50%, 20-40%, 20-30%, 30-60%, 30-50%, or 30-40% of the submonomers are negatively charged.

In some embodiments, out of the total submonomers present in a peptoid of the invention, and described herein, less than 20%, less than 25%, less than 30%, less than 25% of the submonomers are neutrally charged.

In some embodiments, the ratio of positive:neutral, negative:neutral, or positive:negative submonomers is 0.001:1, 0.01:1, 0.1:1, 0.5:1; 1:1, 1:3, 1:5, 1:10, or a range in between.

In some embodiments, the ratio of neutral submonomers to charged submonomers is approximately 1:1. In some embodiments, the ratio of neutral submonomers to charged submonomers is approximately 2-5:1.

In some embodiments, out of the total submonomers present in a peptoid of the invention, 20-80%, 30-80%, or 40-80% of the total submonomer content includes oligo-ethylene glycol.

In a preferred embodiment, N-substituted glycine, L-amino acid, D-amino acid and analogue thereof (e.g., aliphatic guanidines) are preferred to be incorporated as the charged motifs that facilitate peptoid interactions with the surfaces of drug/gene carriers. More specific to peptoid-DNA origami interactions, the positively charged submonomers are not limited to functional groups, including the amino, guanidino, hydrazido, and amidino groups. These functional groups can be aromatic or aliphatic and may include enantiomers (e.g., L-amino acid and D-amino acid).

The peptoid sequences can be chemically conjugated with polyalkylene glycol, in particular, polyethylene glycol is preferred and typically has a molecular weight from 2 to 50 kDa. The peptoid sequences can also be chemically conjugated to mono-, di-, or polysaccharide. This may include chitosan, alginate, heparin, hyaluronic acid, chondroitin sulfate, cyclodextrin, pectin, amylose, dextran and analog thereof. Finally, the peptoid designs also permit crosslinking between the polymers, for example, through disulfide bond at the terminating group or side chains.

The amount of neutrally charged functional groups in a peptoid sequence 12 repeating units can be less than 30% in order to ensure peptoid-DNA binding by the positively charged moieties and DNA origami stabilization by the oligo-ethylene glycol moieties. In some embodiments, a peptoid sequence having 12 repeating units the amount of neutrally charged functional groups is less than 35%. In some embodiments, a peptoid sequence having 12 repeating units the amount of neutrally charged functional groups is less than 25%.

In one embodiment, the composition of the invention includes a compound of Formula (III).

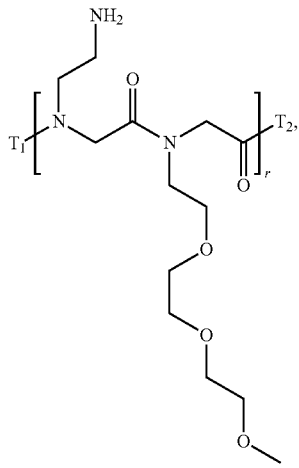

wherein r is 1, 2, 3, 4, 5, 6, 7, 8, 9, 10, 11, 12, 13, 14, 15, 20, 25, 50, 100, or 200;
$T_1$ is

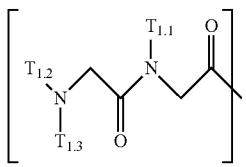

or H; and
$T_2$ is

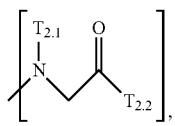

H, —OH, or $NH_2$;
wherein
$T_{1.1}$, $T_{1.2}$, $T_{1.3}$, $T_{2.1}$, and $T_{2.2}$ are independently —($CH_2$)—$NH_2$, —(($CH_2$)$_2$—O)$_3$—$CH_3$, —($C_1$-$C_6$)alkylene($NR_{17}R_{18}$), —$NR_{14}R_{15}$, ($C_1$-$C_6$)alkylene-C(O)$R_{16}$, —C(O)($C_1$-$C_6$)alkyl, —C(O)$NR_{17}R_{18}$, $SO_2$, —OH, —SH, —COOH, —($C_1$-$C_6$)alkylene-$N_3$, —($C_2$-$C_6$)alkynyl, or alkyl, alkenyl, alkynyl, alkylene, or alkoxy that is substituted with at least one of biotinyl, sulfhydryl, cyano, hydrazido, carbodiimide, halo, succinimide, and maleimide; and
$R_{14}$, $R_{15}$, $R_{16}$, $R_{17}$, and $R_{18}$ are each independently H, ($C_1$-$C_6$)alkyl, ($C_2$-$C_6$)alkenyl, ($C_2$-$C_6$)alkynyl, or halo-substituted ($C_1$-$C_6$)alkyl;
wherein formula (III) defines a peptoid, and
wherein $T_1$ and $T_2$ define terminal groups.

As used herein, and with reference to Formulas (I), (II), and (III), $T_1$ defines the N-terminus and $T_2$ defines the C-terminus.

In some embodiments, the peptoid includes 1, 2, 3, 4, or more functional groups. The functional groups may be located exclusively at a single terminus, both termini, internal to the peptoid sequence, or combinations thereof.

The peptoid sequences of the present disclosure can be up to 200 monomer units in length. Typically, the length of the peptoid sequence is at least 2 monomers; at least 3 monomers; more usually 4 monomers, more usually 6-12 monomers and preferably 24-48 monomers. In addition, the typical repeating units of peptoid sequences comprise 2 monomers including 1 positively-charged and 1 neutrally-charged monomer, 3 monomers including 1 positively-charged and 2 neutrally-charged monomers, and 4 monomers including 2 positive-charged and 2 neutrally-charged monomers. As used herein, a "monomer" means one N-substituted glycine unit. By way of example, referencing Formula (I), $A_m$, $E_n$, $G_p$, $J_q$, $L_r$, $M_s$, $Q_t$, and $U_u$ each define a monomer.

In some embodiments, the present invention includes a peptoid according to Formula (I), (II), and (III), wherein a peptoid is conjugated to a chemical compound, imaging reagent, targeting ligand, protein, peptide, aptamer, peptide nucleic acid, dendrimer, oligomer, polymer, antibody, antibody fragment, another peptoid, a biomaterial as disclosed herein, or combinations thereof. Examples of suitable chemical compounds for conjugation include hormones, steroids, estrogens, androgens, thyroid hormone, vitamins, or folic acid.

The conjugation may be by way of a functional group, as described herein and commonly known in the art.

Peptoid synthesis follows the solid-phase peptoid synthesis which is well known in the art, see, e.g., reference nos. 25, 26; where the designed functionality is incorporated during synthesis, enabling controlled peptoid components and architectures.

The peptoids disclosed herein can be prepared by solid-phase synthesis and polymerization methods. The solid-phase synthesis includes methods developed by 1) Merrifield (36), which involves coupling amino acid units (commonly protected by Fmoc) to the growing chain anchored on a resin; and 2) the "submonomer method" developed by Zuckermann (26), which builds peptoid sequences using acylation and nucleophilic displacement with bromoacetic acid and secondary amines. In the polymerization method, peptoids with high molecular weights can be synthesized through ring-opening polymerizations of N-substituted N-carboxyanhydride monomers (37-40) or N-thiocarboxyanhydrides (41-43).

Regardless of type of peptoid monomers, the full-length peptoids described herein may be produced by the same general procedure which includes repeating a two-step or three step cycle wherein a new monomer unit is added in each cycle until a desired length is obtained.

With regards to Formulas (I), (II), and (III) as described herein. When the specific number denoting a chemical group is the integer 0 (zero), a bond is intended to link the adjacent groups onto which the said group is substituted. For example, "(G1)(G2)$_0$(G3)" is equivalent to "G1-G3". Wherein G1 and G3 are adjacent to the subject chemical group G1 (wherein 0 is the specific number denoting the chemical group).

Stabilized Biomaterials

In some embodiments, the present invention provides a stabilized biomaterial and methods for generating the same.

Biomaterials

As used herein, biomaterials include materials useful for biomedical applications. Examples of biomaterials include nucleic acid (DNA and RNA) based nano-structures; lipid based nanostructures; and nanoparticles.

The nucleic acid based nano-structure may be a pre-defined nucleic acid nanostructure. An example of a pre-defined nucleic acid nanostructure includes pre-defined DNA nanostructure. The terms "DNA origami" and "pre-defined DNA nanostructure" are used interchangeably herein.

As used herein, pre-defined nucleic acid nanostructure includes a polynucleotide molecule that has been rationally designed to self-assemble into a pre-defined shape or structure.

The pre-defined nucleic acid nanostructure in accordance with the present disclosure has a size of 1 to 2000 nm, 1 to 1000 nm, 1 to 900 nm, 1 to 800 nm, 1 to 700 nm, 1 to 600 nm, 1 to 500 nm, 1 to 400 nm, 1 to 300 nm, 1 to 200 nm, 1 to 100 nm, or 1 to 50 nm. The size of the pre-defined nucleic acid nanostructure is determined by the longest length of the structure.

As used herein, "self-assemble" refers to the ability of a single-strand of nucleic acid to anneal to itself or another single-strand of nucleic acid, in a sequence-specific manner, in a predicted and non-arbitrary manner, and without external physical control.

In some embodiments, the nucleic acid based nanostructure is double stranded DNA.

In some embodiments, the pre-defined nucleic acid nanostructure is an octahedral-shaped DNA structure having a size of approximately ~60 nm. (29, 30)

In some embodiments, the pre-defined nucleic acid nanostructure is a lattice-based DNA structure that includes a template DNA and staple DNAs with defined shapes and sizes.

In some embodiments, the pre-defined nucleic acid nanostructure is a large-scale DNA structure formed by self-assembly of several smaller pre-defined DNA nanostructures.

The term "lipid" as used herein refers to any suitable material resulting in a single to multi-layered structures such that a hydrophobic portion of the lipid material orients toward the inner lipid layer while a hydrophilic portion orients toward the aqueous phase. An example of a single layer lipid structure includes micelle. Lipids include highly hydrophobic compounds such as triglycerides, phospholipids, glycolipids, and sterols such as cholesterol and amphipathic lipids. An example of a lipid-based structure includes liposomes.

As used herein, the terms "liposome" and "liposomes" refer to a spherical structure having at least one lipid bilayer. A liposome can be used for the administration of therapeutic agents. A liposome can comprise a combination of one or more phospholipids, an optional lipid that is not a phospholipid, such as sterols, glycolipids, amphipathic lipids, pegylated lipids, or a combination thereof. As used herein, a liposome may have a diameter of about 20 nm to about 3,000 nm. In one embodiment, the diameter of the liposomes is about 75 nm to about 600 nm. In certain embodiments, the liposomes can have diameters precisely falling within 110 nm and 125 nm.

In one embodiment, the invention includes stabilized nanoparticles. The nanoparticles are metallic (e.g., monometallic, bimetallic, or polymetallic), and may be inorganic or organic. In some embodiments, the nanoparticles comprise gold, silver, copper, iron oxide, titanium nanoparticles, or alloys thereof, ceramics, carbon, or silica nano- or microparticles. In particular embodiments the nanoparticles are gold or silver nanoparticles.

In some embodiments, the present invention includes a composition having a compound of Formula (I), Formula (II), or Formula (III) and a biomaterial, wherein the compound of Formula (I), Formula (II), or Formula (III) is complexed with a biomaterial. In some embodiments, the complex further includes a small molecule therapeutic or protein. Such a complex defines a drug carrier complex according to the present disclosure.

In embodiments wherein the biomaterial is a nucleic acid, the complex between the peptoid of Formula (I), Formula (II), or Formula (III) and the biomaterial can be characterized as having a molar ratio of peptoid amines to nucleic acid phosphates (N/P).

The following values for N/P be combined in any manner to create a range with a minima and maxima for ratio necessary for a stable complex between the peptoid and nucleic acid biomaterial: 0.001, 0.01, 0.1, 0.125, 0.25, 0.5, 1, 2, 3, 4, 5, 8, and 10. As an example, the N/P may be between 0.001 and 3, 0.001 and 2, 0.01 and 2, or 0.1 and 2.

In some embodiments, the N/P is less than 4, less than 3, less than 2, or less than 1.

In some embodiments, the biomaterial is a pre-defined nucleic acid nanostructure and the complex with a peptoid of the present invention includes a N/P of less than 3 or less than 2.

In an embodiment of the invention, the peptoid sequences comprise 1 to 100 (or any range in between) of the repeating dimers, trimers or tetramers. Optionally, the designs are not limited to peptoid sequences that contain only the positively-, negatively- or neutrally charged monomers, excluding the terminal groups for specific purposes.

As used herein, the submonomers and peptoids are referenced as having a charge. The net charges are also determined by the solution pH, in which the physiologically relevant pH is at least 4 and is no more than 8.5.

Method of Stabilizing

In some embodiments, the present invention includes a method of stabilizing a biomaterial, said method includes complexing with the biomaterial with a composition including a compound of Formula (I), (II), or (III), as described herein.

As used herein, "complexing" means forming a complex of two or more components. As used herein, "complex" refers to a combination of two or more components having intramolecular or intermolecular covalent or noncovalent interactions. The complexed components are said to be stabilized. As used herein, "stabilized" means that the component that is stabilized has improved properties as compared to properties of the non-stabilized or non-complexed component. By way of example, and as described herein, a biomaterial is stabilized if it has increased nuclease resistance. By way of further example, a stabilized pre-defined DNA nanostructure has increased structural integrity in environments with low salt or low monovalent or bivalent ions.

In one embodiment, complexing includes (i) contacting the biomaterial with a composition with a compound of Formula (I), (II), or (III). The contacting conditions include with compound of Formula (I), (II), or (III) for between 0.5 and 20, 10 and 20, 8 and 12, or 0.5 and 4 hours; and at a temperature of between 1° C. and 4° C., 20° C. and 40° C., or 2° C. and 10° C.

In one embodiment, the method includes a method of stabilizing a pre-defined nucleic acid nanostructure. In some aspects of this embodiment, the contacting and complexing include a ratio of Formula (I), (II), or (III) amines to nucleic acid phosphates is less than 20, less than 15, less than 10, less than 8, less than 5, or less than 2. In some aspects of this embodiment, the contacting includes a ratio of Formula (I), (II), or (III) amines to nucleic acid phosphates of the pre-defined nucleic acid nanostructure is between 3 and 0.01, 3 and 0.1, or 2 and 0.2.

Formation of the origami nanostructures can include and without limitation to basically negatively charged "polynucleotide" or "nucleic acid", which refers to DNA, RNA, peptide nucleic acids and their analogues thereof. In addition, the nucleic acids may be single-stranded, double-stranded or combination of the two types of molecules.

Throughout this specification, quantities are defined by ranges having a lower boundary and upper boundary, and by lower or upper boundaries. Each lower boundary can be combined with each upper boundary to define a range. Two lower boundary values can be combined to define a range, and two upper boundary values can be combined to define a range. The lower and upper boundaries should each be taken as a separate element.

Examples

Materials

All single-stranded DNA (ssDNA) sequences were purchased from Integrated DNA Technologies and the M13mp18 ssDNA scaffold was purchased from Bayou Biolabs. 2-(2-(2-methoxyethoxy)ethoxy)ethanamine was purchased from Aurum Pharmatech. Rink Amide resin, 2-methoxyethylamine, propargylamine, magnesium chloride ($MgCl_2$), copper (II) sulphate ($CuSO_4$), aminoguanidine hydrochloride, DNase I, doxorubicin, agarose (medium EEO), bovine serum albumin, trypsin and phosphate buffer saline (PBS) were purchased from Sigma Aldrich.

Method

Preparation of octahedra-shaped DNA origamis (OCs). OCs were folded by mixing 20 nM of M13mp18 scaffold DNA and 100 nM of each staple oligonucleotides in TAE (1×) buffer containing 12.5 mM $MgCl_2$. The mixed solution was then cooled from 90° C. to room temperature over 20 hours to obtain the target OC structure. After synthesis, OCs were purified using the Amicon 100 k centrifugal filter units (Millipore Sigma) and centrifuged at 400 g and at 4° C. The purification process was repeated 6 times by adding fresh TAE (1×) buffer containing 12.5 mM $MgCl_2$ in each cycle.

OC Sequence

```
OC-staple-1
                                      (SEQ ID NO: 2)
TCAAAGCGAACCAGACCGTTTTATATAGTC OC-staple-2
                                      (SEQ ID NO: 3)
GCTTTGAGGACTAAAGAGCAACGGGGAGTT OC-staple-3
                                      (SEQ ID NO: 4)
GTAAATCGTCGCTATTGAATAACTCAAGAA OC-staple-4
                                      (SEQ ID NO: 5)
AAGCCTTAAATCAAGACTTGCGGAGCAAAT OC-staple-5
                                      (SEQ ID NO: 6)
ATTTTAAGAACTGGCTTGAATTATCAGTGA OC-staple-6
                                      (SEQ ID NO: 7)
GTTAAAATTCGCATTATAAACGTAAACTAG OC-staple-7
                                      (SEQ ID NO: 8)
AGCACCATTACCATTACAGCAAATGACGGA OC-staple-8
                                      (SEQ ID NO: 9)
ATTGCGTAGATTTTCAAAACAGATTGTTTG OC-staple-9
                                      (SEQ ID NO: 10)
TAACCTGTTTAGCTATTTTCGCATTCATTC OC-staple-10
                                      (SEQ ID NO: 11)
GTCAGAGGGTAATTGAGAACACCAAAATAG OC-staple-11
                                      (SEQ ID NO: 12)
CTCCAGCCAGCTTTCCCCTCAGGACGTTGG OC-staple-12
                                      (SEQ ID NO: 13)
GTCCACTATTAAAGAACCAGTTTTGGTTCC OC-staple-13
                                      (SEQ ID NO: 14)
TAAAGGTGGCAACATAGTAGAAAATAATAA OC-staple-14
                                      (SEQ ID NO: 15)
GATAAGTCCTGAACAACTGTTTAAAGAGAA OC-staple-15
                                      (SEQ ID NO: 16)
GGTAATAGTAAAATGTAAGTTTTACACTAT OC-staple-16
                                      (SEQ ID NO: 17)
TCAGAACCGCCACCCTCTCAGAGTATTAGC OC-staple-17
                                      (SEQ ID NO: 18)
AAGGGAACCGAACTGAGCAGACGGTATCAT OC-staple-18
                                      (SEQ ID NO: 19)
GTAAAGATTCAAAAGGCCTGAGTTGACCCT OC-staple-19
                                      (SEQ ID NO: 20)
AGGCGTTAAATAAGAAGACCGTGTCGCAAG OC-staple-20
                                      (SEQ ID NO: 21)
CAGGTCGACTCTAGAGCAAGCTTCAAGGCG OC-staple-21
                                      (SEQ ID NO: 22)
CAGAGCCACCACCCTCTCAGAACTCGAGAG OC-staple-22
                                      (SEQ ID NO: 23)
TTCACGTTGAAAATCTTGCGAATGGGATTT OC-staple-23
                                      (SEQ ID NO: 24)
AAGTTTTAACGGGGTCGGAGTGTAGAATGG OC-staple-24
                                      (SEQ ID NO: 25)
TTGCGTATTGGGCGCCCGCGGGGTGCGCTC OC-staple-25
                                      (SEQ ID NO: 26)
GTCACCAGAGCCATGGTGAATTATCACCAATCAGAAAAGCCT OC-staple-26
                                      (SEQ ID NO: 27)
GGACAGAGTTACTTTGTCGAAATCCGCGTGTATCACCGTACG
```

OC-staple-27
(SEQ ID NO: 28)
CAACATGATTTACGAGCATGGAATAAGTAAGACGACAATAAA

OC-staple-28
(SEQ ID NO: 29)
AACCAGACGCTACGTTAATAAAACGAACATACCACATTCAGG

OC-staple-29
(SEQ ID NO: 30)
TGACCTACTAGAAAAAGCCCCAGGCAAAGCAATTTCATCTTC

OC-staple-30
(SEQ ID NO: 31)
TGCCGGAAGGGGACTCGTAACCGTGCATTATATTTTAGTTCT

OC-staple-31
(SEQ ID NO: 32)
AGAACCCCAAATCACCATCTGCGGAATCGAATAAAAATTTTT

OC-staple-32
(SEQ ID NO: 33)
GCTCCATTGTGTACCGTAACACTGAGTTAGTTAGCGTAACCT

OC-staple-33
(SEQ ID NO: 34)
AGTACCGAATAGGAACCCAAACGGTGTAACCTCAGGAGGTTT

OC-staple-34
(SEQ ID NO: 35)
CAGTTTGAATGTTTAGTATCATATGCGTAGAATCGCCATAGC

OC-staple-35
(SEQ ID NO: 36)
AAGATTGTTTTTTAACCAAGAAACCATCGACCCAAAAACAGG

OC-staple-36
(SEQ ID NO: 37)
TCAGAGCGCCACCACATAATCAAAATCAGAACGAGTAGTATG

OC-staple-37
(SEQ ID NO: 38)
GATGGTTGGGAAGAAAAATCCACCAGAAATAATTGGGCTTGA

OC-staple-38
(SEQ ID NO: 39)
CTCCTTAACGTAGAAACCAATCAATAATTCATCGAGAACAGA

OC-staple-39
(SEQ ID NO: 40)
AGACACCTTACGCAGAACTGGCATGATTTTCTGTCCAGACAA

OC-staple-40
(SEQ ID NO: 41)
GCCAGCTAGGCGATAGCTTAGATTAAGACCTTTTTAACCTGT

OC-staple-41
(SEQ ID NO: 42)
CCGACTTATTAGGAACGCCATCAAAAATGAGTAACAACCCCA

OC-staple-42
(SEQ ID NO: 43)
GTCCAATAGCGAGAACCAGACGACGATATTCAACGCAAGGGA

OC-staple-43
(SEQ ID NO: 44)
CCAAAATACAATATGATATTCAACCGTTAGGCTATCAGGTAA

OC-staple-44
(SEQ ID NO: 45)
AACAGTACTTGAAAACATATGAGACGGGTCTTTTTTAATGGA

OC-staple-45
(SEQ ID NO: 46)
TTTCACCGCATTAAAGTCGGGAAACCTGATTTGAATTACCCA

OC-staple-46
(SEQ ID NO: 47)
GAGAATAGAGCCTTACCGTCTATCAAATGGAGCGGAATTAGA

OC-staple-47
(SEQ ID NO: 48)
ATAATTAAATTTAAAAAACTTTTTCAAACTTTTAACAACGCC

OC-staple-48
(SEQ ID NO: 49)
GCACCCAGCGTTTTTTATCCGGTATTCTAGGCGAATTATTCA

OC-staple-49
(SEQ ID NO: 50)
GGAAGCGCCCACAAACAGTTAATGCCCCGACTCCTCAAGATA

OC-staple-50
(SEQ ID NO: 51)
GTTTGCCTATTCACAGGCAGGTCAGACGCCACCACACCACCC

OC-staple-51
(SEQ ID NO: 52)
CGCGAGCTTAGTTTTTCCCAATTCTGCGCAAGTGTAAAGCCT

OC-staple-52
(SEQ ID NO: 53)
AGAAGCAACCAAGCCAAAAGAATACACTAATGCCAAAACTCC

OC-staple-53
(SEQ ID NO: 54)
ATTAAGTATAAAGCGGCAAGGCAAAGAAACTAATAGGGTACC

OC-staple-54
(SEQ ID NO: 55)
CAGTGCCTACATGGGAATTTACCGTTCCACAAGTAAGCAGAT

OC-staple-55
(SEQ ID NO: 56)
ATAAGGCGCCAAAAGTTGAGATTTAGGATAACGGACCAGTCA

OC-staple-56
(SEQ ID NO: 57)
TGCTAAACAGATGAAGAAACCACCAGAATTTAAAAAAAGGCT

OC-staple-57
(SEQ ID NO: 58)
CAGCCTTGGTTTTGTATTAAGAGGCTGACTGCCTATATCAGA

OC-staple-58
(SEQ ID NO: 59)
CGGAATAATTCAACCCAGCGCCAAAGACTTATTTTAACGCAA

OC-staple-59
(SEQ ID NO: 60)
CGCCTGAATTACCCTAATCTTGACAAGACAGACCATGAAAGA

OC-staple-60
(SEQ ID NO: 61)
ACGCGAGGCTACAACAGTACCTTTTACAAATCGCGCAGAGAA

OC-staple-61
(SEQ ID NO: 62)
CAGCGAACATTAAAAGAGAGTACCTTTACTGAATATAATGAA

OC-staple-62
(SEQ ID NO: 63)
GGACGTTTAATTTCGACGAGAAACACCACCACTAATGCAGAT

OC-staple-63
(SEQ ID NO: 64)
AAAGCGCCAAAGTTTATCTTACCGAAGCCCAATAATGAGTAA

OC-staple-64
(SEQ ID NO: 65)
GAGCTCGTTGTAAACGCCAGGGTTTTCCAAAGCAATAAAGCC

OC-staple-65
(SEQ ID NO: 66)
AATTATTGTTTTCATGCCTTTAGCGTCAGATAGCACGGAAAC

OC-staple-66
(SEQ ID NO: 67)
AAGTTTCAGACAGCCGGGATCGTCACCCTTCTGTAGCTCAAC

-continued

OC-staple-67

(SEQ ID NO: 68)
ACAAAGAAATTTAGGTAGGGCTTAATTGTATACAACGGAATC

OC-staple-68

(SEQ ID NO: 69)
AACAAAAATAACTAGGTCTGAGAGACTACGCTGAGTTTCCCT

OC-staple-69

(SEQ ID NO: 70)
CATAACCTAAATCAACAGTTCAGAAAACGTCATAAGGATAGC

OC-staple-70

(SEQ ID NO: 71)
CACGACGAATTCGTGTGGCATCAATTCTTTAGCAAAATTACG

OC-staple-71

(SEQ ID NO: 72)
CCTACCAACAGTAATTTTATCCTGAATCAAACAGCCATATGA

OC-staple-72

(SEQ ID NO: 73)
GATTATAAAGAAACGCCAGTTACAAAATTTACCAACGTCAGA

OC-staple-73

(SEQ ID NO: 74)
AGTAGATTGAAAAGAATCATGGTCATAGCCGGAAGCATAAGT

OC-staple-74

(SEQ ID NO: 75)
TAGAATCCATAAATCATTTAACAATTTCTCCCGGCTTAGGTT

OC-staple-75

(SEQ ID NO: 76)
AAAGGCCAAATATGTTAGAGCTTAATTGATTGCTCCATGAGG

OC-staple-76

(SEQ ID NO: 77)
CCAAAAGGAAAGGACAACAGTTTCAGCGAATCATCATATTCC

OC-staple-77

(SEQ ID NO: 78)
GAAATCGATAACCGGATACCGATAGTTGTATCAGCTCCAACG

OC-staple-78

(SEQ ID NO: 79)
TGAATATTATCAAAATAATGGAAGGGTTAATATTTATCCCAA

OC-staple-79

(SEQ ID NO: 80)
GAGGAAGCAGGATTCGGGTAAAATACGTAAAACACCCCCCAG

OC-staple-80

(SEQ ID NO: 81)
GGTTGATTTTCCAGCAGACAGCCCTCATTCGTCACGGGATAG

OC-staple-81

(SEQ ID NO: 82)
CAAGCCCCCACCCTTAGCCCGGAATAGGACGATCTAAAGTTT

OC-staple-82

(SEQ ID NO: 83)
TGTAGATATTACGCGGCGATCGGTGCGGGCGCCATCTTCTGG

OC-staple-83

(SEQ ID NO: 84)
CATCCTATTCAGCTAAAAGGTAAAGTAAAAAGCAAGCCGTTT

OC-staple-84

(SEQ ID NO: 85)
CAGCTCATATAAGCGTACCCCGGTTGATGTGTCGGATTCTCC

OC-staple-85

(SEQ ID NO: 86)
CATGTCACAAACGGCATTAAATGTGAGCAATTCGCGTTAAAT

OC-staple-86

(SEQ ID NO: 87)
AGCGTCACGTATAAGAATTGAGTTAAGCCCTTTTTAAGAAAG

-continued

OC-staple-87

(SEQ ID NO: 88)
TATAAAGCATCGTAACCAAGTACCGCACCGGCTGTAATATCC

OC-staple-88

(SEQ ID NO: 89)
ATAGCCCGCGAAAATAATTGTATCGGTTCGCCGACAATGAGT

OC-staple-89

(SEQ ID NO: 90)
AGACAGTTCATATAGGAGAAGCCTTTATAACATTGCCTGAGA

OC-staple-90

(SEQ ID NO: 91)
AACAGGTCCCGAAATTGCATCAAAAAGATCTTTGATCATCAG

OC-staple-91

(SEQ ID NO: 92)
ACTGCCCTTGCCCCGTTGCAGCAAGCGGCAACAGCTTTTTCT

OC-staple-92

(SEQ ID NO: 93)
TCAAAGGGAGATAGCCCTTATAAATCAAGACAACAACCATCG

OC-staple-93

(SEQ ID NO: 94)
GTAATACGCAAACATGAGAGATCTACAACTAGCTGAGGCCGG

OC-staple-94

(SEQ ID NO: 95)
GAGATAACATTAGAAGAATAACATAAAAAGGAAGGATTAGGA

OC-staple-95

(SEQ ID NO: 96)
CAGATATTACCTGAATACCAAGTTACAATCGGGAGCTATTTT

OC-staple-96

(SEQ ID NO: 97)
CATATAACTAATGAACACAACATACGAGCTGTTTCTTTGGGG

OC-staple-97

(SEQ ID NO: 98)
ATGTTTTGCTTTTGATCGGAACGAGGGTACTTTTTCTTTTGATAAGAGGT
CATT

OC-staple-98

(SEQ ID NO: 99)
GGGGTGCCAGTTGAGACCATTAGATACAATTTTCACTGTGTGAAATTGTT
ATCC

OC-staple-99

(SEQ ID NO: 100)
CTTCGCTGGGCGCAGACGACAGTATCGGGGCACCGTCGCCATTCAGGCTG
CGCA

OC-staple-100

(SEQ ID NO: 101)
TCAGAGCTGGGTAAACGACGGCCAGTGCGATCCCCGTAGTAGCATTAACA
TCCA

OC-staple-101

(SEQ ID NO: 102)
TTAGCGGTACAGAGCGGGAGAATTAACTGCGCTAATTTCGGAACCTATTA
TTCT

OC-staple-102

(SEQ ID NO: 103)
GATATTCTAAATTGAGCCGGAACGAGGCCCAACTTGGCGCATAGGCTGGC
TGAC

OC-staple-103

(SEQ ID NO: 104)
TGTCGTCATAAGTACAGAACCGCCACCCATTTTCACAGTACAAACTACAACGCC

OC-staple-104

(SEQ ID NO: 105)
CGATTATAAGCGGAGACTTCAAATATCGCGGAAGCCTACGAAGGCACCAACCTA

OC-staple-105

(SEQ ID NO: 106)
AACATGTACGCGAGTGGTTTGAAATACCTAAACACATTCTTACCAGTATAAAGC

OC-staple-106

(SEQ ID NO: 107)
GTCTGGATTTTGCGTTTTAAATGCAATGGTGAGAAATAAATTAATGCCGGAGAG

OC-staple-107

(SEQ ID NO: 108)
GCCTTGAATCTTTTCCGGAACCGCCTCCCAGAGCCCAGAGCCGCCGCCAGCATT

OC-staple-108

(SEQ ID NO: 109)
CGCTGGTGCTTTCCTGAATCGGCCAACGAGGGTGGTGATTGCCCTTCACCGCCT

OC-staple-109

(SEQ ID NO: 110)
TGATTATCAACTTTACAACTAAAGGAATCCAAAAAGTTTGAGTAACATTATCAT

OC-staple-110

(SEQ ID NO: 111)
ACATAACTTGCCCTAACTTTAATCATTGCATTATAACAACATTATTACAGGTAG

OC-staple-111

(SEQ ID NO: 112)
GTAGCGCCATTAAATTGGGAATTAGAGCGCAAGGCGCACCGTAATCAGTAGCGA

OC-staple-112

(SEQ ID NO: 113)
TTATTTTTACCGACAATGCAGAACGCGCGAAAAATCTTTCCTTATCATTCCAAG

OC-staple-113

(SEQ ID NO: 114)
TTTCAATAGAAGGCAGCGAACCTCCCGATTAGTTGAAACAATAACGGATTCGCC

OC-staple-114

(SEQ ID NO: 115)
GGGCGACCCCAAAAGTATGTTAGCAAACTAAAAGAGTCACAATCAATAGAAAAT

OC-staple-115

(SEQ ID NO: 116)
AGCCGAAAGTCTCTCTTTTGATGATACAAGTGCCTTAAGAGCAAGAAACAATGA

OC-staple-116

(SEQ ID NO: 117)
GTGGGAAATCATATAAATATTTAAATTGAATTTTTGTCTGGCCTTCCTGTAGCC

OC-staple-117

(SEQ ID NO: 118)
CCCACGCGCAAAATGGTTGAGTGTTGTTCGTGGACTTGCTTTCGAGGTGAATTT

OC-staple-118

(SEQ ID NO: 119)
ATGACCACTCGTTTGGCTTTTGCAAAAGTTAGACTATATTCATTGAATCCCCCT

OC-staple-119

(SEQ ID NO: 120)
TCCAAATCTTCTGAATTATTTGCACGTAGGTTTAACGCTAACGAGCGTCTTTCC

OC-staple-120

(SEQ ID NO: 121)
GGGTTATTTAATTACAATATATGTGAGTAATTAATAAGAGTCAATAGTGAATTT

Note:
To encapsulate Au NPs and BSA inside the OCs, add
(SEQ ID NO: 122)
'ATCCATCACTTCATACTCTACGTTGTTGTT' in front of the red-marked sequences.

M13mp18 scaffold DNA sequence.

>FOUNDATION_ssDNA_7249

(SEQ ID NO: 123)
TGATAGACGGTTTTTCGCCCTTTGACGTTGGAGTCCACGTTCTTTAATAGT
GGACTCTTGTTCCAAACTGGAACAACACTCAACCCTATCTCGGGCTATTCT
TTTGATTTATAAGGGATTTTGCCGATTTCGGAACCACCATCAAACAGGATT
TTCGCCTGCTGGGGCAAACCAGCGTGGACCGCTTGCTGCAACTCTCTCAGG
GCCAGGCGGTGAAGGGCAATCAGCTGTTGCCCGTCTCACTGGTGAAAAGAA
AAACCACCCTGGCGCCCAATACGCAAACCGCCTCTCCCCGCGCGTTGGCCG
ATTCATTAATGCAGCTGGCACGACAGGTTTCCCGACTGGAAAGCGGGCAGT
GAGCGCAACGCAATTAATGTGAGTTAGCTCACTCATTAGGCACCCCAGGCT
TTACACTTTATGCTTCCGGCTCGTATGTTGTGTGGAATTGTGAGCGGATAA
CAATTTCACACAGGAAACAGCTATGACCATGATTACGAATTCGAGCTCGGT
ACCCGGGGATCCTCTAGAGTCGACCTGCAGGCATGCAAGCTTGGCACTGGC
CGTCGTTTTACAACGTCGTGACTGGGAAAACCCTGGCGTTACCCAACTTAA
TCGCCTTGCAGCACATCCCCCTTTCGCCAGCTGGCGTAATAGCGAAGAGGC
CCGCACCGATCGCCCTTCCCAACAGTTGCGCAGCCTGAATGGCGAATGGCG
CTTTGCCTGGTTTCCGGCACCAGAAGCGGTGCCGGAAAGCTGGCTGGAGTG
CGATCTTCCTGAGGCCGATACTGTCGTCGTCCCCTCAAACTGGCAGATGCA
CGGTTACGATGCGCCCATCTACACCAACGTGACCTATCCCATTACGGTCAA
TCCGCCGTTTGTTCCCACGGAGAATCCGACGGGTTGTTACTCGCTCACATT
TAATGTTGATGAAAGCTGGCTACAGGAAGGCCAGACGCGAATTATTTTTGA

-continued

TGGCGTTCCTATTGGTTAAAAAATGAGCTGATTTAACAAAAATTTAATGCG
AATTTTAACAAAATATTAACGTTTACAATTTAAATATTTGCTTATACAATC
TTCCTGTTTTTGGGGCTTTTCTGATTATCAACCGGGGTACATATGATTGAC
ATGCTAGTTTTACGATTACCGTTCATCGATTCTCTTGTTTGCTCCAGACTC
TCAGGCAATGACCTGATAGCCTTTGTAGATCTCTCAAAAATAGCTACCCTC
TCCGGCATTAATTTATCAGCTAGAACGGTTGAATATCATATTGATGGTGAT
TTGACTGTCTCCGGCCTTTCTCACCCTTTTGAATCTTTACCTACACATTAC
TCAGGCATTGCATTTAAAATATATGAGGGTTCTAAAAATTTTTATCCTTGC
GTTGAAATAAAGGCTTCTCCCGCAAAAGTATTACAGGGTCATAATGTTTTT
GGTACAACCGATTTAGCTTTATGCTCTGAGGCTTTATTGCTTAATTTTGCT
AATTCTTTGCCTTGCCTGTATGATTTATTGGATGTTAATGCTACTACTATT
AGTAGAATTGATGCCACCTTTTCAGCTCGCGCCCCAAATGAAAATATAGCT
AAACAGGTTATTGACCATTTGCGAAATGTATCTAATGGTCAAACTAAATCT
ACTCGTTCGCAGAATTGGGAATCAACTGTTATATGGAATGAAACTTCCAGA
CACCGTACTTTAGTTGCATATTTAAAACATGTTGAGCTACAGCATTATATT
CAGCAATTAAGCTCTAAGCCATCCGCAAAAATGACCTCTTATCAAAGGAG
CAATTAAAGGTACTCTCTAATCCTGACCTGTTGGAGTTTGCTTCCGGTCTG
GTTCGCTTTGAAGCTCGAATTAAAACGCGATATTTGAAGTCTTTCGGGCTT
CCTCTTAATCTTTTTGATGCAATCCGCTTTGCTTCTGACTATAATAGTCAG
GGTAAAGACCTGATTTTTGATTTATGGTCATTCTCGTTTTCTGAACTGTTT
AAAGCATTTGAGGGGGATTCAATGAATATTTATGACGATTCCGCAGTATTG
GACGCTATCCAGTCTAAACATTTTACTATTACCCCCTCTGGCAAAACTTCT
TTTGCAAAAGCCTCTCGCTATTTTGGTTTTTATCGTCGTCTGGTAAACGAG
GGTTATGATAGTGTTGCTCTTACTATGCCTCGTAATTCCTTTTGGCGTTAT
GTATCTGCATTAGTTGAATGTGGTATTCCTAAATCTCAACTGATGAATCTT
TCTACCTGTAATAATGTTGTTCCGTTAGTTCGTTTTATTAACGTAGATTTT
TCTTCCCAACGTCCTGACTGGTATAATGAGCCAGTTCTTAAAATCGCATAA
GGTAATTCACAATGATTAAAGTTGAAATTAAACCATCTCAAGCCCAATTTA
CTACTCGTTCTGGTGTTTCTCGTCAGGGCAAGCCTTATTCACTGAATGAGC
AGCTTTGTTACGTTGATTTGGGTAATGAATATCCGGTTCTTGTCAAGATTA
CTCTTGATGAAGGTCAGCCAGCCTATGCGCCTGGTCTGTACACCGTTCATC
TGTCCTCTTTCAAAGTTGGTCAGTTCGGTTCCCTTATGATTGACCGTCTGC
GCCTCGTTCCGGCTAAGTAACATGGAGCAGGTCGCGGATTTCGACACAATT
TATCAGGCGATGATACAAATCTCCGTTGTACTTTGTTTCGCGCTTGGTATA
ATCGCTGGGGGTCAAAGATGAGTGTTTTAGTGTATTCTTTTGCCTCTTTCG
TTTTAGGTTGGTGCCTTCGTAGTGGCATTACGTATTTTACCCGTTTAATGG
AAACTTCCTCATGAAAAAGTCTTTAGTCCTCAAAGCCTCTGTAGCCGTTGC
TACCCTCGTTCCGATGCTGTCTTTCGCTGCTGAGGGTGACGATCCCGCAAA
AGCGGCCTTTAACTCCCTGCAAGCCTCAGCGACCGAATATATCGGTTATGC
GTGGGCGATGGTTGTTGTCATTGTCGGCGCAACTATCGGTATCAAGCTGTT
TAAGAAAATTCACCTCGAAAGCAAGCTGATAAACCGATACAATTAAAGGCTC

-continued

CTTTTGGAGCCTTTTTTTTGGAGATTTTCAACGTGAAAAAATTATTATTCG
CAATTCCTTTAGTTGTTCCTTTCTATTCTCACTCCGCTGAAACTGTTGAAA
GTTGTTTAGCAAAATCCCATACAGAAAATTCATTTACTAACGTCTGGAAAG
ACGACAAAACTTTAGATCGTTACGCTAACTATGAGGGCTGTCTGTGGAATG
CTACAGGCGTTGTAGTTTGTACTGGTGACGAAACTCAGTGTTACGGTACAT
GGGTTCCTATTGGGCTTGCTATCCCTGAAAATGAGGGTGGTGGCTCTGAGG
GTGGCGGTTCTGAGGGTGGCGGTTCTGAGGGTGGCGGTACTAAACCTCCTG
AGTACGGTGATACACCTATTCCGGGCTATACTTATATCAACCCTCTCGACG
GCACTTATCCGCCTGGTACTGAGCAAAACCCCGCTAATCCTAATCCTTCTC
TTGAGGAGTCTCAGCCTCTTAATACTTTCATGTTTCAGAATAATAGGTTCC
GAAATAGGCAGGGGGCATTAACTGTTTATACGGGCACTGTTACTCAAGGCA
CTGACCCCGTTAAAACTTATTACCAGTACACTCCTGTATCATCAAAAGCCA
TGTATGACGCTTACTGGAACGGTAAATTCAGAGACTGCGCTTTCCATTCTG
GCTTTAATGAGGATTTATTTGTTTGTGAATATCAAGGCCAATCGTCTGACC
TGCCTCAACCTCCTGTCAATGCTGGCGGCGGCTCTGGTGGTGGTTCTGGTG
GCGGCTCTGAGGGTGGTGGCTCTGAGGGTGGCGGTTCTGAGGGTGGCGGCT
CTGAGGGAGGCGGTTCCGGTGGTGGCTCTGGTTCCGGTGATTTTGATTATG
AAAAGATGGCAAACGCTAATAAGGGGGCTATGACCGAAAATGCCGATGAAA
ACGCGCTACAGTCTGACGCTAAAGGCAAACTTGATTCTGTCGCTACTGATT
ACGGTGCTGCTATCGATGGTTTCATTGGTGACGTTTCCGGCCTTGCTAATG
GTAATGGTGCTACTGGTGATTTTGCTGGCTCTAATTCCCAAATGGCTCAAG
TCGGTGACGGTGATAATTCACCTTTAATGAATAATTTCCGTCAATATTTAC
CTTCCCTCCCTCAATCGGTTGAATGTCGCCCTTTTGTCTTTGGCGCTGGTA
AACCATATGAATTTTCTATTGATTGTGACAAAATAAACTTATTCCGTGGTG
TCTTTGCGTTTCTTTTATATGTTGCCACCTTTATGTATGTATTTTCTACGT
TTGCTAACATACTGCGTAATAAGGAGTCTTAATCATGCCAGTTCTTTTGGG
TATTCCGTTATTATTGCGTTTCCTCGGTTTCCTTCTGGTAACTTTGTTCGG
CTATCTGCTTACTTTTCTTAAAAAGGGCTTCGGTAAGATAGCTATTGCTAT
TTCATTGTTTCTTGCTCTTATTATTGGGCTTAACTCAATTCTTGTGGGTTA
TCTCTCTGATATTAGCGCTCAATTACCCTCTGACTTTGTTCAGGGTGTTCA
GTTAATTCTCCCGTCAATGCGCTTCCCTGTTTTTATGTTATTCTCTCTGT
AAAGGCTGCTATTTTCATTTTTGACGTTAAACAAAAAATCGTTTCTTATTT
GGATTGGGATAAATAATATGGCTGTTTATTTTGTAACTGGCAAATTAGGCT
CTGGAAAGACGCTCGTTAGCGTTGGTAAGATTCAGGATAAAATTGTAGCTG
GGTGCAAAATAGCAACTAATCTTGATTTAAGGCTTCAAAACCTCCCGCAAG
TCGGGAGGTTCGCTAAAACGCCTCGCGTTCTTAGAATACCGGATAAGCCTT
CTATATCTGATTTGCTTGCTATTGGGCGCGGTAATGATTCCTACGATGAAA
ATAAAAACGGCTTGCTTGTTCTCGATGAGTGCGGTACTTGGTTTAATACCC
GTTCTTGGAATGATAAGGAAAGACAGCCGATTATTGATTGGTTTCTACATG
CTCGTAAATTAGGATGGGATATTATTTTTCTTGTTCAGGACTTATCTATTG

```
                                -continued
TTGATAAACAGGCGCGTTCTGCATTAGCTGAACATGTTGTTTATTGTCGTC

GTCTGGACAGAATTACTTTACCTTTTGTCGGTACTTTATATTCTCTTATTA

CTGGCTCGAAAATGCCTCTGCCTAAATTACATGTTGGCGTTGTTAAATATG

GCGATTCTCAATTAAGCCCTACTGTTGAGCGTTGGCTTTATACTGGTAAGA

ATTTGTATAACGCATATGATACTAAACAGGCTTTTTCTAGTAATTATGATT

CCGGTGTTTATTCTTATTTAACGCCTTATTTATCACACGGTCGGTATTTCA

AACCATTAAATTTAGGTCAGAAGATGAAATTAACTAAAATATATTTGAAAA

AGTTTTCTCGCGTTCTTTGTCTTGCGATTGGATTTGCATCAGCATTTACAT

ATAGTTATATAACCCAACCTAAGCCGGAGGTTAAAAAGGTAGTCTCTCAGA

CCTATGATTTTGATAAATTCACTATTGACTCTTCTCAGCGTCTTAATCTAA

GCTATCGCTATGTTTTCAAGGATTCTAAGGGAAAATTAATTAATAGCGACG

ATTTACAGAAGCAAGGTTATTCACTCACATATATTGATTTATGTACTGTTT

CCATTAAAAAAGGTAATTCAAATGAAATTGTTAAATGTAATTAATTTTGTT

TTCTTGATGTTTGTTTCATCATCTTCTTTTGCTCAGGTAATTGAAATGAAT

AATTCGCCTCTGCGCGATTTTGTAACTTGGTATTCAAAGCAATCAGGCGAA

TCCGTTATTGTTTCTCCCGATGTAAAAGGTACTGTTACTGTATATTCATCT

GACGTTAAACCTGAAAATCTACGCAATTTCTTTATTTCTGTTTTACGTGCA

AATAATTTTGATATGGTAGGTTCTAACCCTTCCATTATTCAGAAGTATAAT

CCAAACAATCAGGATTATATTGATGAATTGCCATCATCTGATAATCAGGAA

TATGATGATAATTCCGCTCCTTCTGGTGGTTTCTTTGTTCCGCAAAATGAT

AATGTTACTCAAACTTTTAAAATTAATAACGTTCGGGCAAAGGATTTAATA

CGAGTTGTCGAATTGTTTGTAAAGTCTAATACTTCTAAATCCTCAAATGTA

TTATCTATTGACGGCTCTAATCTATTAGTTGTTAGTGCTCCTAAAGATATT

TTAGATAACCTTCCTCAATTCCTTTCAACTGTTGATTTGCCAACTGACCAG

ATATTGATTGAGGGTTTGATATTTGAGGTTCAGCAAGGTGATGCTTTAGAT

TTTTCATTTGCTGCTGGCTCTCAGCGTGGCACTGTTGCAGGCGGTGTTAAT

ACTGACCGCCTCACCTCTGTTTTATCTTCTGCTGGTGGTTCGTTCGGTATT

TTTAATGGCGATGTTTTAGGGCTATCAGTTCGCGCATTAAAGACTAATAGC

CATTCAAAAATATTGTCTGTGCCACGTATTCTTACGCTTTCAGGTCAGAAG

GGTTCTATCTCTGTTGGCCAGAATGTCCCTTTTATTACTGGTCGTGTGACT

GGTGAATCTGCCAATGTAAATAATCCATTTCAGACGATTGAGCGTCAAAAT

GTAGGTATTTCCATGAGCGTTTTTCCTGTTGCAATGGCTGGCGGTAATATT

GTTCTGGATATTACCAGCAAGGCCGATAGTTTGAGTTCTTCTACTCAGGCA

AGTGATGTTATTACTAATCAAAGAAGTATTGCTACAACGGTTAATTTGCGT

GATGGACAGACTCTTTTACTCGGTGGCCTCACTGATTATAAAACACTTCT

CAGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGTC

AAAGCAACCATAGTACGCGCCCTGTAGCGGCGCATTAAGCGCGGCGGGTGT

GGTGGTTACGCGCAGCGTGACCGCTACACTTGCCAGCGCCCTAGCGCCCGC

TCCTTTCGCTTTCTTCCCTTCCTTTCTCGCCACGTTCGCCGGCTTTCCCCG

-continued
TCAAGCTCTAAATCGGGGGCTCCCTTTAGGGTTCCGATTTAGTGCTTTACG

GCACCTCGACCCCAAAAAACTTGATTTGGGTGATGGTTCACGTAGTGGGCC

ATCGCCC
```

Peptoid Synthesis and Purification.

Peptoids were synthesized by solid phase peptoid synthesis on the Symphony X (Gyros Protein Technologies) and the synthesis procedure followed the method previously described (1). All solvents and reagents were purchased from commercial sources and used without further purification. Briefly, 200 mg of Rink amide polystyrene resin (0.61 mmol/g, Novabiochem) was swelled in DMF and the Fmoc group was deprotected in 20% (v/v) 4-methylpiperidine/DMF prior to the submonomer cycle. The acylation step was performed on the amino resin by the addition of 1.0 mL of 0.8 M bromoacetic acid and 1.0 mL of 0.8 M N,N'-diisopropylcarbodiimide in DMF and agitated with N2 for 20 min. Displacement of the bromide with the submonomers was performed by adding 1 M solution of the primary amine in N-methyl-2-pyrrolidone followed by agitation for 30 min. The peptoids were cleaved from the resin by the addition of trifluoroacetic acid/triisopropylsilane/deionized water (95:2.5:2.5, v/v/v) solution for ~2 h, followed by evaporation using the Biotage V10 Evapoator and precipitation with an excess of cold diethyl ether. The crude peptoids were re-dispersed in deionized water followed by lyophilization. Finally, the peptoids were purified by reverse-phase high-performance liquid chromatography (HPLC, Shimadzu) using a linear gradient of 5-95% acetonitrile in water with 0.1% TFA. The Phenomenex C18 Gemini NX column was 150×21.2 mm and had a 5 m pore size and 100 Å particle size.

Preparation of peptoid-coated OCs. The synthesized peptoids were dissolved in deionized water at a concentration of 10 mM and stored at 4° C. For all experiments, peptoids at different concentrations based on the target ratios between the free peptoid amine and DNA phosphate (N/P) were mixed with OCs (5-45 nM) and incubated overnight (≥12 h) at 4° C. in TAE (1×) buffer.

The buffer is TAE (1×) buffer composed of 40 mM tris base, 20 mM acetic acid and 1 mM of ethylenediaminetetraacetic acid (EDTA) sodium salt dihydrate, and containing 12.5 mM magnesium chloride.

Negative-stained TEM imaging. The peptoid-coated OC structures were typically confirmed using negative-stained TEM imaging. In brief, 5 L of the peptoid-coated OC (5-10 nM) solution was dropped on a carbon film for 1-3 min and the residual liquid was removed with a piece of filter paper. After that, the grid was washed with 5 L of deionized water followed by staining with 5 L of 2 wt % uranyl acetate for 15 sec. The excess liquid was removed with filter papers. TEM imaging was performed on a JEOL 1400 TEM with an acceleration voltage of 120 kV.

Agarose Gel Electrophoresis (AGE).

In a typical experiment, agarose (0.8 wt %) was prepared in TBE (1×) buffer containing 12.5 mM $MgCl_2$ and 1×SYBR Gold dye. OCs (4.3 nM, ~40 L) were mixed with 1× BlueJuice gel loading buffer (Thermo Fisher Scientific) prior to loading into the gel. The gel electrophoresis was performed at 60 V on ice to prevent heating damage.

SYBR Green I (SG) fluorescence assay of OCs. OCs (1 nM) were mixed with peptoids in PBS (1×) buffer at an N/P of 0.125 and incubated overnight at room temperature. Prior to measuring fluorescence, 0.8×SG was added to the peptoid-coated OC solutions for 2 h at room temperature. The fluorescence signal was recorded from 37° C. to 85° C. at a step of 0.03° C./sec by LightCycler 480 (Roche).

SYBR Green I (SG) Fluorescence of Duplex DNA (dsDNA).

A15-bp dsDNA was designed with a sequence of 5'-ATTACCGTATAGCAT-3' (SEQ ID NO: 124) with a complementary sequence of 5'-ATGCTATACGGTAAT-3' (SEQ ID NO: 125). The dsDNA (500 μM) was formed in PBS (1×) buffer and cooled from 70° C. to room temperature over 11 h. Next, the dsDNA (100 nM) solution was mixed with different peptoid solutions at varied concentrations in PBS overnight at room temperature. Prior to measuring fluorescence, SG (1×) was added to the dsDNA/peptoid mixtures for 2 h at room temperature. The fluorescence signal was recorded from 37° C. to 85° C. at a step of 0.03° C./sec by LightCycler 480. The concentrations of only peptoids in solution were the same as those in the N/P of 8, which were 3.43 μM for PE1, PE3, PE4, PE5, and 1.85 μM for PE2, respectively.

Molecular dynamics (MD) simulation of peptoid-DNA interactions.

All-atom MD simulations were performed to investigate the mechanisms of interactions and binding of brush-type PE1 and block-type PE4 peptoids with DNA in explicit solvent. The 15-bp dsDNA (5'-ATT ACC GTA TAG CAT-3') (SEQ ID NO: 126) structure was generated using the nab program available through AMBER18 (2). The peptoids were build using the Dassault Systemes BIOVIA Materials Studio package (3), and their atomic charges were calculated with B3LYP/6-31G* level of theory using the RESP procedure (4) and Gaussian16 (5). The force field parameters for the peptoids, except the atomic charges, were generated using antechamber (6) and gaff (7). The ParmBSC1 force field (8) was employed to model the dsDNA. The molecular structures of the dsDNA, PE1 and PE4 peptoids are shown in FIG. 19. Each peptoid was placed in a triclinic simulation cell ~11 Å away from the pre-equilibrated dsDNA structure to avoid any initial interactions. To solvate the systems, explicit water (TIP3P) molecules were added to the simulation cell to a corresponding water density of ~1.0 g/cm$^3$. Counter-ions (Na$^+$) were included to neutralize the net negative charge of the system, and 150 mM NaCl to represent physiological environment.

All simulations were performed using the GROMACS simulations package (9). Particle mesh Ewald (PME) (10) electrostatic summation was truncated at 11 Å, while a force-switched cut-off starting at 9 Å and ending at 10 Å was used for the Lennard-Jones non-bonded interactions. Cubic interpolation was used with 10 Å Fourier spacing and an Ewald tolerance of 10$^{-6}$. The MD simulations were performed in the NPT (isothermal-isobaric) ensemble. The temperature of the system was coupled at 300 K using the Nosè-Hoover thermostat (11) and pressure was maintained at 1 bar using the Parinello-Rahman barostat (12). An integration time-step of 2 fs was applied with all hydrogen bond lengths constrained using the LINCS algorithm (13). Each system was energy minimized using the steepest descent approach with a convergence criteria of 500 kJ mol$^{-1}$ nm$^{-1}$ to remove any steric clashes. Following the energy minimization, a 200 ps of MD simulation was performed with position restraints applied to the solute to allow the solvent to equilibrate. Initial unrestrained MD simulations were performed on the dsDNA for 50 ns to equilibrate its structure. A peptoid was then added to the simulation box sufficiently apart to prevent any initial interactions with the dsDNA. To further emulate spontaneous DNA-peptoid binding and explore wider conformational space four different starting arrangements were simulated, where the peptoid was positioned at 0°, 90°, 180°, and 270° relative to the dsDNA. A 100 ns unrestrained MD was conducted for each peptoid arrangement where the peptoid was allowed to spontaneously adsorb onto the DNA from solution. The simulation trajectories from all four starting arrangements per dsDNA/peptoid complex were concatenated for further analysis. A total of 800 ns of simulation data was collected.

The different modes of interaction between the peptoids and dsDNA were investigated using contact analysis. The total time each peptoid was in contact with the dsDNA was determined, and these frames were extracted for further analysis. A contact was defined when any peptoid atom was within 4 Å of any DNA atom. The number of positively charged (Nae) residues and ethylene glycol (Nte) chains interacting with DNA and their contact stabilities was calculated. The preference of binding to specific structural features of DNA was also determined by calculating the total time each peptoid was interacting exclusively with the major or minor groove, or with both simultaneously (atomic definition for the DNA grooves is provided in the caption of Table S1). The average contact area between each peptoid and DNA was also determined. The average solvent accessible surface area of each peptoid while bound to dsDNA was calculated using a probe radius of 1.4 Å (water) and Lennard-Jones hard-shell radii for each atom to define the surface of the peptoid. The elongation or compactness of the peptoid was estimated by measuring the average distance between the outermost nitrogen atoms of the peptoid backbone. Visualization of the trajectories and analysis was performed using the VMD software (14).

TABLE S1

Peptoid-DNA interaction characterization and properties.

| Properties | PE1 | PE4 |
|---|---|---|
| $^a$Persistent Contact (%) | 98.2% | 98.7% |
| $^b$Minor/Major groove interactions | | |
| $^c$Minor Groove Contacts (%) | 28.5% | 24.0% |
| $^d$Major Groove Contacts (%) | 6.1% | 39.6% |
| Major and Minor Groove Contacts (%) | 48.8% | 18.5% |
| $^b$Nte/Nae residue interaction time | | |
| Nte Contact (%) | 98.01% | 70.39% |
| Nte (1 residue) | 12.55% | 30.45% |
| Nte (2 residues) | 74.75% | 24.94% |
| Nte (3 residues) | 31.79% | 11.82% |
| Nte (4 residues) | 20.19% | 2.90% |
| Nte (5 residues) | 8.07% | 0.28% |
| Nte (6 residues) | 0.67% | 0.00% |
| Nae Contact Time (%) | 98.08% | 99.90% |
| Nae (1 residue) | 14.79% | 0.66% |
| Nae (2 residues) | 25.53% | 3.87% |
| Nae (3 residues) | 31.53% | 12.74% |
| Nae (4 residues) | 19.87% | 28.43% |
| Nae (5 residues) | 6.45% | 35.86% |
| Nae (6 residues) | 0.41% | 18.33% |
| Average contact area (nm$^2$) | 2.88 ± 1.11 | 2.54 ± 1.05 |
| Peptoid solvent accessible surface area (nm$^2$) | 18.82 ± 1.47 | 17.81 ± 1.64 |
| Average separation distance of outermost nitrogens $d_{N2-N19}$ (nm) | 2.33 ± 0.6 | 2.20 ± 0.6 |

Magnesium depletion assays.

Bare OCs and peptoid-coated OCs were diluted in TAE (1×) buffer, PBS (1×) buffer, Roswell Park Memorial Institute 1640 medium (RPMI, Thermo Fisher Scientific) and the Dulbecco's Modified Eagle Medium (DMEM, Gibco) such that the final concentrations of origami and MgCl$_2$ were 4.3 nM and 1.25 mM, respectively. The samples were incubated at 4° C. (TAE and PBS) or 37° C. (RPMI and DMEM) for 24 h and characterized by AGE and negative-stained TEM imaging. In all figures of AGE analyses, label "+" represents the final $MgCl_2$ concentration of 12.5 mM; label "−" represents depleted $Mg^{2+}$ and the final $MgCl_2$ concentration was 1.25 mM. To prepare samples for TEM imaging, OCs were extracted from the agarose gels using the Freeze 'N Squeeze™ DNA Gel Extraction Spin Columns (Bio Rad) and centrifuged at 1000 rcf for 3 min at room temperature.

Figure 4A:
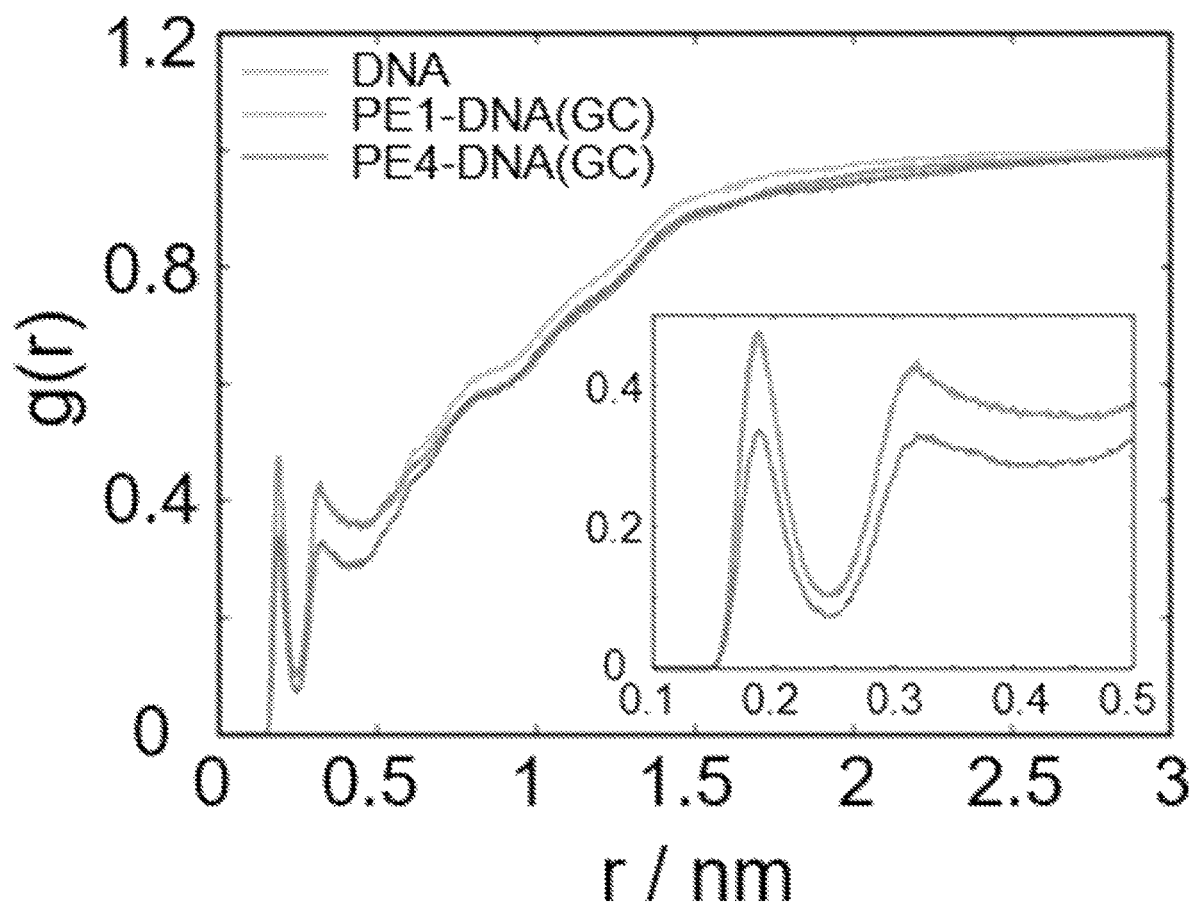
FIG. 4. Analysis of peptoid-coated OCs in low $Mg^{2+}$ solution. (A) Schematic view showing peptoid-coated OCs (OC/peptoid) was protected against $Mg^{2+}$ depletion. (B, C) Agarose gel electrophoresis (AGE) was used to analyze the structural integrity of OCs in TAE buffer at $MgCl_2$ concentrations of 12.5 mM (+) and 1.25 mM (−). In (c), the electrophoretic shift was measured from the reference band at 0.5 kb and the relative value was calculated from that of the control OCs (n=3). (D) TEM imaging was performed on OCs extracted from the agarose gels (bands a and b in B). Scale bars: 200 nm. The insets show magnified images of the OC structures (scale bars: 100 nm). (E) Dynamic light scattering (DLS) and (F) in situ small angle X-ray scattering (SAXS) spectra show bare OCs and OC/PE2 treated with EDTA (5 or 10 mM) for 20-30 min at room temperature.
Figure 4B:
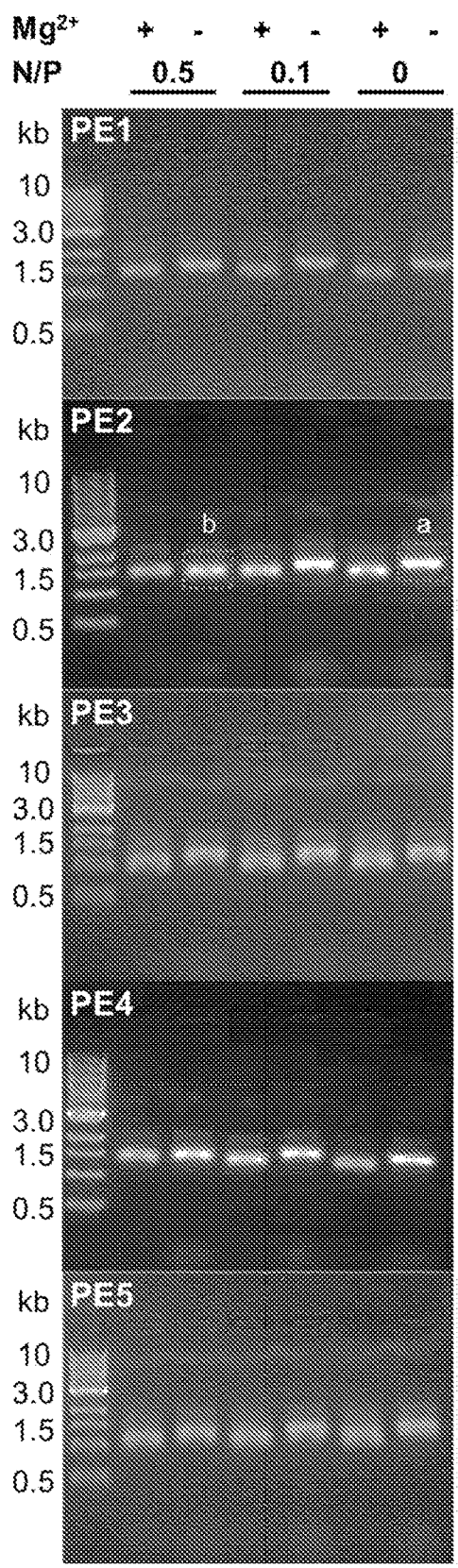
Figure 4C:
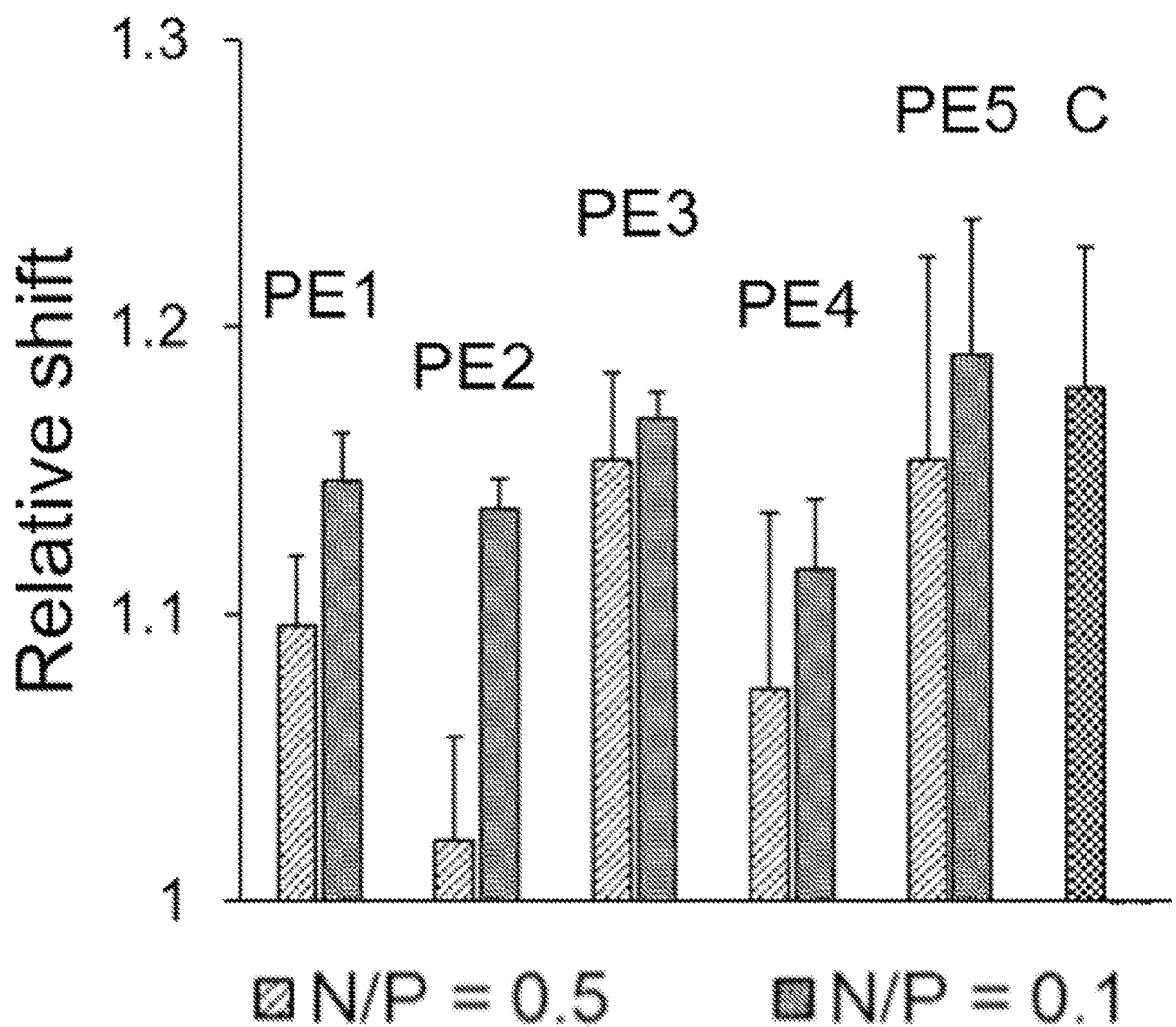
Figure 4D:
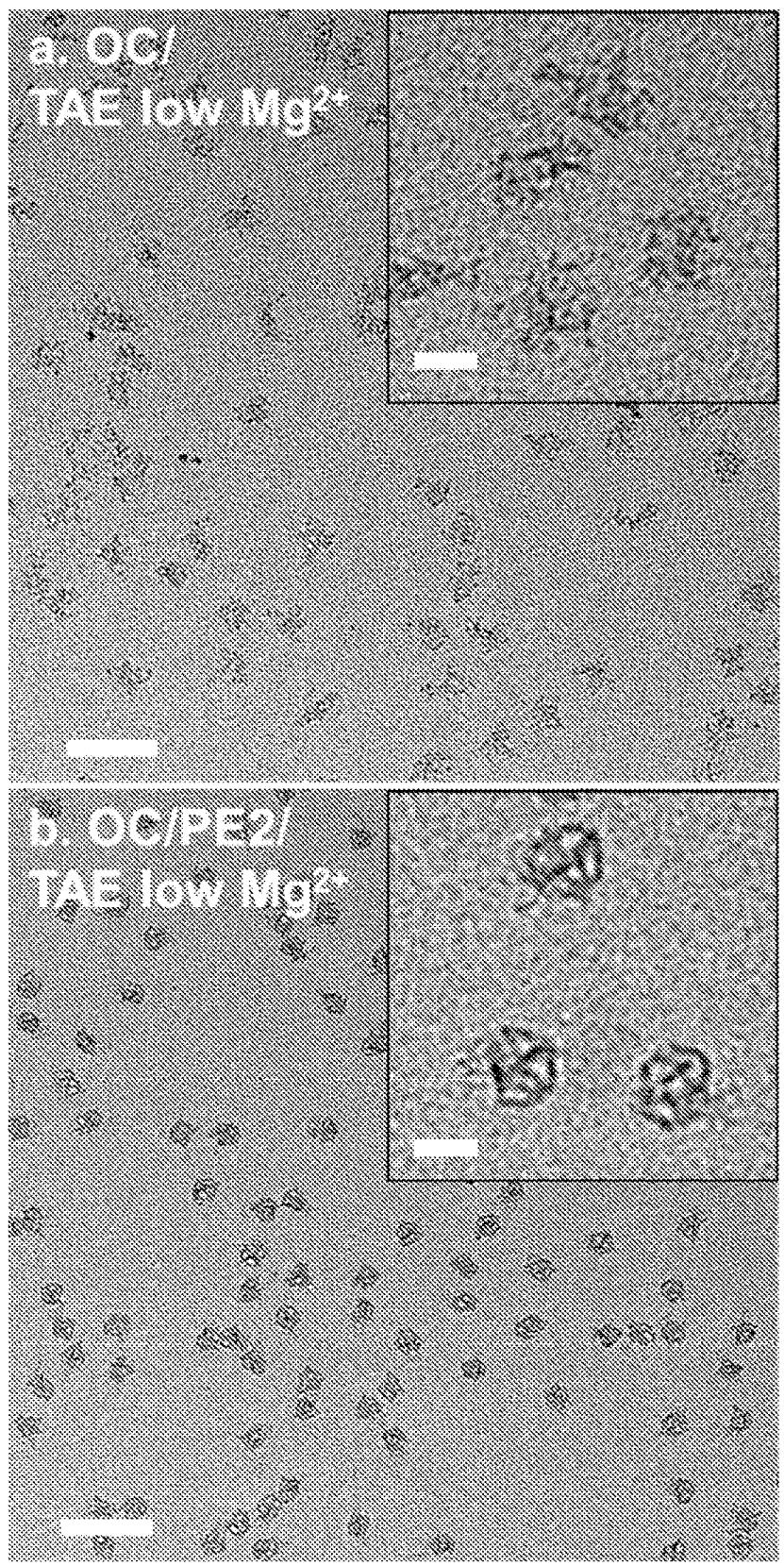
Figure 4E:
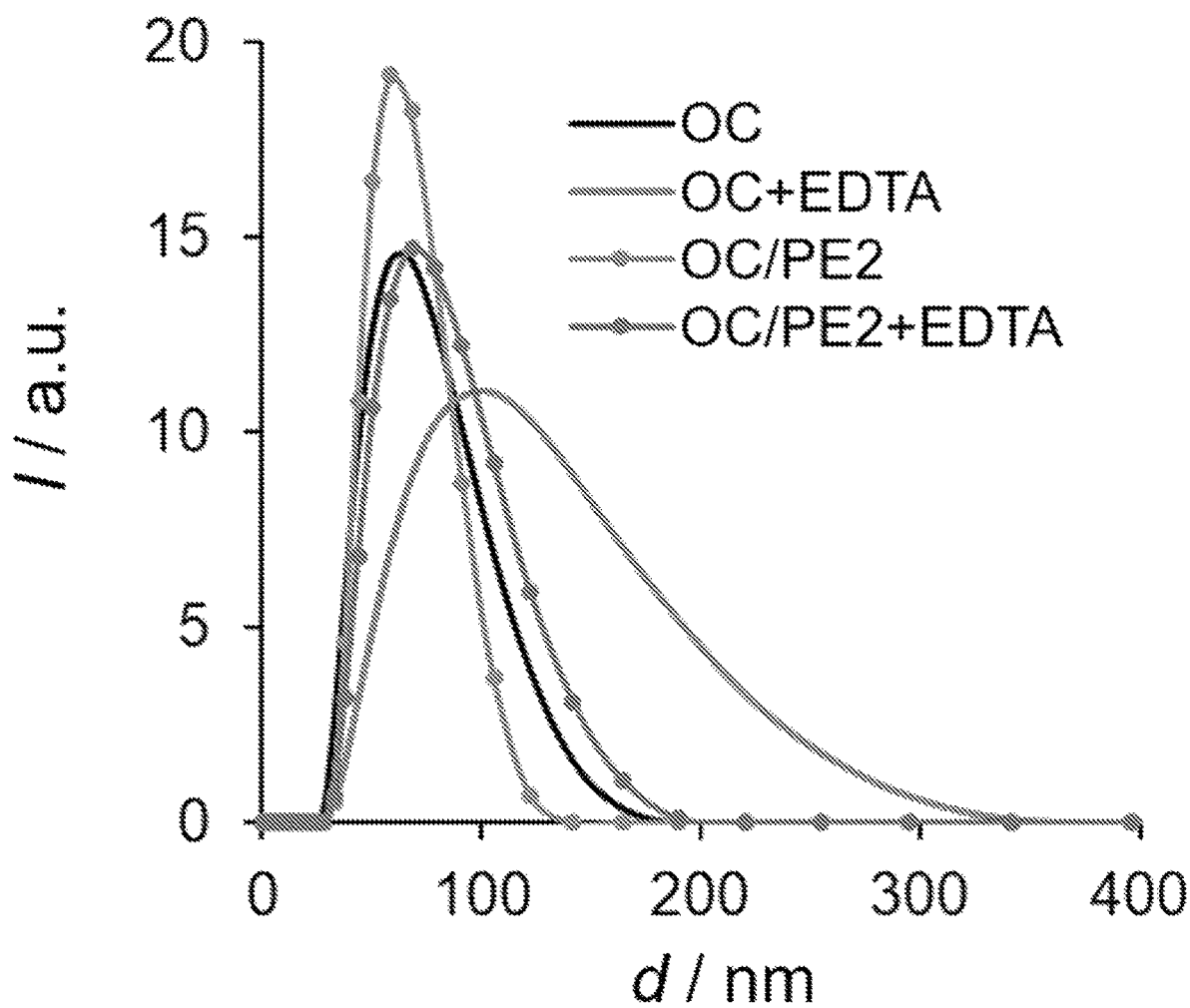
Figure 35A:
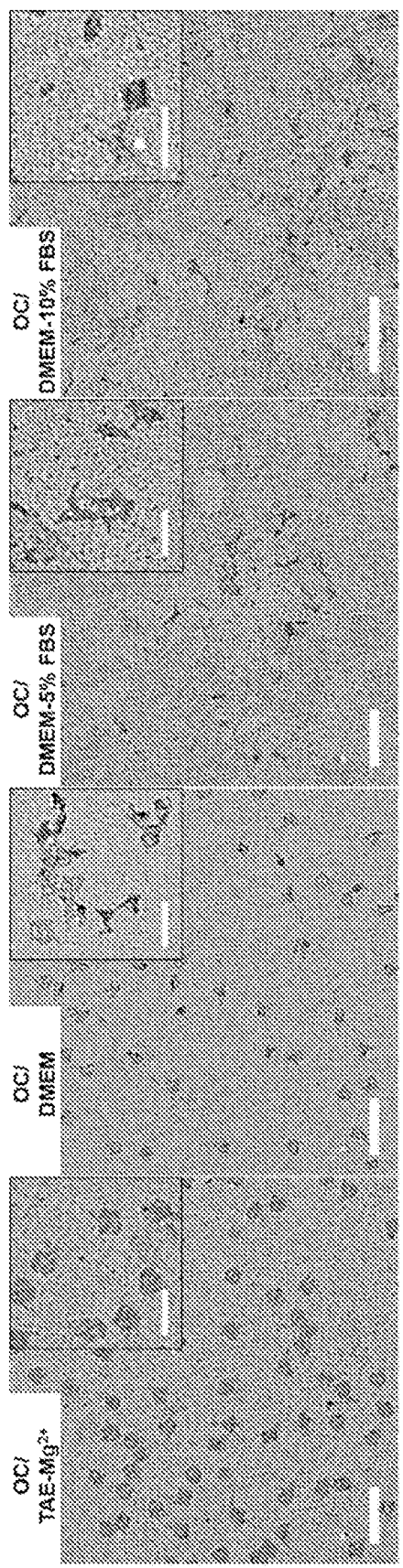
FIG. 35 Negative-stained TEM images of (A) bare OCs and (B) PE2-coated OCs in DMEM cell media containing FBS (0%, 5%, and 10%). The final concentration of $MgCl_2$ was 1.25 mM. TEM samples were extracted from the agarose gels (scale bars: 200 nm). The insets show the magnified images of the OC structures (scale bars: 100 nm).
Figure 35B:
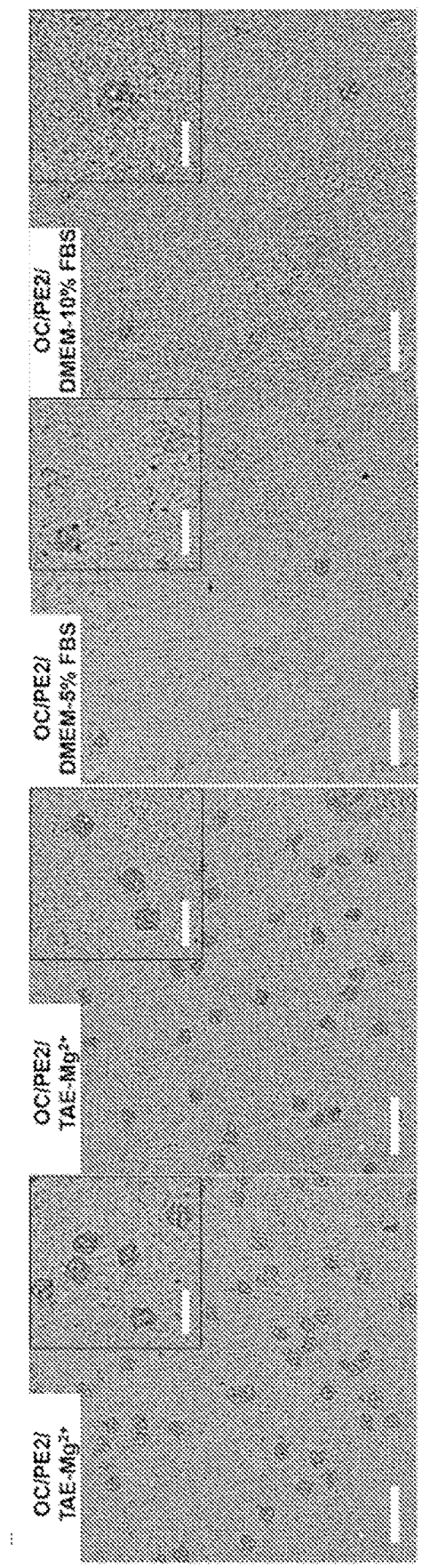

Dynamic light scattering (DLS). In FIG. 4E, bare (4 nM) and PE2-coated OCs (4 nM, N/P: 0.5) in TAE (1×) buffer containing 12.5 mM $MgCl_2$ were incubated with EDTA (10 mM) for ~30 min prior to DLS measurement. In FIG. 35, bare (4 nM) and PE2-coated OC solutions (4 nM, N/P: 0.5) were incubated with DN of 15 and 20 µg/mL at 37° C. for 30 min prior to measurement. The concentration of $MgCl_2$ in the TAE buffer was 12.5 mM. The samples were measured 3 times with Zetasizer Nano Z (Malvern Panalytical) with an equilibrium time of 120 sec. Small-angle X-ray scattering (SAXS). Solution Scattering data was collected at the Life Sciences X-ray Scattering beamline (LiX) at NSLSII, Brookhaven National Laboratory, Upton, N.Y. LiX utilizes an undulator source and a Si(111) monochromator. KB mirrors focus the beam on a secondary source and X-ray energy was 12 keV with a beamsize of ~400 um. An in-house solution scattering box houses a movable 3 channel flow cell such that proteins in solution flow through the beam during collection. Data is collected on 3 Pilatus detectors (SAXS: Pilatus 1M, 2 offset WAXS detectors: Pilatus 300K) https://doi.org/10.1063/1.4952872. The data was merged, averaged, subtracted and packed into HDF5 format using our in-house py4xs software https://doi.org/10.1107/S0909049512048984, with data visualization in jupyter notebook. Bare (28 nM) and PE2-coated OCs (28 nM, N/P: 0.5) in TAE (1×) buffer containing 12.5 mM $MgCl_2$ were mixed with EDTA (10 mM) and immediately loaded to the SAXS flow cell. The total processing time prior to measurement is ~20-30 min. For each sample exposed to the X-ray beam, five frames, with an exposure time of 1 sec was collected and processed using the py4xs software. TAE (1×) buffer containing 12.5 mM $MgCl_2$ was used as reference and was subtracted from the samples.

Nuclease degradation assays.

Bare OCs (4.3 nM) and peptoid-coated OCs (4.3 nM, N/P: 0.5) were mixed with different concentrations of deoxyribonuclease I (DN) in TAE (1×) buffer containing 12.5 mM $MgCl_2$. The samples were incubated at 37° C. for 30 min at 650 rpm on a thermal cycler (Eppendorf) and characterized using AGE and negative-stained TEM imaging.

Encapsulation of 10 nm gold nanoparticles (Au NPs) in OCs.

(1) Peptide Synthesis.

Solid-phase peptide synthesis was performed to synthesize the azido peptide (CALDDK(N3)) for Au NP functionalization. Briefly, Rink Amide resins and the protected amino acids were added to the growing peptide chain with the activating reagent 2-(1H-benzotriazol-1-yl)-1,1,3,3-tetramethyluronium hexafluorophosphate (HBTU). Following addition of the submonomers, the Fmoc group was removed under 20% piperidine in DMF deprotection conditions. The peptides were cleaved by trifluoroacetic acid/triisopropylsilane/deionized water (95:2.5:2.5, v/v/v). The crude peptide was precipitated by cold ether several times and lyophilized. The as-synthesized peptides were purified by reverse-phase high-performance liquid chromatography (HPLC, Shimadzu). The Phenomenex C18 Gemini NX column was 150×21.2 mm and had a 5 m pore size and 100 Å particle size.

(2) Au NP Functionalization.

First, 990 L of 10 nm Au NPs (9.5 nM, BBI solutions) were mixed with 10 L of peptide CALDDK(N3) (pep, 1 mM) overnight at room temperature (~12 h). The solution was washed 3 times with 10 mM phosphate buffer (pH 7.4) by centrifugation at 10,000 rcf and at 4° C. Next, DBCO-modified single-stranded DNA (ssDNA, 5'-TATGAAGT-GATGGATGAT/3DBCO/)) (SEQ ID NO: 1) was added to the Au NP-pep solution at concentration ratio of 300:1 in 10 mM phosphate buffer (pH 7.4) and incubated at least 4 h at room temperature. A final concentration of 100 mM of NaCl was added to the Au NP-solution and left incubating overnight. The solution was washed 3 times with 10 mM phosphate (pH 7.4) containing 100 mM NaCl by centrifugation at 10,000 rcf and at 4° C. UV-vis spectroscopy (Lambda 25, PerkinElmer) was used to calculate the final Au NP-pep-ssDNA concentration.

(3) Au NP-pep-ssDNA Encapsulation in OCs.

OCs (40 nM) were mixed with the Au NP-pep-ssDNA (48 nM) and cooled from 50° C. to room temperature over a time course of 40 h.

Doxorubicin (Dox) release from bare OCs and peptoid-coated OCs. OCs (10 nM) were incubated with doxorubicin (Dox, 0.1 mM) at room temperature for 24 h and purified 3 times with TAE (1×) buffer containing 12.5 mM $MgCl_2$ using a 100 kDa filter and centrifuged at 400 rcf and at 15° C. OCs were concentrated to 50 nM in the final centrifugation. PE2-coated OCs were prepared by mixing PE2 (27.7 µM) with Dox-loaded OCs (50 nM) overnight (~12 h) at room temperature. Dox-loaded bare and PE2-coated OCs were diluted in PBS (1×) at pH 7 or 5.5 and incubated at 37° C. for 48 h, followed by centrifugation with 50 kDa filters at 1000 rcf for 30 min at room temperature, of which the supernatant solution was collected. Fluorescence spectra were measured in a 384 well plate (Corning) using the Spark microplate reader (Tecan). The $\lambda_{ex}$ and $\lambda_{em}$ were 485 nm and 515-800 nm, respectively with a step size of 2 nm.

Encapsulation of fluorescein-modified bovine serum albumin (BSA) in OCs.

First, NHS-fluorescein (240 µM) and NHS-PEG-azide (60 µM) was mixed with BSA (10 µM) in PBS (1×) buffer for 3 h at room temperature. The solution was purified 8 times with PBS using a 50 kDa filter and centrifuged at 3000 rcf and at 4° C. Next, the DBCO-modified single-stranded DNA (ssHy, 5'-TATGAAGTGATGGATGAT/3DBCO/, 250 µM) (SEQ ID NO: 1) was mixed with the BSA solution (10 µM) overnight (~12 h) at 4° C. The solution was purified 8 times with PBS using a 50 kDa filter and centrifuged at 3000 rcf at 4° C. Finally, the surface-modified BSA (200 nM) was added to the OCs (40 nM) and the solution was cooled down from 45° C. to room temperature over a time course of 60 h. The solution was purified 2 times with TAE (1×) buffer containing 12.5 mM $MgCl_2$ using a 100 kDa filter and centrifuged at 400 rcf and at 4° C.

Fluorescence Assay for Tryptic Digestion of BSA.

(1) The fluorescein-modified BSA (80 nM) solution without OCs was incubated at 37° C. in the presence or absence of trypsin (50 nM) overnight ~12 h prior to fluorescence measurement. Fluorescence spectra were measured with excitation and emission wavelengths of 490 nm and 510-750 nm, respectively and a step size of 2 nm. (2) The fluorescein-modified BSA encapsulated OCs (20 nM) were incubated at 37° C. in the presence or absence of trypsin (50 nM) in a 384 well plate. The fluorescence kinetics were measured at $\lambda_{ex}$ and $\lambda_{em}$ of 490 nm and 525 nm, respectively and time interval of 3 min. Fluorescence spectra were measured after 15 h at excitation and emission wavelengths of 490 nm and 510-800 nm, respectively and a step size of 2 nm. TAE (1×) buffer containing 12.5 mM $MgCl_2$ was used for both experiments.

Surface conjugation of peptoid-protected OCs with azide fluor 488.

Alkyne-modified peptoids (PE8 and PE9, 20 µM) were mixed with azide fluor 488 (60 µM), 0.1 mM $CuSO_4$, 0.5 mM THPTA, 5 mM aminoguanidine and 5 mM sodium ascorbate in 100 mM sodium phosphate buffer (pH=7.4) for 2 h at room temperature. The peptoid-fluorophore (PE8-FL and PE9-FL) conjugates were dialyzed against deionized water with 0.2 mM EDTA for 12 h at room temperature using a 3,500 Da membrane, followed by dialysis against deionized water for 24 h at room temperature.

Synthesis of Trastuzumab-azide.

Trastuzumab expressed with two heavy chain C-terminal formylglycine residues (SMARTag antibody CT) was a gift from David Rabuka (Catalent) (15). A small molecule azide linker with a hydrazino moiety was synthesized in 9 steps as described previously (16, 17). The trastuzumab-aldehyde was reacted with the azide via the hydrazino-iso-Pictet Spengler ligation as described previously (17). Briefly, trastuzumab with C-terminal heavy-chain formylglycine residues was buffer exchanged via PD-10 column (GE Life Sciences, 17085101) into 50 mM sodium citrate (Millipore Sigma C8532). To trastuzumab fGly (182.7 nmol, 2.19 mL, 1 equiv.) in sodium citrate buffer was added the azide molecule (4 µmol, 135 µL, 21.9 equiv.) freshly dissolved in DMSO in a falcon tube. The falcon tube was closed after flushing with argon gas, and the reaction was mixed 250 rpm in the dark at 37° C. for 22 h. Following this, the reaction was buffer exchanged via PD-10 desalting columns into PBS (Corning, 21-040-CM), with ~90% recovery.

Trastuzumab-azide was analyzed by mass spectrometry to confirm the azide addition, with no detected unmodified trastuzumab-azide remaining. Trastuzumab-azide (20 L in PBS was treated with 0.75 L PNGaseF (NEB, P0704S) at 37° C. overnight in an eppendorf tube. After 16 h, the DTT was added (30 mM, 0.6 L from frozen stock solution in water) (Thermo Fisher Scientific, 15508013), and the antibody was heated at 65° C. for 5 min using a Thermomixer. Antibody was placed on ice and analyzed in the same day at the SUMS facility at Stanford University by ESI-LC/MS on an Agilent 1260 HPLC and Bruker MicroTOF-Q II time-of-flight mass spectrometer. A Waters BioResolve RP mAb Polyphenyl 450 Å 2.7 m 100×2.1 mm column was maintained at 50° C. Five microliters of reduced, de-glycosylated antibody conjugate were injected at a flow rate of 0.3 mL/min at 95% solvent A (0.05% trifluoroacetic acid in water) and 5% solvent B (0.1% formic acid in acetonitrile). This was held for 1.5 min, then ramped to 35% B at 2 min, 46% B at 10 min, and 95% B at 11 min, which was held for 1 min. Data was collected in full scan MS mode with a mass range of 400-4000 Da and Collision RF setting equal to 800 V.

Surface conjugation of peptoid-protected OCs with Trastuzumab.

Alkyne-modified peptoids (PE8 and PE9, 30 µM) were mixed with azide-modified Trastuzumab (10 µM), 0.1 mM $CuSO_4$, 0.5 mM THPTA, 5 mM aminoguanidine and 5 mM sodium ascorbate in 100 mM sodium phosphate buffer (pH=7.4) for 2 h at room temperature. The peptoid-Trastuzumab (PE8-Tz and PE9-Tz) conjugates were dialyzed against PBS (1×) buffer with 0.2 mM EDTA for 12 h at 4° C. using a 100-500 Da membrane for 2 times, followed by dialysis against PBS (1×) buffer for 24 h at 4° C.

Results and Discussion

Two types of polycationic peptoids were designed to protect DNA origamis by multivalent peptoid-DNA interactions and compact surface coating (FIGS. 1A and 13). In the brush-type peptoids (PE1-3), positively charged (2-aminoethyl)glycine (Nae) and neutrally charged N-2-(2-(2-methoxyethoxy)ethoxy)ethylglycine (Nte) moieties were assembled alternately. In the block-type peptoids (PE4-5), Nae and Nte clustered together to form a peptoid having positively-charged submonomers clustered at the N-terminus and neutrally charged submonomers clustered at the C-terminus.

These polycationic peptoids are proposed to electrostatically bind to the anionic phosphate backbone of the DNA and compensate charge repulsions between DNA strands. In addition, incorporation of neutral oligo-Nte is expected to prevent aggregation of the DNA origami structures. The anti-fouling oligo-Nte can also prevent adsorption of biomolecules in physiological environments (51, 52) and enzymatic degradation of DNA origamis triggered by protease and nuclease.

In this disclosure, the interactions between a duplex DNA and peptoids were first studied by comprehensive spectroscopic approach and molecular dynamics simulations. The enhanced stability of 3D octahedra-shaped DNA origamis (OCs) was then investigated by surface coating with peptoids in physiological solutions, including the depletion of magnesium ions, the presence of nuclease and the addition of cell culture media. The effect of different peptoid structures on OC protection was discussed. Next, the functionality of peptoid-stabilized OCs was explored, where controlled release of anti-cancer drug and tryptic digestion of proteins encapsulated in OC nanostructures were examined. Finally, alkyne modified peptoids were used to conjugate functional biomolecules and present them on the surface of peptoid-coated OCs.

Figure 2A:
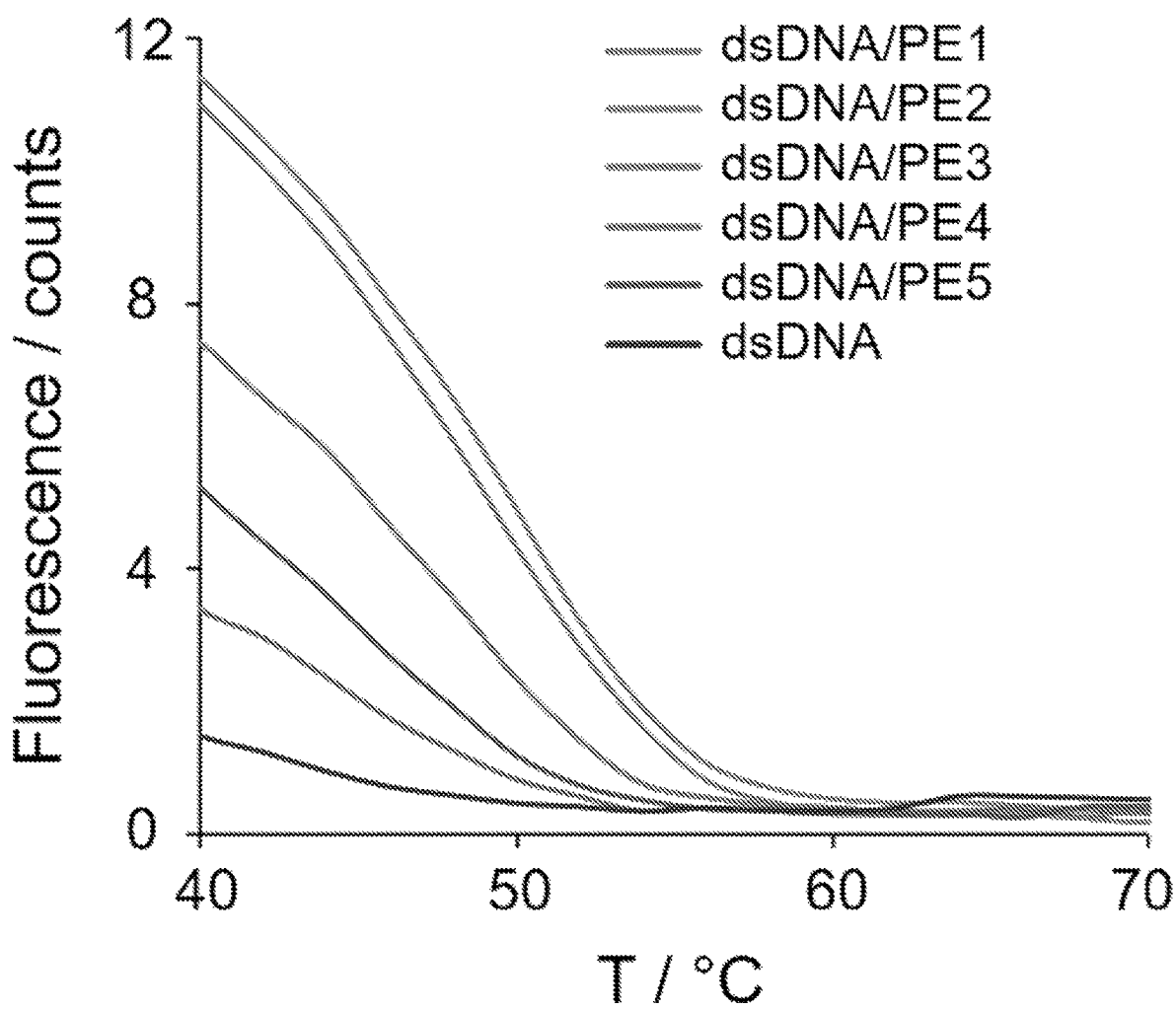
FIG. 2. Fluorescence assay monitoring peptoid-stabilized duplex DNA (dsDNA). Real-time SYBR Green I (SG) fluorescence assay of a 15-bp dsDNA (500 μM) in the presence of peptoids at different ratios of peptoid amines to phosphate groups of the DNA (N/P). The fluorescence signals of (A) dsDNA/peptoid complexes at N/P of 4 and (B) dsDNA/PE2 complexes at different N/P are plotted against the increasing temperature.
Figure 2B:
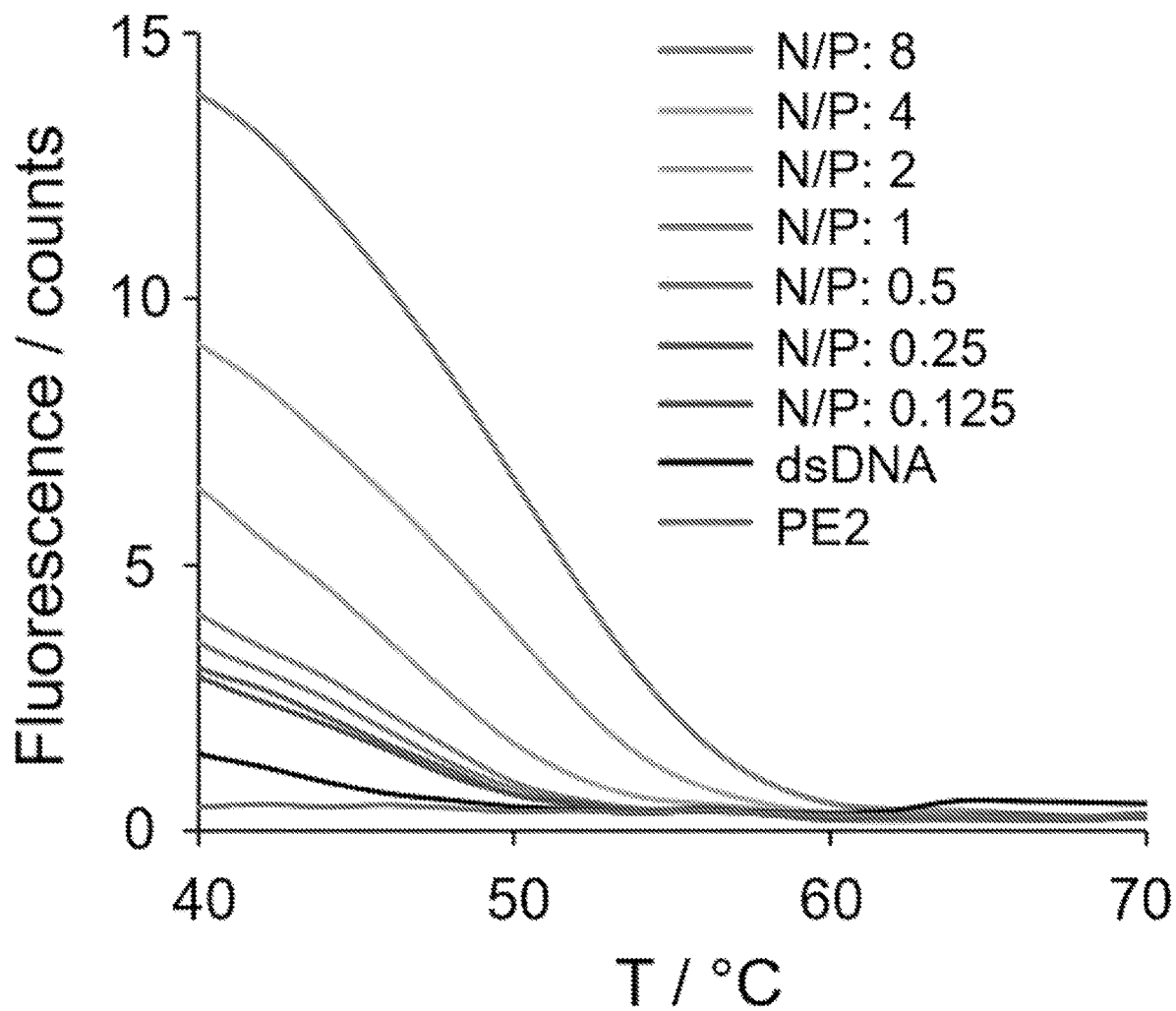
Figure 3A:
FIG. 3 Molecular dynamics (MD) simulations of the interactions of PE1 and PE4 with dsDNA. Molecular representation of the most visited binding sites and structures of (A) PE1 and (B) PE4 with dsDNA. The most visited binding sites represented as occupancy volume areas (shown as transparent white) where the peptoids were present for at least 6% of total contact time. (C-F) Radial distribution functions (RDF) of water near the (C, D) minor and (E, F) major grooves of the dsDNA. RDFs were calculated on the H (donor) atoms of water and the N and O (acceptor) atoms of (C, E) AT and (D, F) GC base-pairs. The structuring of water around DNA only is shown in FIG. 3C-F, lines labeled DNA, while for the dsDNA/PE1 and dsDNA/PE4 complexes are shown in FIG. 3C-F, lines labeled PE1-DNA and PE4-DNA, where the AT and GC base-pairs are distinguished by light and dark colors respectively.
Figure 3B:
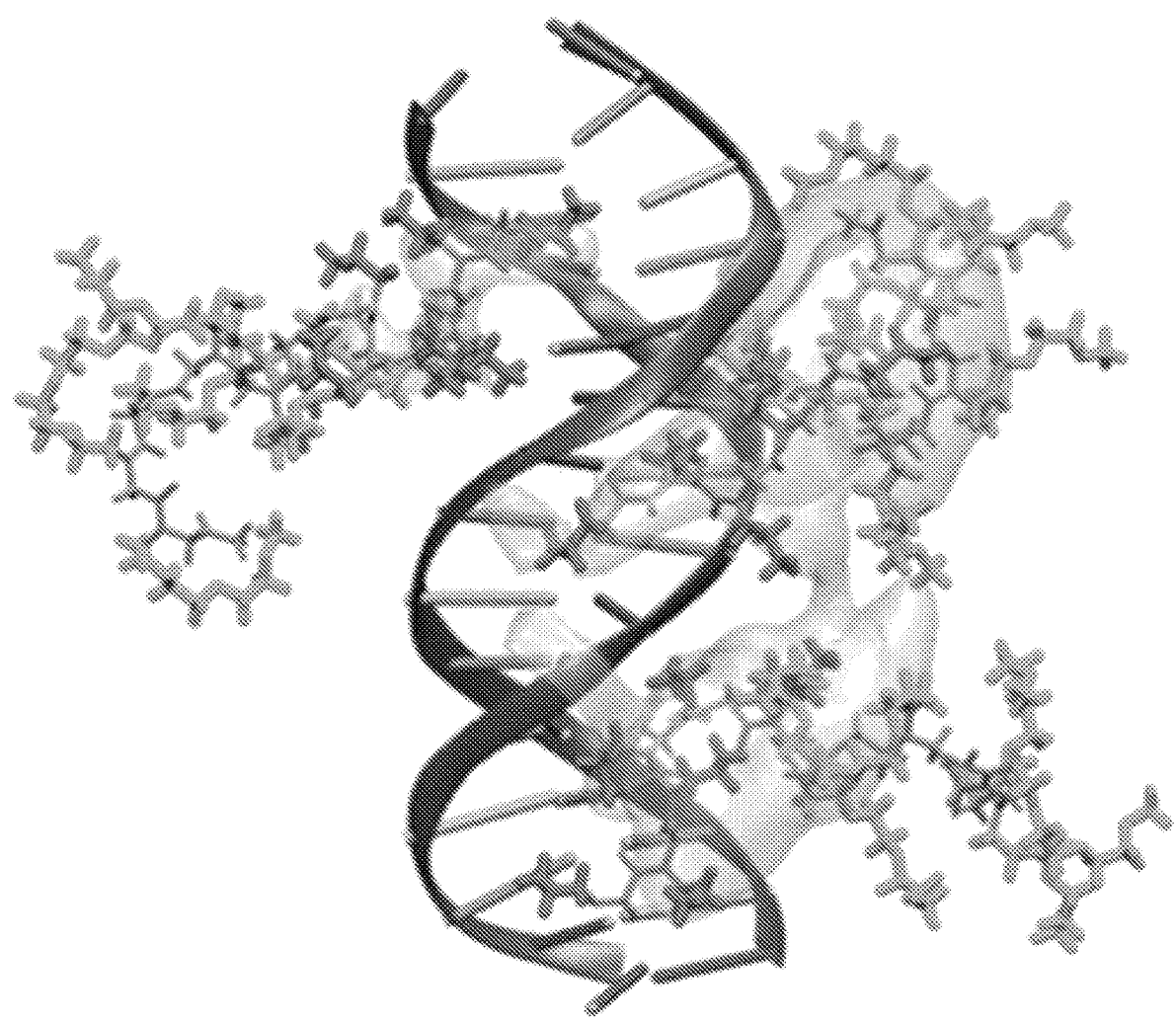
Figure 3C:
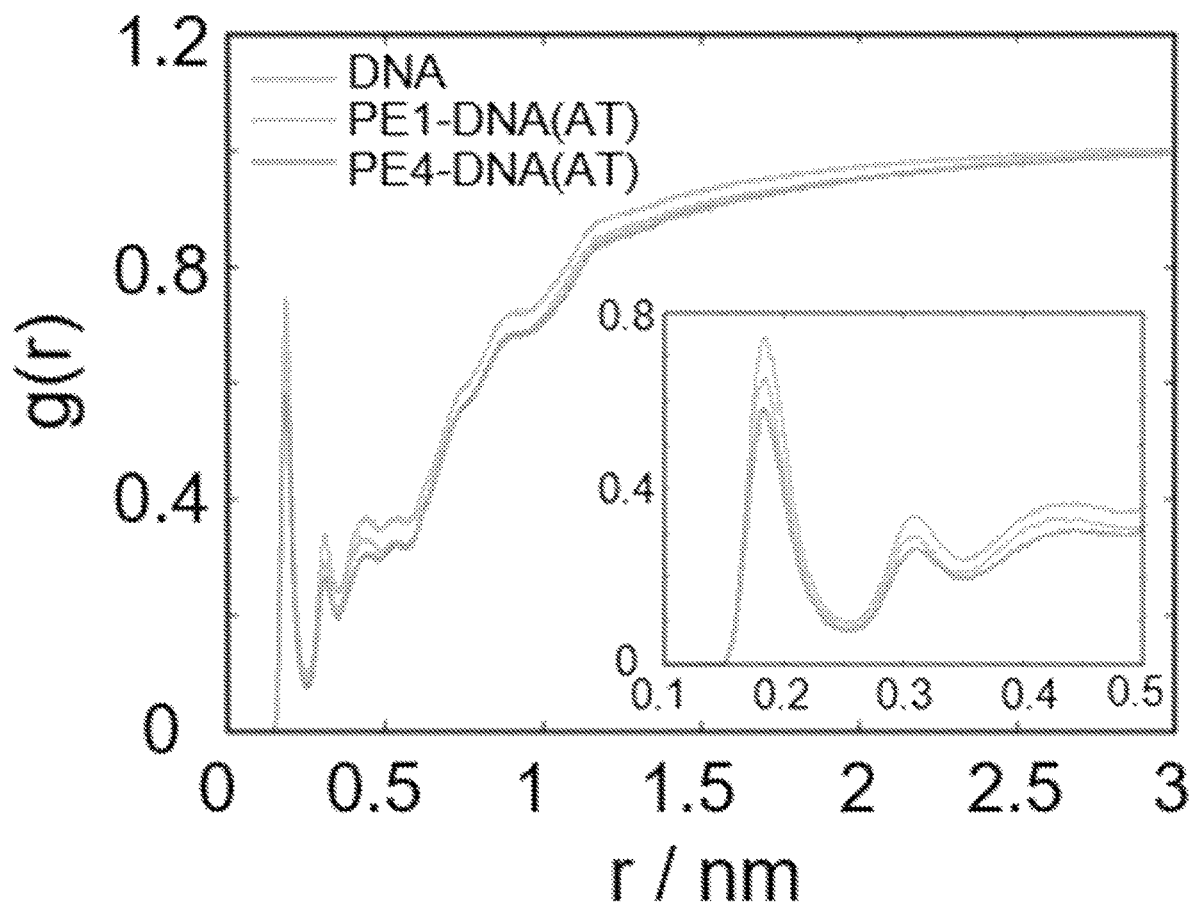
Figure 3D:
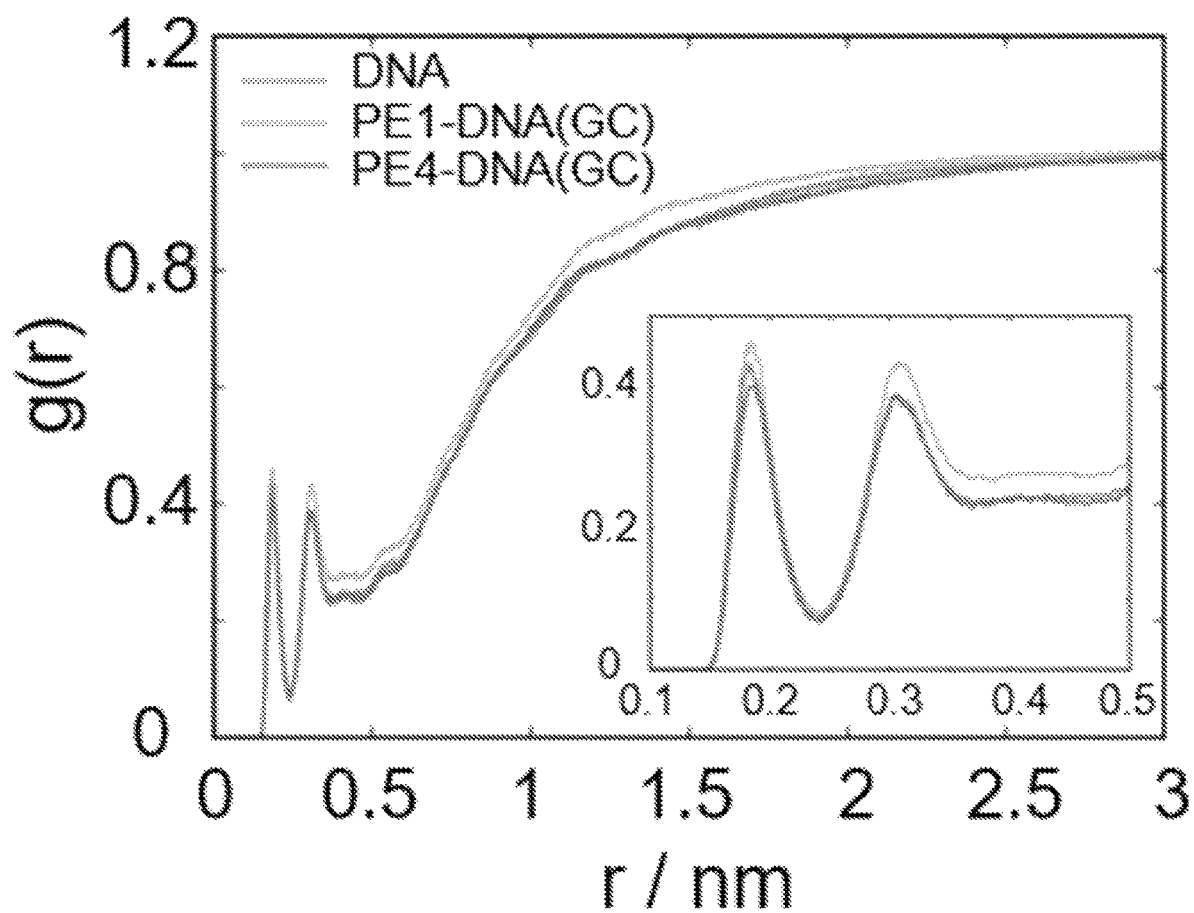
Figure 3E:
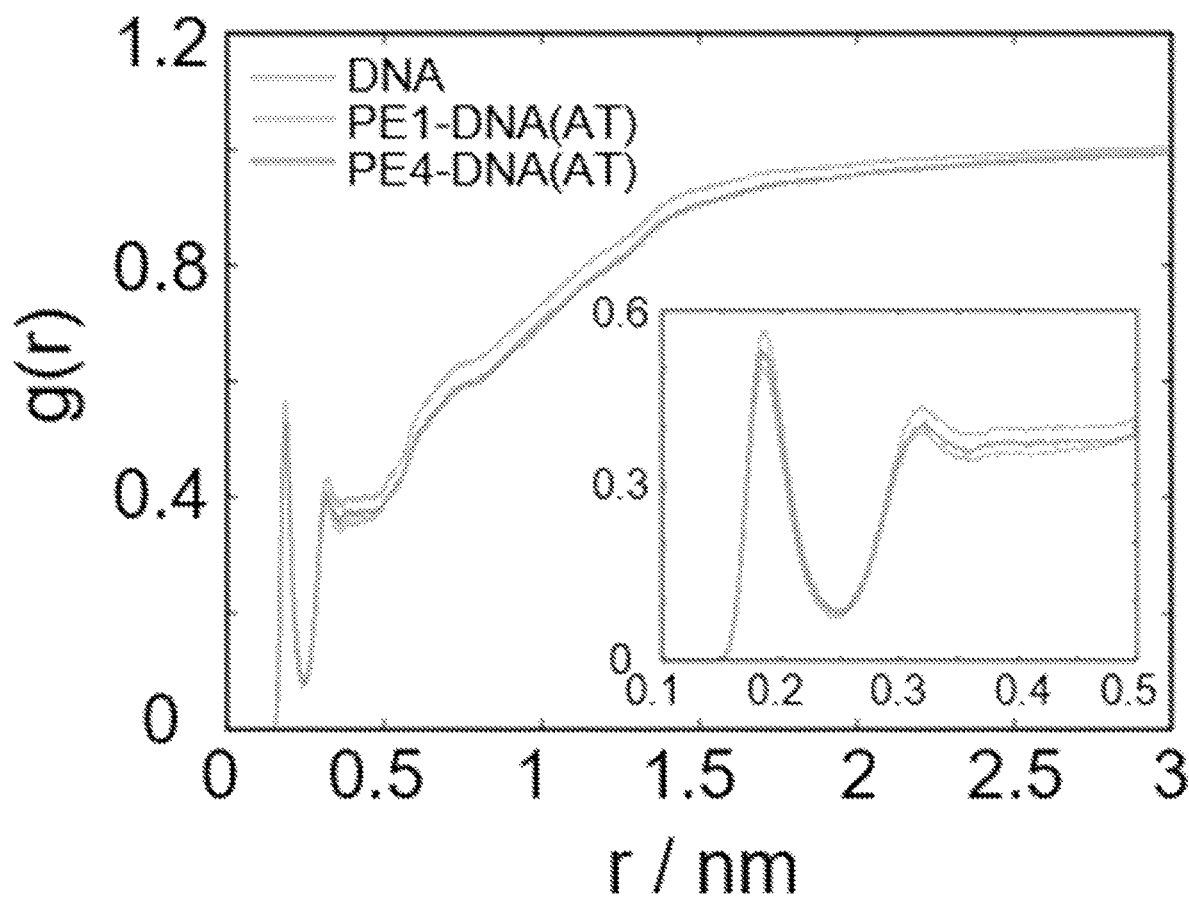
Figure 3F:
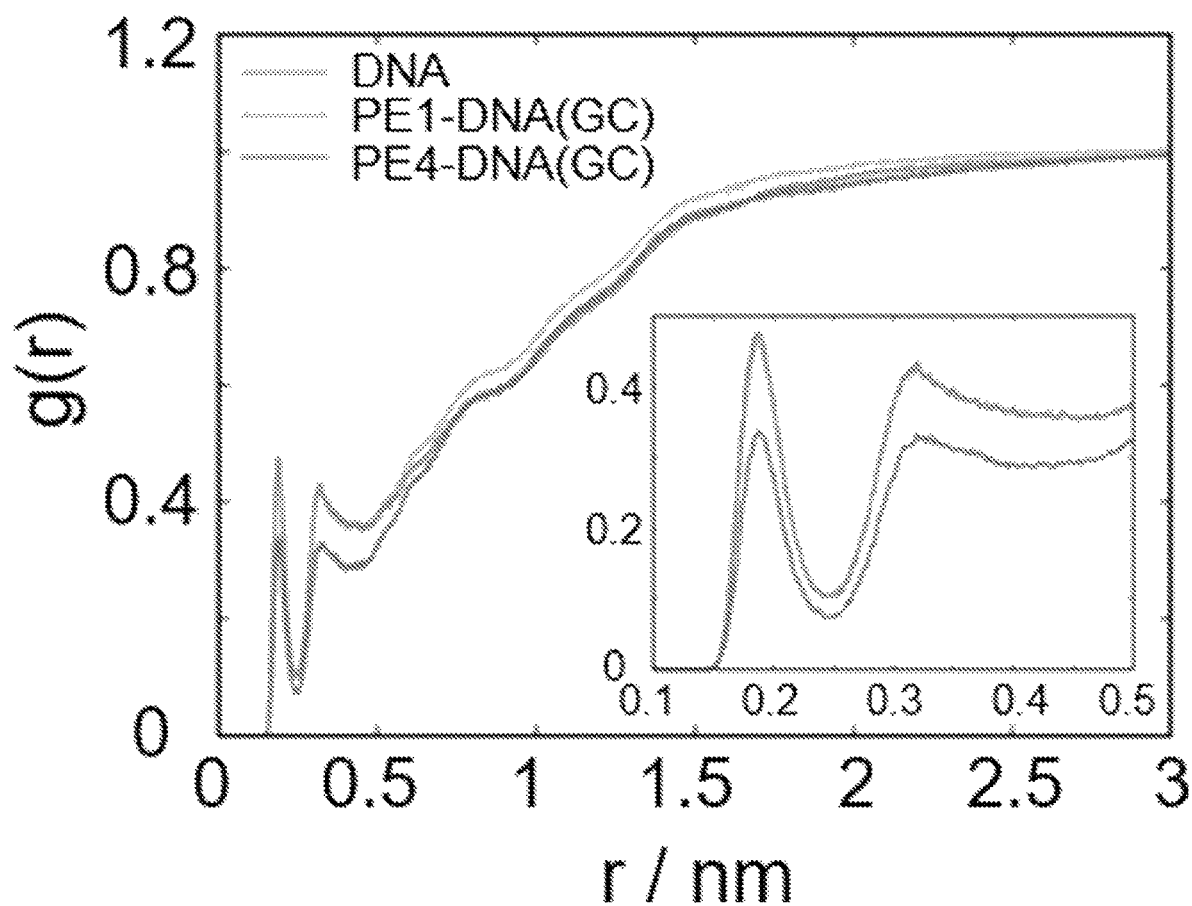
Figure 15A:
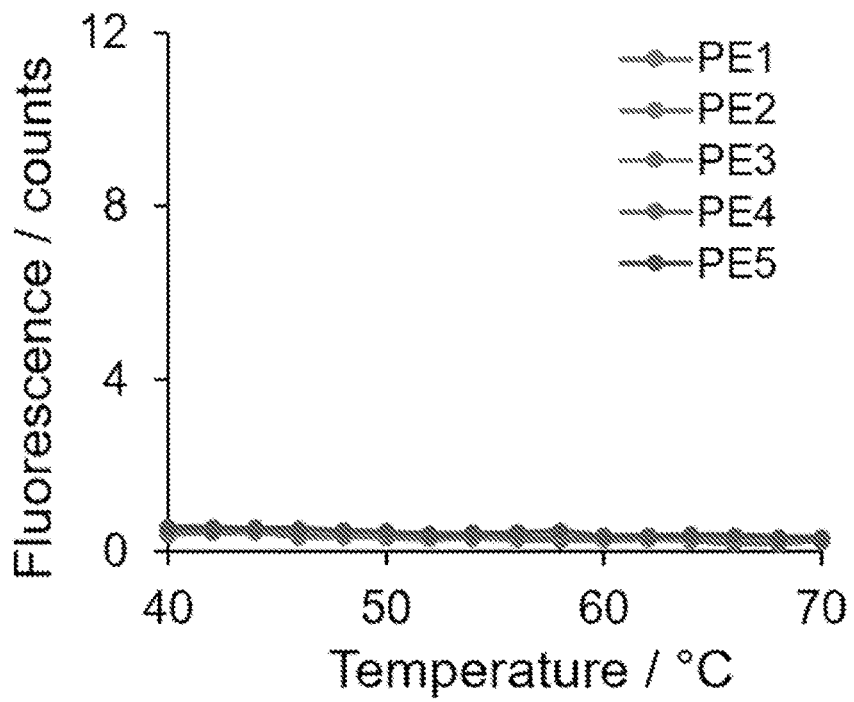
FIG. 15 Real-time SG fluorescence assay of peptoid only. (A) Fluorescence intensities and (B) derivatives of the fluorescence intensities were plotted against the increasing temperature.
Figure 15B:
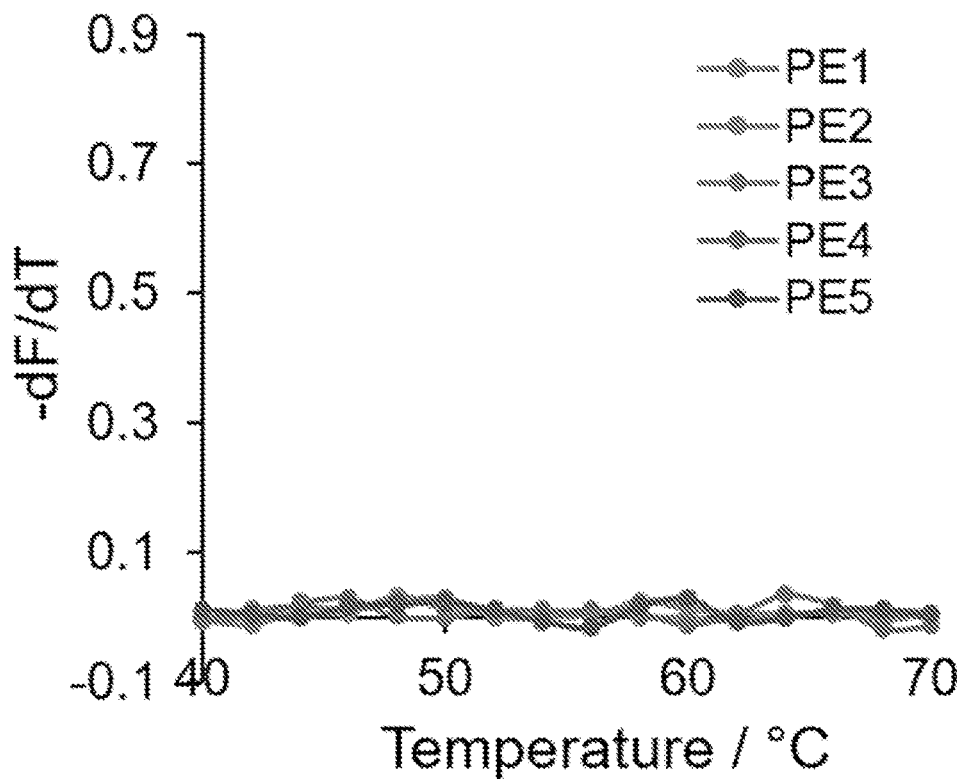
Figure 16A:
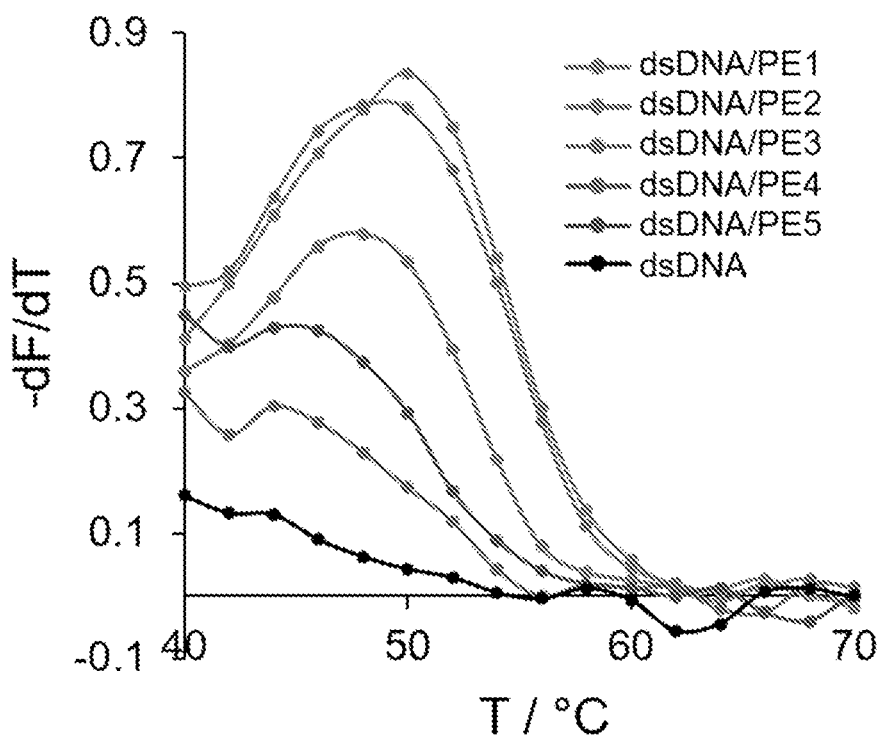
FIG. 16 Real-time SG fluorescence assay of 15-bp dsDNA in the presence of (A) PE1-5 at N/P of 4 (B) PE2 at different N/P as in FIGS. 2A and 2B, respectively. Derivatives of fluorescence intensities were plotted against the increasing temperature.
Figure 16B:
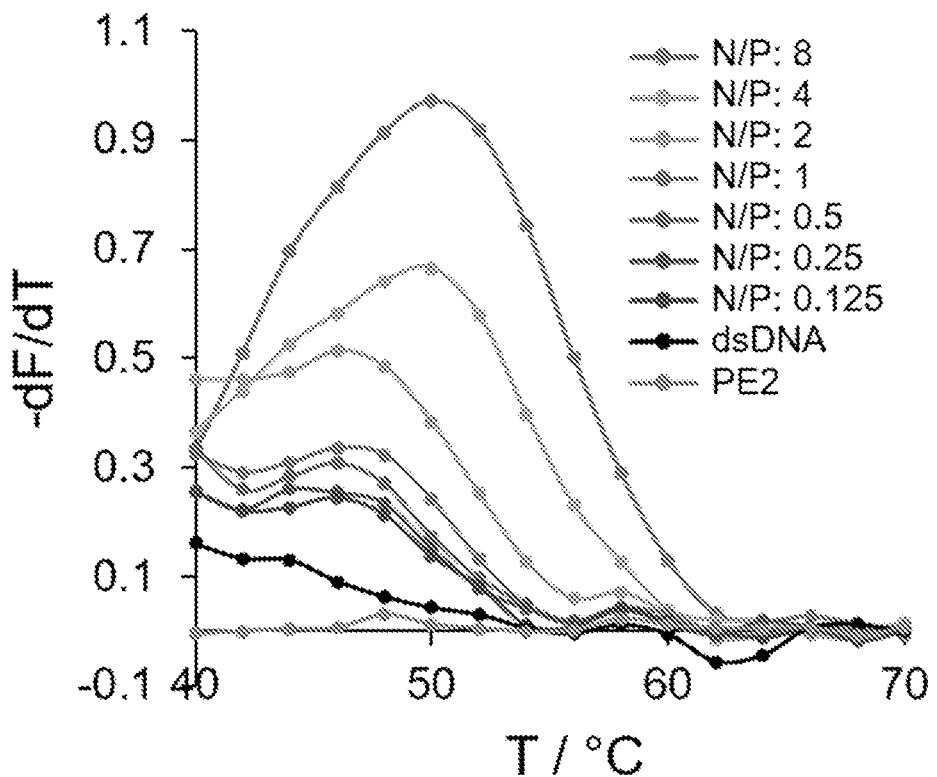

The effect of the two types (i.e., brush and block) of peptoids on stabilizing duplex DNA (dsDNA) was investigated by real-time SYBR Green I (SG) fluorescence assay. SG is known to have a stronger affinity toward dsDNA than to single-stranded DNA (ssDNA) due to the favored intercalation between base pairs and increased stability of the SG/dsDNA complex. The enhanced SG fluorescence in complex with dsDNA is due to the dampening of its intramolecular motions (53, 54). Here, a 15-base pair dsDNA with a melting temperature (Tm) of ~44° C. was designed to study dsDNA stability in the presence of peptoids at varied molar ratios of peptoid amines to phosphate groups of the DNA (i.e., N/P). As shown in FIGS. 2A and 14, fluorescence signals of SG/dsDNA complexes were observed to increase in the presence of peptoids, indicating enhanced stability of DNA base-pairing as the temperature approaches Tm of the dsDNA. The increase of fluorescence signal was believed to originate from the association of SG with dsDNA (53) since no signal was observed when mixing SG with peptoids only (FIG. 15). Tm of dsDNA/peptoid complexes was presented by the derivatives of fluorescence intensities plotted against temperature. As shown in FIGS. 2B, 14 and 16, depending on the amount of peptoid added, Tm of the dsDNA increased 1-6° C. Among the sequences, PE2 exhibited the highest performance in raising the Tm of the dsDNA, where the Tm shifted from 44° C. to 50° C. as the N/P increased from 0.125 to 8 (FIGS. 2B and 16). Moreover, brush-type peptoids were observed to confer higher stability of the dsDNA compared to block-type peptoids, where Tm (dsDNA/PE2)>Tm (dsDNA/PE1)>Tm (dsDNA/PE4) and Tm (dsDNA/PE3)>Tm (dsDNA/PE5).

Figure 17:
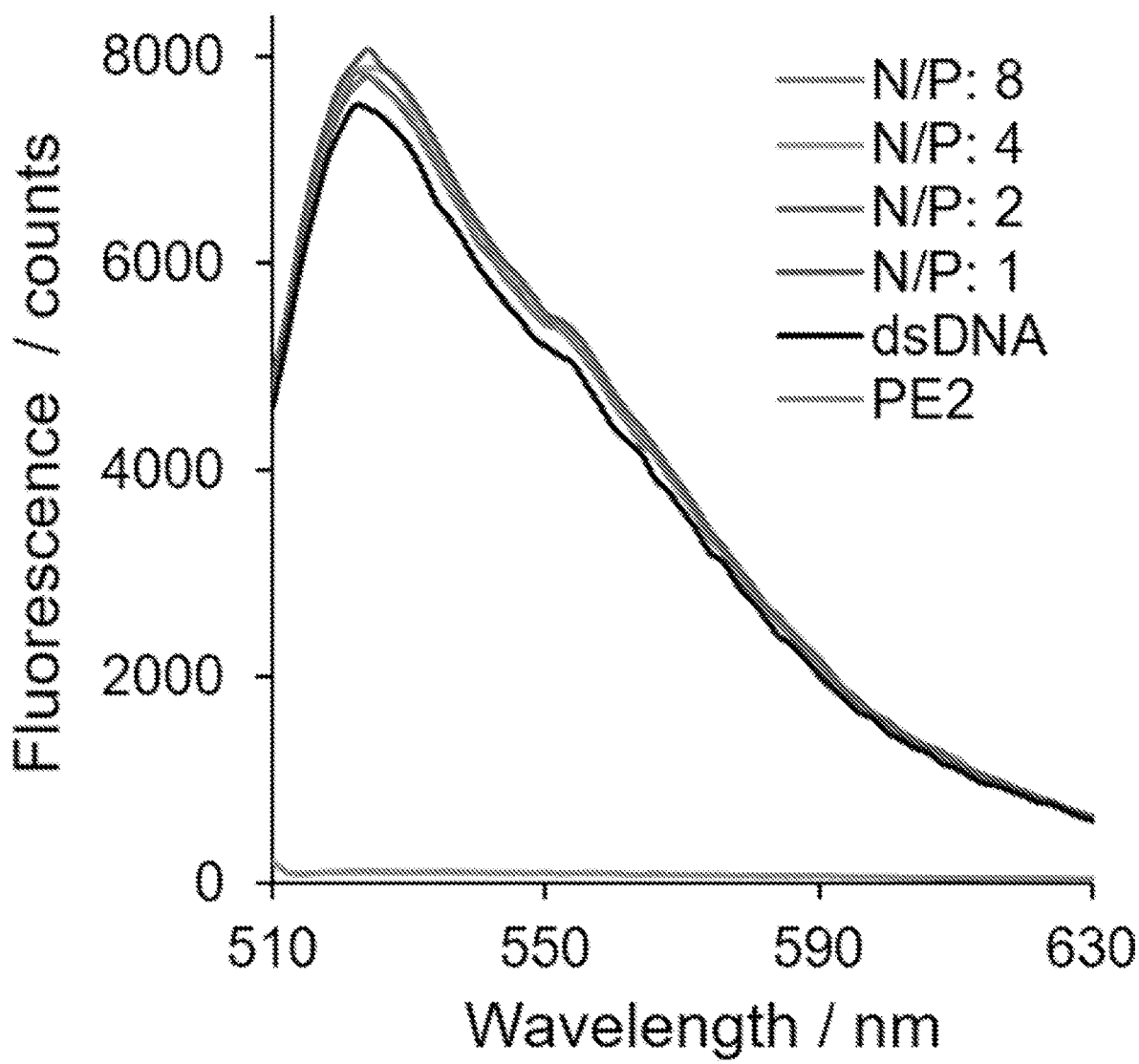
FIG. 17 Fluorescence spectra of the 15-bp dsDNA in the presence of SG and PE2 at different N/P. Sample preparation and fluorescence measurements were performed at room temperature ($\lambda_{ex}$=495 nm and $\lambda_{em}$=510-650 nm). The concentration of PE2 only in solution was the same as that of N/P of 8, which was 1.85 µM.
Figure 18A:
FIG. 18 AGE shows the electrophoretic shift of dsDNA/peptoid complexes. (A) dsDNA/peptoid of 0.5; (B) dsDNA/PE2 at different N/P.
Figure 18B:
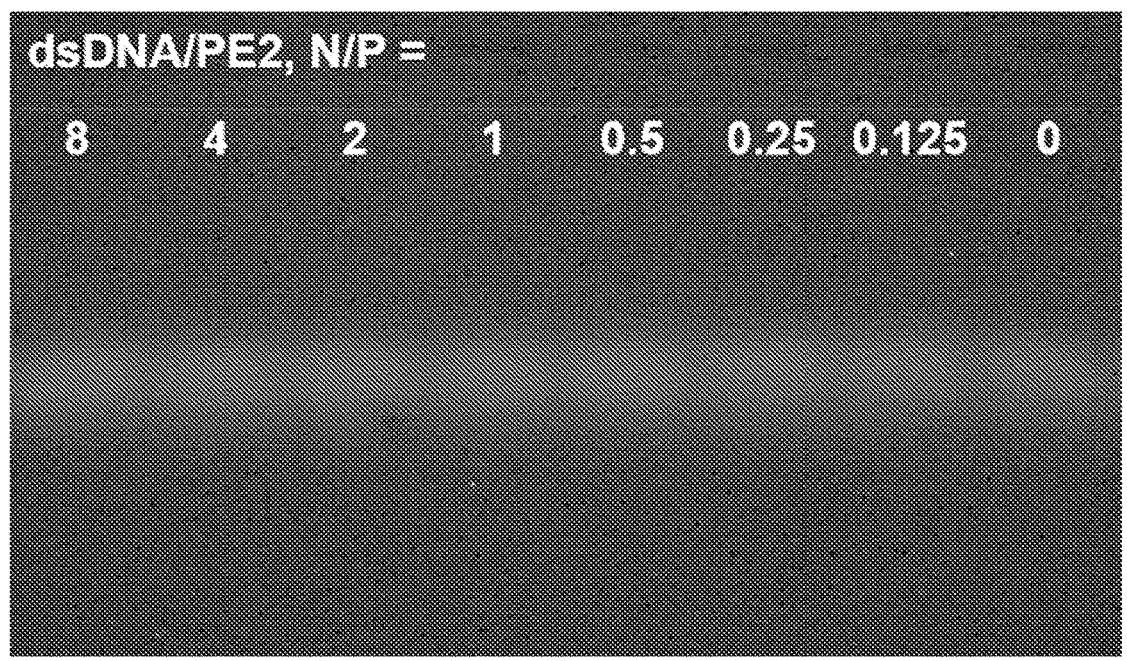
Figure 19A:
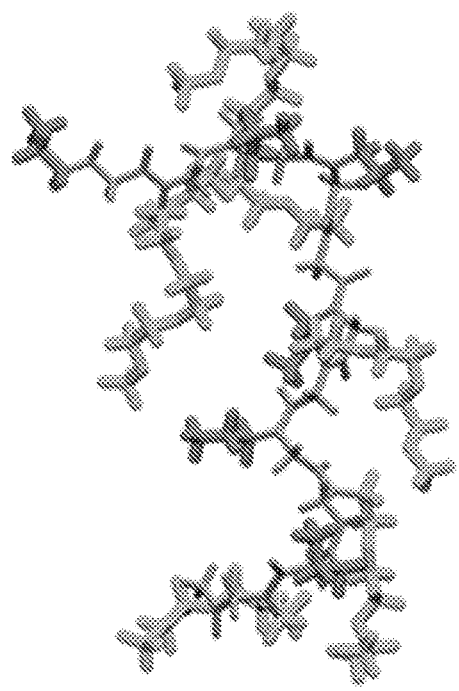
FIG. 19 Atomistic structures of the peptoid and dsDNA models used in the MD simulations. The peptoids (A) PE1 and (B) PE4 are shown in FIG. 19A and FIG. 19B. (C) Molecular and (D) cartoon representation of the dsDNA model are shown in FIGS. 19C and 19D.
Figure 19B:
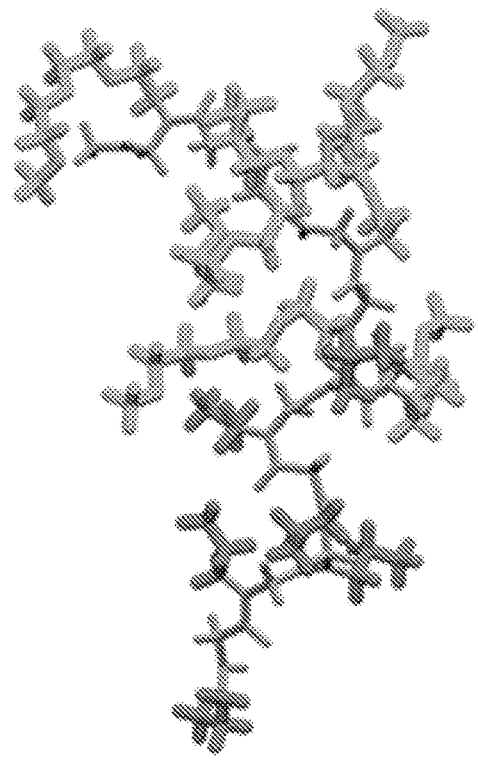
Figure 19C:
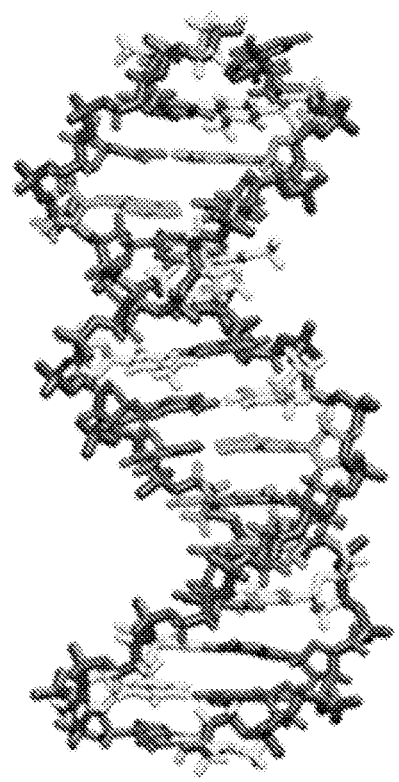
Figure 19D:
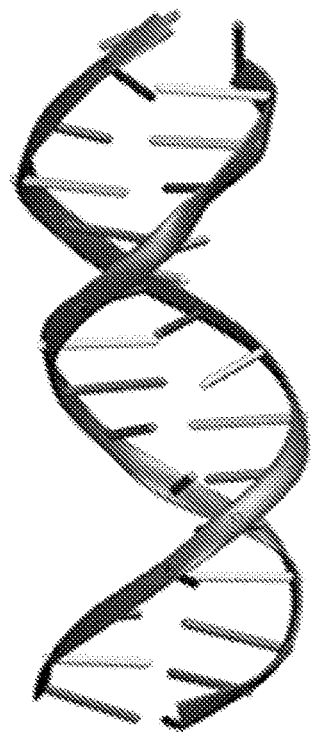

Polycationic polymers and lipids often cause DNA to form polyplexes which can significantly quench the DNA-binding fluorophores (55). Here, the oligo-Nte motifs are expected to inhibit DNA condensation and polyplex formation. Indeed, the fluorescence of SG intercalated inside the dsDNA remained unchanged after the addition of PE2 at room temperature (25° C.) (FIG. 17). This was confirmed by agarose gel electrophoresis (AGE), where no aggregation of dsDNA/PE2 was noted at N/P from 0.125 to 8 (FIG. 18). These indicated that the peptoid-dsDNA interactions did not induce DNA condensation at this level.

Explicit solvent molecular dynamics (MD) simulations were performed to investigate the binding mechanisms of brush-type PE1 and block-type PE4 with dsDNA in solution (FIG. 3A, 3B, 19 and FIG. 13). The simulations showed strong binding affinities of both peptoids to dsDNA, of which PE1 and PE4 exhibited persistent contacts (cut-off=4 Å) for 98.2% and 98.7% of the total simulation time, respectively. The peptoids experienced almost immediate binding to the dsDNA regardless of their starting structures in the simulations. This strong attraction was due to the electrostatic attractive forces between the positively charged Nae residues of the peptoids and negatively charged phosphate groups of the DNA backbone.

PE1 and PE4 exhibited distinct differences in the binding mechanisms to dsDNA. PE1 demonstrated persistent interactions (~98% of the total contact time) with DNA via both the Nae and Nte motifs, where at least 58% (Nae) and 61% (Nte) of the time, 3 or more residues were in close contact with the dsDNA. In addition, the "brush" arrangement facilitated PE1 to spread across the DNA backbone where it interacted with both major and minor grooves concurrently (48.8% of the total contact time), while a preferred binding toward the minor groove (28.5%) exclusively over the major groove (6.1%) of the dsDNA was also observed.

In contrast, the PE4-dsDNA interactions dominated binding through the Nae moieties (~100% of the total contact time), where 4 or more Nae residues were in close contact with the dsDNA for more than 85% of the time. Meanwhile, the Nte moieties exhibited significantly less persistent interactions with DNA, where only the closest two Nte residues were involved in binding for 55% of the total contact time. In addition, the "block" arrangement facilitated the Nte end of PE4 to be solvent exposed, and therefore PE4 was observed to embed in either the major (39.6%) or minor (24%) grooves of the dsDNA, while simultaneous interactions with both major and minor grooves (18.5%) were less favored. As expected, PE1 formed a larger contact area with dsDNA (2.88±1.11 nm$^2$) compared to PE4 (2.54±1.05 nm$^2$), whereas PE4 had lower average solvent accessible surface area than PE1 due to a more compact structure overall while bound to DNA (PE1: 18.82±1.47 nm$^2$ and PE4: 17.81±1.64 nm$^2$) (Table S). Interestingly, MD simulations showed the PE1 structure to be more flexible and dynamic while interacting with the dsDNA compared to PE4, which was frequently restrained due to the embedding of the Nae end within the DNA grooves (demonstrated by the larger occupancy volume areas adopted by PE4 compared to PE1 in FIGS. 3A and 3B).

Without wishing to be bound by theory, it is believed that water plays an important role in the binding phenomena of the architecturally different peptoids with dsDNA. The structuring of water surrounding the pristine dsDNA in respective to the dsDNA/peptoid complex was investigated through radial distribution functions (RDFs). FIG. 3C-F showed a higher density of water molecules surrounding the AT base-pairs versus GC base-pairs with notable preference for the minor grooves of the AT base-pairs. The higher solvation of the minor groove vis-à-vis major groove of DNA was reported previously (56). Interestingly, the binding of PE4 contributed to significant expulsion of water from the dsDNA, with most evident reduction in water density at the minor grooves of the AT base-pairs and major grooves of the GC base-pairs. Without wishing to be bound by theory, it is believed that this was due to the "block" arrangement of PE4, where the "block" comprised osmotic ethylene glycol residues which could alter the surrounding dielectric constant, resulting in effective displacement of water molecules from the DNA structure (57, 58). On the other hand, PE1 was observed to have the least effect on the structuring of water surrounding the dsDNA, suggesting that such "brush" arrangement of PE1 did not affect the water uptake by dsDNA. At the same time, water facilitated the interactions of the polar Nte moieties to achieve a close (albeit dynamic) binding and larger contact area with the dsDNA. Since it is known that DNA hydration directly relates with the stability of duplex formation specifically through Watson-Crick base pairs (59), the observed differences in water structuring and binding mechanisms of PE1 and PE4 to dsDNA play important roles in the stability of dsDNA and thus DNA origamis, as observed from the SG fluorescence assays (FIG. 2).

Figure 1B:
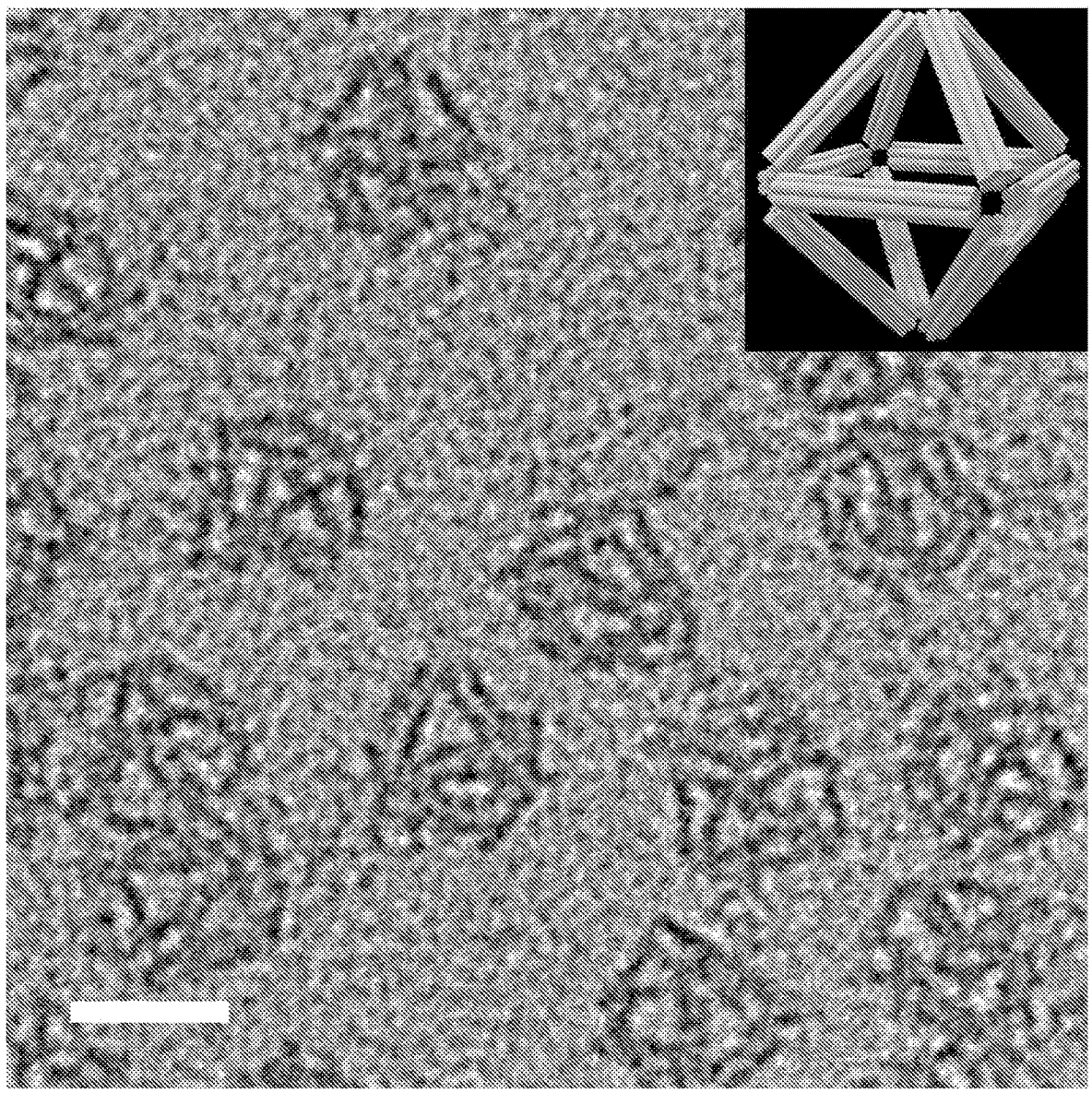
Figure 1C:
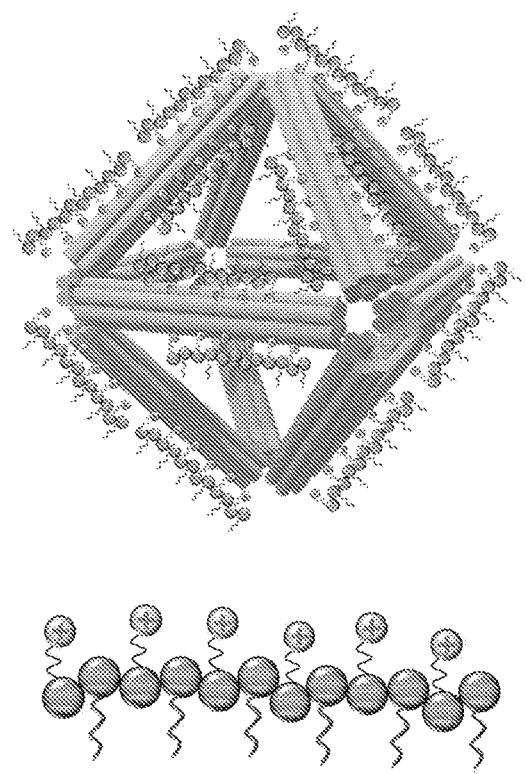
Figure 1C:
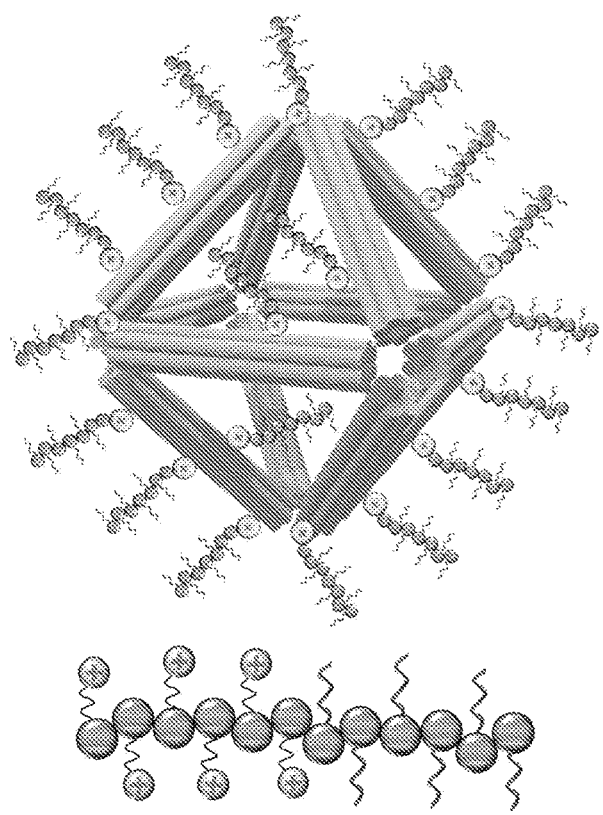
Figure 20:
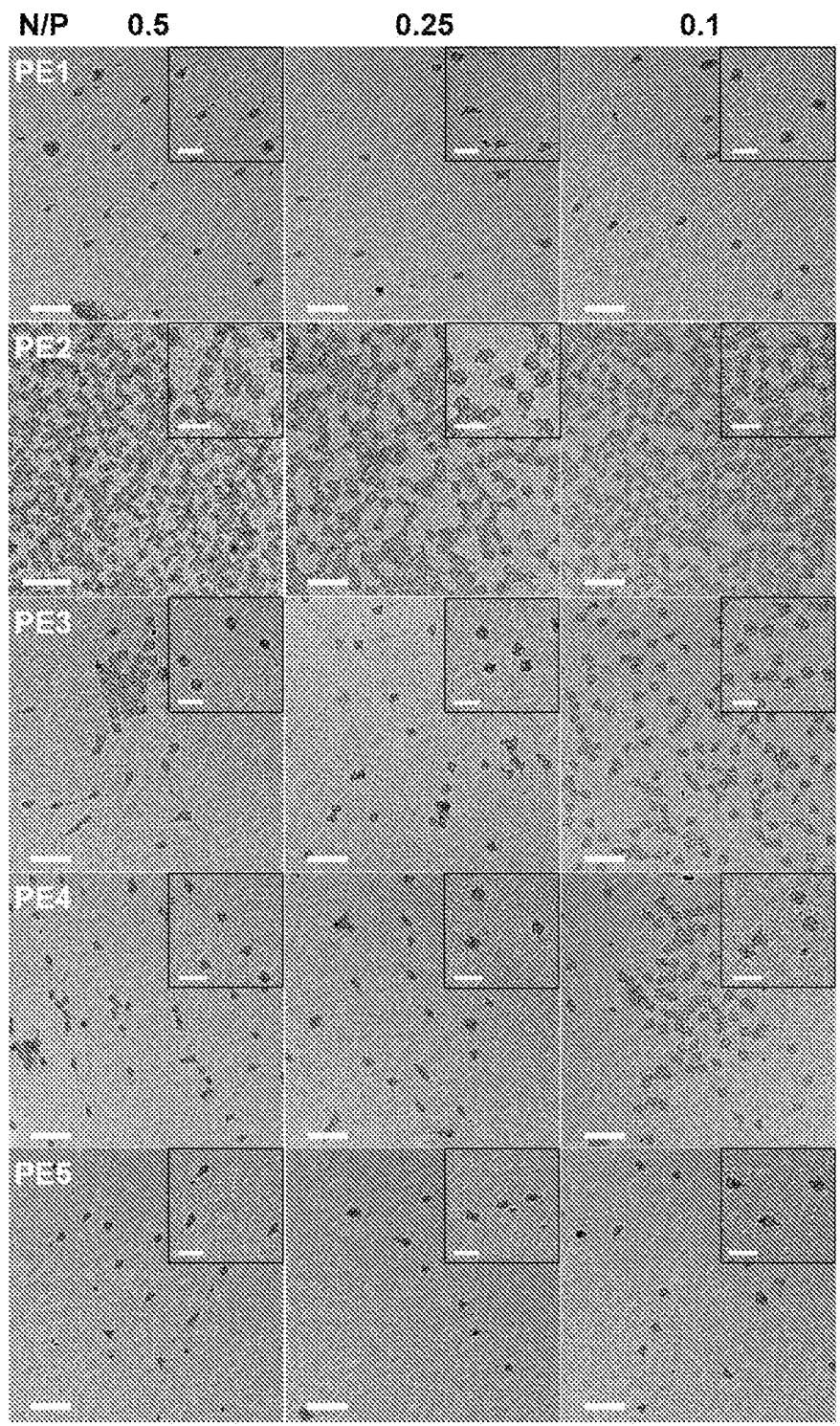
FIG. 20 Negative-stained TEM images show peptoid-coated OCs at N/P of 0.5, 0.25 and 0.1 (scale bars: 200 nm). The insets show magnified images of the OC structures (scale bars: 100 nm).
Figure 21A:
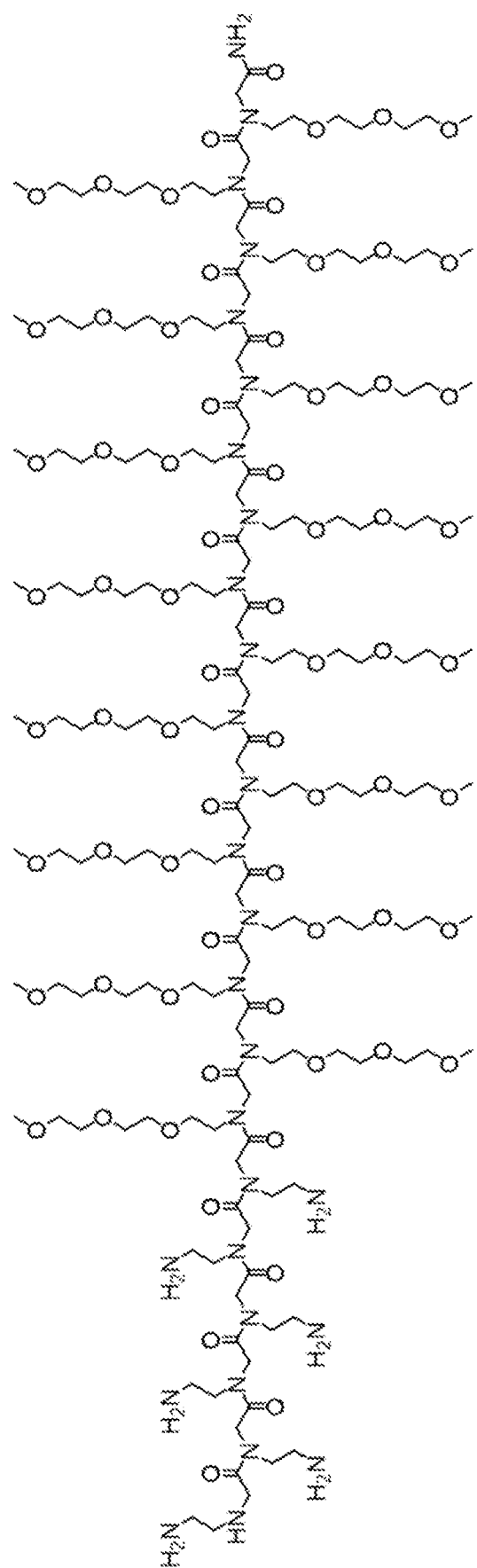
FIG. 21 (A) Chemical structure of the Nae6-Nte16 block peptoid and (B) negative-stained TEM images of $Nae_6$-$Nte_{16}$ block-coated OCs at N/P of 0.5 (scale bar: 200 nm). The inset shows magnified image of the OC structures (scale bar: 100 nm).
Figure 21B:
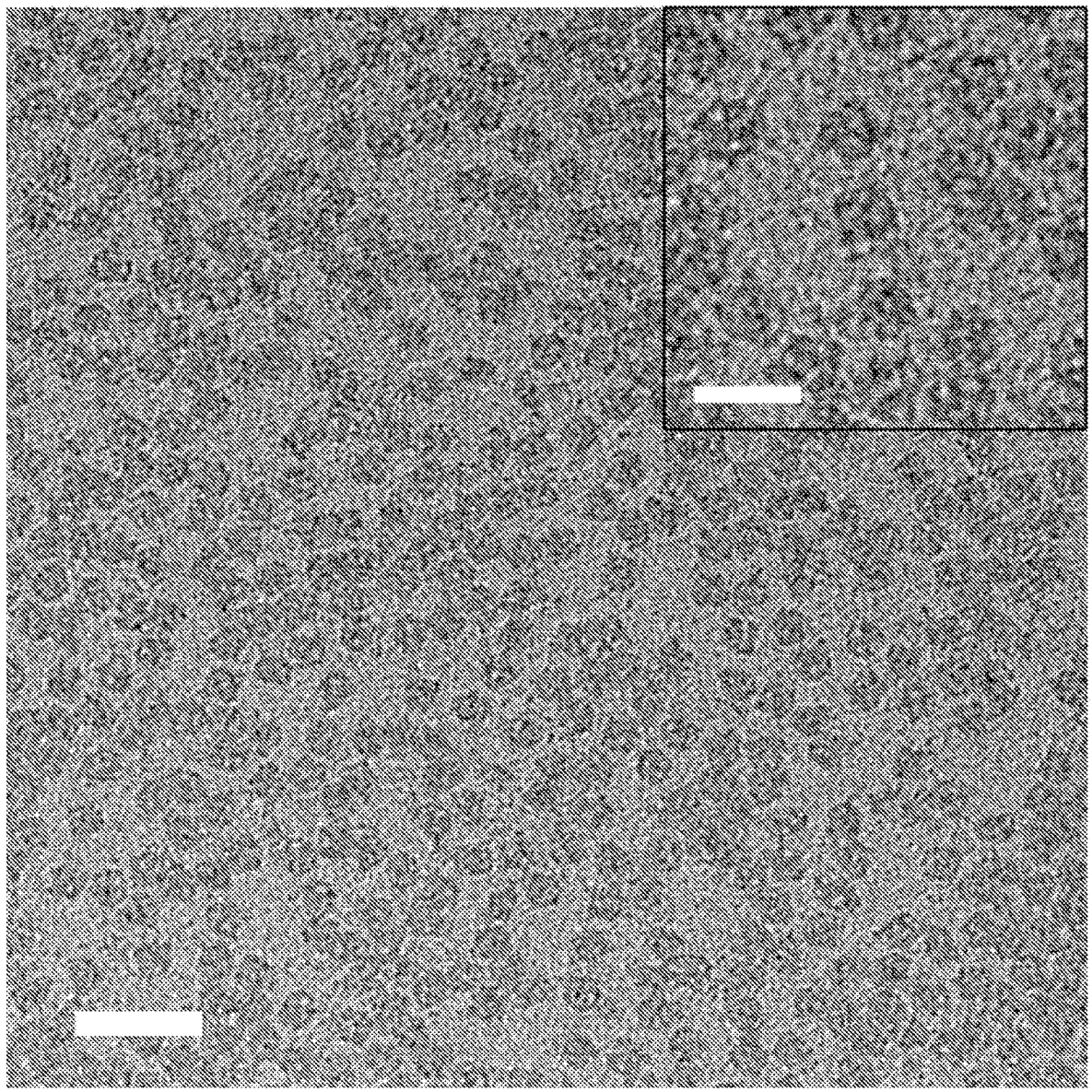
Figure 22:
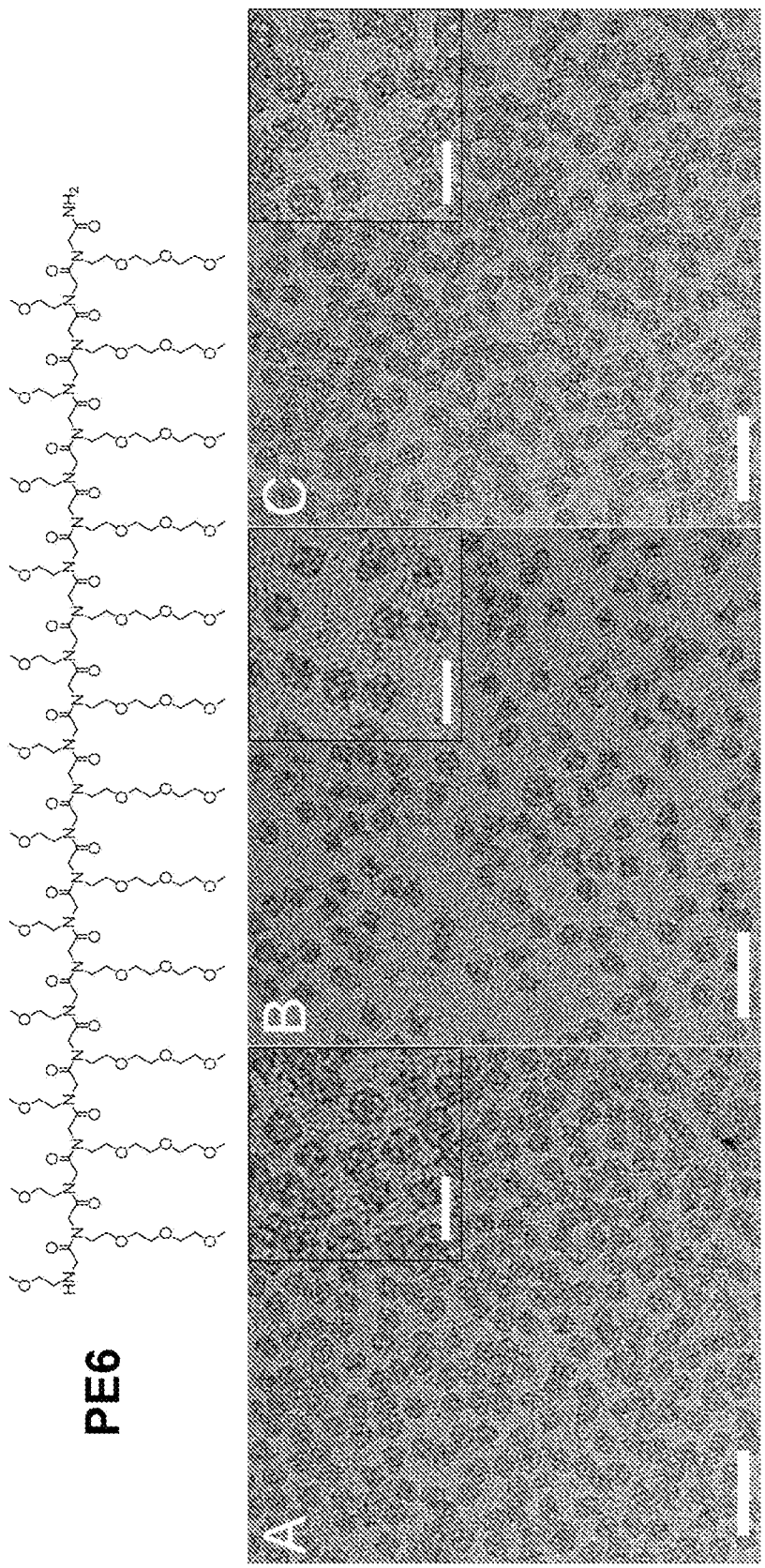
FIG. 22 Top: Molecular structure of PE6. Bottom: Negative-stained TEM images of PE6-coated OC structures at N/P of (A) 2, (B) 1 and (C) 0.5 (scale bars: 200 nm). The insets show magnified images of the OC structures (scale bars: 100 nm).
Figure 23:
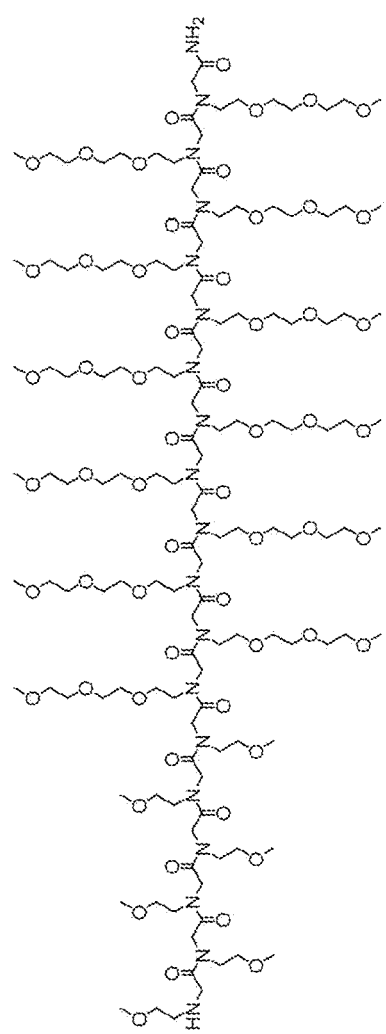
FIG. 23 Top: molecular structure of PE7. Bottom: negative-stained TEM images of PE7-coated OCs at N/P of (A) 2, (B) 1 and (C) 0.5 (scale bars: 200 nm). The insets show magnified images of the OC structures (scale bars: 100 nm).
Figure 23:
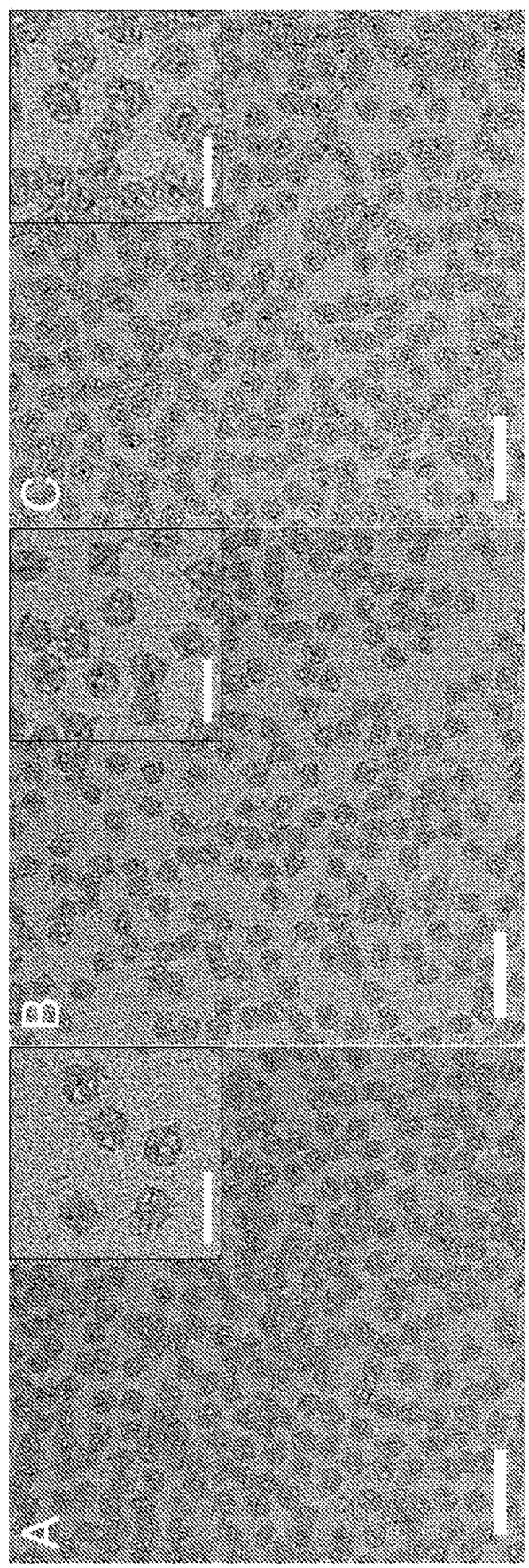

The polycationic peptoids were then applied to protect OCs, which possessed six DNA bundles at each edge that confers rigidity of the 3D nanostructure (FIG. 1B). The structural stability of OCs in the presence of peptoids was evaluated. As shown in FIG. 20, transmission electron microscopic (TEM) imaging showed that the morphology of OCs was maintained when N/P was not higher than 0.5. Higher N/P could lead to aggregation, while this was improved by increasing the number of Nte residues, of which PE2 (Nae$_{12}$-Nte$_{12}$ brush) and PE3 (Nae$_6$-Nte$_{12}$ brush) coated OCs exhibited less aggregation than PE1 (Nae$_6$-Nte$_6$ brush). Similarly, increasing the number of Nte residues in the block-type peptoids, PE4 (Nae$_6$-Nte$_6$ block) and PE5 (Nae$_6$-Nte$_{12}$ block), to further of 16 Nte residues enabled more stable OC structures (FIGS. 20 and 21). This implied that incorporation of the hydrophilic Nte motifs could reduce aggregation of DNA origamis. On the other hand, PE6 and PE7 peptoids, where the positively charged Nae residues was substituted by neutrally charged N-(2-methoxyethyl)glycine (Nme) residues on the peptoid backbone, exhibited no obvious structural changes at even higher N/P (i.e., 2, 1, and 0.5, FIGS. 22 and 23). This supported that the Nae moieties were the primary driving force for the peptoid-DNA interactions as demonstrated by MD simulations (FIG. 3). ξ-potential was also analyzed (n=3), where bare OCs, PE2- and PE3-coated OCs were measured at −13.3±0.34, −11.7±0.42, and −12.6±0.40, respectively. The low ξ-potential of OCs was likely due to the high ionic strength and Mg$^{2+}$ content of the buffer, which effectively shielded the surface charge of OCs.

Figure 24:
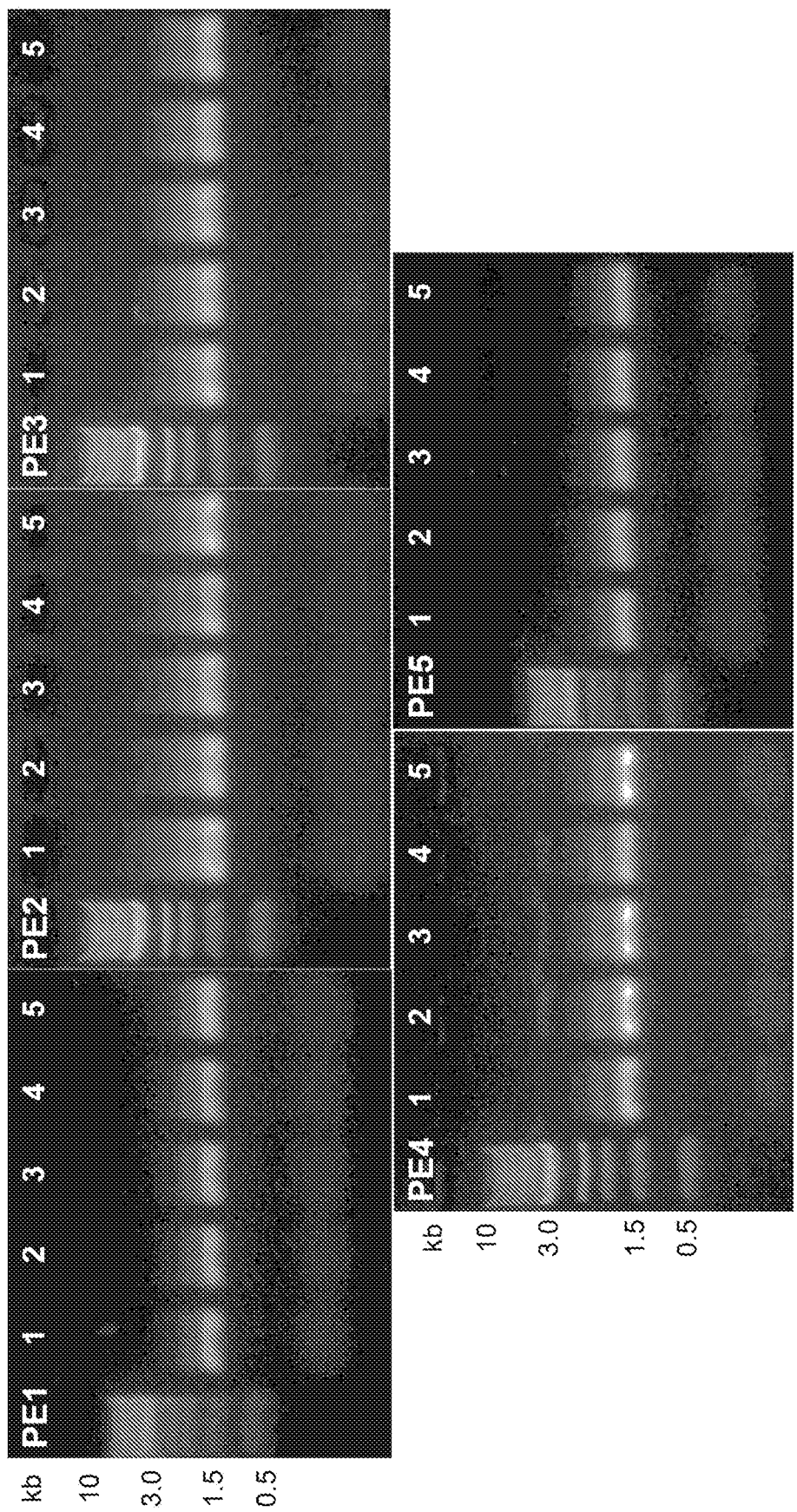
FIG. 24 AGE showing the electrophoretic shift of peptoid-coated OCs (4.3 nM). Lanes 1-3: N/P of 0.5, 0.25, and 0.1, respectively; Lane 4: peptoid/OC=1; and Lane 5: OC only.
Figure 25:
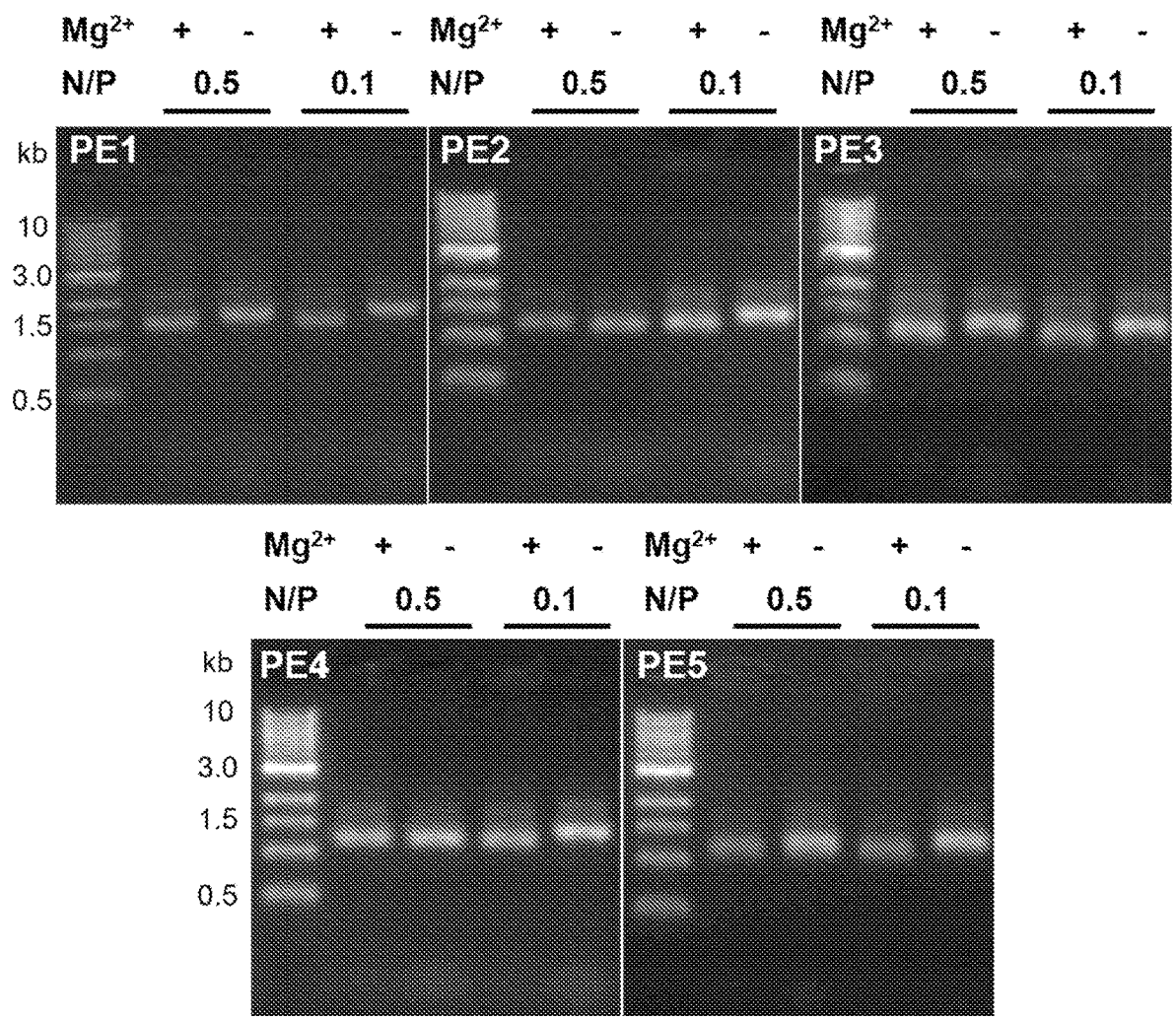
FIG. 25 AGE of OC/peptoid in TAE buffer. The final concentration of $MgCl_2$ was 1.25 mM. The result was used in the calculation of electrophoretic shift in FIG. 4C.
Figure 26:
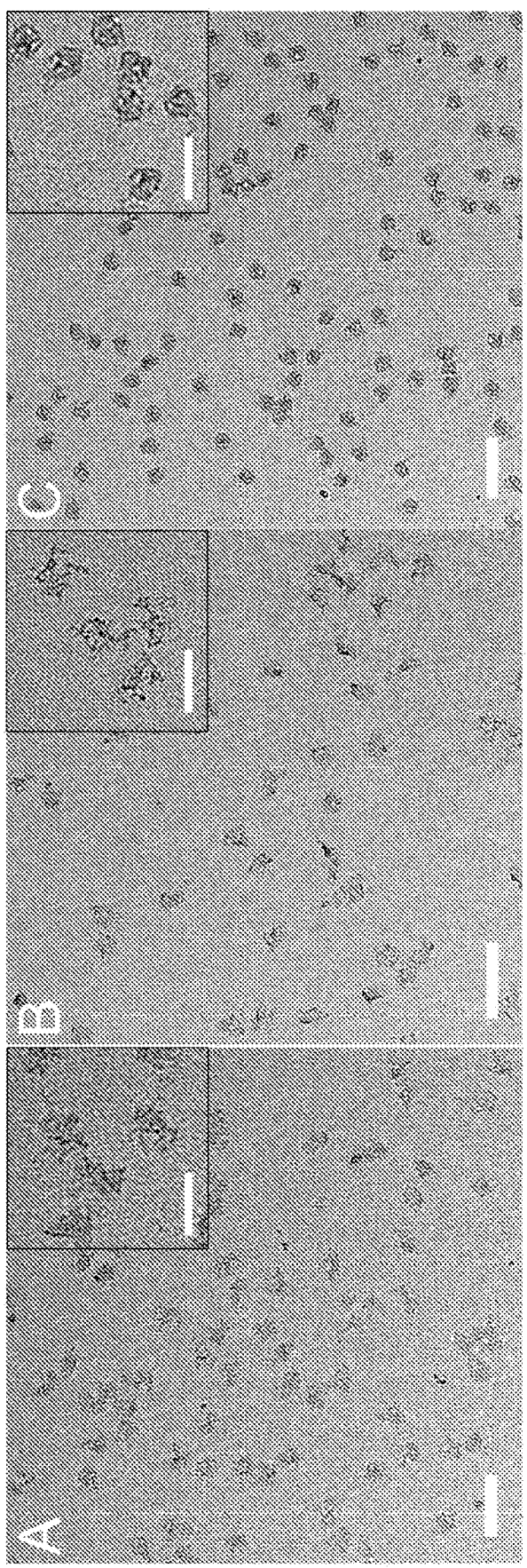
FIG. 26 Negative-stained TEM images of (A) bare OCs and OC/PE2 at (B) N/P of 0.1 and (C) N/P of 0.5. The final concentration of $MgCl_2$ in TAE buffer was 1.25 mM. TEM samples were extracted from the agarose gels (scale bars: 200 nm). The insets show magnified images of the OC structures (scale bars: 100 nm).
Figure 27:
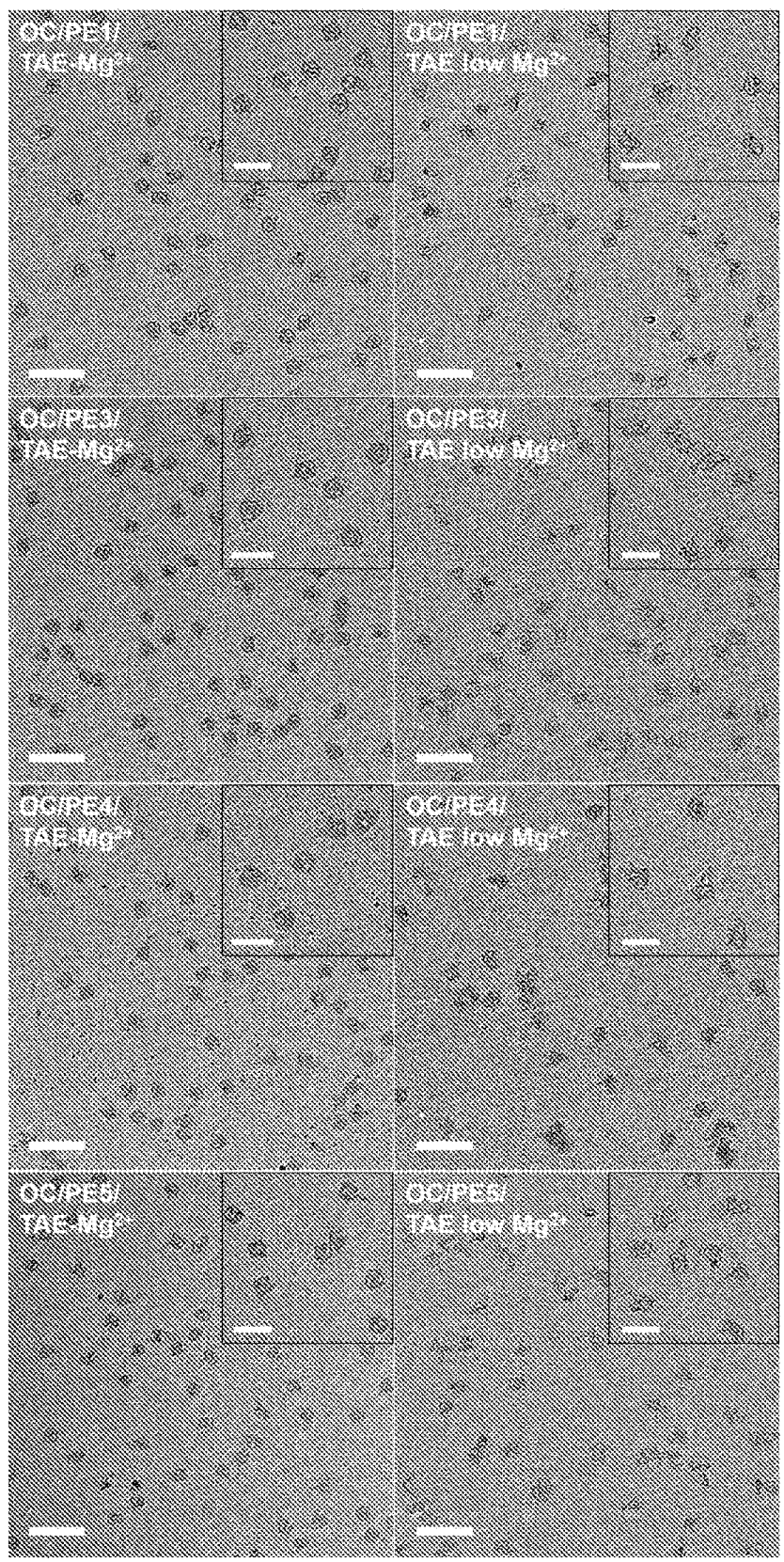
FIG. 27 Negative-stained TEM images of peptoid (PE1, PE3, PE4, and PE5)-coated OCs in TAE buffer. The final concentrations of $MgCl_2$ were 12.5 mM (TAE-$Mg^{2+}$) and 1.25 mM (TAE low $Mg^{2+}$). TEM samples were extracted from the agarose gels (scale bars: 200 nm). The insets show magnified images of the OC structures (scale bars: 100 nm).
Figure 28:
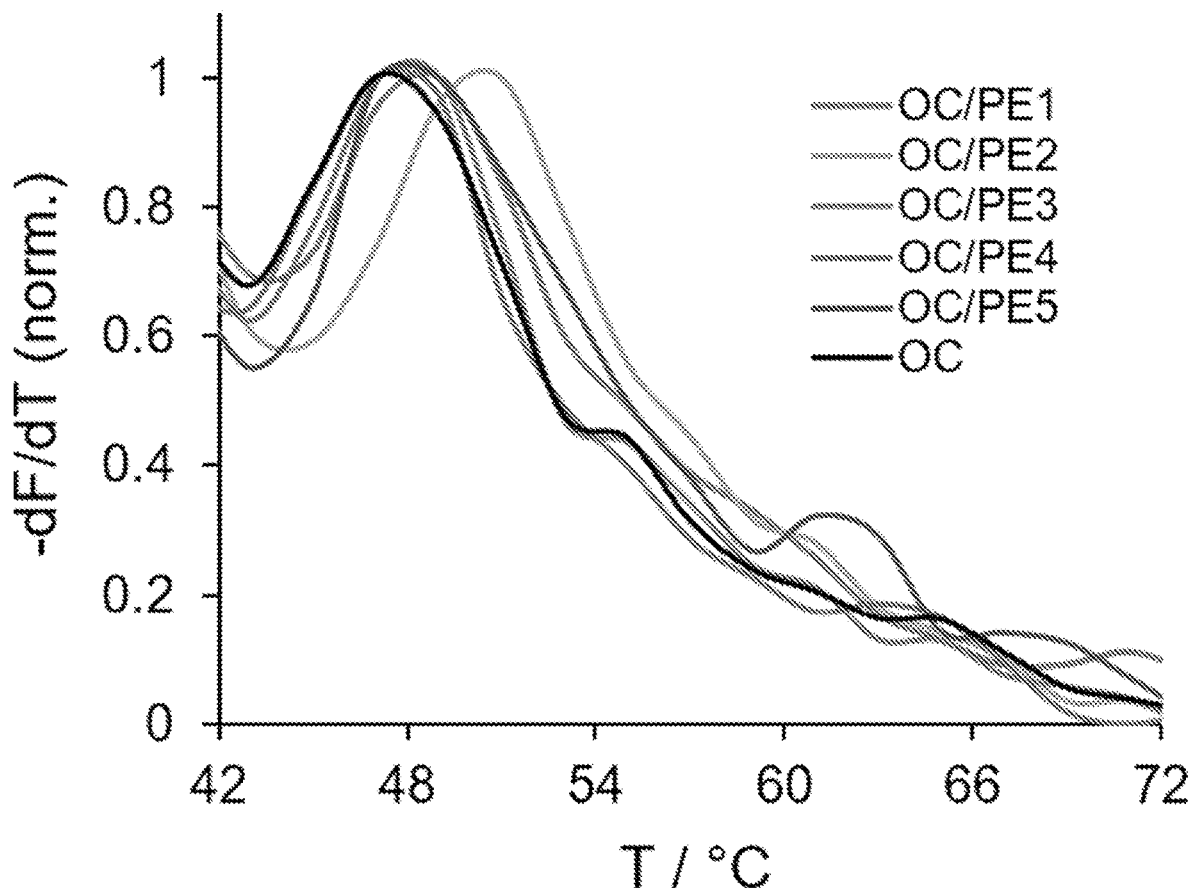
FIG. 28 Real-time SG fluorescence assay of bare and peptoid-coated OCs (1 nM, N/P: 0.125) in PBS buffer. Derivatives of the fluorescence intensities were normalized to 0-1 range and plotted against the increasing temperature.

Mg$^{2+}$ is known to play the central role for the integrity of DNA origami nanostructures by stabilizing DNA base-pairing (28). Here, a Mg$^{2+}$ depleted condition was generated by diluting the bare OCs and peptoid-coated OCs (OC/peptoid) so that the final concentration of magnesium chloride (MgCl2) in solution was 1.25 mM (FIG. 4). The structural integrity of OCs was first assessed by agarose gel electrophoresis (AGE). The peptoid-protected OCs show bands on the agarose gel similar to bare OCs, confirming the intact OC nanostructures (FIG. 24). However, when MgCl$_2$ concentration was reduced from 12.5 mM to 1.25 mM, a notable electrophoretic band shift in the agarose gel was observed (FIGS. 4B, 4C, and 25), indicating the damage of OCs. At N/P of 0.5, OC/peptoid showed less electrophoretic shift than bare OCs, indicating an improved stability in the presence of peptoids (FIG. 4C). Among the peptoid sequences, OC/PE2 showed the least electrophoretic shift at N/P of 0.5, while the protection effect was significantly reduced at N/P of 0.1, supporting that higher concentration of positively charged moieties could compensate the depletion of $Mg^{2+}$. TEM imaging was further performed on bare OCs and OC/peptoid extracted from the agarose gel. As shown in FIG. 4D and S14A, the structure of bare OCs in a low $Mg^{2+}$ condition was significantly distorted and expanded. At an N/P of 0.5, TEM imaging ensured the dense coating of PE2 did not comprise the structural integrity of OCs in the $Mg^{2+}$ depleted solution (FIGS. 4D and 26), while the protection effect was not observed in other peptoid sequences (FIG. 27). This stronger PE2-DNA interaction was consistent with result obtained from the SG fluorescence assay (FIG. 2). In fact, the assay was performed on OC/peptoid at an N/P of 0.125, in which only OC/PE2 exhibited a clear Tm shift from 48° C. to 52° C. (FIG. 28).

Figure 4F:
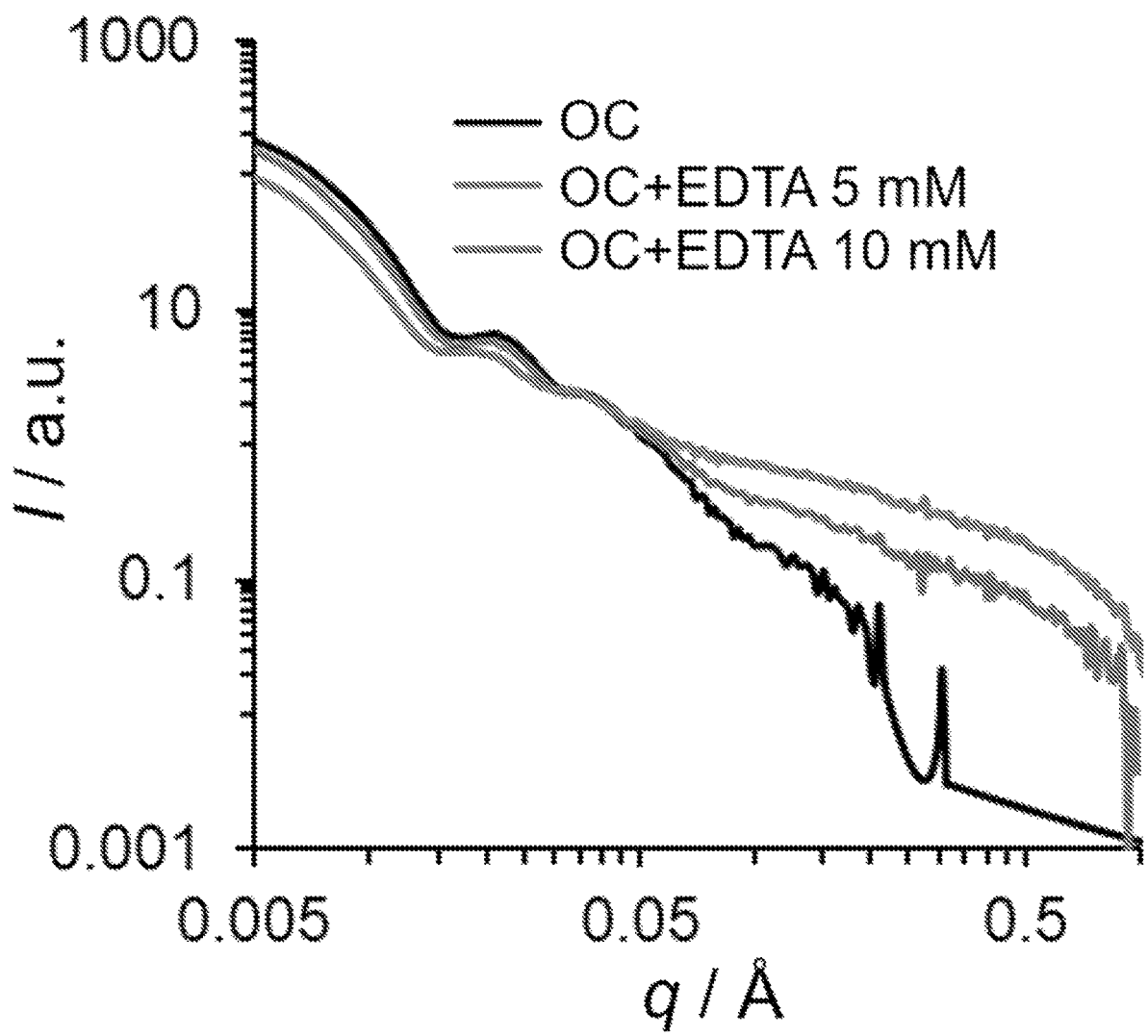
Figure 4G:
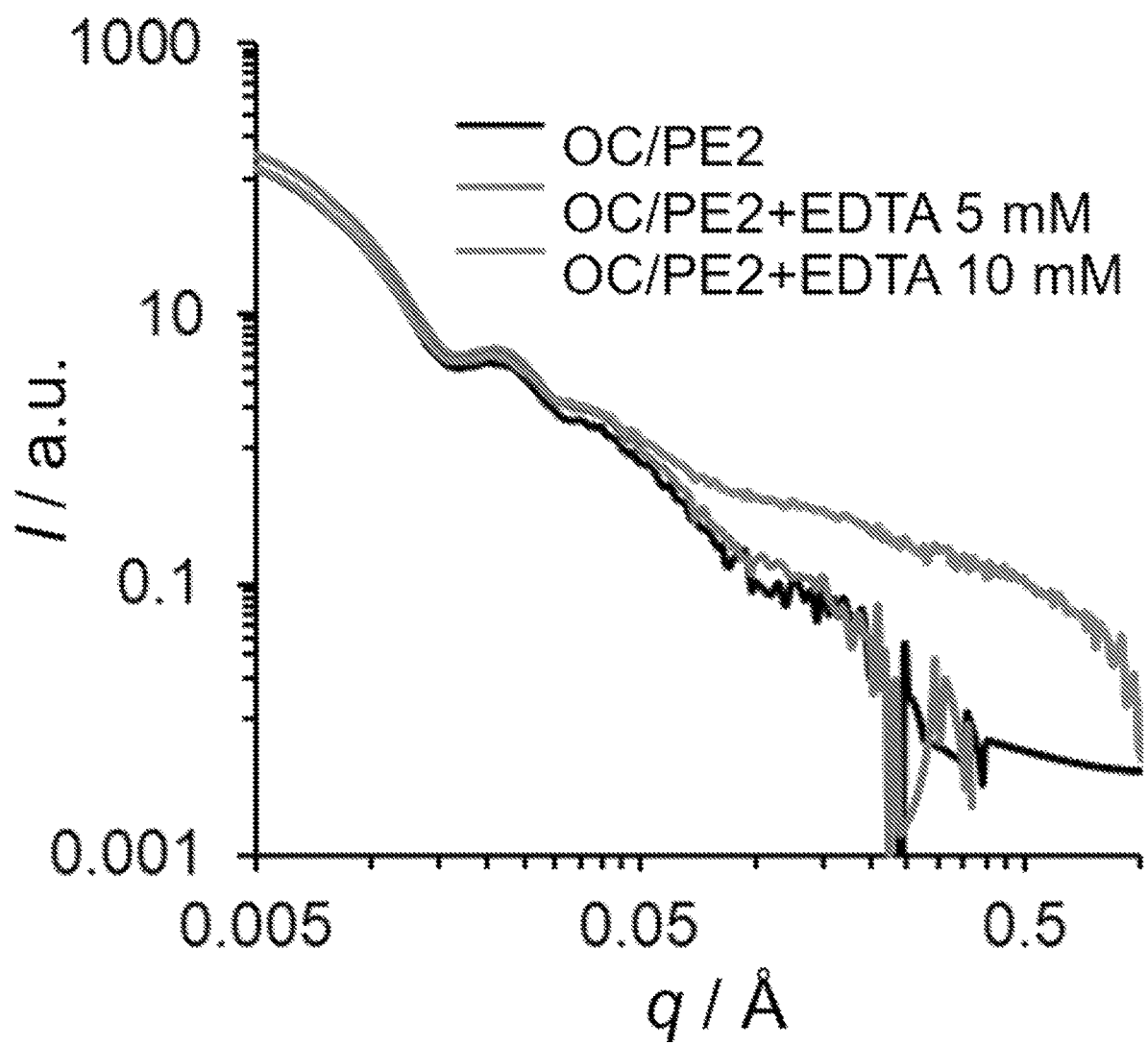
Figure 29:
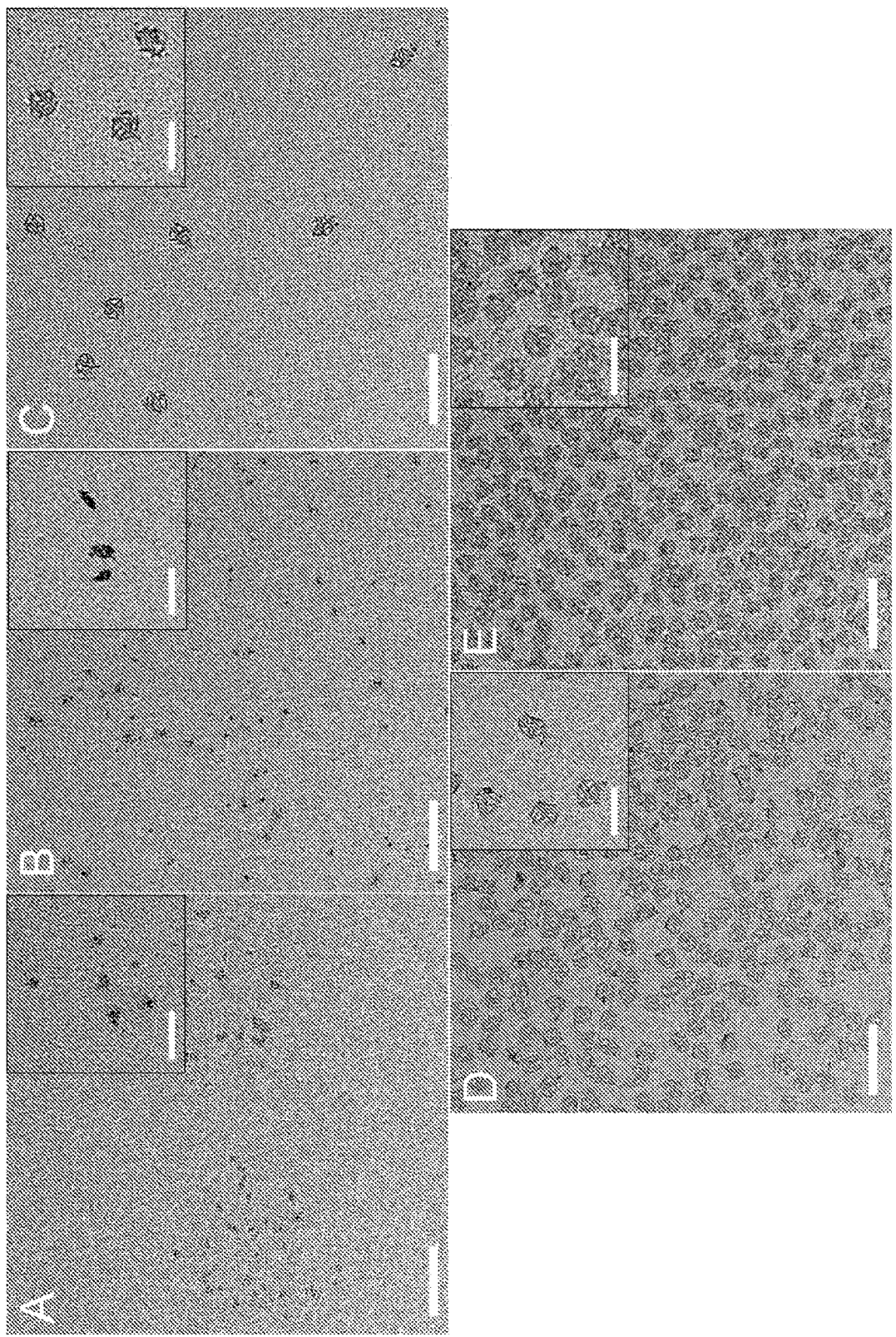
FIG. 29 Negative-stained TEM images of OCs in the presence of different amounts of EDTA: (A) 12.5 mM, (B) 10 mM, (C) 6.25 mM, (D) 3.5 mM and (E) 0 mM. The concentration of $MgCl_2$ in TAE buffer was 12.5 mM. EDTA was added to the OC solution and left undisturbed for ~4 h at room temperature prior to TEM samples preparation (scale bars: 200 nm). The insets show magnified images of the OC structures (scale bars: 100 nm).
Figure 30:
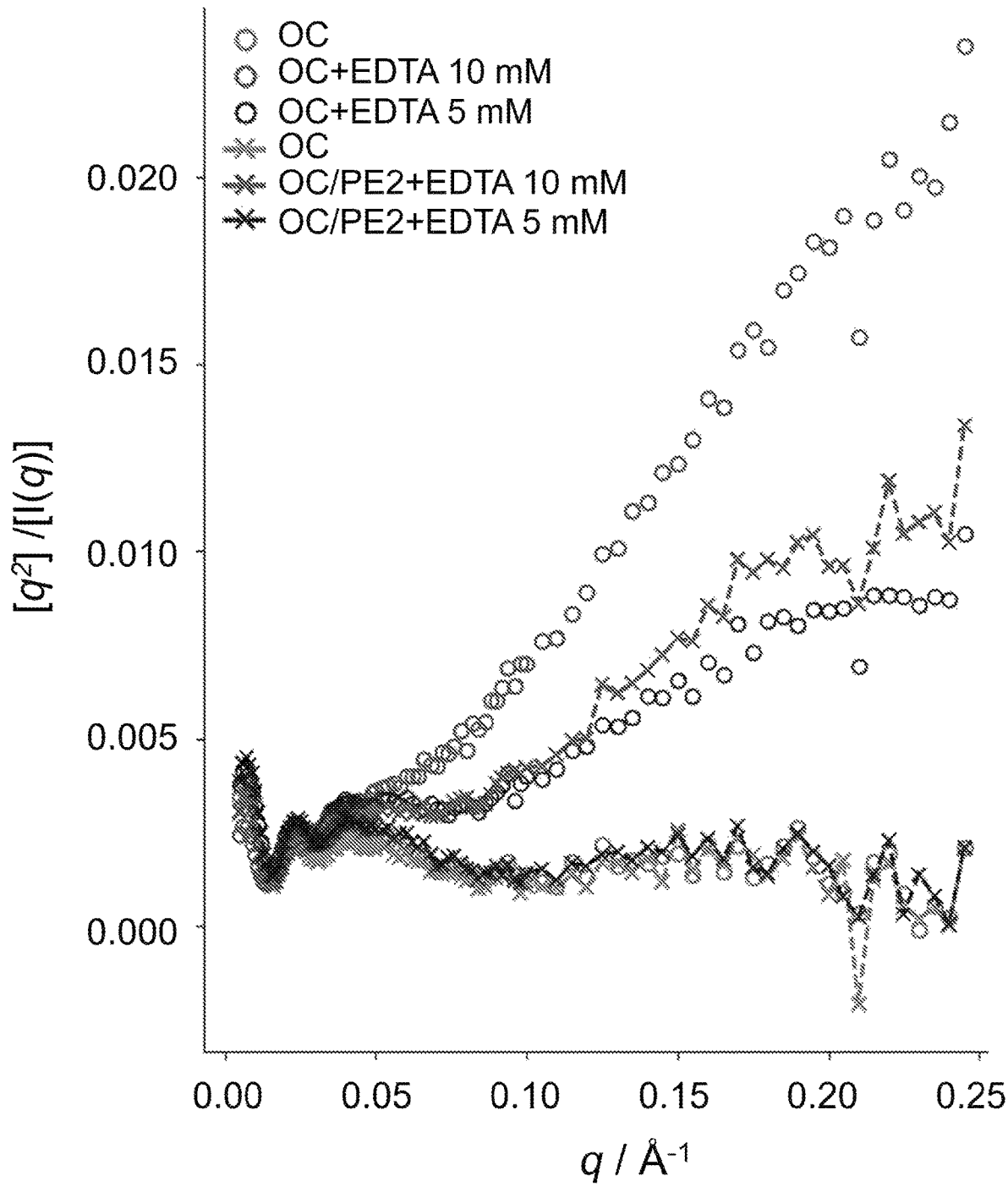
FIG. 30 Kratky analysis of SAXS data in FIGS. 4F and G. Bare OCs appeared to be more flexible upon treatment with EDTA and did not plateau at higher q compared to the PE2-coated OCs.

Dynamic light scattering (DLS) and in situ small angle X-ray scattering (SAXS) were used to analyze the overall average size and structure of bare OCs and OC/PE2 in solution, respectively. Here, ethylenediaminetetraacetic acid (EDTA), a strong metal ion chelating reagent, was used to remove $Mg^{2+}$ from the solution, where TEM images showed that the extent of damaged OCs increased with the concentration of EDTA (FIG. 29). As shown in FIG. 4E, DLS revealed a broadened peak width when the bare OCs were treated with high concentration of EDTA (10 mM), indicating distorted OCs and increased structural heterogeneity. On the other hand, peak broadening was inhibited by PE2 coating, suggesting that OC stability was significantly improved in the presence of PE2. Similarly, SAXS showed that the q value at $0.021$ $Å^{-1}$, representing the shape factor of OCs, continued to shift toward the lower q-regime in the presence of EDTA (5 and 10 mM). While some destabilization was observed in OC/PE2 at higher amount of EDTA, it is clear that the structural changes of OCs were effectively inhibited by PE2 coating (FIGS. 4F and 4G). The flexibility or "unfoldedness" of the OC structures obtained from SAXS were also assessed using the Kratky analysis. As shown in FIG. 30, bare OCs became more flexible and did not plateau at higher q upon treatment with EDTA while this effect was inhibited by PE2 coating. These results were consistent with AGE and TEM imaging (FIG. 4A-C).

Figure 31:
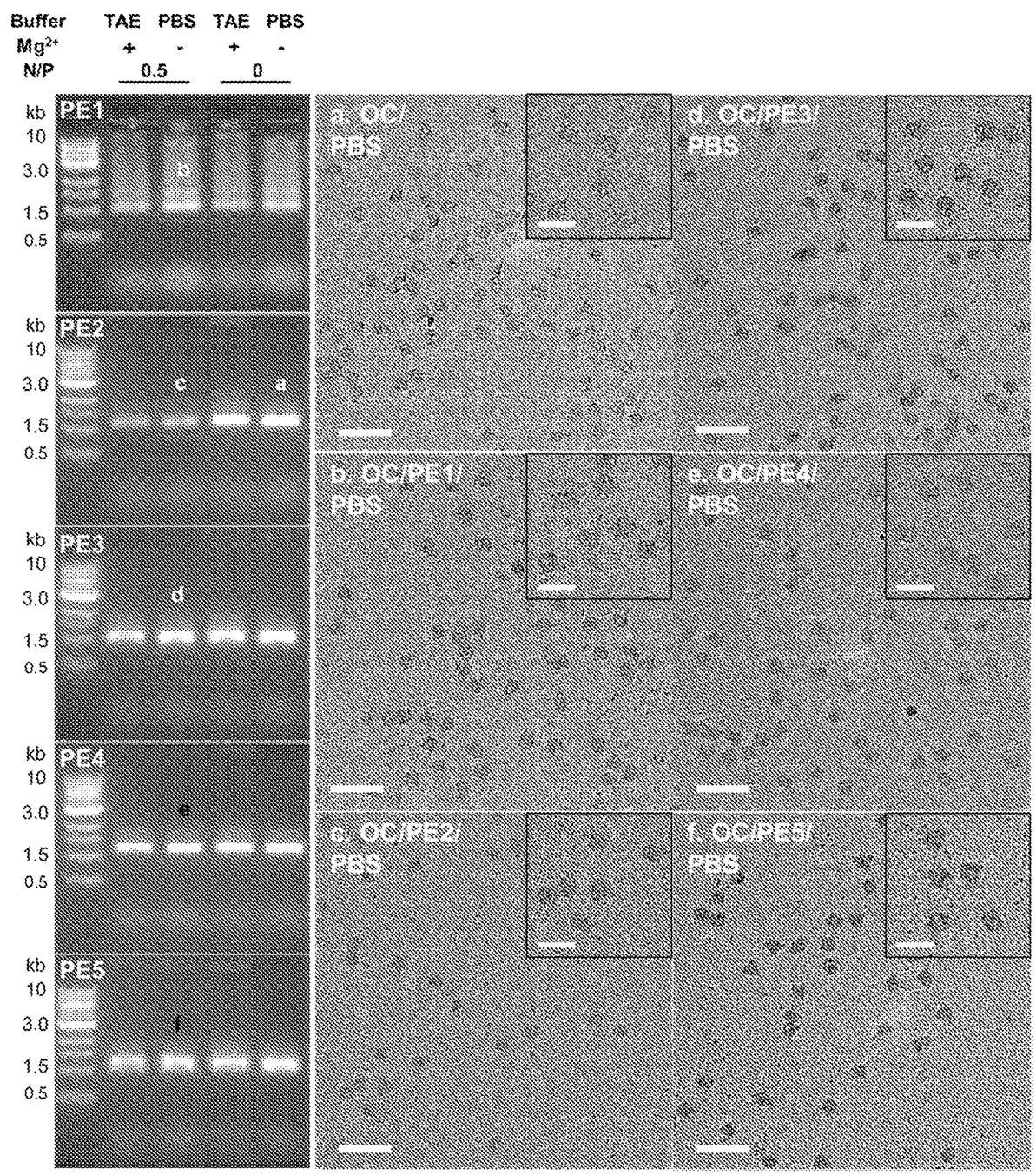
FIG. 31 Left: AGE of bare and peptoid-coated OCs in PBS buffer. The final concentration of $MgCl_2$ was 1.25 mM. Right: TEM samples were extracted from the agarose gels (bands a-f). Scale bars: 200 nm. The insets show magnified images of the OC structures (scale bars: 100 nm).

When bare OCs and OC/peptoid were dispersed in phosphate buffered saline (PBS) at low $Mg^{2+}$ content, all OC/peptoid exhibited more stable structures compared to those observed in TAE buffer (FIG. 31). This was likely due to the Na+ in PBS buffer compensated the loss of $Mg^{2+}$ and assisted the stability of OC structures.

Figure 5A:
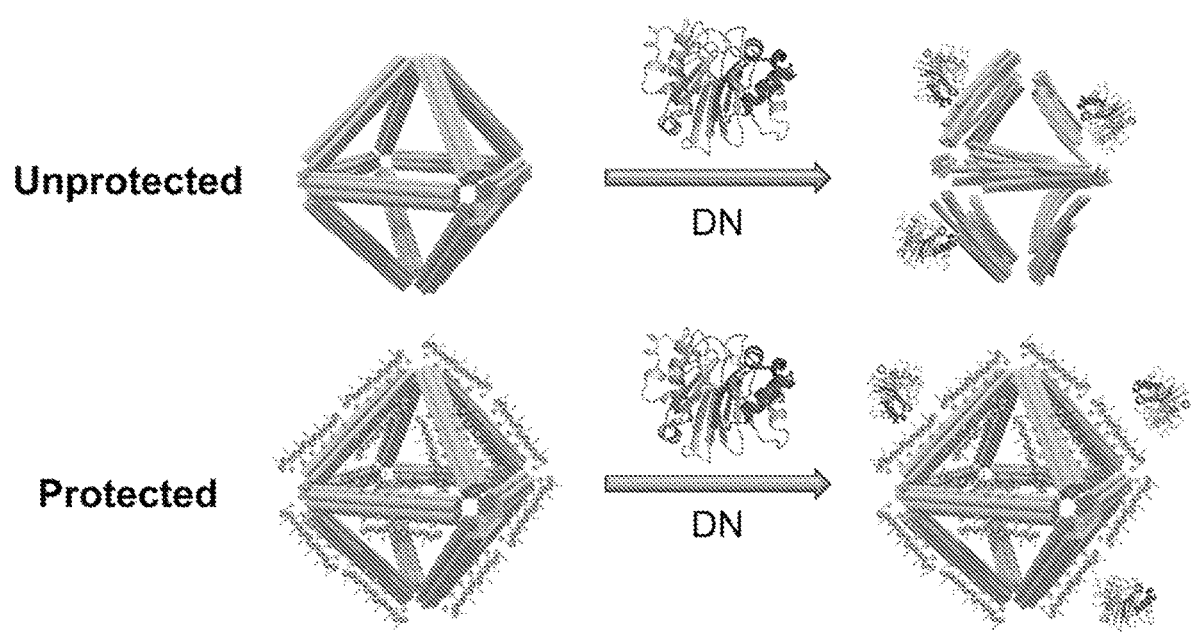
FIG. 5. Analysis of peptoid-coated OCs in the presence of deoxyribonuclease (DN). (A) Schematic view showing peptoid-coated OCs (OC/peptoid) were protected against DN (image obtained from PDB: 2DNJ) degradation. (B) TEM images show bare OCs and OC/peptoid (N/P: 0.5) in solution containing DN of 15 g/mL. Imaging was performed on samples extracted from the agarose gel (scale bars: 200 nm). The insets show magnified images of the OC structures (scale bars: 100 nm).
Figure 5B:
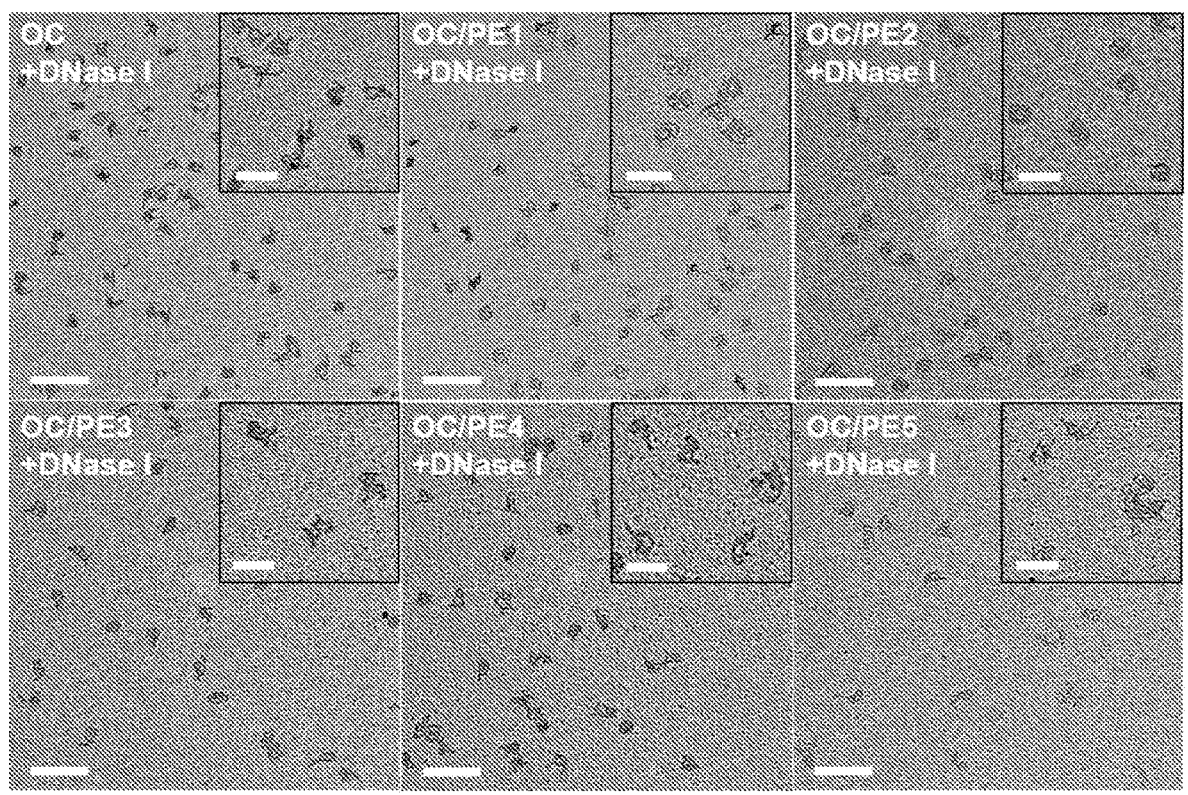
Figure 32:
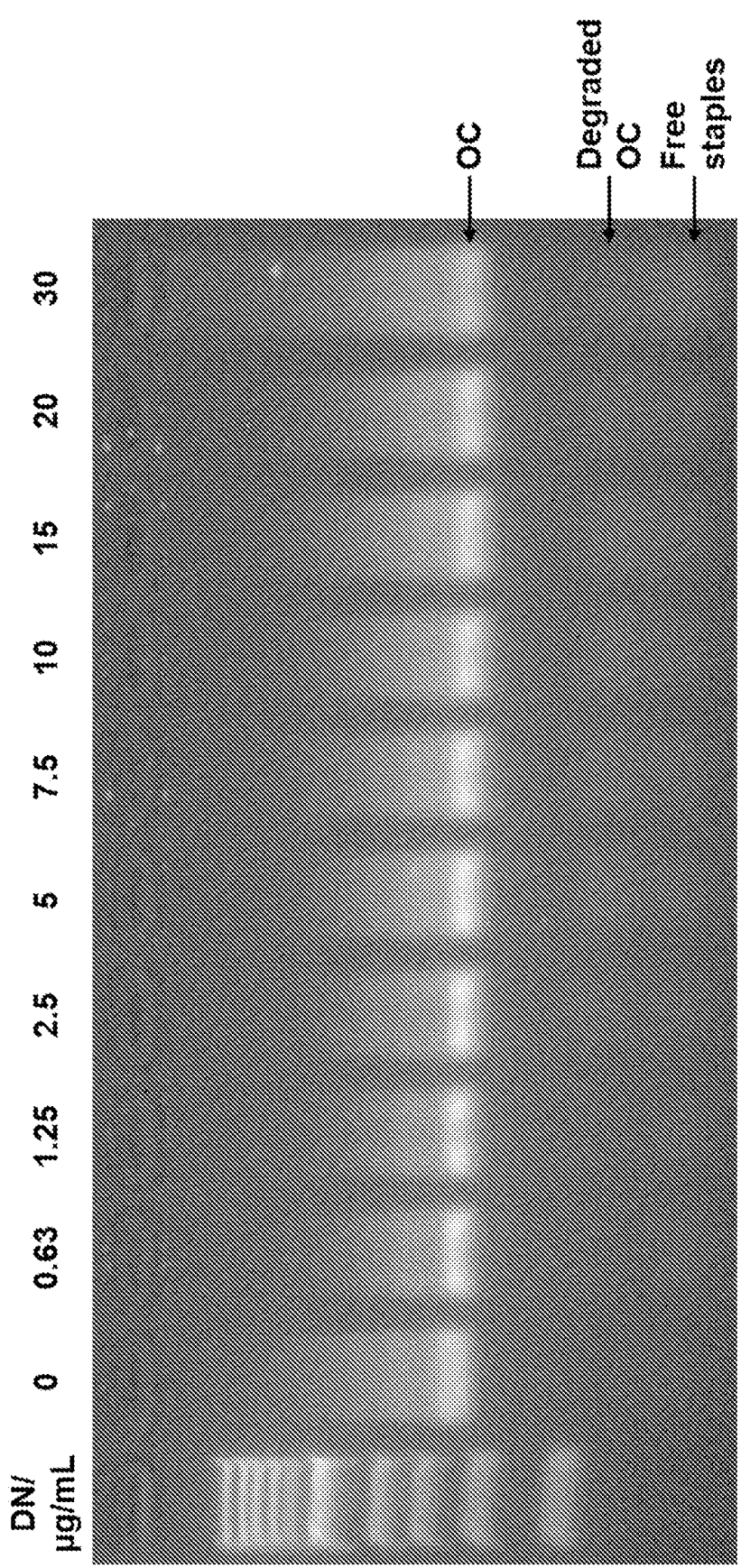
FIG. 32 AGE of OCs in the presence of different concentrations of deoxyribonuclease I (DN). Degradation of OC nanostructures by DN was shown by the electrophoretic shift toward the end of lower molecular weight and the presence of new bands representing degraded OCs.
Figure 33:
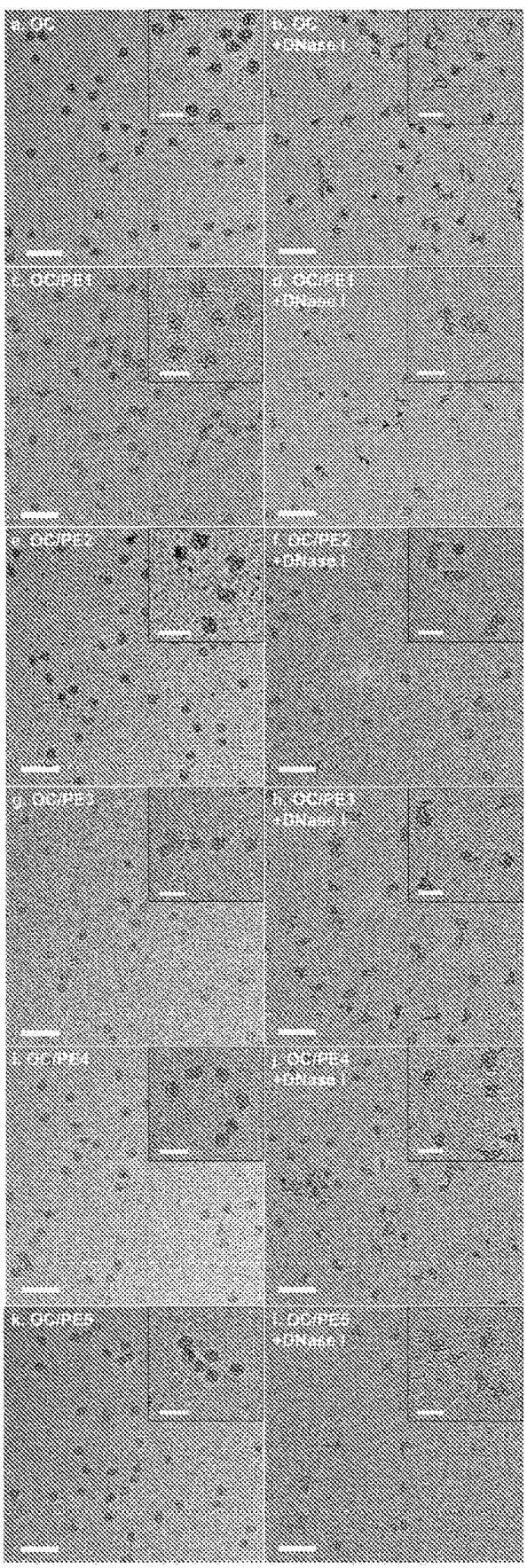
FIG. 33 TEM images of bare OCs and peptoid-coated OCs in the absence (left) and presence of DN (15 µg/mL, right). The samples were extracted from agarose gels. The concentration of $MgCl_2$ in TAE buffer was 12.5 mM (scale bars: 200 nm). The insets show magnified images of the OC structures (scale bars: 100 nm). Among the peptoid sequences, only OC/PE2 showed protection of the OC nanostructures.
Figure 34A:
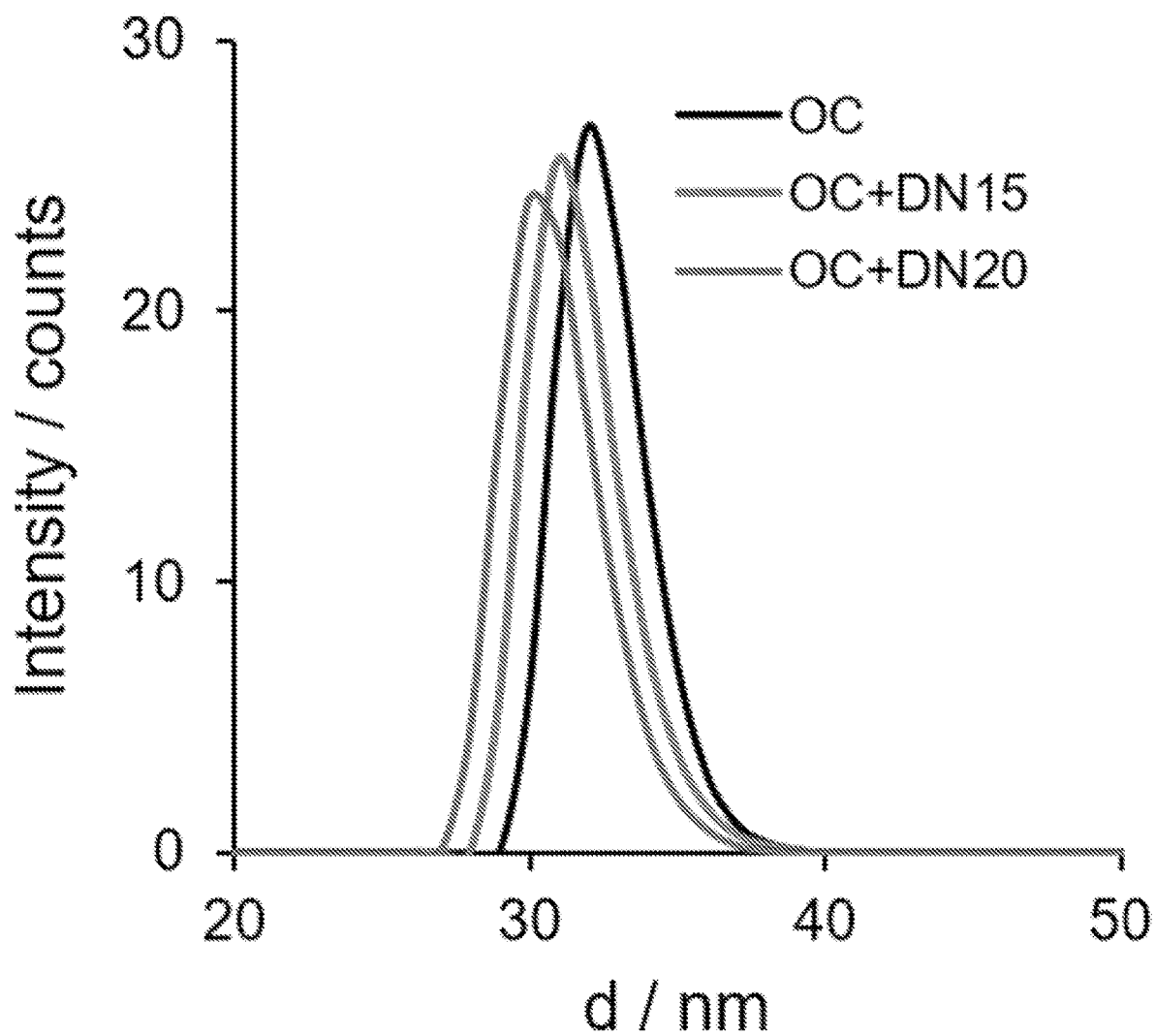
FIG. 34 DLS of (A) bare and (B) PE2-coated OCs (N/P: 0.5) in the presence of DN. The extent of size reduction represents degradation of the OC nanostructures by DN.
Figure 34B:
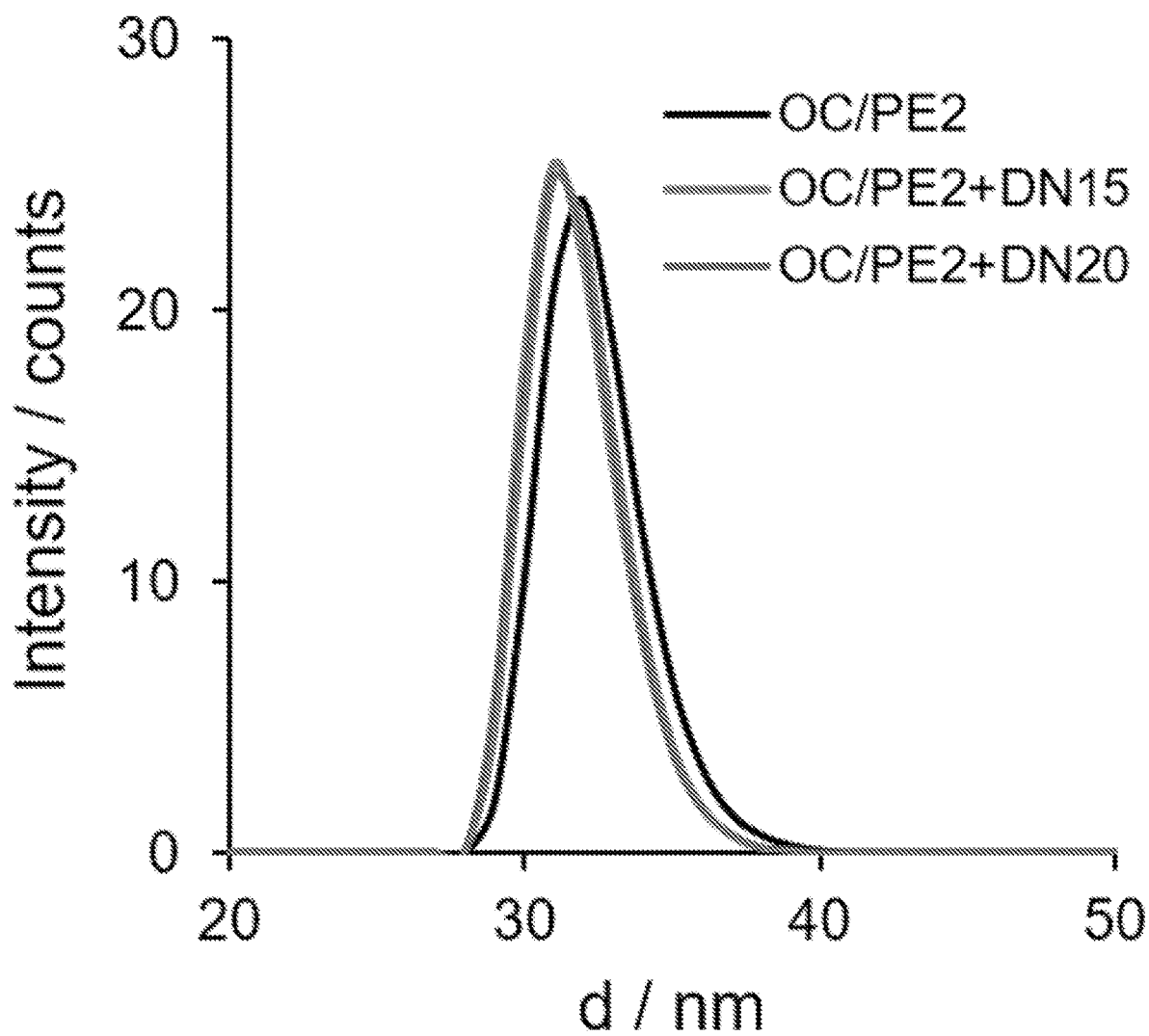

Next, the stability of OC/peptoid against enzymatic degradation was investigated in solution containing deoxyribonuclease I (DN). As shown in AGE, bare OCs could be degraded by DN at a concentration as low as 2.5 μg/mL, where the increased electrophoretic mobility indicated dissociation of staple strands from the OCs (FIG. 32). To demonstrate the protecting effect of peptoids, bare OCs and OC/peptoid were incubated with DN (15 μg/mL) for 30 min at 37° C. and inspected by TEM imaging (FIGS. 5 and 33). As expected, bare OC structures were degraded, and the octahedra shape was damaged after incubating with DN. In the presence of peptoids, the OC/PE2 structure remained intact and PE1, PE3, and PE4 show some extents of capability to preserve the origami structure. DLS also confirmed a smaller size reduction of the OC/PE2 at DN levels of 15 and 20 μg/mL compared to bare OCs (FIG. 34). Without wishing to be bound by theory, it is believed that the stronger multivalent interactions in the OC/PE2 system is required to prevent DN adsorption and degradation. The oligo-Nte of the peptoid sequences is also likely to provide steric shielding to reduce DN binding to the DNA backbone.

Figure 6A:
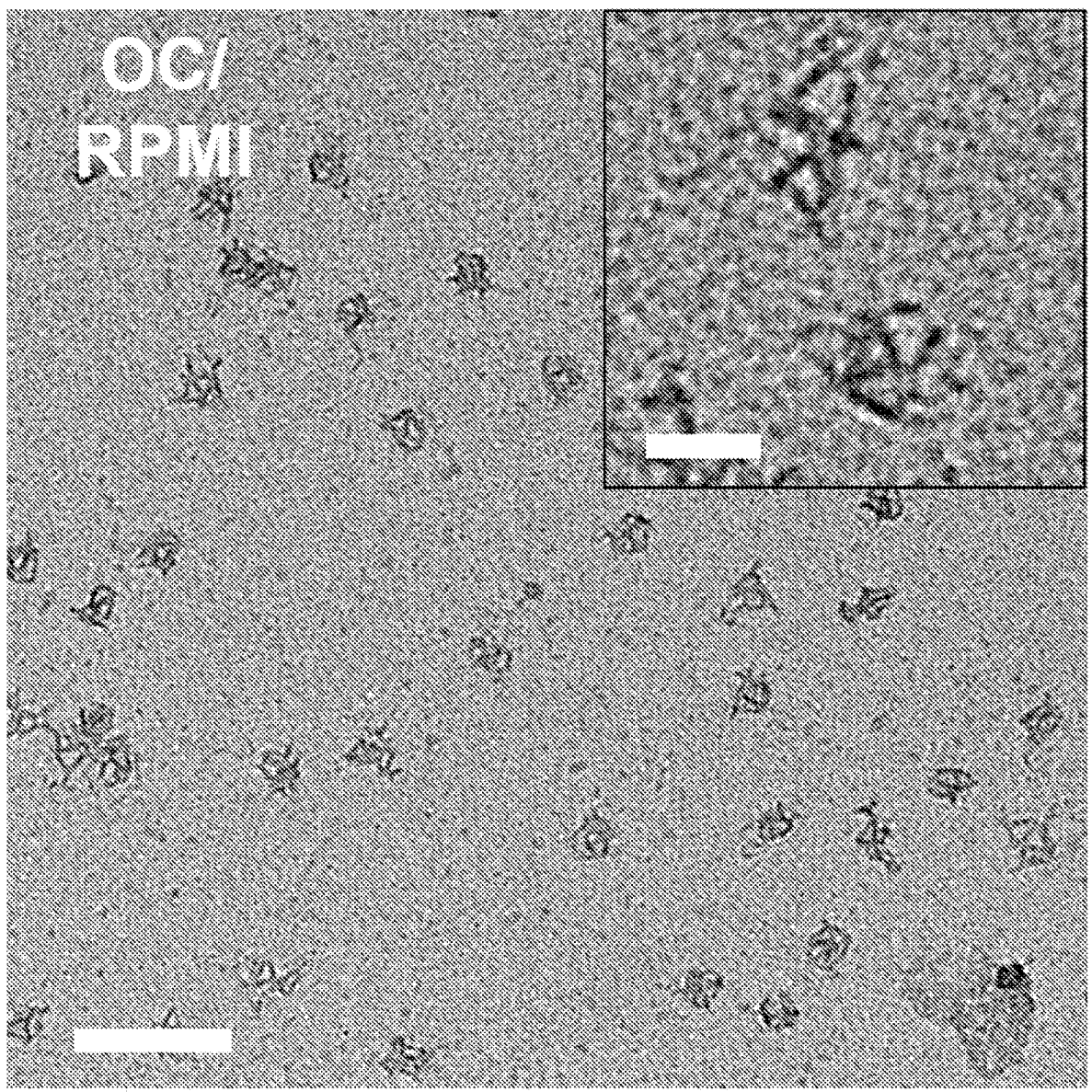
FIG. 6. Analysis of peptoid-coated OCs in cell media and presence of serum nuclease. TEM images show (A, C) bare OCs and (B, D) PE2-coated OCs (OC/PE2) in (A, B) Roswell Park Memorial Institute (RPMI) 1640 medium and (C, D) Dulbecco's Modified Eagle Medium (DMEM) containing 0%, 5%, and 10% of fetal bovine serum (FBS) and incubated for 24 h at 37° C. The final concentrations of $MgCl_2$ were 1.25 mM. Imaging was performed on samples extracted from the agarose gels (scale bars: 200 nm). The insets show magnified images of the OC structures (scale bars: 50 nm).
Figure 6B:
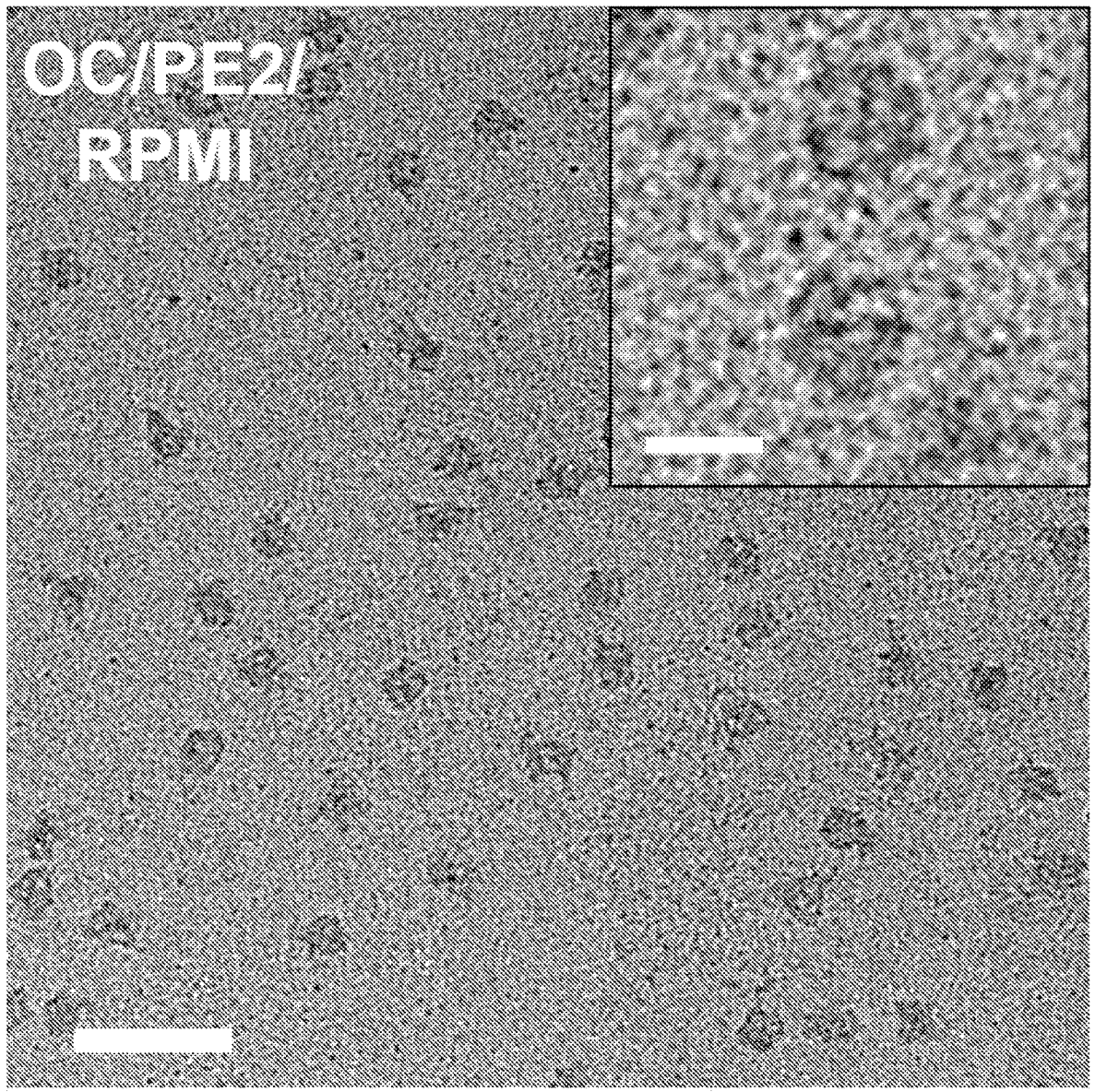
Figure 6C:
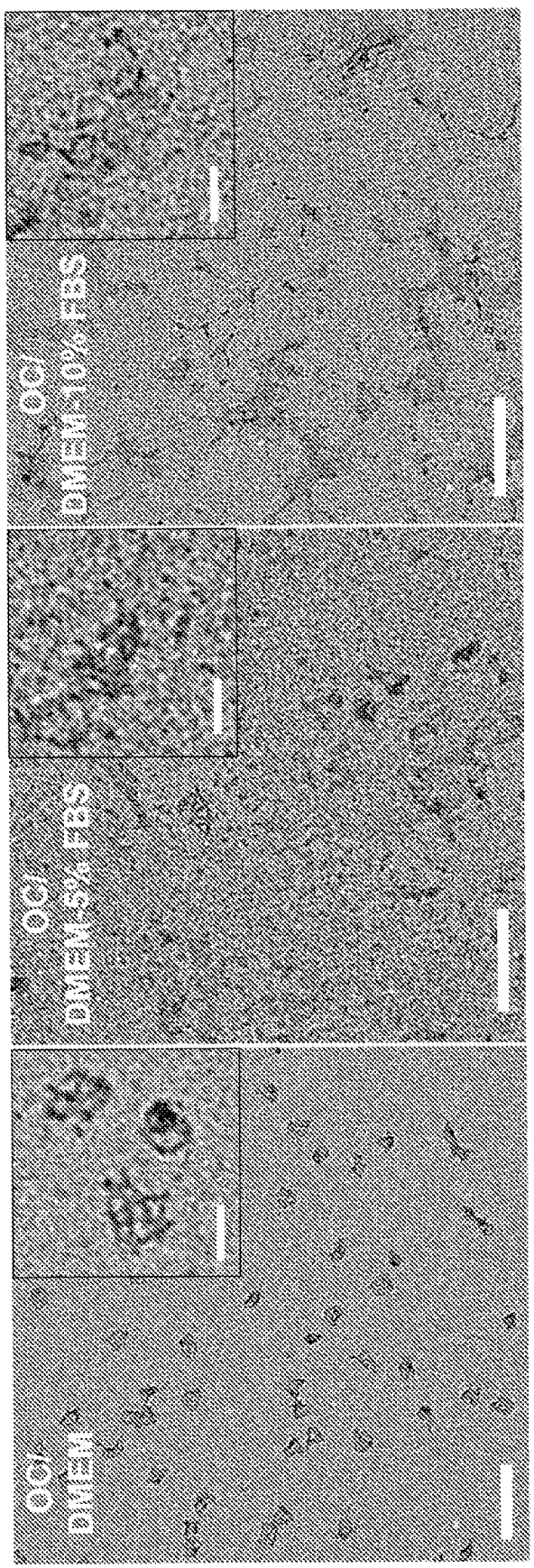
Figure 6D:
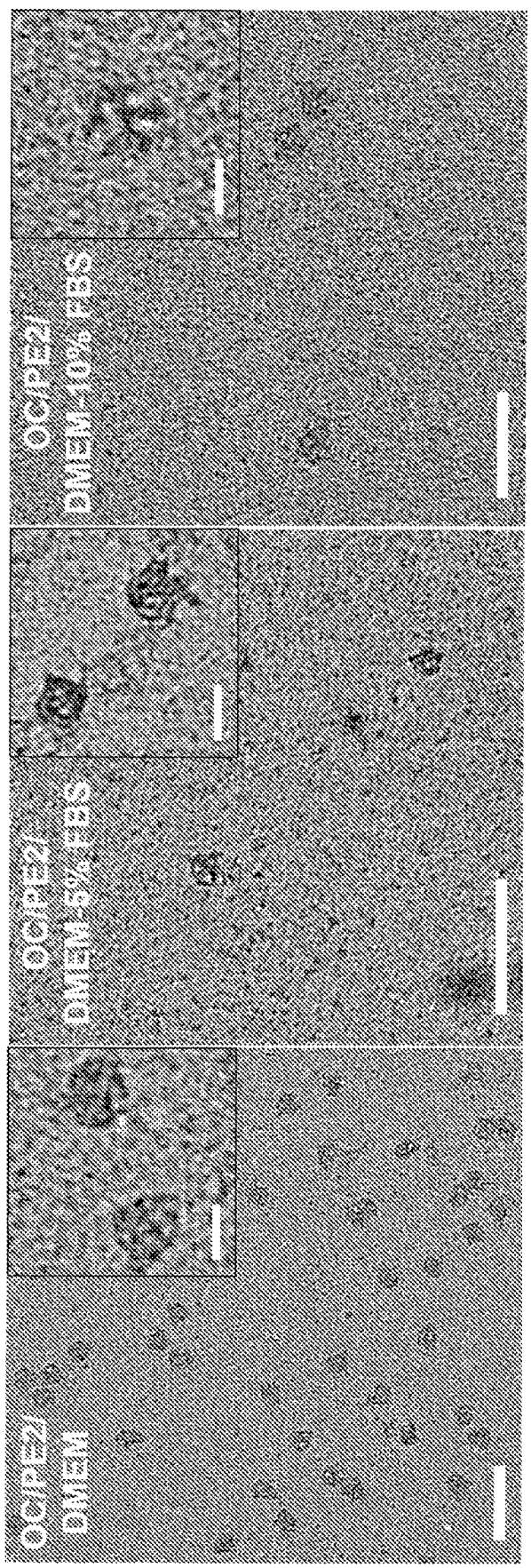
Figure 36:
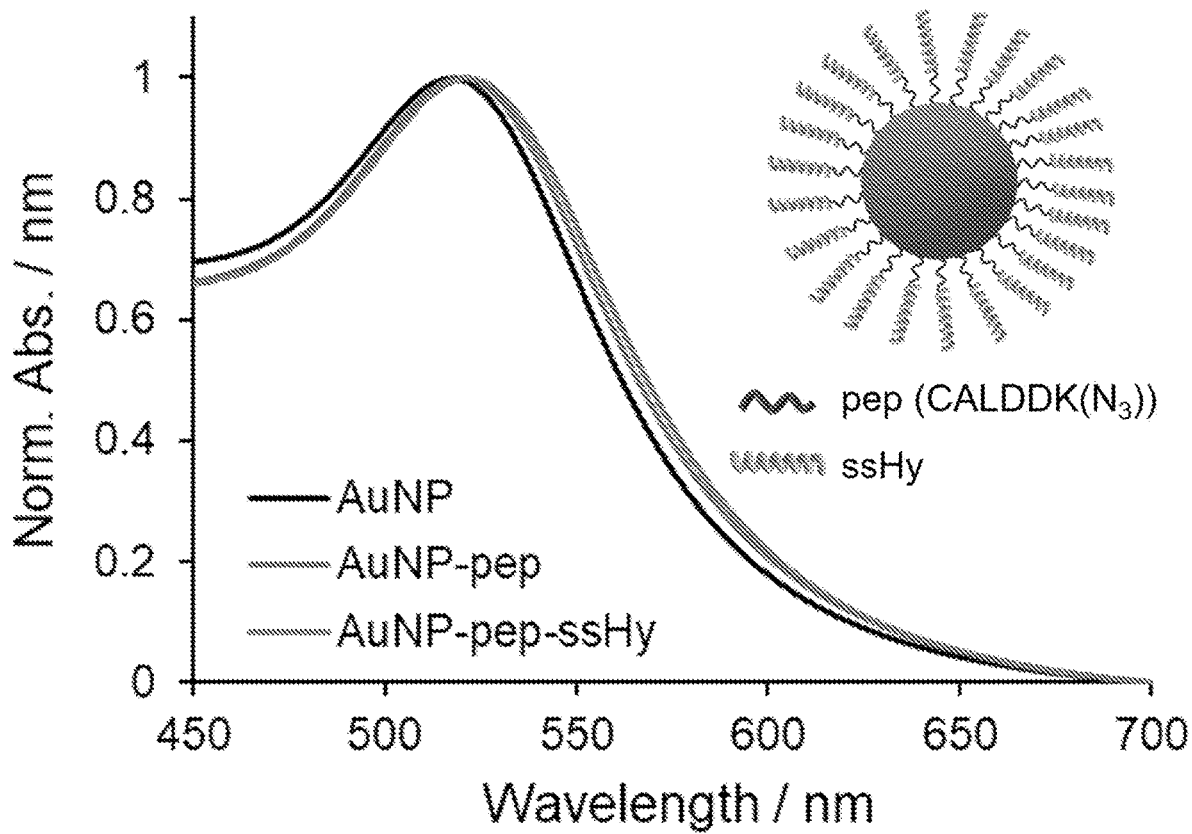
FIG. 36 UV-vis spectra of step-wise functionalization of 10 nm gold nanoparticles (Au NPs) with Cys-Ala-Leu-Asp-Asp-Lys(N3) (SEQ ID NO: 127) (pep) and followed by a DBCO-modified single-stranded DNA (ssDNA, 5'-TATGAAGTGATGGATGAT/3DBCO/), (SEQ ID NO: 1) which complemented with the eight ssDNAs located in the OCs.
Figure 37A:
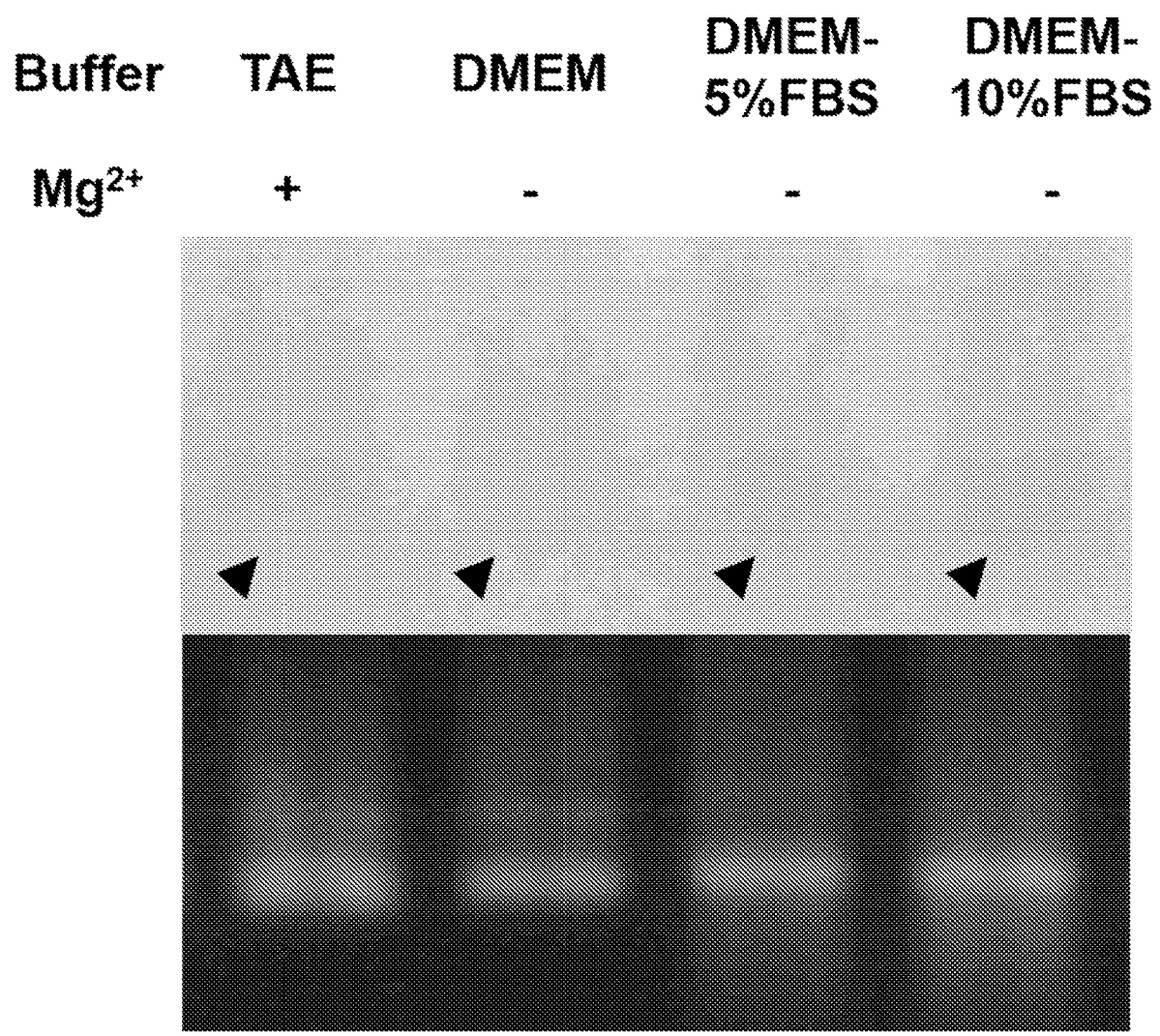
FIG. 37 (A) AGE and (B) TEM images show PE2 coated and Au NP-encapsulated OCs in DMEM media containing FBS (0%, 5%, and 10%). AGE was performed and imaged by white light (top) and UV light (bottom). TEM samples were extracted from the agarose gels (scale bars: 200 nm). The insets show magnified images of the OC structures (scale bars: 50 nm).
Figure 37B:
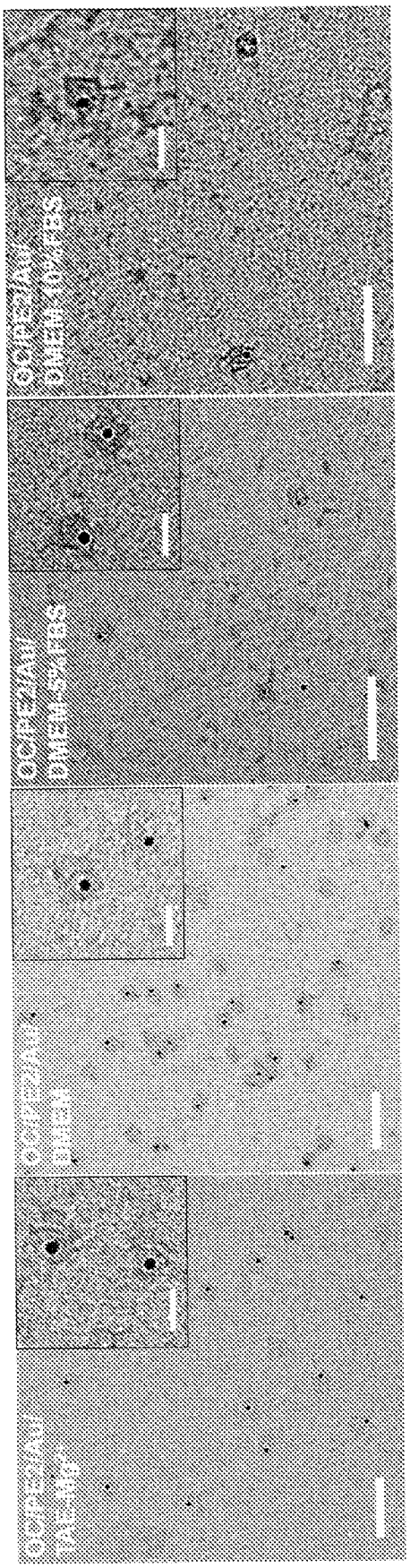
Figure 38A:
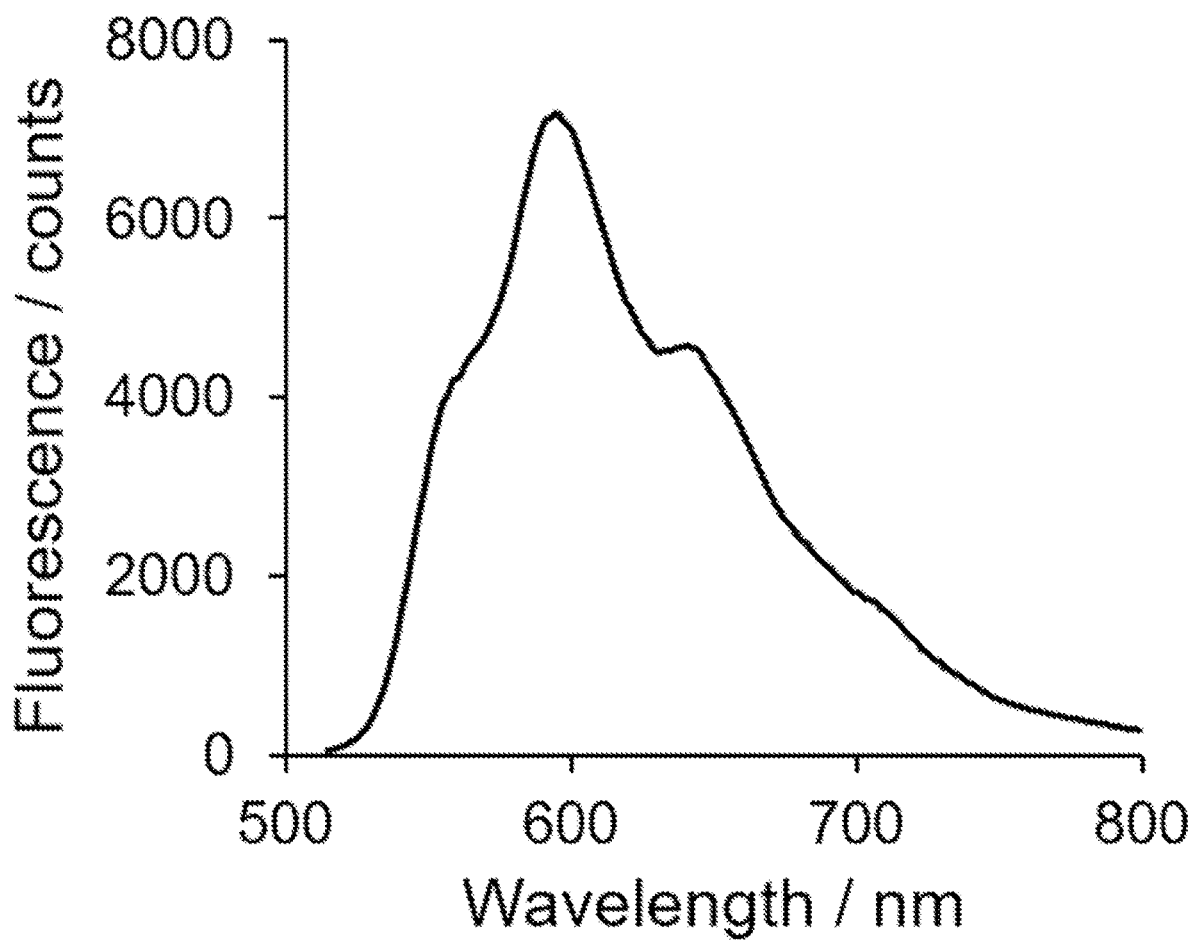
FIG. 38 (A) Fluorescence spectrum of doxorubicin (Dox, 100 µM) in PBS buffer. Excitation and emission wavelengths were measured at 485 nm and 510-800 nm, respectively. (B) Fluorescence signals at 597 nm were plotted against Dox concentrations ([Dox]). A linear relationship between fluorescence signal and [Dox] was observed below 3.2 µM.
Figure 38B:
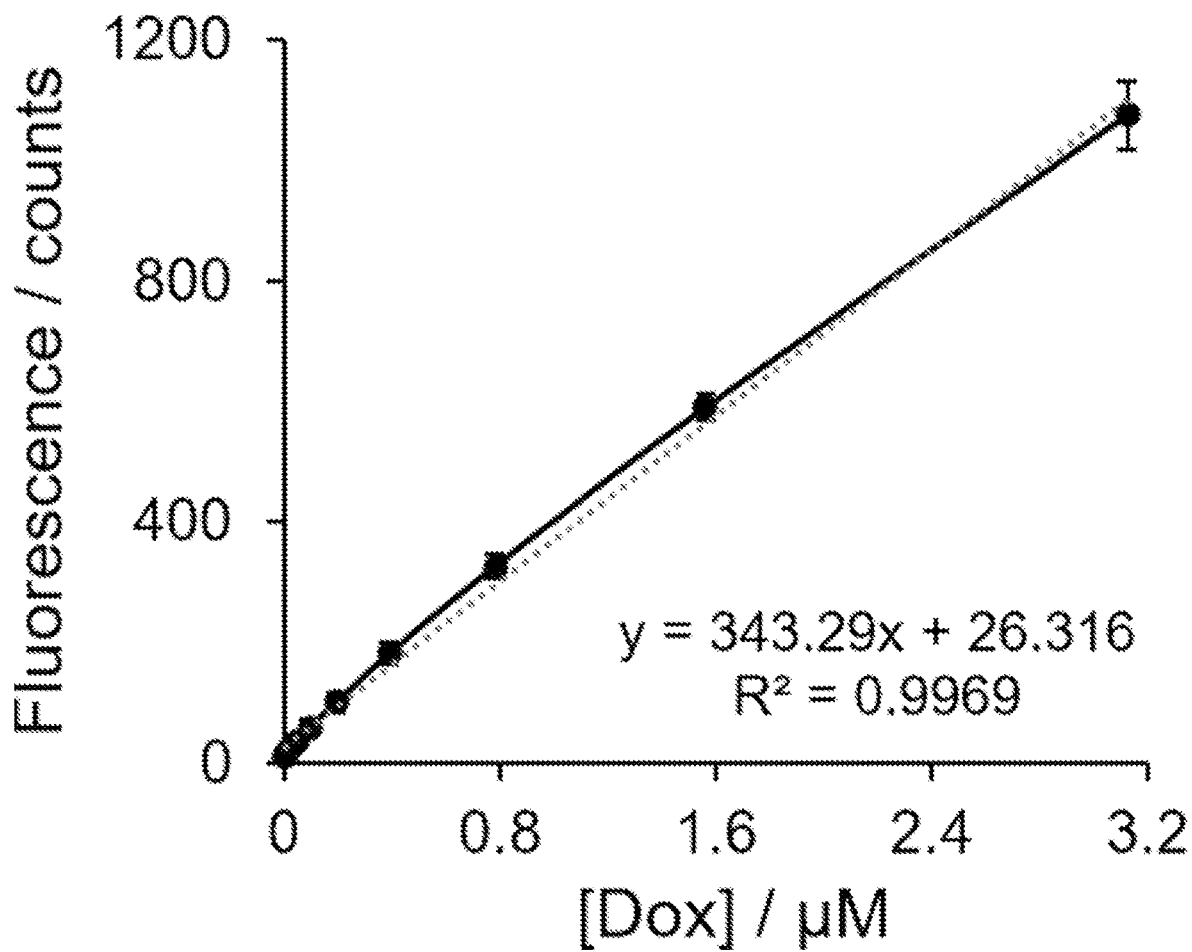
Figure 39:
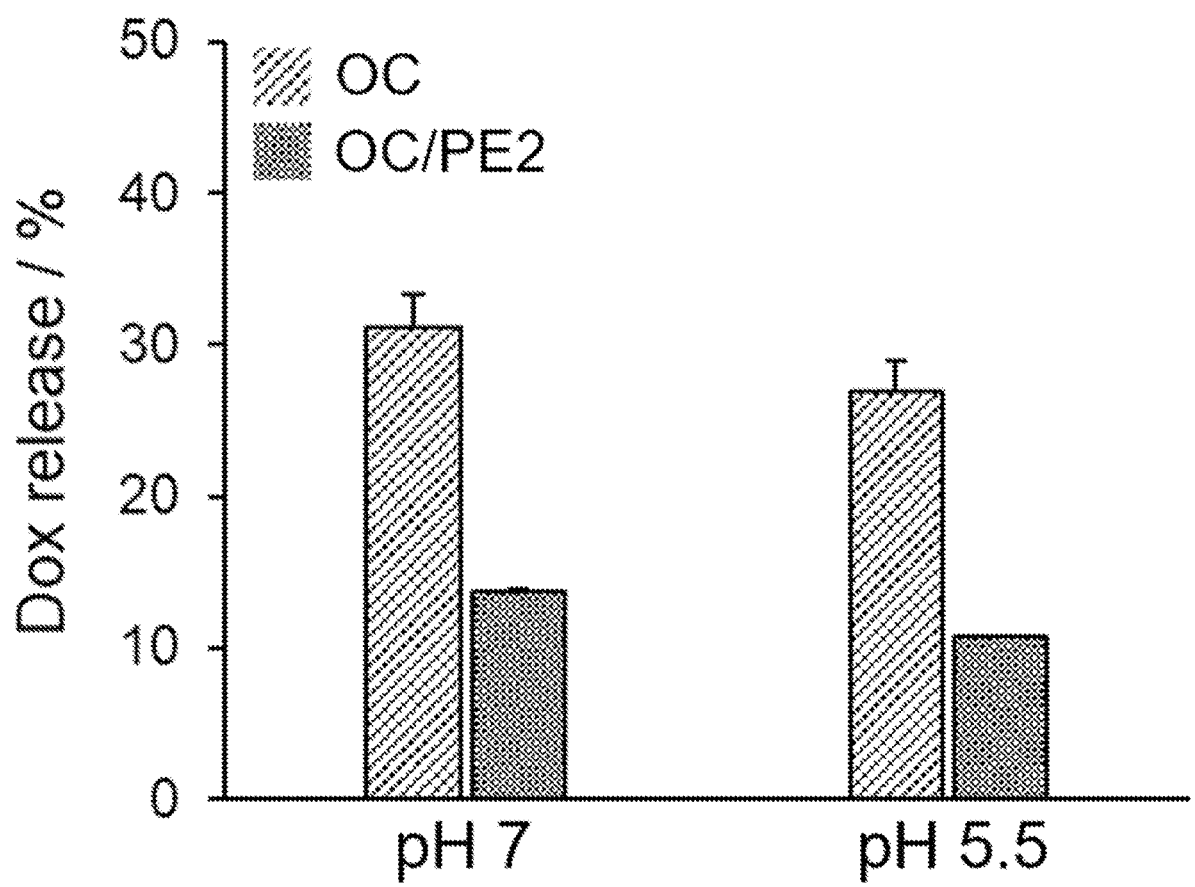
FIG. 39 Plot showing the total Dox release from bare OCs and OC/PE2 (n=2). The Dox release was determined by the remaining fluorescence of OCs after incubating in PBS buffer at 37° C. for 48 h. A reduction of total Dox release from the OC/PE2 compared to bare OCs was observed at both pH 7 and 5.5.

Since PE2 exhibited the best protection of OC structures, the stability of OC/PE2 in cell media was investigated, including the Dulbecco's Modified Eagle Medium (DMEM) (FIGS. 6C, 6D and 35) and Roswell Park Memorial Institute (RPMI) 1640 medium (FIGS. 6A and 6B) in a low $Mg^{2+}$ condition. TEM images showed that OC/PE2 (N/P: 0.5) were protected after incubating in both the RPMI and DMEM media for 24 h at 37° C., while the OC structures were distorted without PE2 coating (FIGS. 6 and 35). In the presence of fetal bovine serum (FBS), the combination of $Mg^{2+}$ depletion and FBS nuclease led to enhanced structural damages of bare OCs beyond recognition (FIG. 6C). On the other hand, TEM imaging showed presence of stable OC/PE2 in the DMEM-FBS media although reduced numbers of OCs were found after incubation for 24 h at 37° C. (FIG. 6D). The protection is expected to be further improved by increasing the length of PE2 sequence, enabling stronger peptoid-DNA interactions whilst preventing OC aggregation and condensation, which requires further experimentation. In an independent experiment, 10 nm gold nanoparticles (Au NPs) were encapsulated in the OC structures by surface functionalization of Au NPs with single-stranded DNAs (ssDNAs) that complemented eight ssDNA linkers located in the OCs prior to PE2 coating (FIG. 36). As shown in FIG. 37, the Au NPs remained encapsulated in the OC/PE2 after incubation in the DMEM and DMEM-FBS media for 24 h at 37° C., which supported the protection by PE2 coating. The resistance of OC/PE2 against $Mg^{2+}$ depletion, change in buffer component and nuclease degradation makes it an attractive candidate for biomedical applications. In fact, OC has a size of ~60 nm which is ideal for encapsulation/immobilization of biomolecules and drugs of a range of sizes. Doxorubicin (Dox), a common anti-cancer drug used in chemotherapy, was loaded to bare OCs and OC/PE2 (N/P: 0.5) and measured its release from the OC structures. Dox-loaded DNA origamis have been reported in the literature, where the molecule intercalates the DNA backbone and releases from the origamis structures over time (24-26). The intrinsic Dox fluorescence can be used to measure the loading and release from the OCs (24-26), where the fluorescence intensity was proportional to the Dox concentration in the sub-micromolar range (FIG. 38). In our case, -10% of Dox was loaded onto the OCs. As shown in FIG. 39, a reduction of the total Dox release from the OC/PE2 (~10% release) compared to bare OCs (~30% release) was observed at both pH 7 and 5.5 after incubating for 48 hrs at 37° C. in PBS buffer. This property may be useful for modulating the desired release during the drug delivery processes.

Figure 7A:
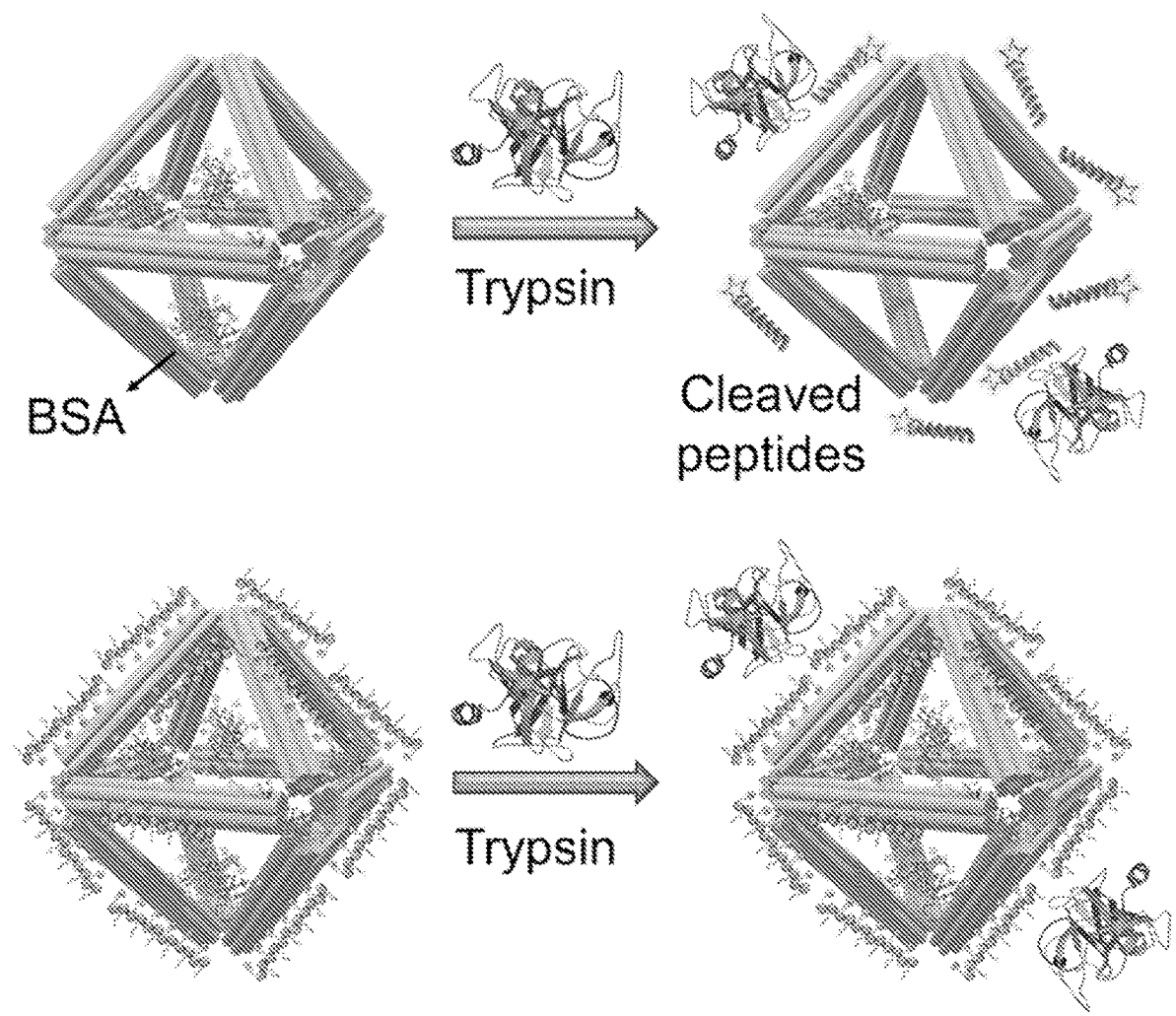
FIG. 7. Protection of protein-encapsulated in OCs by PE2 coating. (A) Schematic view showing that OC/PE2 reduce trypsin (image obtained from PDB: 1S0Q) digestion of fluorescein labeled BSA encapsulated in the OCs. (B) Fluorescence kinetics show enhanced fluorescence of the fluorescein labeled BSA upon trypsin cleavage ($\lambda_{ex}$=490 nm and $\lambda_{em}$=525 nm, 37° C.).
Figure 7B:
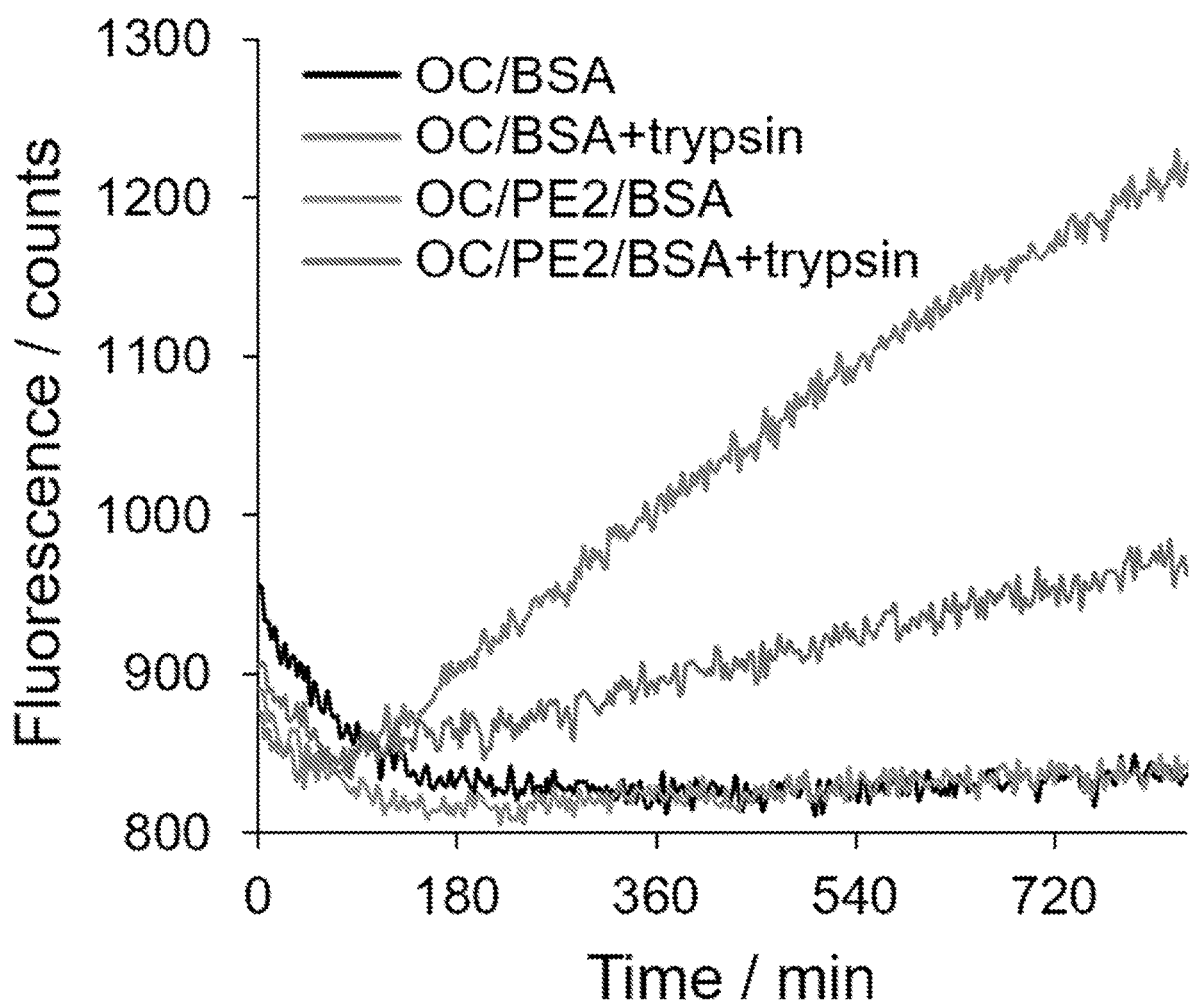
Figure 40:
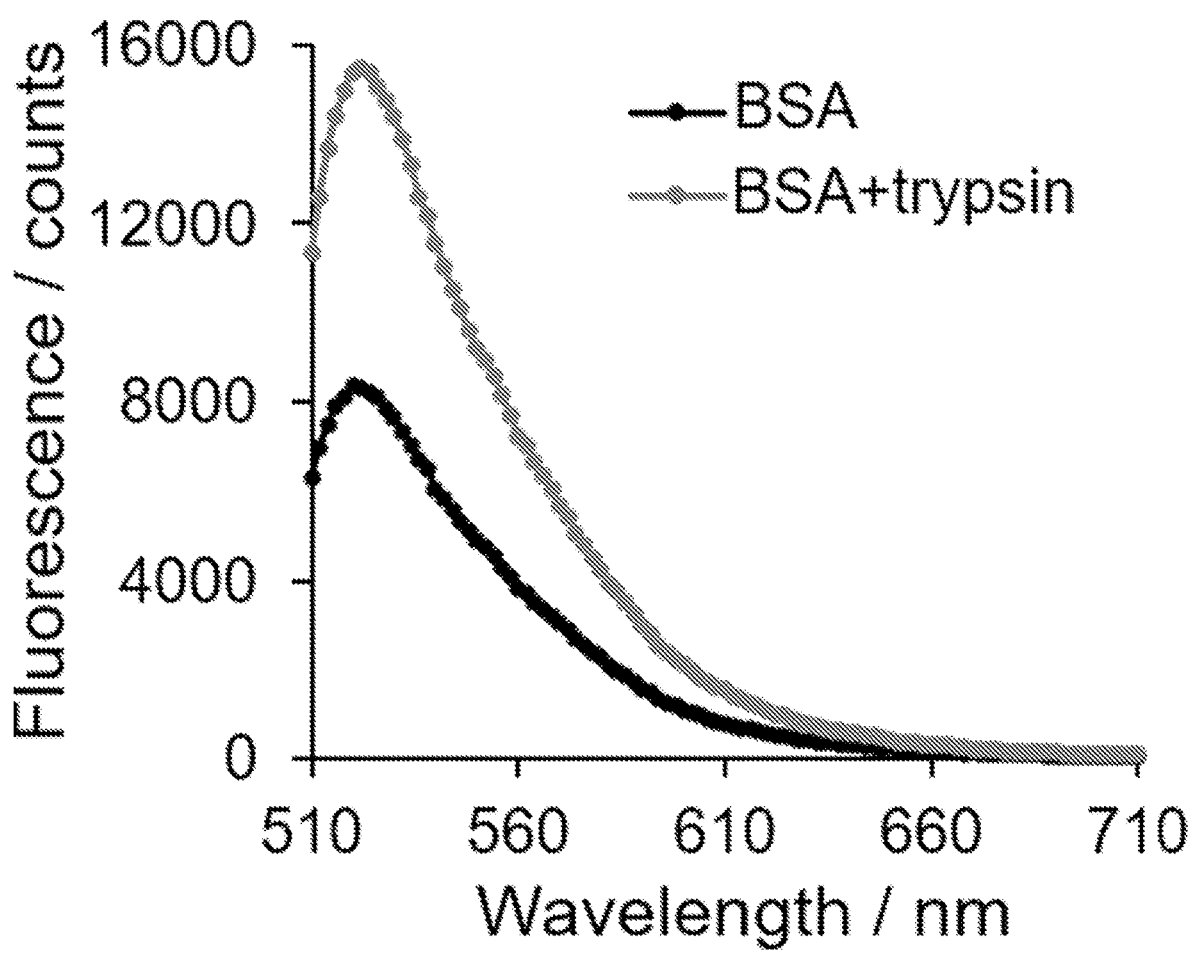
FIG. 40 Fluorescence enhancement of fluorescein labeled BSA (80 nM) in the presence and absence of trypsin (50 nM). The concentration of $MgCl_2$ in TAE buffer was 12.5 mM. The solution was incubated overnight (>12 h) at 37° C. prior to fluorescence measurement ($\lambda_{ex}$=490 nm and $\lambda_{em}$=510-800 nm).
Figure 41:
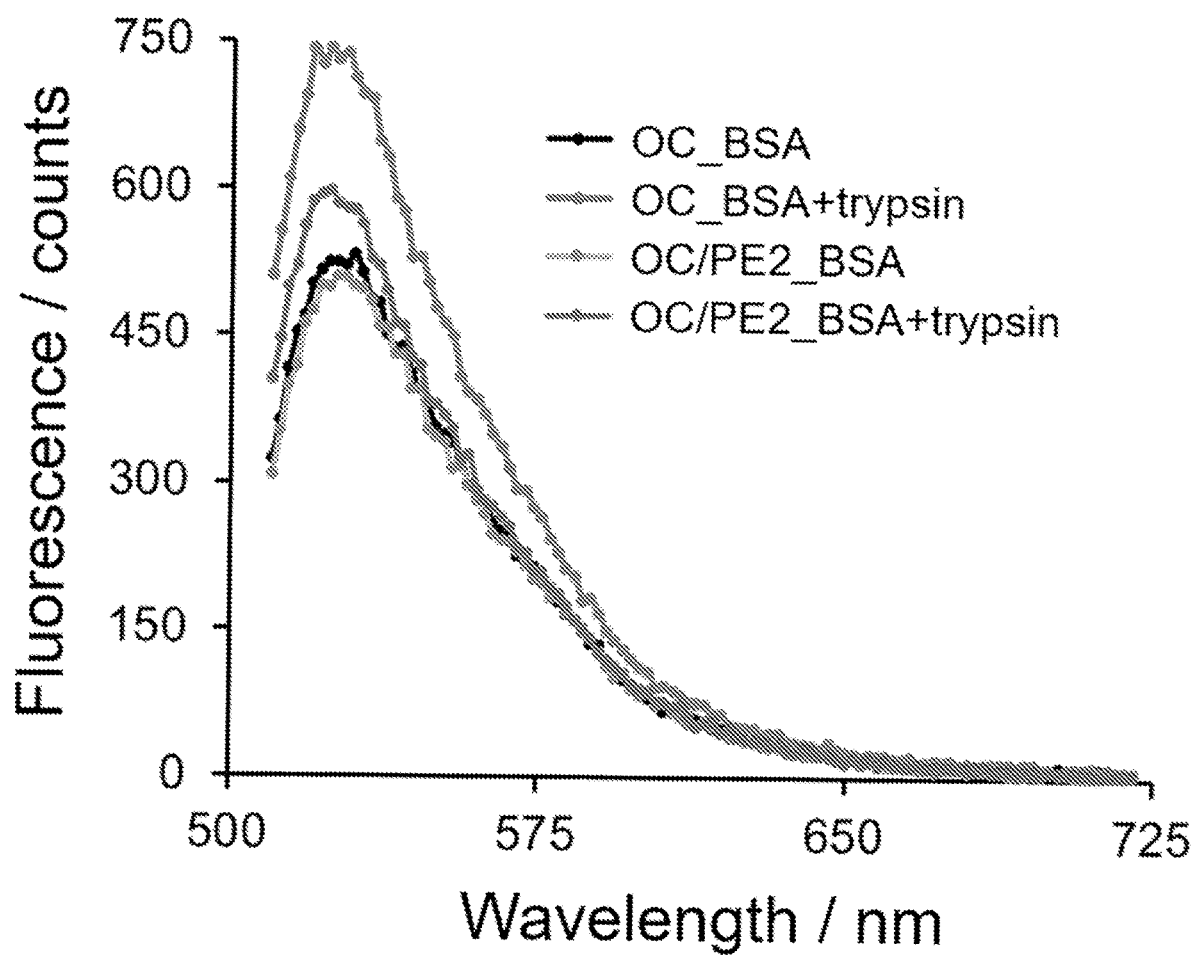
FIG. 41 Fluorescence spectra of fluorescein-labelled BSA encapsulated in bare and PE2-coated OCs (20 nM) in the presence and absence of trypsin (50 nM). The concentration of $MgCl_2$ in TAE buffer was 12.5 mM. The mixtures were incubated at 37° C. for ~15 h prior to fluorescence measurement ($\lambda_{ex}$=485 nm and $\lambda_{em}$=510-800 nm).
Figure 42:
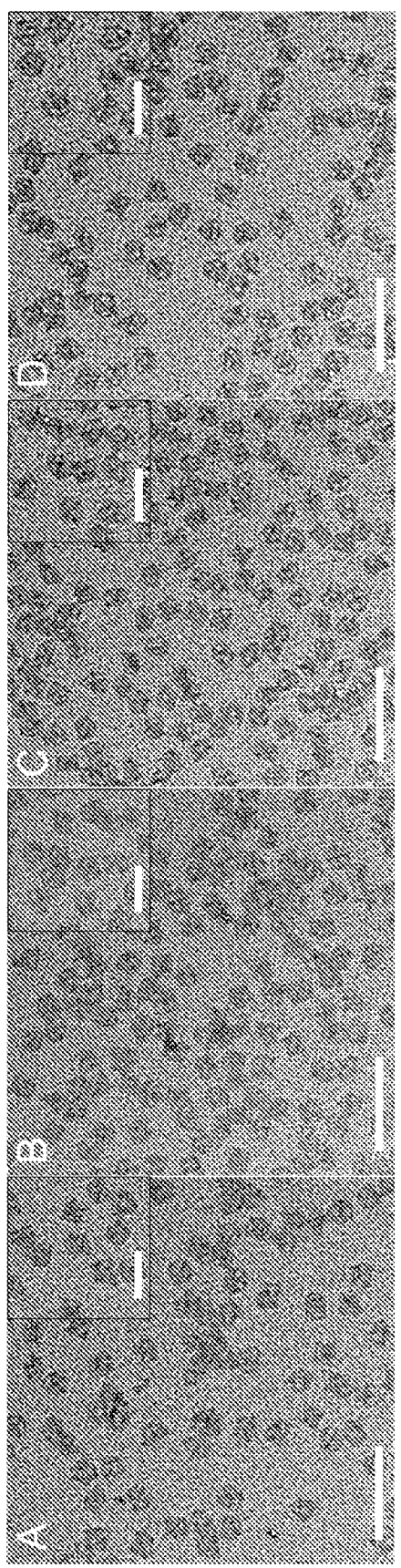
FIG. 42 TEM images of OC in the presence of different trypsin concentrations: (A) 5 µM, (B) 0.5 µM, (C) 0.1 µM and (D) 0 µM (scale bars: 200 nm). The insets show magnified images of the OC structures (scale bars: 100 nm).

It was demonstrated that surface coating of OCs with PE2 provides protease resistance to proteins encapsulated in the OC structures. Here, bovine serum albumin (BSA) was modified with fluorescein and encapsulated in the bare OCs and OC/PE2 via DNA hybridization (see Method). The fluorescence signal was self-quenched due to multiple fluorescein labeled on a single BSA (60). Fluorescence recovery was attained in the presence of trypsin, which catalyzed hydrolysis of BSA preferentially at sites of lysine and arginine (61), and subsequently released the fluorescein-conjugated fragments (FIG. 7A). In the presence of trypsin, an 85% increase in the fluorescence intensity was observed in the fluorescein labeled BSA in solution (FIG. 40). This fluorescence enhancement representing trypsin digestion of the target BSA sequences was reduced to ~40% by protein encapsulation inside the OCs and further reduced to ~14% by PE2 coating on the OC surface (FIG. 41). In addition, the fluorescence kinetics assay showed a slower trypsin digestion with PE2 coating (FIG. 7B). Peptoid coating can increase protection of biological cargos inside OCs from solution environments. Note that higher levels of trypsin (0.1-5 µM) in the OC solution were examined by TEM imaging and no observable effect to the OC structures was found (FIG. 42).

Figure 8A:
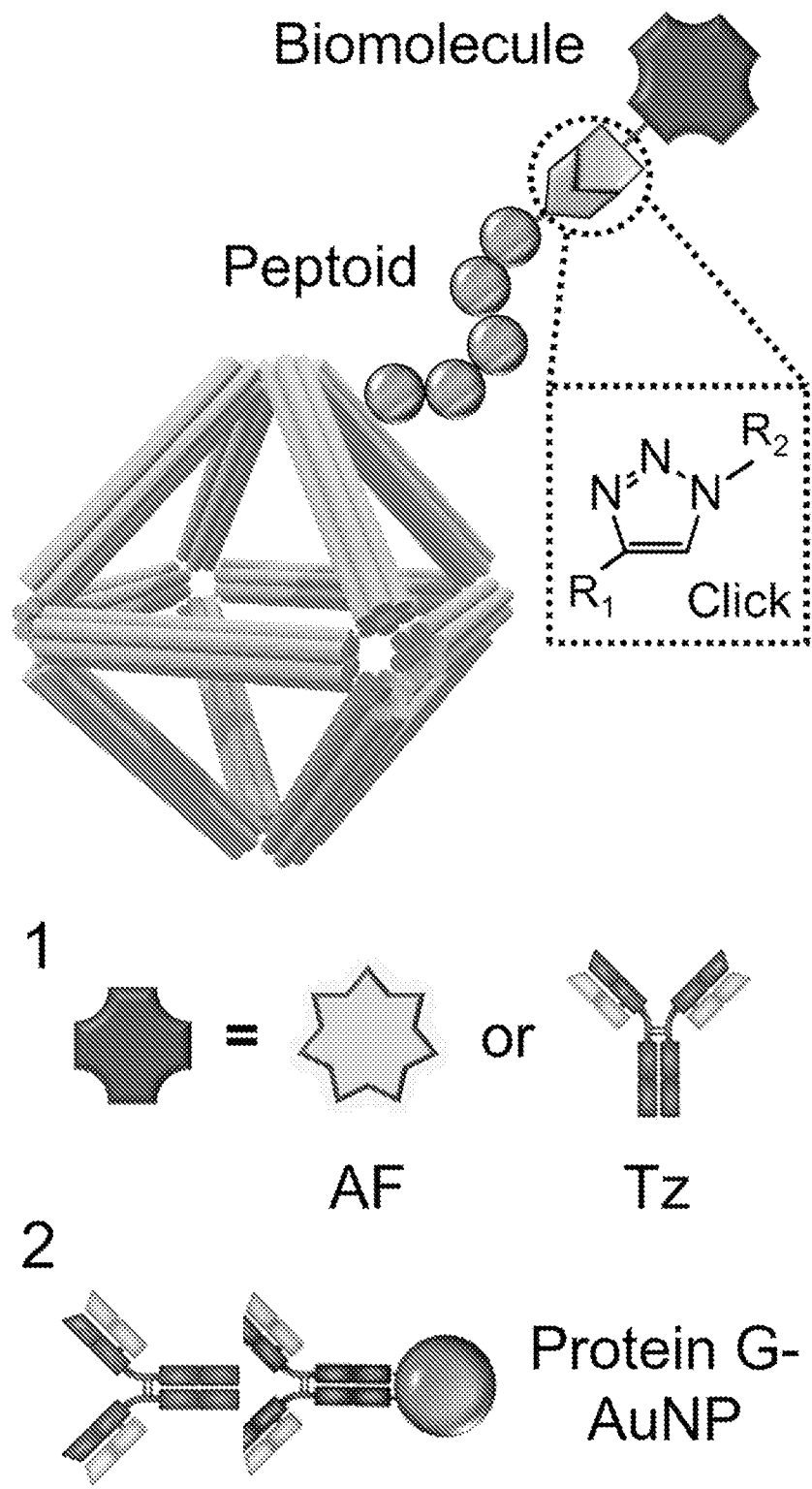
FIG. 8. Surface functionalization of peptoid-stabilized OCs with antibody and fluorophore. (A) Schematic view showing alkyne-modified peptoids conjugates azide-modified cargos through click chemistry. Here, azide fluor 488 (AF) and Trastuzumab (Tz) were used as the presenting cargos (label 1). (B) Chemical structure of PE8 and PE9. (C) Fluorescence assay of bare OCs, OC/PE8-AF and OC/PE9-AF extracted from the agarose gel ($\lambda_{ex}$=485 nm and $\lambda_{em}$=510-800 nm). (D) TEM images show surface coating of OCs with PE8-Tz and PE9-Tz. The samples were labeled with immunogold (label 2 in A) prior to TEM imaging (scale bars: 50 nm).
Figure 8B:
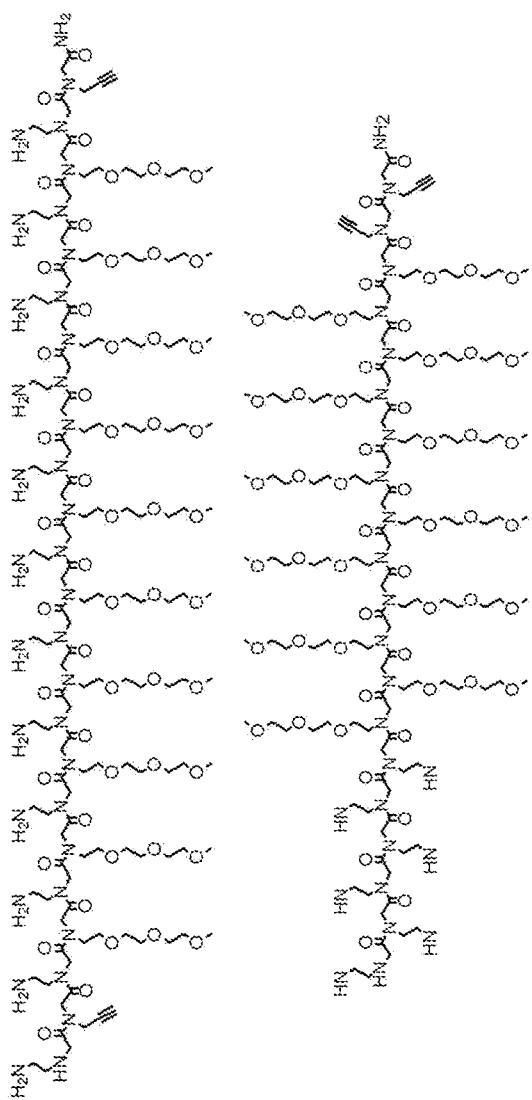
Figure 8B:
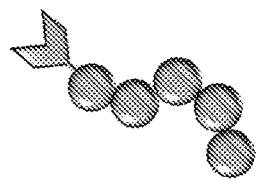
Figure 8C:
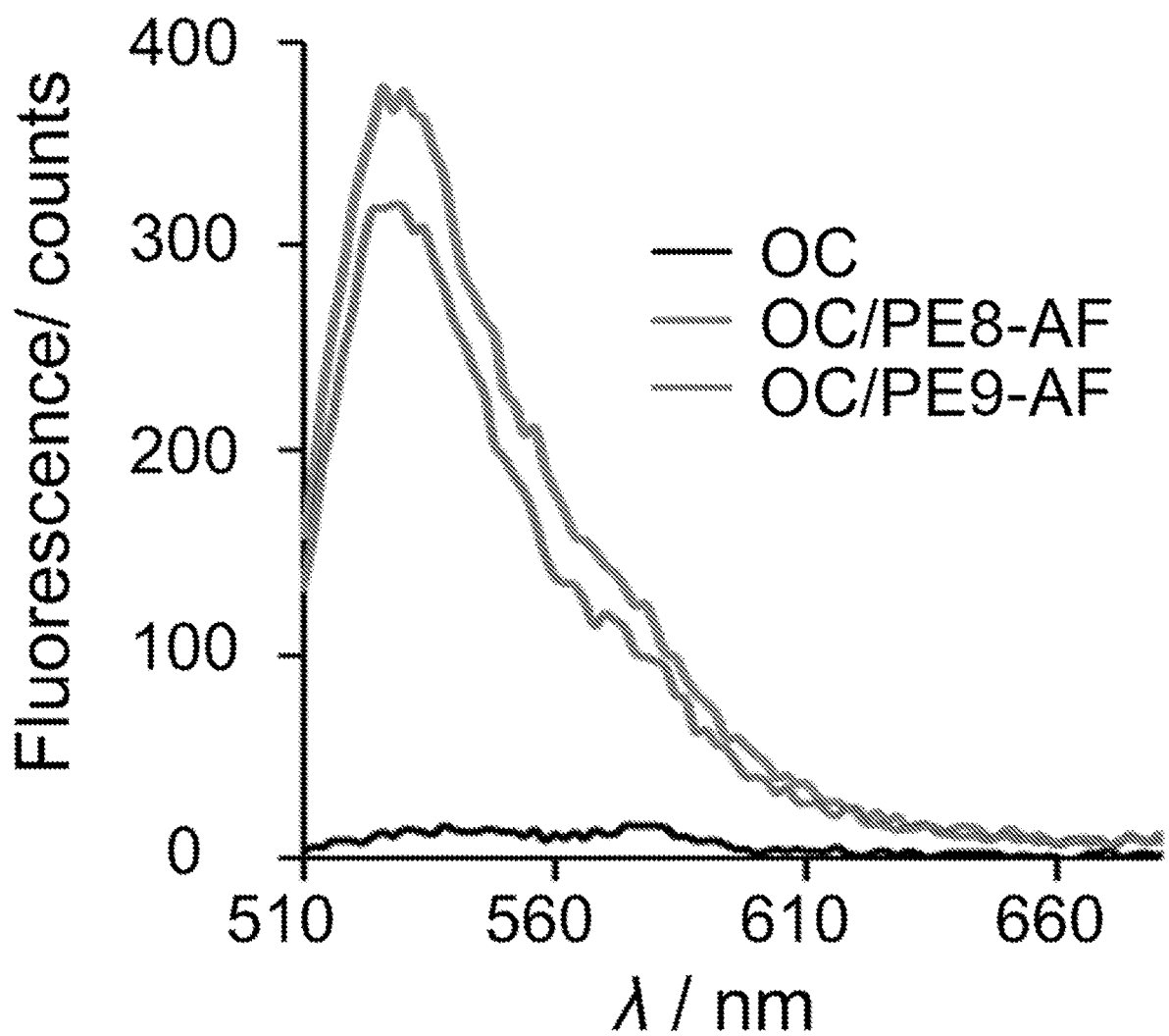
Figure 8D:
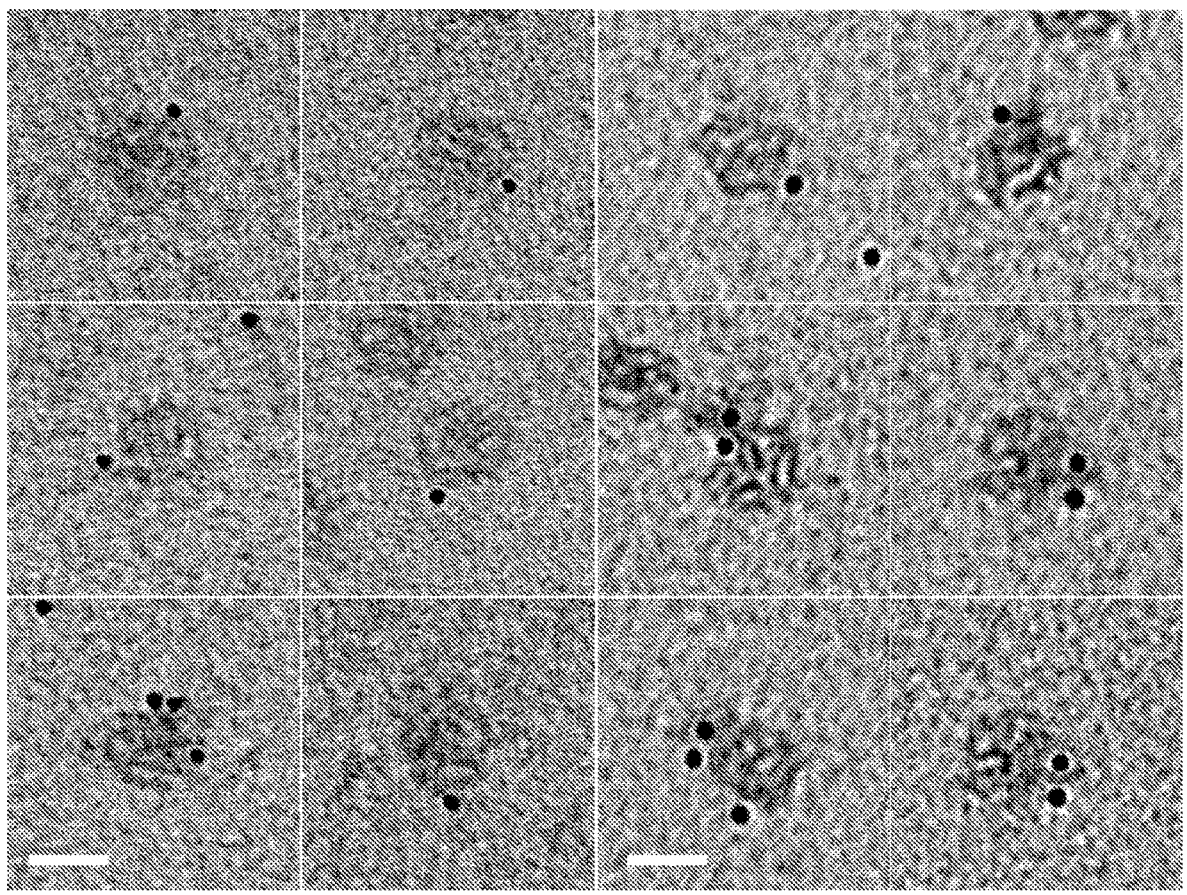
Figure 9A:
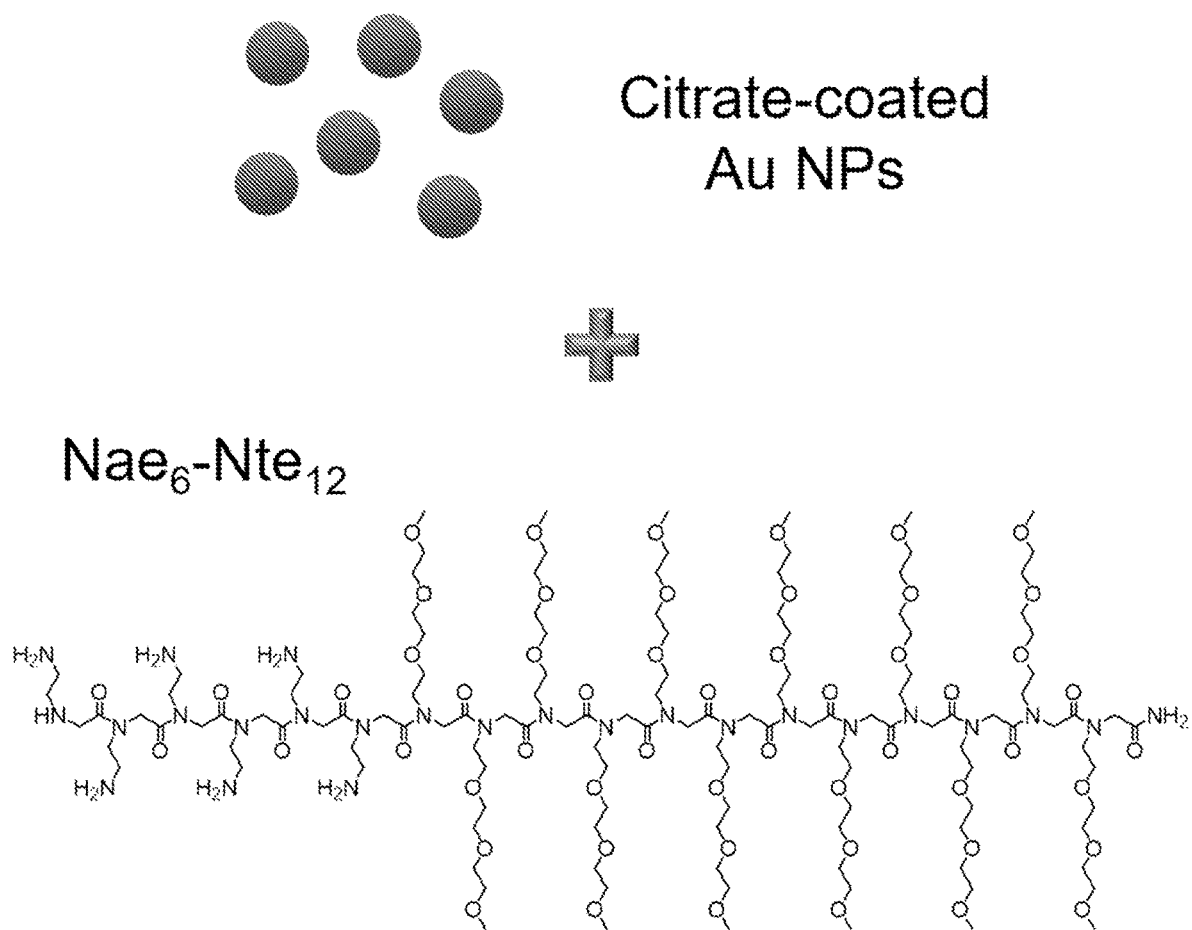
FIG. 9. Stabilization of Au NPs by peptoid coating. (A) Schematic view showing the block-type peptoid $Nae_6$-$Nte_{12}$ was used to stabilize 20 nm citrated-capped gold nanoparticles (Au NPs). (B) UV-visible spectroscopy (UV-vis) showing stable Au NPs (0.5 nM) after coating with $Nae_6$-$Nte_{12}$ block at different concentrations. The buffer was 10 mM phosphate, pH 7.0.
Figure 9B:
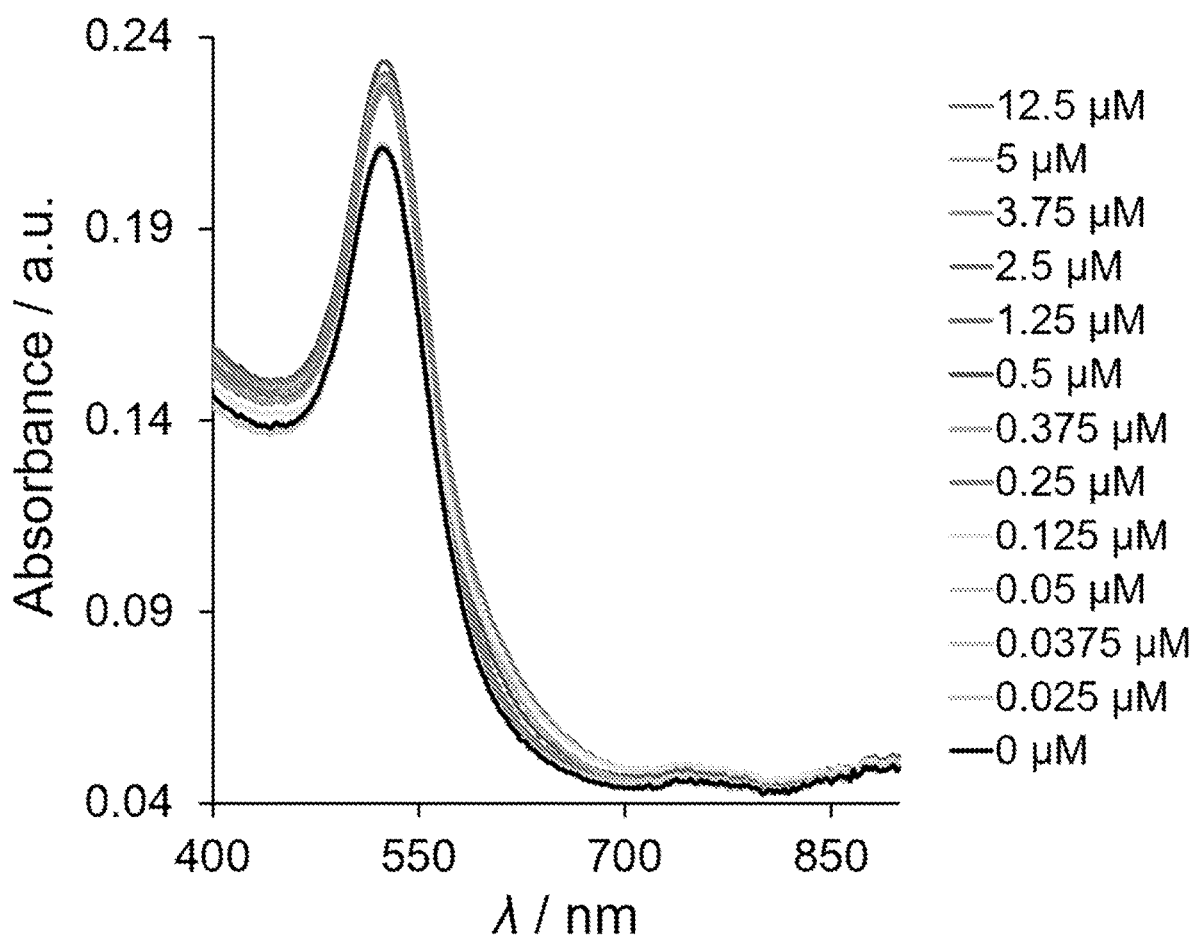
Figure 10:
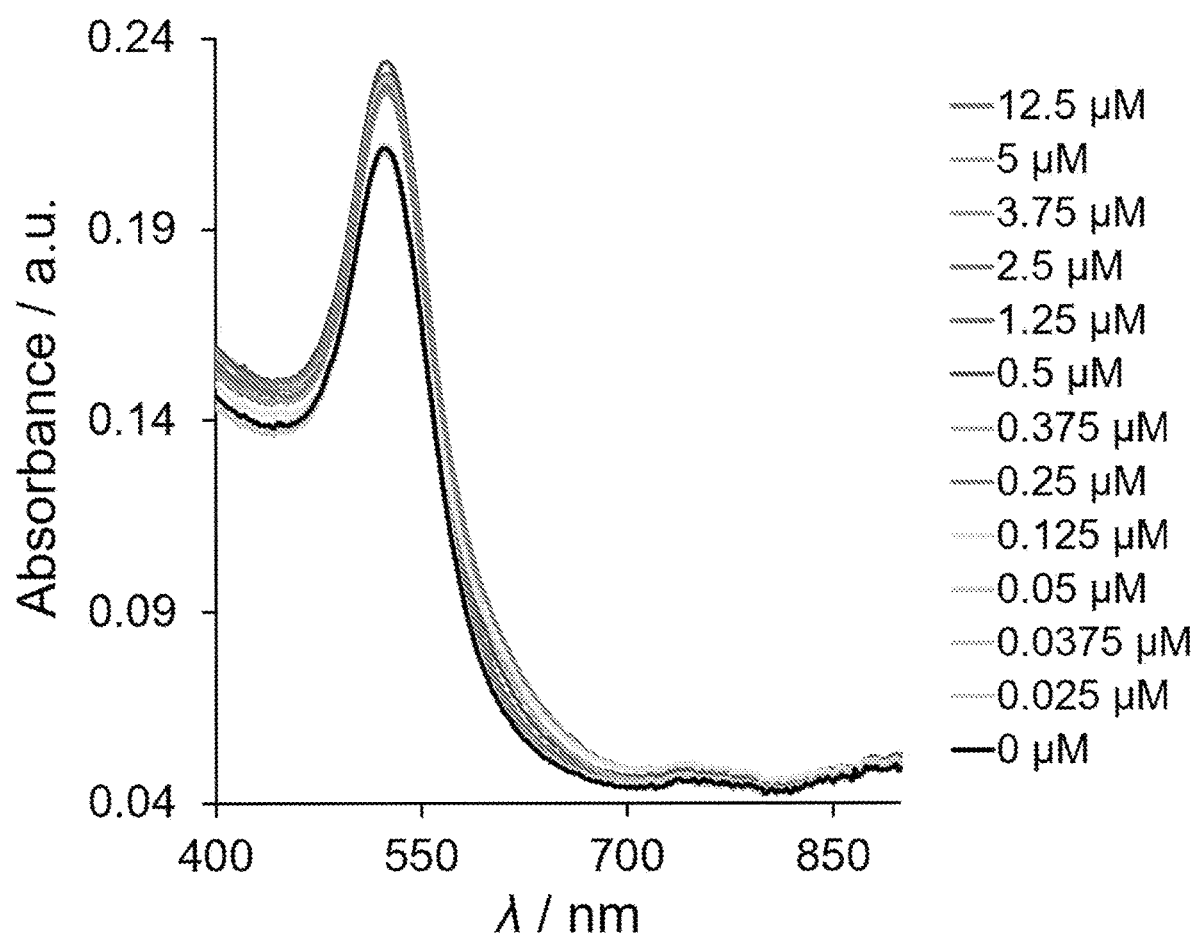
FIG. 10. Peptoid stabilizes Au NPs in solution containing high salt concentration. UV-vis showing that Au NPs remains stable in solution containing 200 mM of sodium chloride after coating with $Nae_6$-$Nte_{12}$ block. Below 0.375 µM of Nae6-Nte12 block, the extent of Au NP aggregation is dependent on the peptoid concentration.
Figure 11:
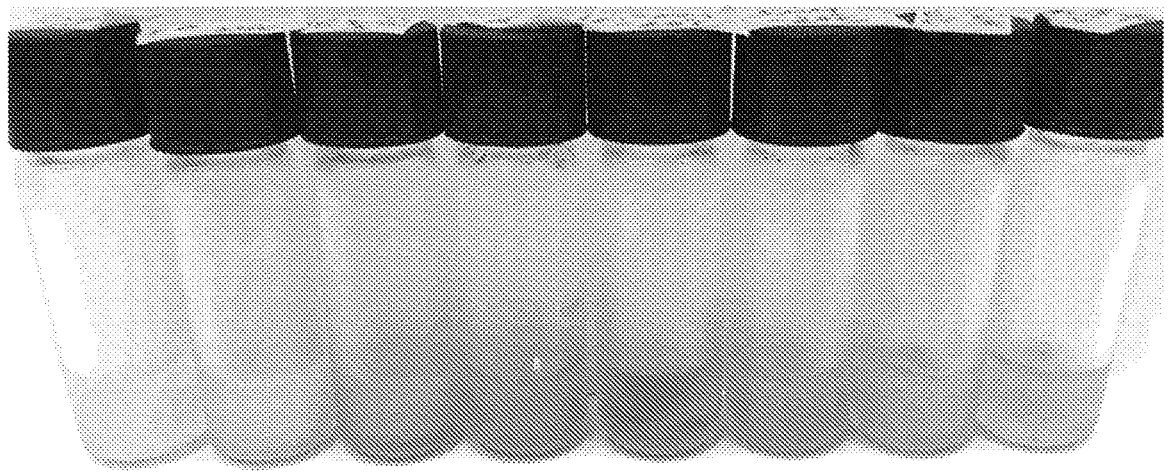
FIG. 11 Cryogenic protection of peptoid stabilized Au NPs. (A) Pictures showing $Nae_6$-$Nte_{12}$ block stabilizes the Au NPs at frozen (top) and melted (bottom) states.
Figure 11:
Figure 11:
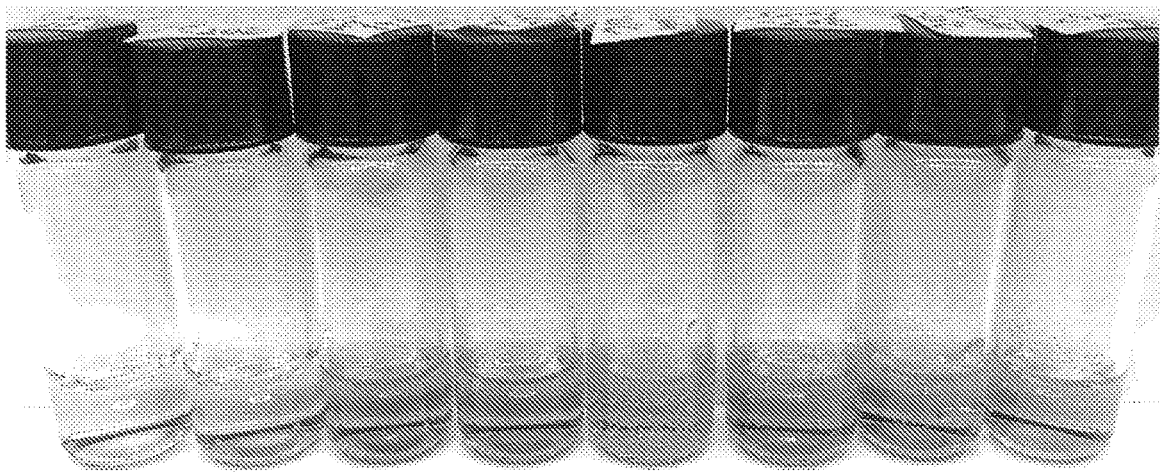
Figure 12:
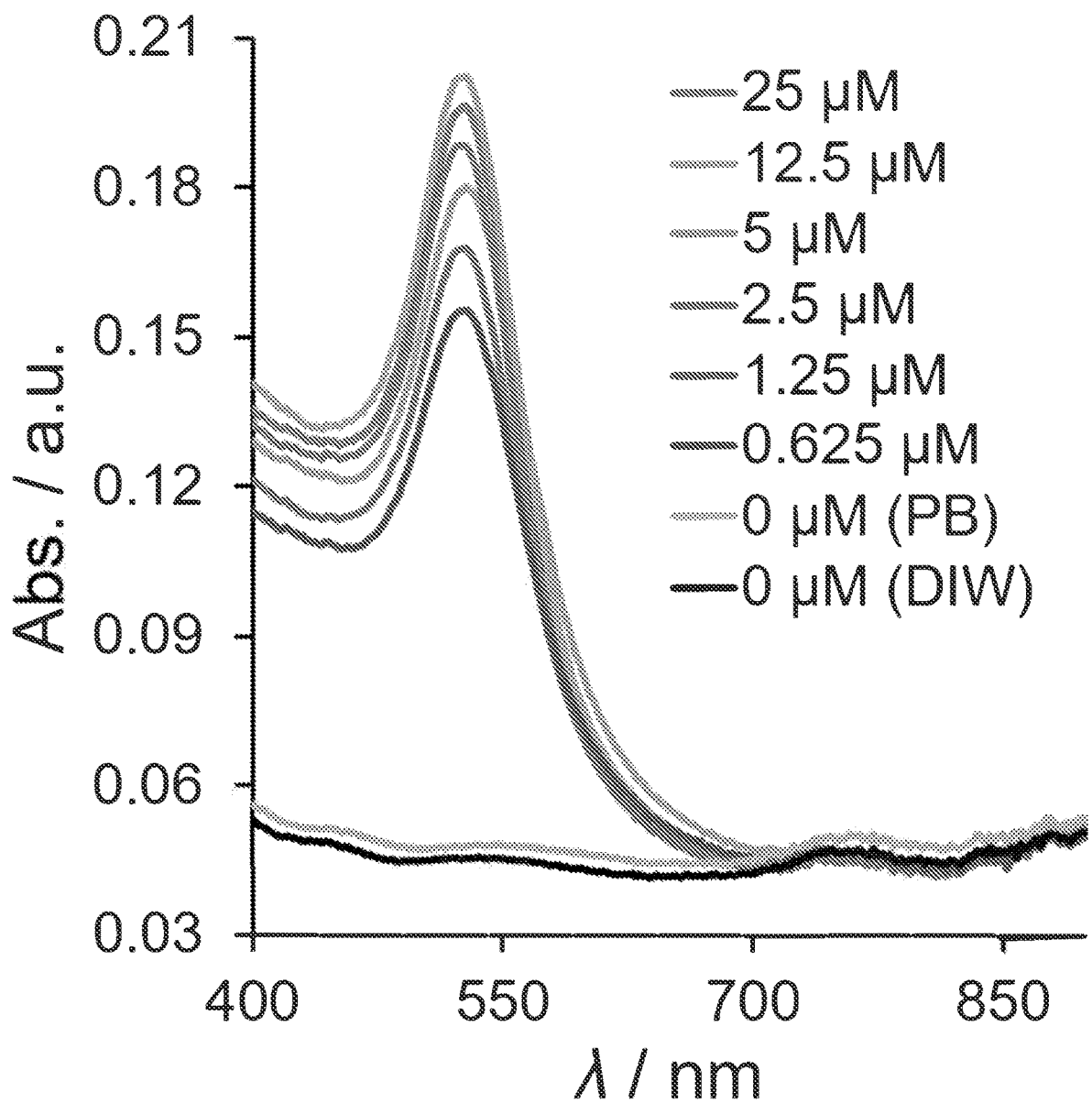
FIG. 12 UV-vis showing stable Au NPs in the melted state with $Nae_6$-$Nte_{12}$ block coating. Higher concentration of peptoid enables higher Au NP stability.
Figure 13A:
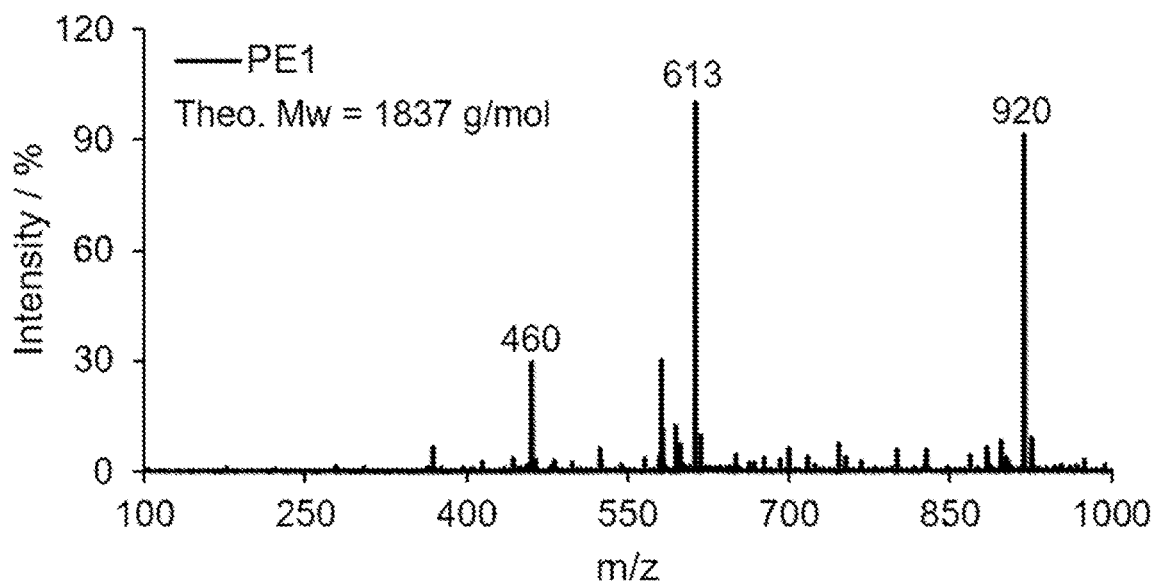
FIG. 13 Mass spectrometry of peptoids PE1-9 prepared by solid phase peptoid synthesis.
Figure 13B:
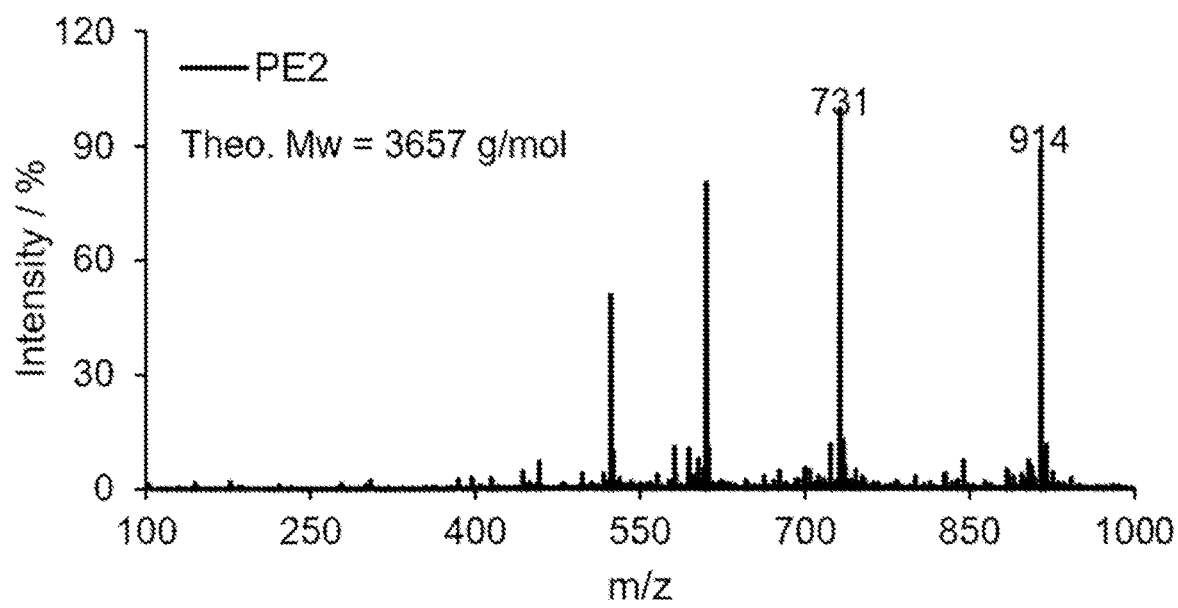
Figure 13C:
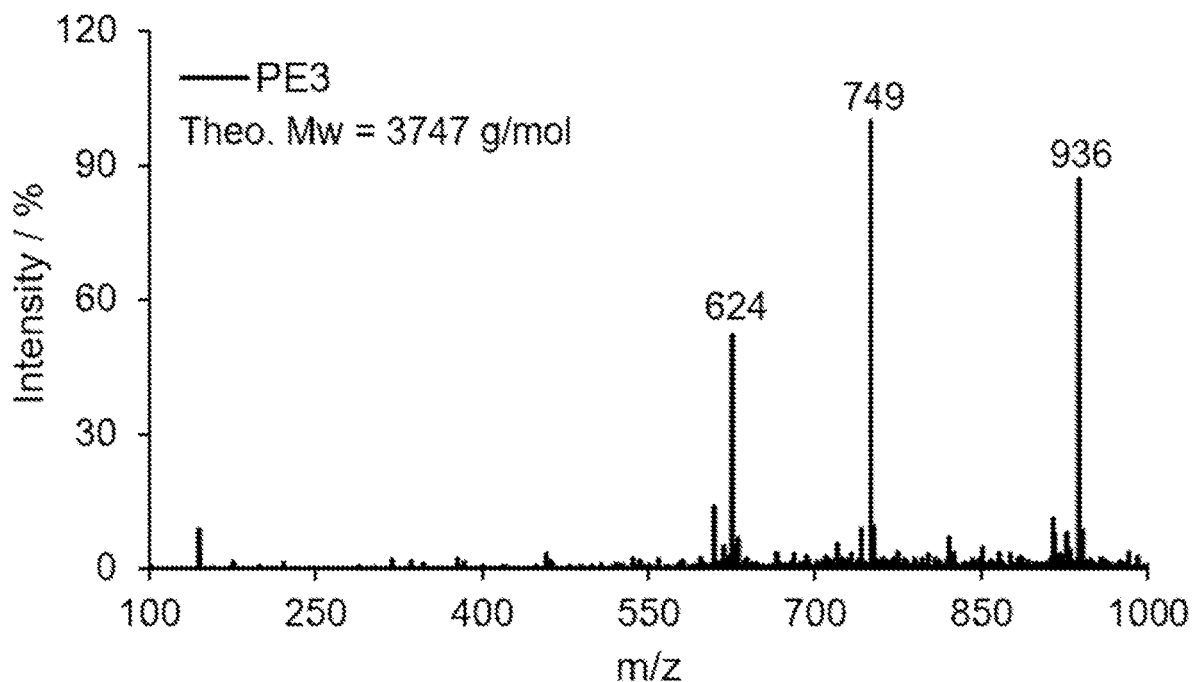
Figure 13D:
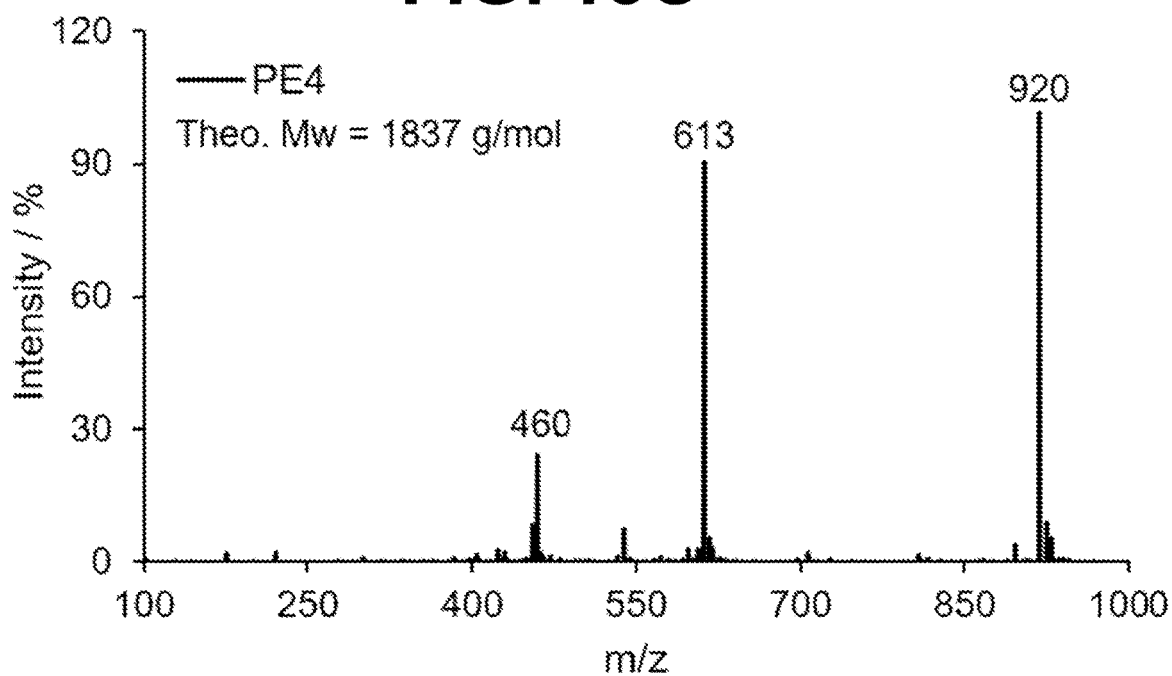
Figure 13E:
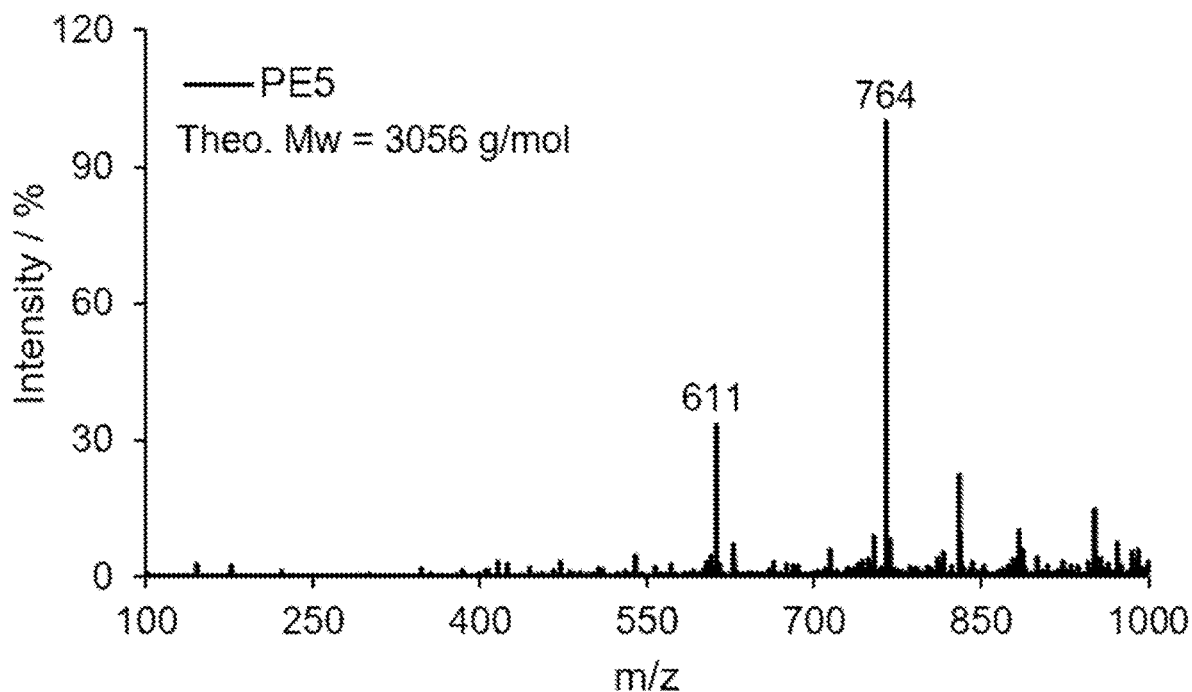
Figure 13F:
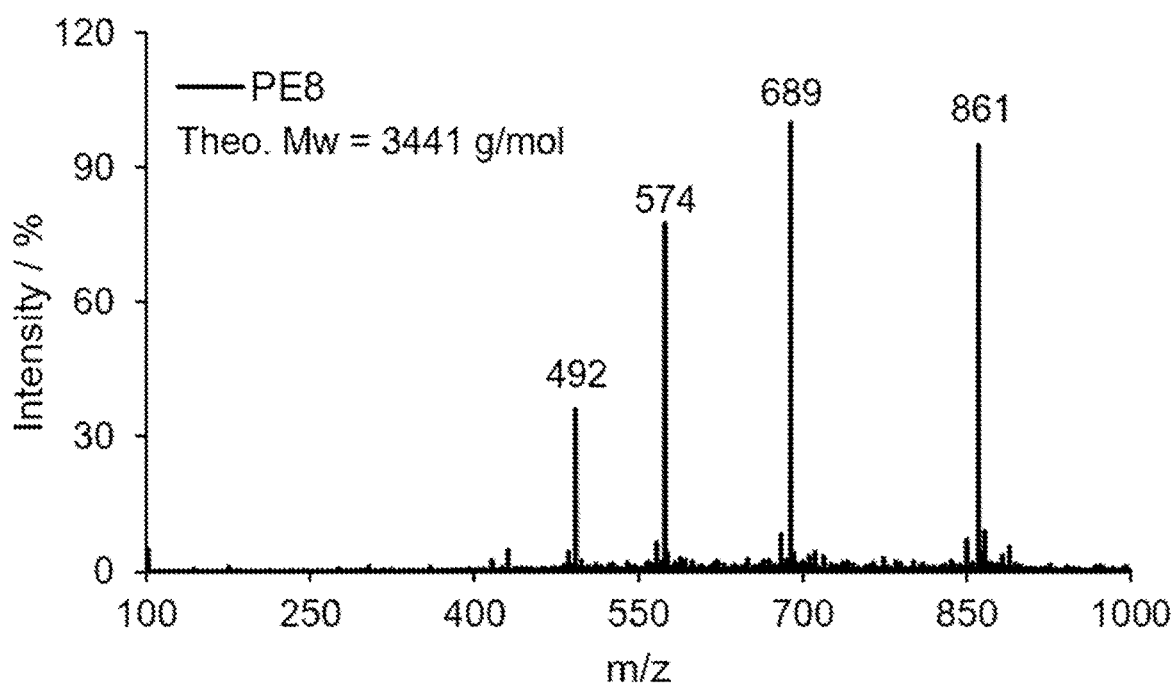
Figure 13G:
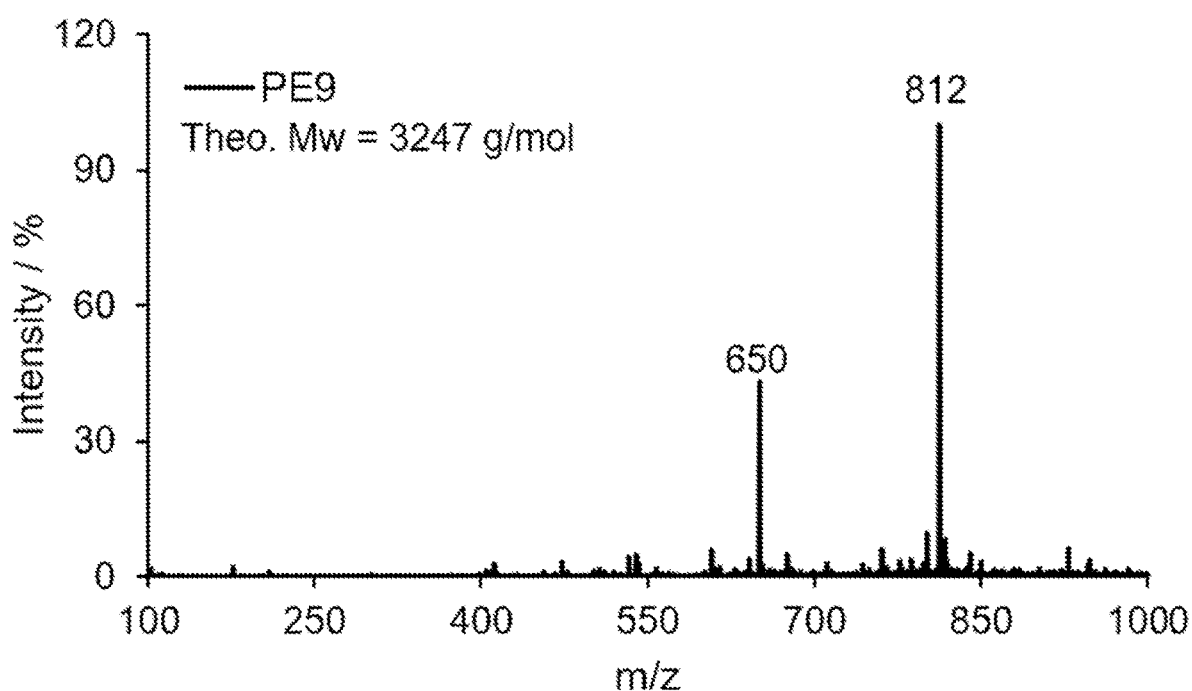
Figure 14A:
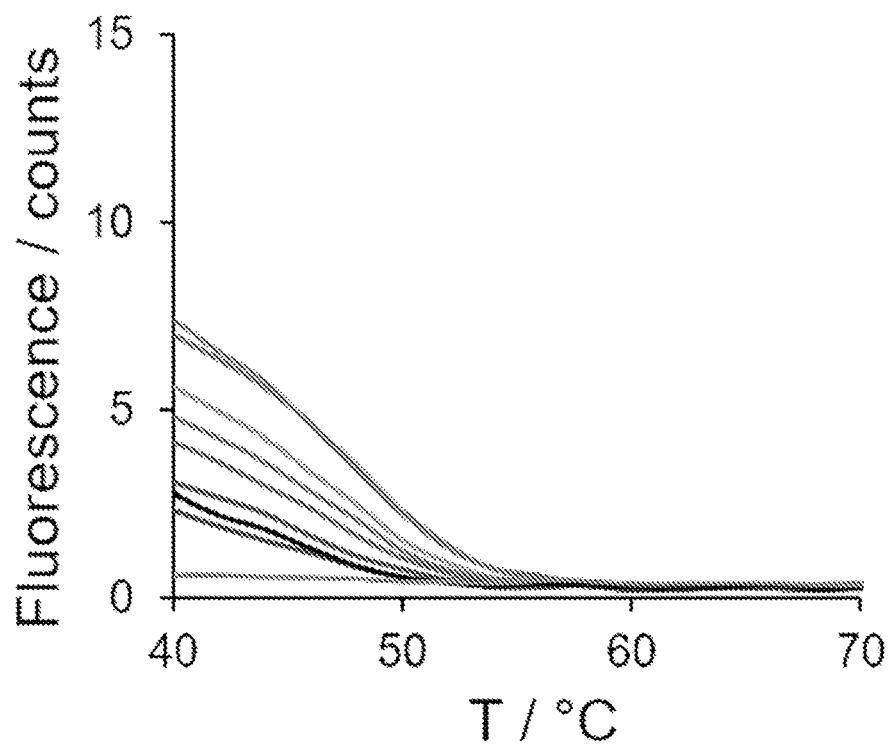
FIG. 14 Real-time SYBR Green I (SG) fluorescence assay of the 15-bp dsDNA in the presence of peptoids (A, B) PE1, (C, D) PE3, (E, F) PE4 and (G, H) PE5 at different N/P. Derivatives of the fluorescence intensities were plotted against the increasing temperature.
Figure 14B:
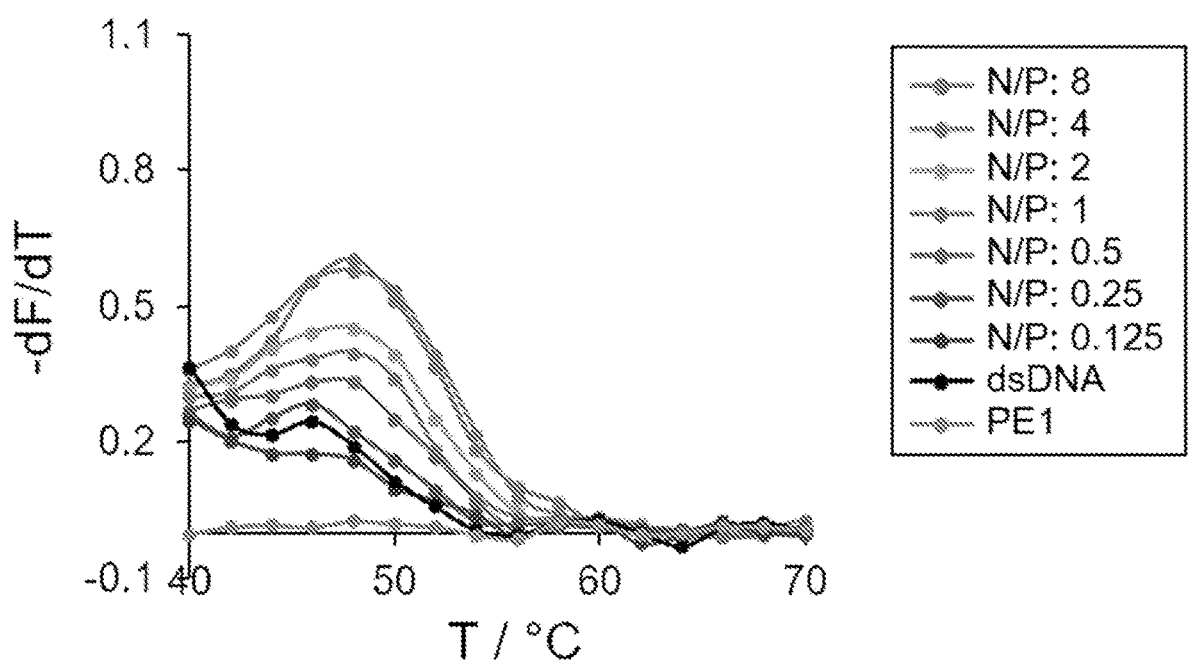
Figure 14C:
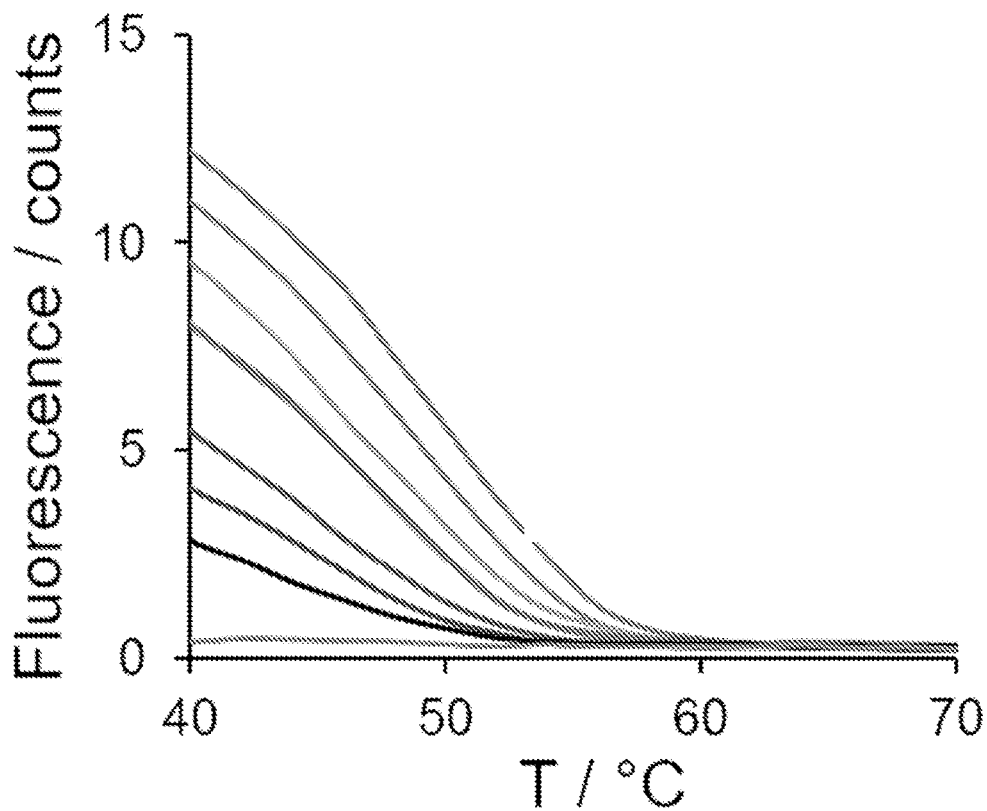
Figure 14D:
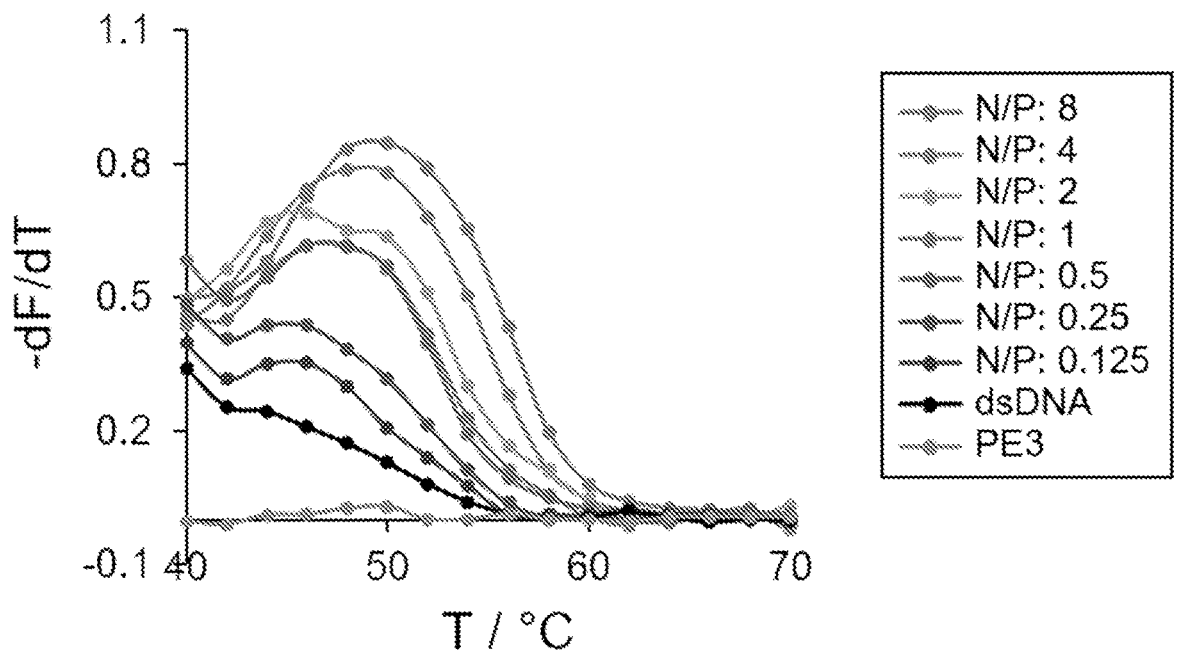
Figure 14E:
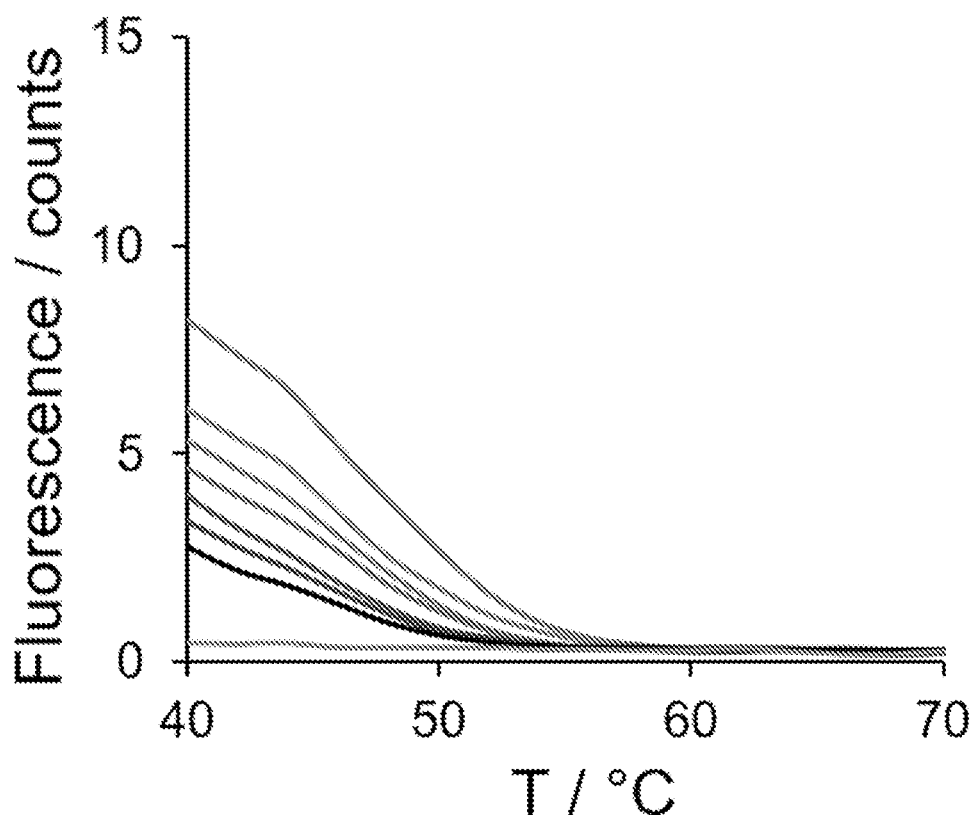
Figure 14F:
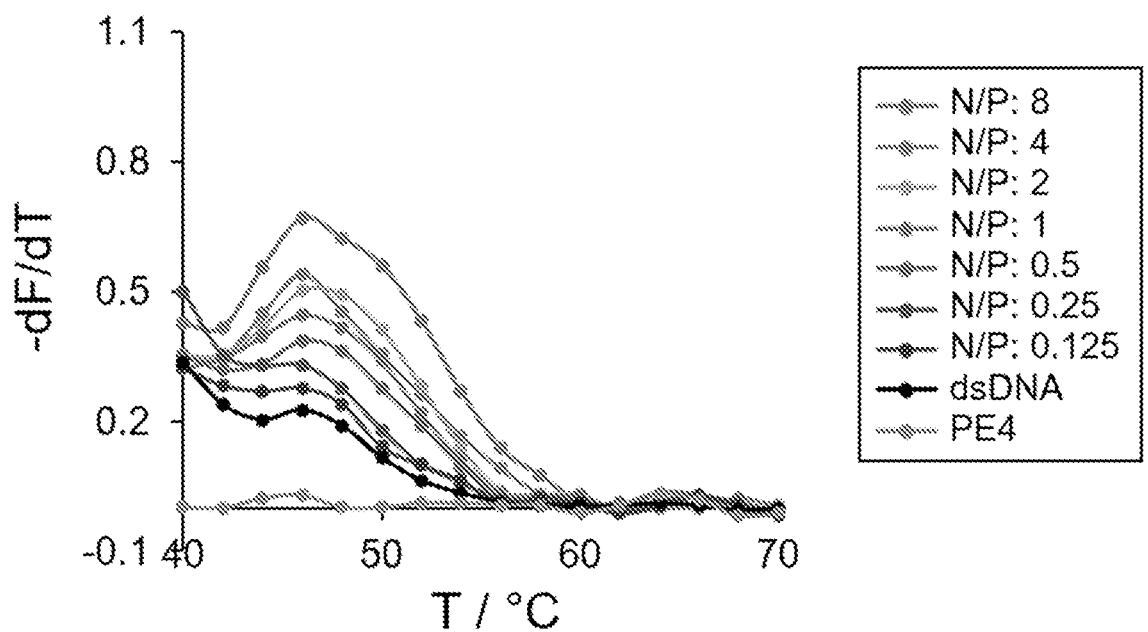
Figure 14G:
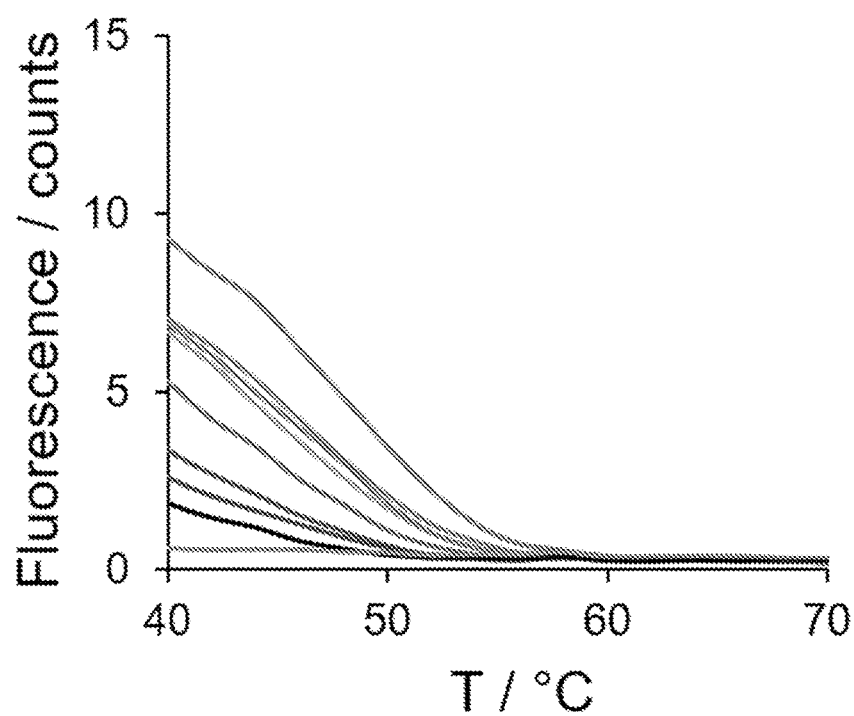
Figure 14H:
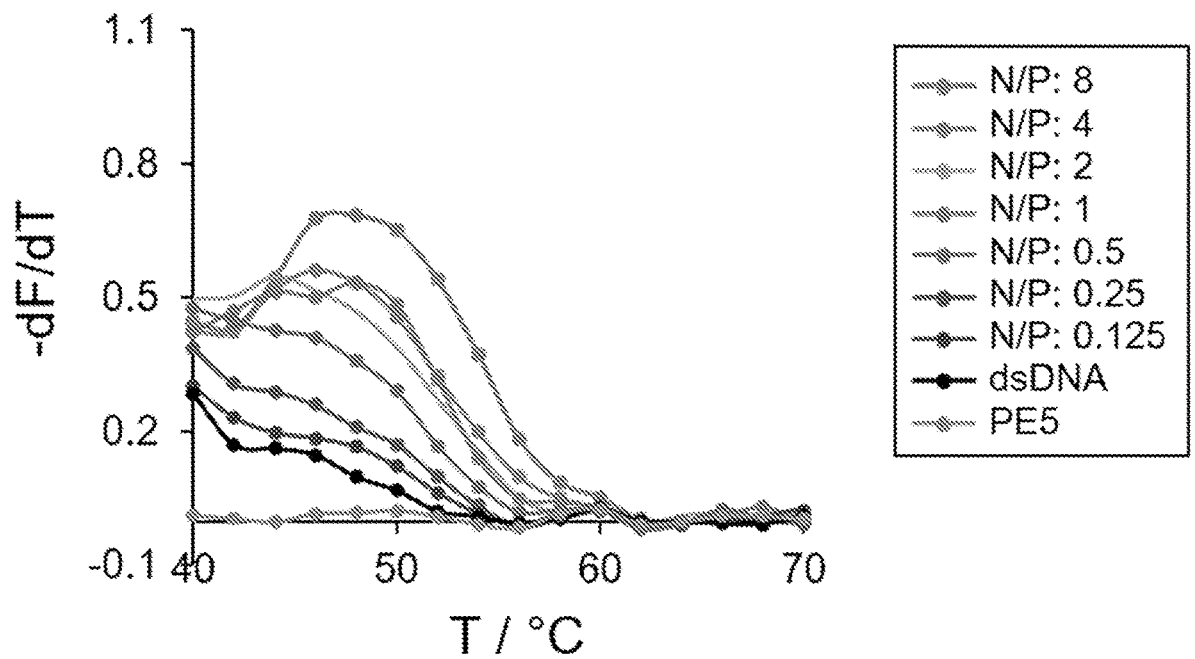
Figure 43:
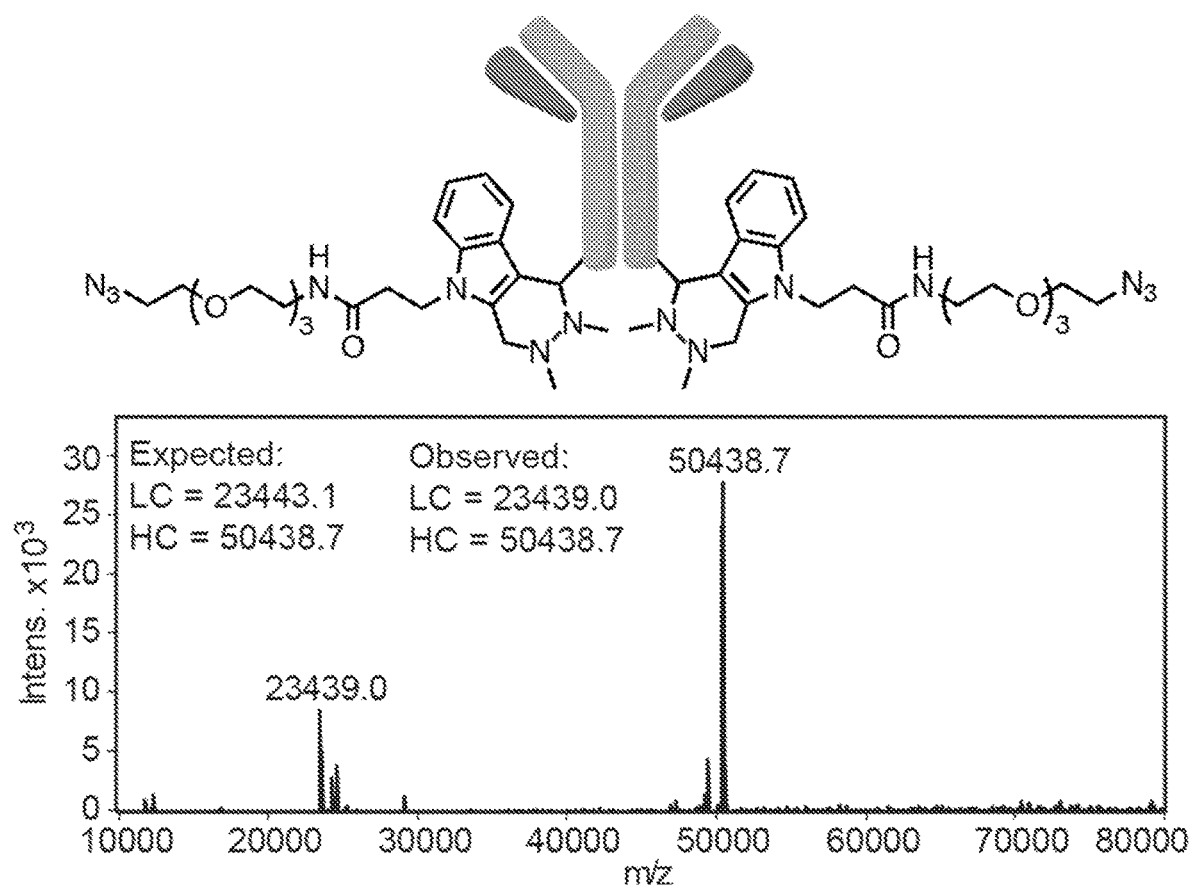
FIG. 43 Site-specific modification of Trastuzumab. Top: schematic view of the modification. Bottom: ESI-LC/MS analyses of the Trastuzumab-azide.

Peptoid-protected OCs can be modified with different biological moieties by incorporating reactive groups into the peptoid sequences. Toward this end, two clickable peptoids (brush and block types, PE8 and PE9) were synthesized (FIG. 8) and used to stabilize OCs. Azide fluor 488 was then conjugated to OCs via copper-catalyzed click chemistry. As shown in FIG. 8C, the success of surface conjugation was confirmed by the increased fluorescence from OCs. The peptoid-protected OCs can also be functionalized with larger biomolecules such as Trastuzumab (Tz), an IgG1 monoclonal antibody used to treat breast cancers that are HER2 receptor positive. To this end, Trastuzumab was expressed with two azide linkers at the C-terminal fGly residue of the Tz sequence prior to peptoid conjugation (62, 63). This allows us to perform site-specific antibody-peptoid conjugation via alkyne-azide reaction (FIG. 43), where the active antibody domains are presented in an orientated fashion. As shown in FIG. 8D, the conjugation of Trastuzumab on OCs was confirmed by immunogold labelling, where the Tz was stained by Au NP (6 nm)-modified protein G and visualized by TEM. The Tz-displaying property of OCs can be potentially combined with the capability of anti-cancer drug loading to provide a combinatory method toward cancer therapy.

SEQUENCE LISTING

A Sequence Listing conforming to the rules of WIPO Standard ST.25 is hereby incorporated by reference. The Sequence Listing has been filed as an electronic document via EFS-Web in ASCII format. The electronic document, created on Sep. 25, 2020, is entitled "SEQ-369-304_ST25.txt", and is 37,860 bytes in size.

REFERENCES

1. Seeman N C (2003) DNA in a material world. *Nature* 421:427.
2. Lin C, Liu Y, Yan H (2009) Designer DNA Nanoarchitectures. *Biochemistry* 48:1663-1674.
3. Pinheiro A V, Han D, Shih W M, Yan H (2011) Challenges and opportunities for structural DNA nanotechnology. *Nat Nanotechnol* 6:763-772.
4. Rothemund P W K (2006) Folding DNA to create nanoscale shapes and patterns. *Nature* 440:297.
5. Mirkin C A, Letsinger R L, Mucic R C, Storhoff J J (1996) A DNA-based method for rationally assembling nanoparticles into macroscopic materials. *Nature* 382:607-609.
6. Niemeyer C M, Burger W, Peplies J (1998) Covalent DNA-Streptavidin Conjugates as Building Blocks for Novel Biometallic Nanostructures. *Angew Chemie Int Ed* 37:2265-2268.
7. Keren K, et al. (2002) Sequence-Specific Molecular Lithography on Single DNA Molecules. *Science* (80-) 297:72 LP-75.
8. Ford W E, Harnack O, Yasuda A, Wessels J M (2001) Platinated DNA as Precursors to Templated Chains of Metal Nanoparticles. *Adv Mater* 13:1793-1797.
9. Alivisatos A P, et al. (1996) Organization of "nanocrystal molecules" using DNA. *Nature* 382:609-611.
10. Nykypanchuk D, Maye M M, van der Lelie D, Gang O (2008) DNA-guided crystallization of colloidal nanoparticles. *Nature* 451:549.
11. Zhang Y, Lu F, Yager K G, van der Lelie D, Gang O (2013) A general strategy for the DNA-mediated self-assembly of functional nanoparticles into heterogeneous systems. *Nat Nanotechnol* 8:865.
12. Chandrasekaran A R, Levchenko O (2016) DNA Nanocages. *Chem Mater* 28:5569-5581.
13. Schneider A-K, Niemeyer C M (2018) DNA Surface Technology: From Gene Sensors to Integrated Systems for Life and Materials Sciences. *Angew Chemie Int Ed* 57:16959-16967.
14. Zhu B, Wang L, Li J, Fan C (2017) Precisely Tailored DNA Nanostructures and their Theranostic Applications. *Chem Rec* 17:1213-1230.
15. Zhang Y, et al. (2018) Programmable and Multifunctional DNA-Based Materials for Biomedical Applications. *Adv Mater* 30:1703658.
16. Fu J, Liu M, Liu Y, Yan H (2012) Spatially-Interactive Biomolecular Networks Organized by Nucleic Acid Nanostructures. *Acc Chem Res* 45:1215-1226.
17. Li J, Fan C, Pei H, Shi J, Huang Q (2013) Smart Drug Delivery Nanocarriers with Self-Assembled DNA Nanostructures. *Adv Mater* 25:4386-4396.
18. Amir Y, et al. (2014) Universal computing by DNA origami robots in a living animal. *Nat 20 Nanotechnol* 9:353.
19. Douglas S M, Bachelet I, Church G M (2012) A Logic-Gated Nanorobot for Targeted Transport of Molecular Payloads. *Science* (80-) 335:831 LP-834.
20. Bujold K E, Hsu JCC, Sleiman H F (2016) Optimized DNA "Nanosuitcases" for Encapsulation and Conditional Release of siRNA. *J Am Chem Soc* 138:14030-14038.
21. Schüller V J, et al. (2011) Cellular Immunostimulation by CpG-Sequence-Coated DNA Origami Structures. *ACS Nano* 5:9696-9702.
22. Grossi G, Dalgaard Ebbesen Jepsen M, Kjems J, Andersen E S (2017) Control of enzyme reactions by a reconfigurable DNA nanovault. *Nat Commun* 8:992.
23. Ora A, et al. (2016) Cellular delivery of enzyme-loaded DNA origami. *Chem Commun* 52:14161-14164.
24. Jiang Q, et al. (2012) DNA Origami as a Carrier for Circumvention of Drug Resistance. *J Am Chem Soc* 134:13396-13403.
25. Zhang Q, et al. (2014) DNA Origami as an In Vivo Drug Delivery Vehicle for Cancer Therapy. *ACS Nano* 8:6633-6643.
26. Sun W, et al. (2014) Cocoon-Like Self-Degradable DNA Nanoclew for Anticancer Drug Delivery. *J Am Chem Soc* 136:14722-14725.
27. Douglas S M, et al. (2009) Self-assembly of DNA into nanoscale three-dimensional shapes. *Nature* 459:414.
28. Hahn J, Wickham S F J, Shih W M, Perrault S D (2014) Addressing the Instability of DNA Nanostructures in Tissue Culture. *ACS Nano* 8:8765-8775.
29. Kielar C, et al. (2018) On the Stability of DNA Origami Nanostructures in Low-Magnesium Buffers. *Angew Chemie Int Ed* 57:9470-9474.

30. Kim H, Surwade S P, Powell A, O'Donnell C, Liu H (2014) Stability of DNA Origami Nanostructure under Diverse Chemical Environments. *Chem Mater* 26:5265-5273.
31. Benson E, et al. (2018) Effects of Design Choices on the Stiffness of Wireframe DNA Origami Structures. *ACS Nano* 12:9291-9299.
32. Benson E, et al. (2015) DNA rendering of polyhedral meshes at the nanoscale. *Nature* 523:441.
33. Veneziano R, et al. (2016) Designer nanoscale DNA assemblies programmed from the top down. *Science (80-)* 352:1534 LP-1534.
34. Gerling T, Kube M, Kick B, Dietz H (2018) Sequence-programmable covalent bonding of designed DNA assemblies. *Sci Adv* 4:eaau1157.
35. Cassinelli V, et al. (2015) One-Step Formation of "Chain-Armor"-Stabilized DNA Nanostructures. *Angew Chemie Int Ed* 54:7795-7798. 21
36. Ponnuswamy N, et al. (2017) Oligolysine-based coating protects DNA nanostructures from low-salt denaturation and nuclease degradation. *Nat Commun* 8:15654.
37. Kiviaho J K, et al. (2016) Cationic polymers for DNA origami coating—examining their binding efficiency and tuning the enzymatic reaction rates. *Nanoscale* 8:11674-11680.
38. Agarwal N P, Matthies M, Gur F N, Osada K, Schmidt T L (2017) Block Copolymer Micellization as a Protection Strategy for DNA Origami. *Angew Chemie Int Ed* 56:5460-5464.
39. Mikkilä J, et al. (2014) Virus-Encapsulated DNA Origami Nanostructures for Cellular Delivery. *Nano Lett* 14:2196-2200.
40. Auvinen H, et al. (2017) Protein Coating of DNA Nanostructures for Enhanced Stability and Immunocompatibility. *Adv Healthc Mater* 6:1700692.
41. Sun J, Zuckermann R N (2013) Peptoid Polymers: A Highly Designable Bioinspired Material. *ACS Nano* 7:4715-4732.
42. Figliozzi G M, Goldsmith R, Ng S C, Banville S C, Zuckermann RNBT-M in E (1996) [25] Synthesis of N-substituted glycine peptoid libraries. Combinatorial Chemistry (Academic Press), pp 437-447.
43. Webster A M, Cobb S L (2018) Recent Advances in the Synthesis of Peptoid Macrocycles. *Chem—A Eur J* 24:7560-7573.
44. Miller S M, et al. (1994) Proteolytic studies of homologous peptide and N-substituted glycine peptoid oligomers. *Bioorg Med Chem Lett* 4:2657-2662.
45. Wender P A, et al. (2000) The design, synthesis, and evaluation of molecules that enable or enhance cellular uptake: Peptoid molecular transporters. *Proc Natl Acad Sci* 97:13003-13008.
46. Rothbard J B, et al. (2002) Arginine-Rich Molecular Transporters for Drug Delivery: Role of Backbone Spacing in Cellular Uptake. *J Med Chem* 45:3612-3618.
47. Schröder T, et al. (2008) Peptoidic Amino- and Guanidinium-Carrier Systems: Targeted Drug Delivery into the Cell Cytosol or the Nucleus. *J Med Chem* 51:376-379.
48. Murphy J E, et al. (1998) A combinatorial approach to the discovery of efficient cationic peptoid reagents for gene delivery. *Proc Natl Acad Sci* 95:1517-1522.
49. Tian Y, et al. (2015) Prescribed nanoparticle cluster architectures and low-dimensional arrays built using octahedral DNA origami frames. *Nat Nanotechnol* 10:637.
50. Tian Y, et al. (2016) Lattice engineering through nanoparticle-DNA frameworks. *Nat Mater* 15:654.
51. Statz A R, Meagher R J, Barron A E, Messersmith P B (2005) New Peptidomimetic Polymers for Antifouling Surfaces. *J Am Chem Soc* 127:7972-7973.
52. Xuan S, et al. (2017) Synthesis and Characterization of Well-Defined PEGylated Polypeptoids as Protein-Resistant Polymers. *Biomacromolecules* 18:951-964.
53. Dragan, A. I.; Pavlovic, R.; McGivney, J. B.; Casas-Finet, J. R.; Bishop E. S.; Strouse, R. J.; Schenerman M A. GCD (2012) SYBR Green I: Fluorescence Properties and Interaction with DNA. *J Fluoresc* 22:1189-1199.
54. Zipper H, Brunner H, Bernhagen J, Vitzthum F (2004) Investigations on DNA intercalation and surface binding by SYBR Green I, its structure determination and methodological implications. *Nucleic Acids Res* 32:e103-e103.
55. Krishnamoorthy G, Duportail G, M6ly Y (2002) Structure and Dynamics of Condensed DNA Probed by 1,1′-(4,4,8,8-Tetramethyl-4,8-diazaundecamethylene)bis[4-[[3-methylbenz-1,3-oxazol-2-yl]methylidine]-1,4-dihydroquinolinium] Tetraiodide Fluorescence. *Biochemistry* 41:15277-15287.
56. Guarnieri F, Mezei M (1996) Simulated Annealing of Chemical Potential: A General Procedure for Locating Bound Waters. Application to the Study of the Differential Hydration Propensities of the Major and Minor Grooves of DNA. *J Am Chem Soc* 118:8493-8494.
57. Spink C H, Chaires J B (1999) Effects of Hydration, Ion Release, and Excluded Volume on the Melting of Triplex and Duplex DNA. *Biochemistry* 38:496-508.
58. Tateishi-Karimta H, Sugimoto N (2014) Control of stability and structure of nucleic acids using cosolutes. *Methods* 67:151-158.
59. Miyoshi D, Karimata H, Sugimoto N (2006) Hydration Regulates Thermodynamics of G-Quadruplex Formation under Molecular Crowding Conditions. *J Am Chem Soc* 128:7957-7963.
60. Munkholm C, Parkinson D R, Walt D R (1990) Intramolecular fluorescence self-quenching of fluoresceinamine. *J Am Chem Soc* 112:2608-2612.
61. Hu L, et al. (2012) Highly sensitive fluorescent detection of trypsin based on BSA-stabilized gold nanoclusters. *Biosens Bioelectron* 32:297-299.
62. Xiao H, Woods E C, Vukojicic P, Bertozzi C R (2016) Precision glycocalyx editing as a strategy for cancer immunotherapy. *Proc Nat Acad Sci* 113:10304 LP-10309.
63. Gray, Melissa A.; Stanczak Michal A.; Xiao Han; Pijnenborg, Johan F. A.; Malaker, Stacy A.; Tanzo, Julia T.; Ahn, Green; Weidenbacher, Payton A.; Woods, Elliot C.; Laubli H, Bertozzi C R (2019) Targeted desialylation overcomes glyco-immune checkpoints and potentiates the anticancer immune response in vivo. https://doi.org/026434/chemrxiv8l87146.v1.

Thus while there have been described what are presently believed to be preferred embodiments of the invention, those skilled in the art will realize that changes and modifications may be made thereto without departing from the spirit of the invention, and it is intended to claim all such changes and modifications as fall within the true scope of the invention.

What is claimed is:
1. A composition for stabilizing a biomaterial, said composition comprising a compound of Formula (I), wherein Formula (I) comprises:
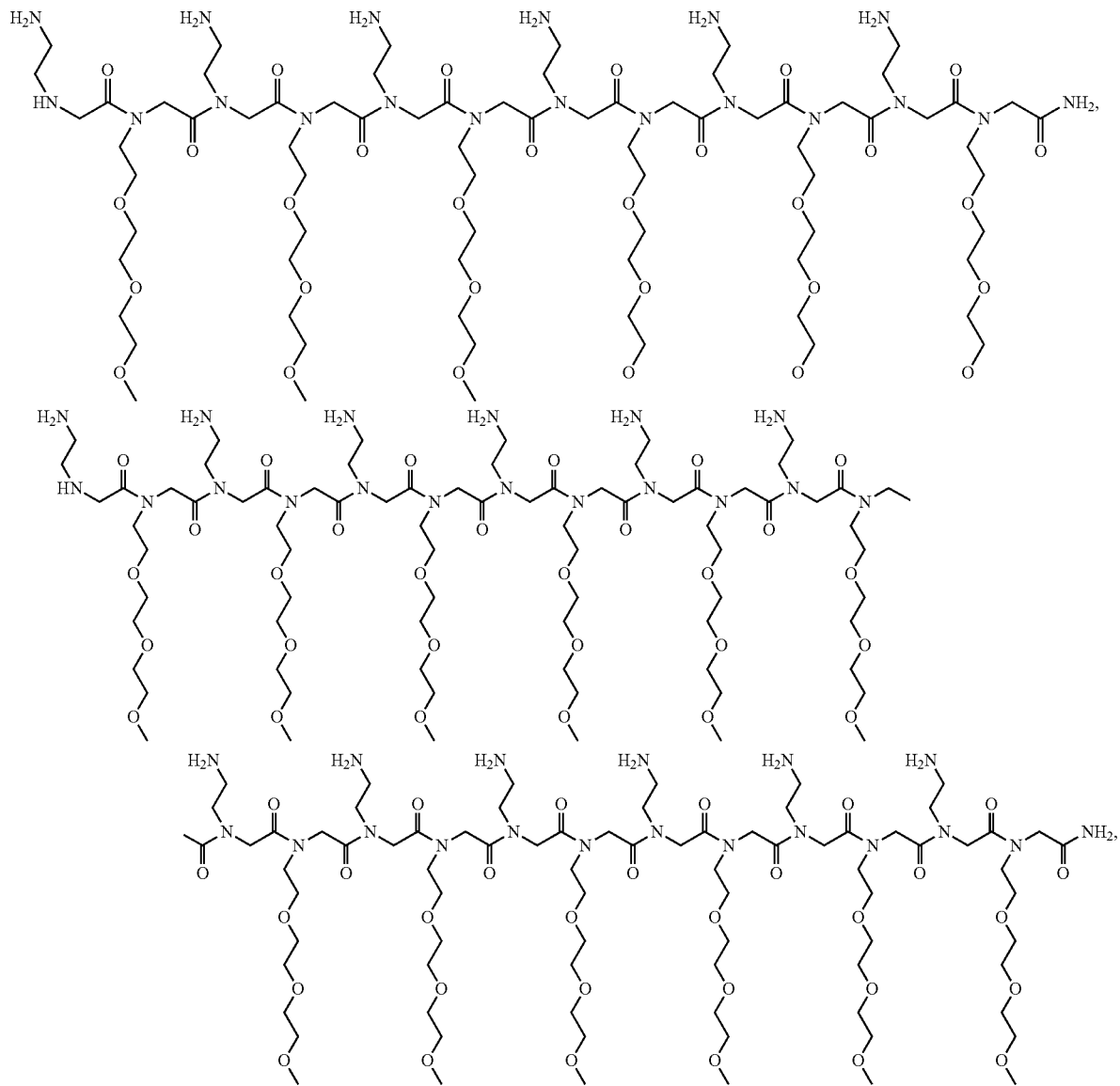
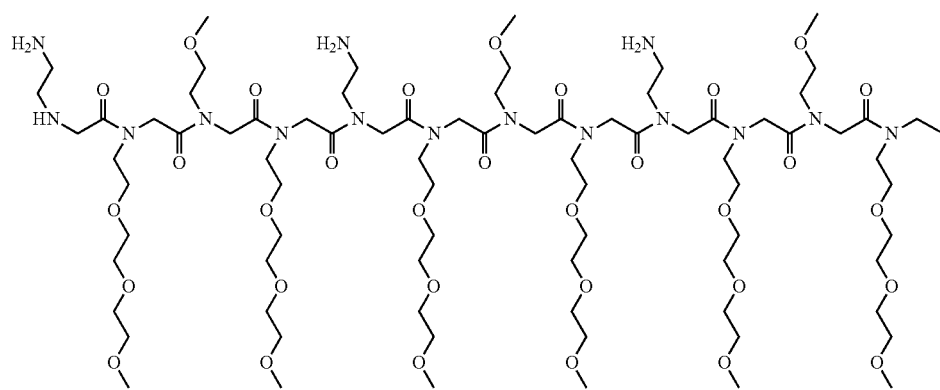

-continued
103
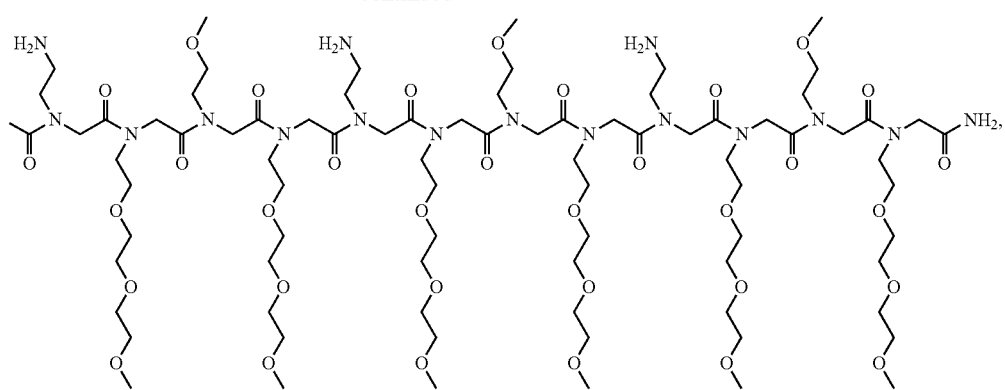
104
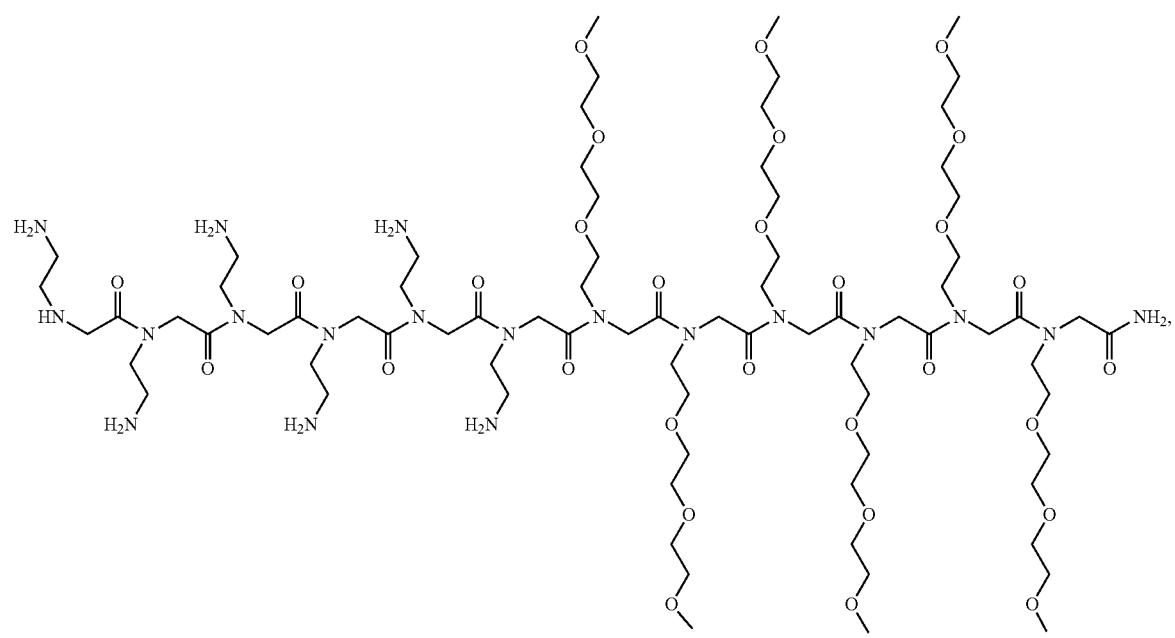
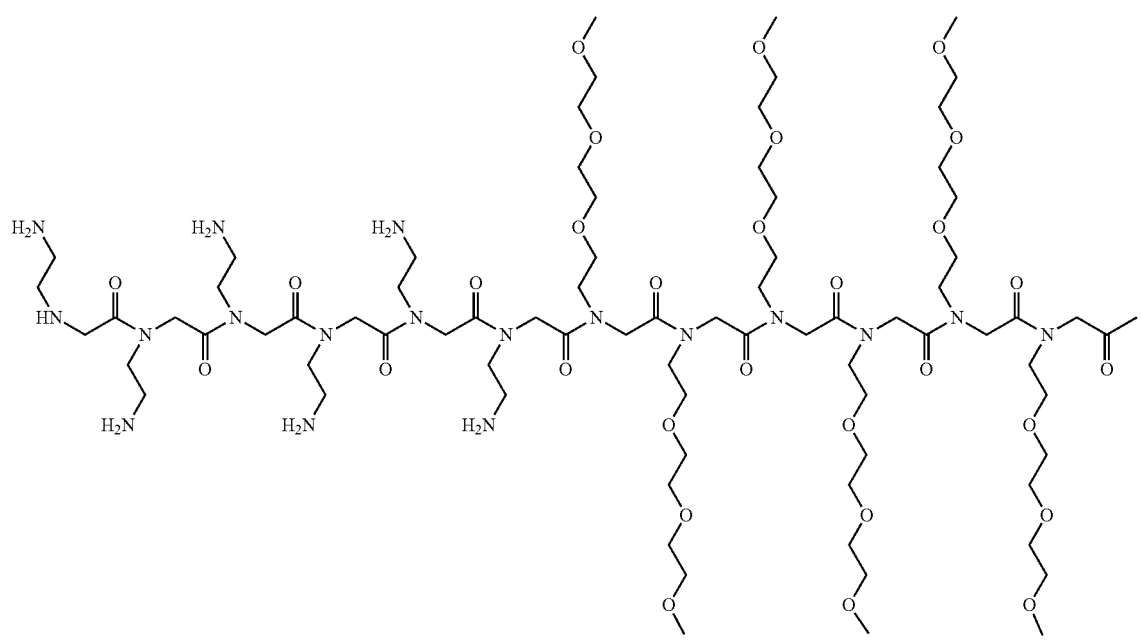

-continued
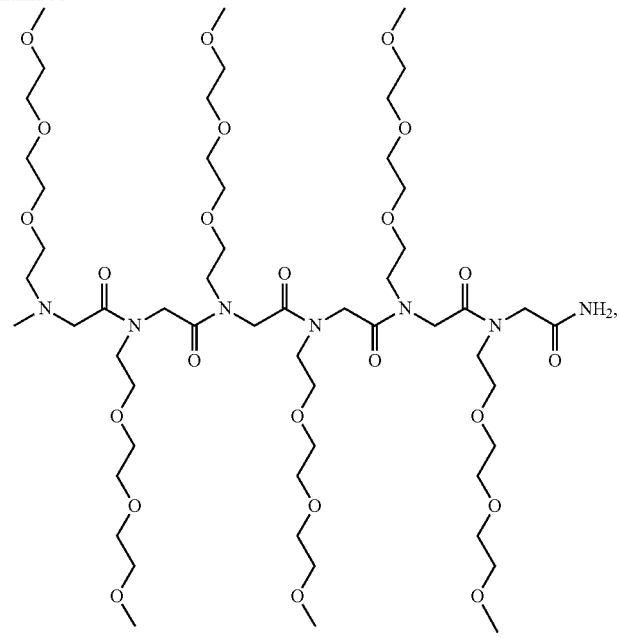
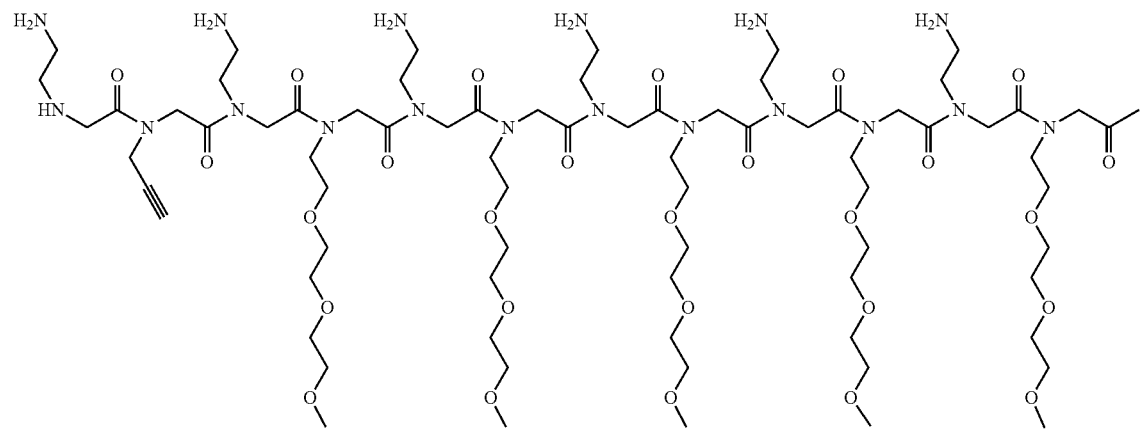
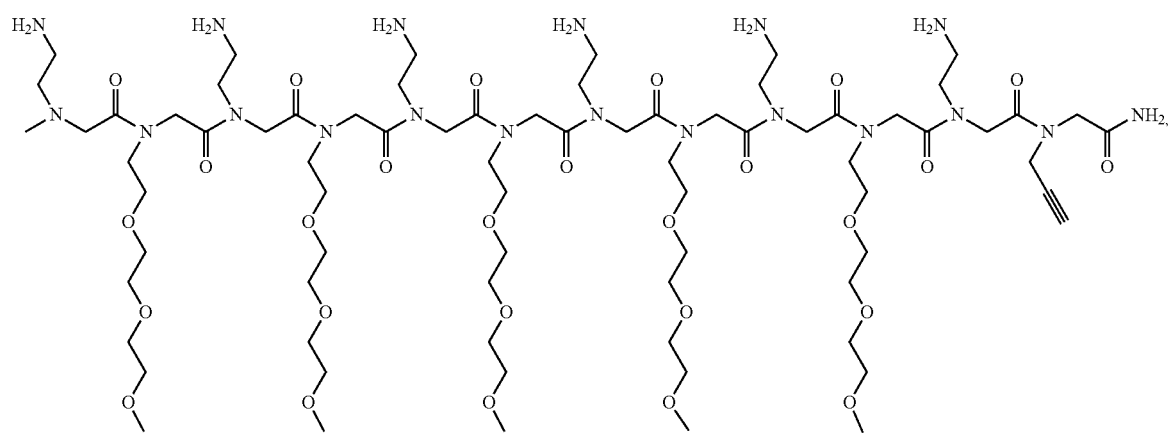

107
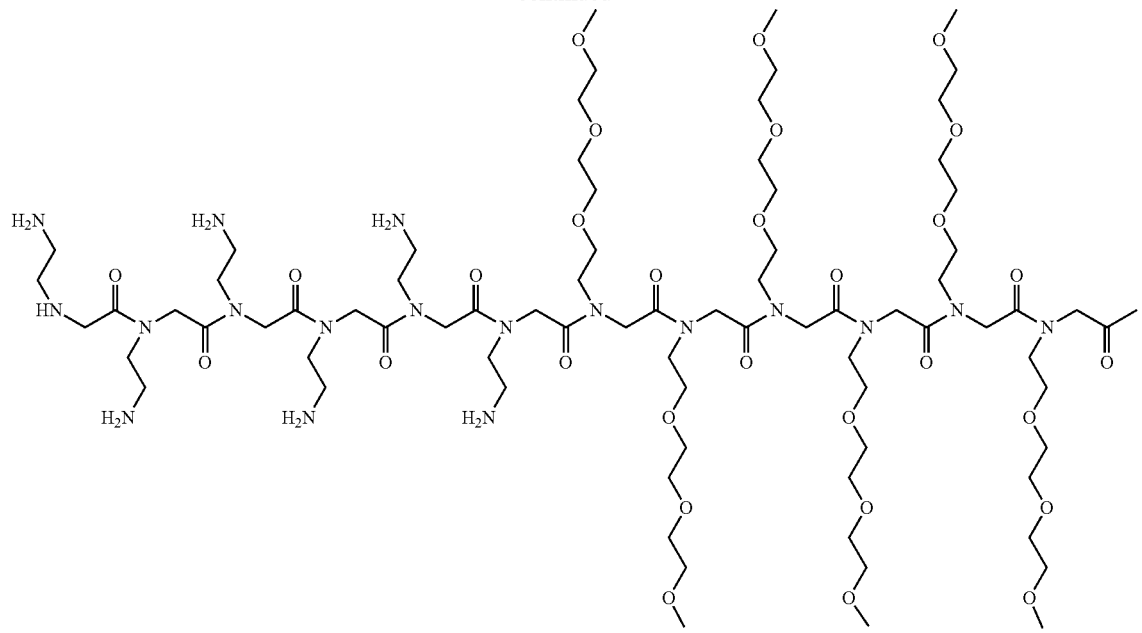
108
-continued
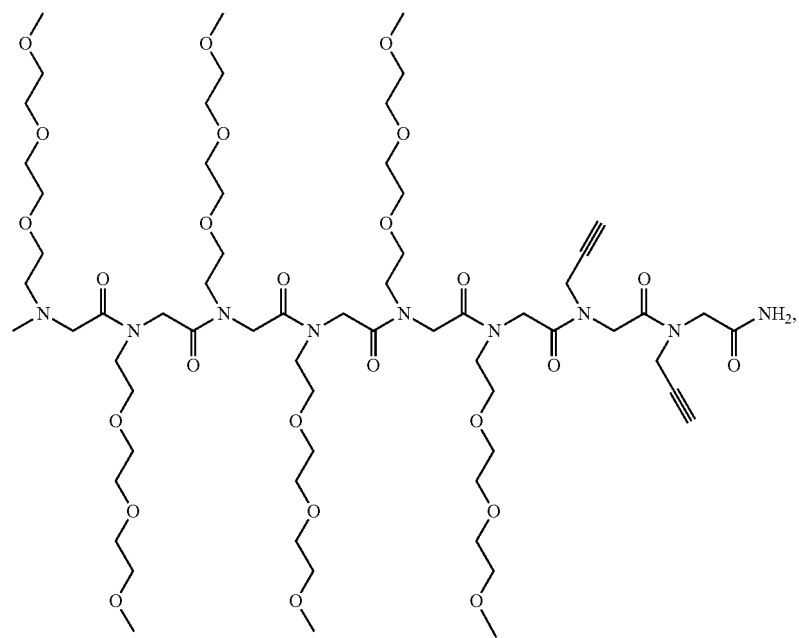

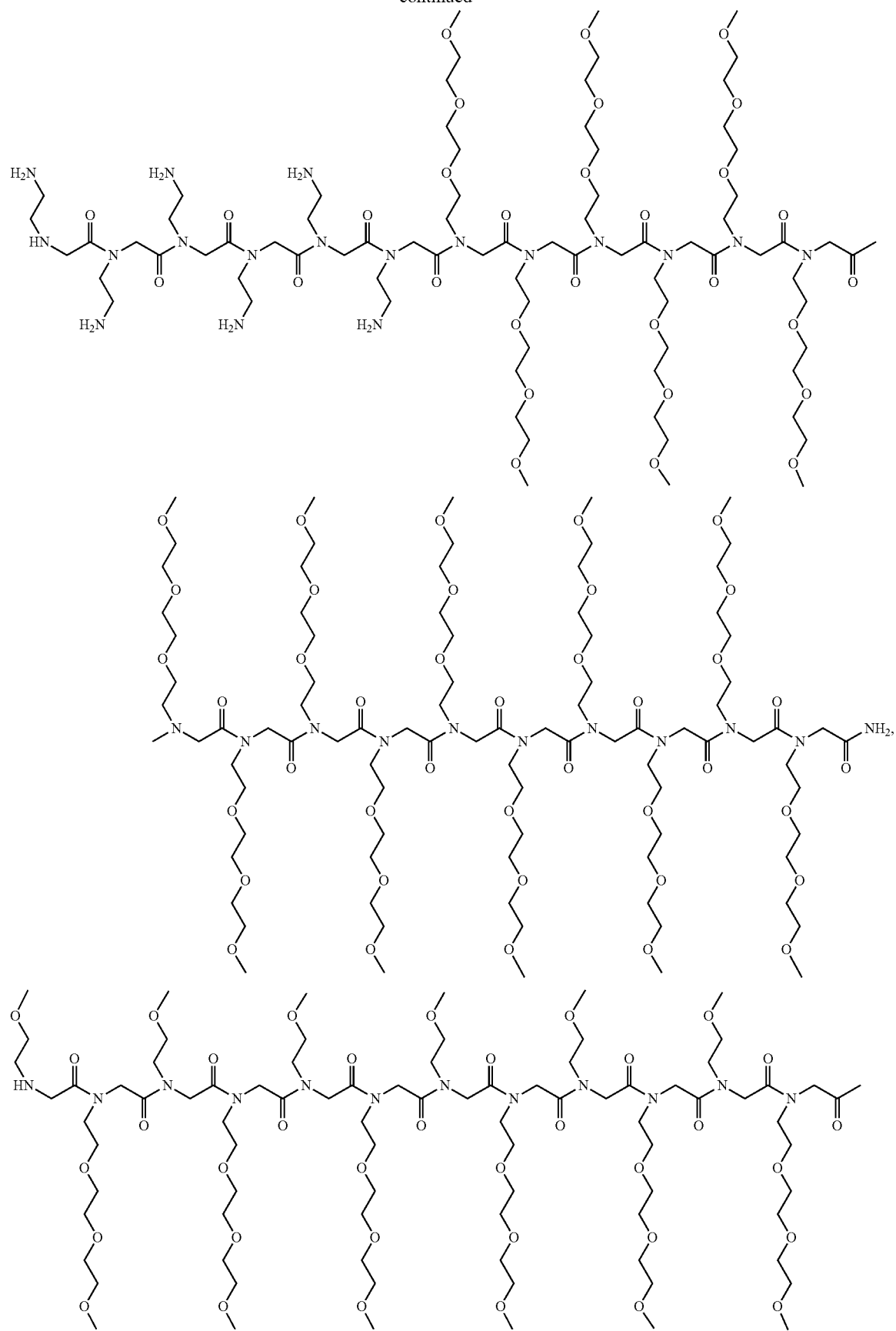

-continued
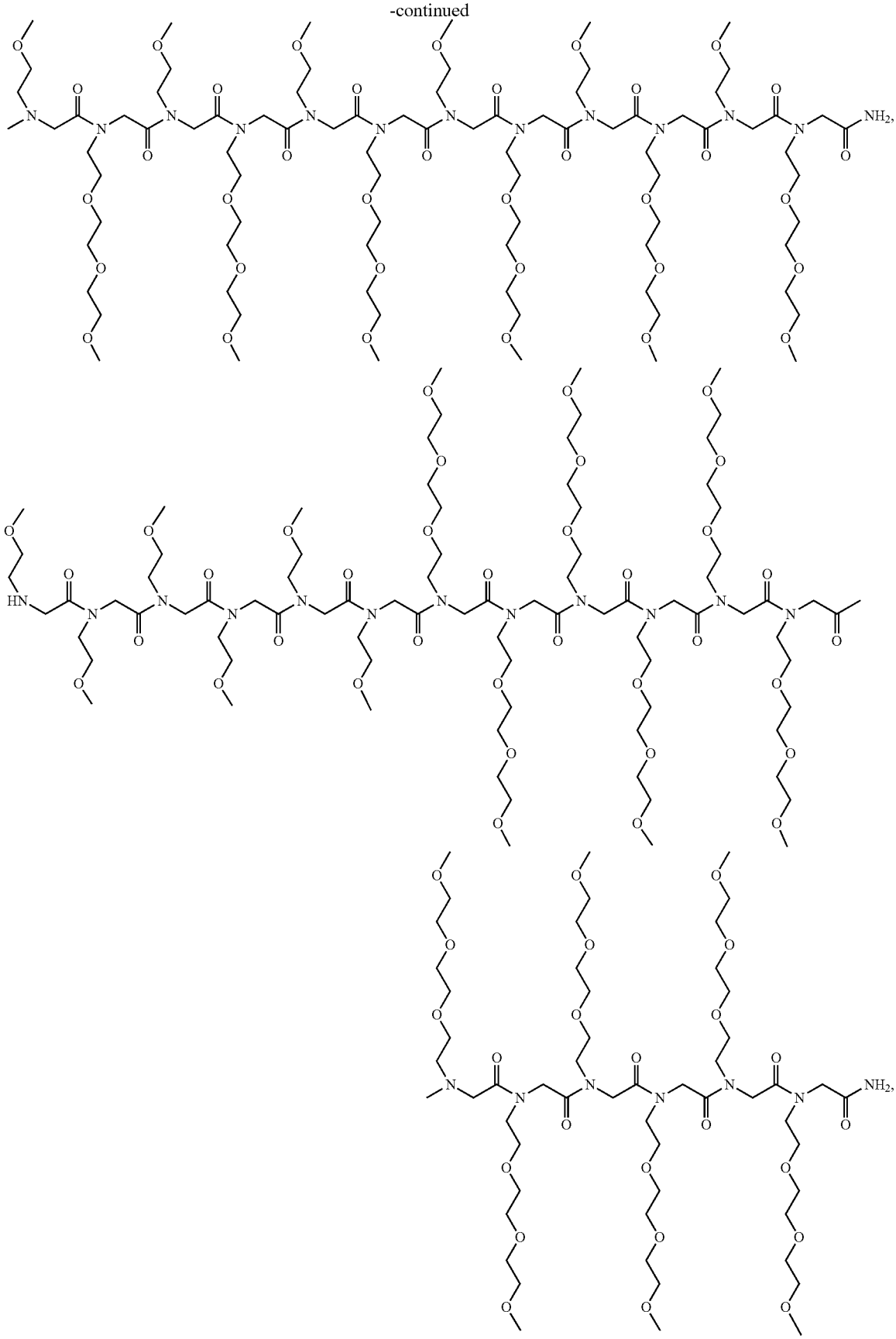

2. A stabilized nanoparticle, wherein the nanoparticle comprises a compound of Formula (I) as described in claim 1.

* * * * *